US008513489B2

(12) United States Patent
Sorek et al.

(10) Patent No.: US 8,513,489 B2
(45) Date of Patent: Aug. 20, 2013

(54) USES OF ANTIMICROBIAL GENES FROM MICROBIAL GENOME

(75) Inventors: Rotem Sorek, Rehovot (IL); Edward M. Rubin, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 607 days.

(21) Appl. No.: 12/519,350

(22) PCT Filed: Dec. 15, 2007

(86) PCT No.: PCT/US2007/087691
§ 371 (c)(1),
(2), (4) Date: Sep. 11, 2009

(87) PCT Pub. No.: WO2008/133749
PCT Pub. Date: Nov. 6, 2008

(65) Prior Publication Data

US 2010/0050303 A1 Feb. 25, 2010

Related U.S. Application Data

(60) Provisional application No. 60/870,322, filed on Dec. 15, 2006.

(51) Int. Cl.
*C12N 15/09* (2006.01)
*C12N 15/82* (2006.01)
*A01H 5/00* (2006.01)
*A01H 5/10* (2006.01)

(52) U.S. Cl.
USPC ........... 800/279; 800/278; 800/298; 800/295; 435/468

(58) Field of Classification Search
None
See application file for complete search history.

(56) References Cited

U.S. PATENT DOCUMENTS

| | | | | |
|---|---|---|---|---|
| 4,873,192 | A | 10/1989 | Kunkel | |
| 6,465,636 | B1 | 10/2002 | Stuiver et al. | |
| 6,534,075 | B1 | 3/2003 | Hei et al. | |
| 7,041,808 | B2 | 5/2006 | Tomie et al. | |
| 2004/0093636 | A1 | 5/2004 | Daniell | |
| 2004/0101876 | A1 * | 5/2004 | Mintz et al. | 435/6 |
| 2004/0235738 | A1 | 11/2004 | Lu et al. | |
| 2006/0014179 | A1 | 1/2006 | Roberts | |
| 2006/0272050 | A1 | 11/2006 | Segura et al. | |

OTHER PUBLICATIONS

Genbank Accession No. NP_049726.1; Mar. 26, 2010.*
Genbank Accession No. CP000360.1. Sep. 10, 2010.*
GenBank Gene ID. 1258703; updated Apr. 3, 2013.*
Aliprandi, P. et al. (May 9, 2008). "S1 Ribosomal Protein Functions in Translation Initiation and Ribonuclease RegB Activation Are Mediated by Similar RNA-Protein Interactions: An NMR and SAXS Analysis," The Journal of Biological Chemistry 283(19):13289-13301.
Miller, E. S. et al. (Mar. 2003). "Bacteriophage T4 Genome," Microbiology and Molecular Biology Reviews 67(1):86-156.
Odaert, B. et al. (2007). "1H, 13C and 15N Resonance Assignment of Phage T4 Endoribonuclease RegB," Biomolecular NMR Assignments 1:73-74.
Piesiniene, L. et al. (2004). "The Sequences and Activities of RegB Endoribonucleases of T4-Related Bacteriophages," Nucleic Acids Research 32(18):5582-5595.
Saida, F. et al. (2004). "First Structural Investigation of the Restriction Ribonuclease RegB: NMR Spectroscopic Conditions, 13C/15N Double-Isotopic Labelling and Two-Dimensional Heteronuclear Spectra," Protein Expression and Purificiation 34:158-165.
Saida, F. et al. (2006). "Expression of Highly Toxic Genes in *E. coli*: Special Strategies and Genetic Tools," Current Protein and Peptide Science 7(1):47-56.
Sorek, R. et al. (Nov. 30, 2007). "Genome-Wide Experimental Determination of Barriers to Horizontal Gene Transfer," Science 318:1449-1452 (and Supporting Online Material, 25 pages).
Altschul, S. F. et al. (1990). "Basic Local Alignment Search Tool," Journal of Molecular Biology 215:403-410.
Bolte, S. et al. (2004). "The N-Myristoylated Rab-GTPase m-Rabmc is Involved in Post-Golgi Trafficking Events to the Lytic Vacuole in Plant Cells," Journal of Cell Science 117(6):943-954.
Brashears, M. M. et al. (2003). "Prevalence of *Escherichia coli* O157:H7 and Performance by Beef Feedlot Cattle Given *Lactobacillus* Direct-Fed Microbials," Journal of Food Protection 66(5):748-754.
Cammue, B. P. A. et al. (Feb. 5, 1992). "Isolation and Characterization of a Novel Class of Plant Antimicrobial Peptides from *Mirabilis jalapa* L Seeds," The Journal of Biological Chemistry 267(4):2228-2233.
Carraro, D. M. et al. (Mar. 2003). "PCR-Assisted Contig Extension: Stepwise Strategy for Bacterial Genome Closure," BioTechniques 34(3):626-632.
Chopin, M. et al. (2005). "Phage Abortive Infection in *Lactococci*: Variations on a Theme," Current Opinion in Microbiology 8:473-479.
Delcher, A. L. et al. (2002). "Fast Algorithms for Large-Scale Genome Alignment and Comparison," Nucleic Acids Research 30(11):2478-2483.
Delves-Broughton, J. et al. (1996). "Applications of the Bacteriocin, Nisin," Antonie van Leeuwenhoek 69:193-202.
Fetter, K. et al. (Jan. 2004). "Interactions between Plasma Membrane Aquaporins Modulate their Water Channel Activity," The Plant Cell 16:215-228.
Frohme, M. et al. (2000). "Mapping Analysis of the *Xylella fastidiosa* Genome," Nucleic Acids Research 28(16):3100-3104.

(Continued)

*Primary Examiner* — Medina A Ibrahim
(74) *Attorney, Agent, or Firm* — Michelle Chew Wong; Lawrence Berkeley National Laboratory

(57) ABSTRACT

We describe a method for mining microbial genomes to discover antimicrobial genes and proteins having broad spectrum of activity. Also described are antimicrobial genes and their expression products from various microbial genomes that were found using this method. The products of such genes can be used as antimicrobial agents or as tools for molecular biology.

10 Claims, 22 Drawing Sheets

(56) References Cited

OTHER PUBLICATIONS

Gillor, O. et al. (2005). Genetically Engineered Bacteriocins and their Potential as the Next Generation of Antimicrobials,' Current Pharmaceutical Design 1:1067-1075.
Hancock, R. E. W. et al. (Sep. 2000). "The Role of Cationic Antimicrobial Peptides in Innate Host Defenses," Trends in Microbiology 8(9):402-410.
Hu, X. et al. (1997). "Cloning and Expression of a PR5-Like Protein from *Arabidopsis*: Inhibition of Fungal Growth by Bacterially Expressed Protein," Plant Molecular Biology 34:949-959.
International Search Report mailed Apr. 16, 2009, for PCT Application No. PCT/US07/87691 filed Dec. 15, 2007, 4 pages.
International Written Opinion mailed Apr. 16, 2009, for PCT Application No. PCT/US07/87691 filed Dec. 15, 2007, 10 pages.
Kato, N. et al. (Jul. 2002). "Spectral Profiling for the Simultaneous Observation of Four Distinct Fluorescent Proteins and Detection of Protein-Protein Interaction via Fluorescence Resonance Energy Transfer in Tobacco Leaf Nuclei," Plant Physiology 129:931-942.
Kneller, D. G. et al. (1990). "Improvements in Protein Secondary Structure Prediction by an Enhanced Neural Network," Journal of Molecular Biology 214:171-182.
Kunkel, T. A. (Jan. 1985). "Rapid and Efficient Site-Specific Mutagenesis without Phenotypic Selection," Proceedings of the National Academy of Sciences of the United States of America 82:488-492.
Kunkel, T. A. et al. (1987). "Rapid and Efficient Site-Specific Mutagenesis without Phenotypic Selection," Methods in Enzymology 154:367-382.
Liu, D. et al. (Mar. 1994). "Osmotin Overexpression in Potato Delays Development of Disease Symptoms," Proceedings of the National Academy of Sciences of the United States of America 91:1888-1892.
Nielsen, H. et al. (1999). "Machine Learning Approaches for the Prediction of Signal Peptides and Other Protein Sorting Signals," Protein Engineering 12(1):3-9.
Penyalver, R. et al. (2000). "Use of Genetically Engineered Agrobacterium strain K1026 for Biological Control of Crown Gall," European Journal of Plant Pathology 106:801-810.
Riley, M. A. et al. (2002). "Bacteriocins: Evolution, Ecology, and Application," Annual Review of Microbiology 56:117-137.
Rutherford, K. et al. (2000). "Artemis: Sequencing Visualization and Annotation," Bioinformatics 16(10):944-945.
Sablon, E. et al. (2000). "Antimicrobial Peptides of Lactic Acid Bacteria: Mode of Action, Genetics and Biosynthesis," Advances in Biochemical Engineering/Biotechnology 68:21-60.
Sanson, B. et al. (1995). "Post-Transcriptional Controls in Bacteriophage T4: Roles of the Sequence-Specific Endoribonuclease RegB," FEMS Microbiology Reviews 17:141-150.
Schuch, R. et al. (Aug. 22, 2002). "A Bacteriolytic Agent that Detects and Kills *Bacillus anthracis*," Nature 418:884-889.
Su, W. W. et al. (Mar. 20, 2004). "High-Level Secretion of Functional Green Fluorescent Protein from Transgenic Tobacco Cell Cultures: Characterization and Sensing," Biotechnology and Bioengineering 85(6):610-619.
Watve, M. G. et al. (2001). "How Many Antibodies are Produced by the genus *Streptomyces*?," Archives of Microbiology 176:386-390.

* cited by examiner

EMTKEEKDQCLLASKNCGMEVDTLQKKIKKLNSEIKKGKKVYSADEIKKLQQKLDEANALLDDILKGGGN (SEQ ID NO:197)

-------------------HHHHHHHHHHHHHHHHHH--------HHHHHHHHHHHHHHHHHHHH-----

No IPTG
250uM IPTG
800uM IPTG

ABB43866
ABB45230
ABB43899

Figure 14

```
SEQ ID NO: 159     TTTTCTTGTGAAGTCGGCGGGGCATTCGTATAATGATCCTCATTGGTTGC
SEQ ID NO: 160     TTTTCTTGTGAAGTCGGCGGGGCATTCGTATAATGATCCTCATTGGTTGC
SEQ ID NO: 161     TTTTCTTGTGGAGTCGGCGACGCGTTCGTATAATGAGCCTCATTGGTTGT
SEQ ID NO: 162     TTTTCTTGTGAAGTCGACGCCCCATTCGTATAATGAGCCTCATTGGTTGT
SEQ ID NO: 163     AGTCGGTA--ACGTACCCAAATCGCTCGTCGCACCGCCCGCCAAGACCGG
SEQ ID NO: 164     GCCCC------CGG--CCAA---GCTCTCCGCACCGCCCGC-AAGAAC--
                                     *    *       **     *    **  *  *

SEQ ID NO: 159     CGCGCTGCGGCAACCTCCGCATGTCTCCTCCACCCTCCTCCTAAGGTGGA
SEQ ID NO: 160     CGCGCTGCGGCAACCTCCGCATGTCTCCTCCACCCTCCTCCTAAGGTGGA
SEQ ID NO: 161     CGCGCTGCGGCAACCTCCGAATGTCTCCTCCACCCTCCTCCTATGGTGGA
SEQ ID NO: 162     CGCGGTGCGACAATCTCCGCATGTCTCCTCCACCCTCCTCCTGAGGTGGA
SEQ ID NO: 163     CCC----CGTCGATCGCCCGGTGTCTCCTCCACCCTCCTCCTTTGGTGGA
SEQ ID NO: 164     -AC----CGTCGGTCTCCCAGTGTCTCCTCCACCCTCCTCCTTTGGTGGA
                      *    ** *   * **   *********************  ******

SEQ ID NO: 159     TT--AAGCCCGAACCAGCCGT--TCGGGCTTTTTTTCGTCCCATGCAAACA
SEQ ID NO: 160     TT--AAGCCCGAACCAGCCGT--TCGGGCTTTTTTTCGTCCCATGCAAACA
SEQ ID NO: 161     TT--AAGCCCGAACCAGCCGT--TCGGGCTTTTTTTCGTCCCATGCAAACA
SEQ ID NO: 162     TT--AAGCCCGAACCAGCCGT--TCGGGCTTTTTTTCGTCCCATGCAATGA
SEQ ID NO: 163     TTCGAA-CCCAAGTCCAACCGACTTGGGTTTTTTTTCGTCTTTTGCAAGGG
SEQ ID NO: 164     TTCAAA-CCCAGGCTAAACCGCC-TGGGTTTTTTTTCGCCCCT-----GT-
                   **   ** ***        *      *** ********* *
```

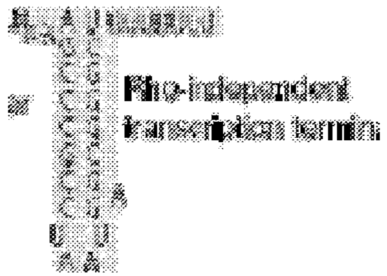

Figure 15

```
Cupriavidus_metallidurans (SEQ ID NO:173)          gccgatatgtataattcaatccaUCGAACGACGGcGCAugagagcgcgcc
Cupriavidus_necator (SEQ ID NO:174)                taccccatgtataattccaatcaUUGAACGACGGcGCA............
Burkholderia_cenocepacia_AU_1054 ((SEQ ID NO:175)  gggcattcgtataatgatcctcaUUGGUUGCCGC.GCU............
Burkholderia_cenocepacia_HI2424 (SEQ ID NO:176)    gggcattcgtataatgatcctcaUUGGUUGCCGC.GCU............
Burkholderia_ambifaria_AMMD ((SEQ ID NO:177)       ccccattcgtataatgagcctcaUUGGUUGUCGC.GGU............
Burkholderia sp 383 (SEQ ID NO:178)                acgcgttcgtataatgagcctcaUUGGUUGUCGC.GCU............
RNA STRUCTURE                                      .......................::<<<<<<<<<.___............

Cupriavidus_metallidurans                          agagugcgaaagcgaaagucgguaacguacccaaaucgcucgucgcaccg
Cupriavidus_necator                                ..gacagcgcgccagagugcgaaagcgaagcccccggccaagcucuccgc
Burkholderia_cenocepacia_AU_1054                   ..................................................
Burkholderia_cenocepacia_HI2424                    ..................................................
Burkholderia_ambifaria_AMMD                        ..................................................
Burkholderia sp 383                                ..................................................
RNA STRUCTURE                                      ..................................................

Cupriavidus_metallidurans                          cccgccaagaccggccCCGUCGAUCGCCCGGUGUCUCCUCCACCCUCCUC
Cupriavidus_necator                                accgcccgcaagaacaCCGUCGGUCUCCCAGUGUCUCCUCCACCCUCCUC
Burkholderia_cenocepacia_AU_1054                   ................GCGGCAACCUCCGCAUGUCUCCUCCACCCUCCUC
Burkholderia_cenocepacia_HI2424                    ................GCGGCAACCUCCGCAUGUCUCCUCCACCCUCCUC
Burkholderia_ambifaria_AMMD                        ................GCGACAAUCUCCGCAUGUCUCCUCCACCCUCCUC
Burkholderia sp 383                                ................GCGGCAACCUCCGAAUGUCUCCUCCACCCUCCUC
RNA STRUCTURE                                      ................>>>>>>>>>,,,,,,,,,,,,<<<<<<______

Cupriavidus_metallidurans                          CUUUGGUGGAUUcgAACCCAAGUC.CAACCGACUUGGGUUUUUUUUC
Cupriavidus_necator                                CUUUGGUGGAUUc.AAACCCAGGCuAAACCGCCUGGGUUUUUUUUCG
Burkholderia_cenocepacia_AU_1054                   CUAAGGUGGAUU..AAGCCCGAAC.CAGCCGUUCGGGCUUUUUUUCG
Burkholderia_cenocepacia_HI2424                    CUAAGGUGGAUU..AAGCCCGAAC.CAGCCGUUCGGGCUUUUUUUCG
Burkholderia_ambifaria_AMMD                        CUGAGGUGGAUU..AAGCCCGAAC.CAGCCGUUCGGGCUUUUUUUCG
Burkholderia sp 383                                CUAUGGUGGAUU..AAGCCCGAAC.CAGCCGUUCGGGCUUUUUUUCG
RNA STRUCTURE                                      ____>>>>>>,,,..<<<<<<<<<<._____>>>>>>>>>>,,,,,,,
```

(SEQ ID NO: 182)

No IPTG 250uM IPTG 800uM IPTG

Burkholderia cenocepacia HI2424 Toxic RNA #1 (SEQ ID NO:182)

Burkholderia cenocepacia HI2424 Toxic RNA #2 (SEQ ID NO:185)

Burkholderia cenocepacia HI2424 Toxic RNA #3 (SEQ ID NO:186)

Ralstonia metallidurans Toxic RNA #1 (SEQ ID NO:179)

SEQUENCE LISTING

```
<160> NUMBER OF SEQ ID NOS: 197

<210> SEQ ID NO 1
<211> LENGTH: 864
<212> TYPE: DNA
<213> ORGANISM: Acidobacterium sp. Ellin 345

<400> SEQUENCE: 1

atgcgcaaaa ttctgttttt caccgtcctg gtgctcggtc tttccgtgtt tagcttcggt     60

caagctagcc gcacttggat ttccggcgtc ggcgacgatg ccaatccctg ctcgcgtacc    120

gcgccttgca aaacgtttgc tggcgccatt tcgaagacag ccccgagcgg cgagatcgat    180

gcccttgatc caggcggatt cggcgctttg acgatcacca agcccattac gctggatggc    240

aataactggg gcagcgttct cgtctccggc accaacggca tcgccatcag caatcccacg    300

ccgacgactc cgatggaagt catcatccgc aacctcagca tcaacgggct caacaccgga    360

atctcaggca tttcgatcgt cagcgctggt gtcgtgctga aggttgagca cgttcaggtc    420

ttcgacttca ccgtggccgg gatcgatatg caatacccga cgaagttcag cgtcgtgaac    480

acagagatca tcggagcagt tgtggccggc atccgatcgg ctagcagcgg cgctgggaac    540

attgtcggaa cccacatctc gaactcgaca aatggcgtgt acgcccttgg caaggtcacc    600

atttccaaca gcaccgtgac cggcgccagc aaccgagcat ttgcgagcga gggaggggca    660

agtctcacac tgcagaactc caccgcctcc gatagcggcg tcggcgtttt tgctacgggc    720

aacgtctaca tgagcaattg cgagatcagc aacaacacca ccgccatcag tatctctgga    780

ggagttgttt actcctacgg caataaccaa ctctctggaa acgttggcaa cggcaacgcc    840

gttacgccgg ccaaccagac ctag                                           864


<210> SEQ ID NO 2
<211> LENGTH: 287
<212> TYPE: PRT
<213> ORGANISM: Acidobacterium sp. Ellin 345

<400> SEQUENCE: 2

Met Arg Lys Ile Leu Phe Phe Thr Val Leu Val Leu Gly Leu Ser Val
1               5                   10                  15

Phe Ser Phe Gly Gln Ala Ser Arg Thr Trp Ile Ser Gly Val Gly Asp
            20                  25                  30

Asp Ala Asn Pro Cys Ser Arg Thr Ala Pro Cys Lys Thr Phe Ala Gly
        35                  40                  45

Ala Ile Ser Lys Thr Ala Pro Ser Gly Glu Ile Asp Ala Leu Asp Pro
    50                  55                  60

Gly Gly Phe Gly Ala Leu Thr Ile Thr Lys Pro Ile Thr Leu Asp Gly
65                  70                  75                  80
```

```
Asn Asn Trp Gly Ser Val Leu Val Ser Gly Thr Asn Gly Ile Ala Ile
                85                  90                  95

Ser Asn Pro Thr Pro Thr Thr Pro Met Glu Val Ile Ile Arg Asn Leu
            100                 105                 110

Ser Ile Asn Gly Leu Asn Thr Gly Ile Ser Gly Ile Ser Ile Val Ser
        115                 120                 125

Ala Gly Val Val Leu Lys Val Glu His Val Gln Val Phe Asp Phe Thr
    130                 135                 140

Val Ala Gly Ile Asp Met Gln Tyr Pro Thr Lys Phe Ser Val Val Asn
145                 150                 155                 160

Thr Glu Ile Ile Gly Ala Val Val Ala Gly Ile Arg Ser Ala Ser Ser
                165                 170                 175

Gly Ala Gly Asn Ile Val Gly Thr His Ile Ser Asn Ser Thr Asn Gly
            180                 185                 190

Val Tyr Ala Leu Gly Lys Val Thr Ile Ser Asn Ser Thr Val Thr Gly
        195                 200                 205

Ala Ser Asn Arg Ala Phe Ala Ser Glu Gly Gly Ala Ser Leu Thr Leu
    210                 215                 220

Gln Asn Ser Thr Ala Ser Asp Ser Gly Val Gly Val Phe Ala Thr Gly
225                 230                 235                 240

Asn Val Tyr Met Ser Asn Cys Glu Ile Ser Asn Asn Thr Thr Ala Ile
                245                 250                 255

Ser Ile Ser Gly Gly Val Val Tyr Ser Tyr Gly Asn Asn Gln Leu Ser
            260                 265                 270

Gly Asn Val Gly Asn Gly Asn Ala Val Thr Pro Ala Asn Gln Thr
        275                 280                 285


<210> SEQ ID NO 3
<211> LENGTH: 1134
<212> TYPE: DNA
<213> ORGANISM: Anaeromyxobacter dehalogenans 2CP-C

<400> SEQUENCE: 3

atggaagcag atcagaagtt caacatggag ttctccgagc agcactacgt cccggtcctg     60

aagtggaagc gcggggaggc gcgcgcgttg aaggacctcg accccgccgt gaaggcggcc    120

tgcacgccct tggtcgaggt cgttcccgtc cccaccgacc ccgagaccgg cgccgccaag    180

aagaccttgt ccaagcacct ggacgacgcc atcgcggaga tgaagtcgag ttggggcacg    240

gcccacccca tcttcgtgga catccgcctc ctgccgccga accaggcgac gggggccacg    300

ctcaccgggc tcttcgaccg gctccgtgcg gcggccatcc tcgccatccc ggtcatctcg    360

accggcgcga cccaggacat cctccaggcc gcggccggca tccacaagaa ggaccggcgg    420

ggcgtctgcc tgcgggaggg cctcgacgcg gtgatggcgc ccgcgttccc ggtggccgtg    480

agcaaggcgc tgctggccac cggcgtcacg cagaagacgg ctgacgtcgt catcgacatg    540

caggacgtgt cggccaacaa gacgaccgtg aacgccgcgt tggcggcgag cgccatcggc    600

aaggtcccga acctgaaggc gtggcggacg ttcaccatcg tcgccacggc gttcccgttg    660

aacctgagcg gcatcgcacc cggggtccac acgctgcctc gcgcggagtg ggcgctctgg    720

aaggccctcg gctccctccc gagacggccc acctacggcg actacgccgt cgcgcactgg    780

gacctccagg agctggaccc gcgcgtcatc ctcatcagcg ccagcatccg gtacacgagc    840

gatgacgagt gggtcatctt ccgcggccgg aacgtcaaga actacggctt cggccagttc    900

accgcgctga gcaagctggt ggtcaagcac ccggcgtact gcgggtcggc gttcagcgcg    960
```

-continued

```
ggcgacgact acatcgcggc gtgcgccagc gggaccgtcg ggtcgggcaa ccacgagacg   1020

tggcggcggg tcgcgaccaa ccaccacatc acgttcgtgg tggaccagct ctccaagctg   1080

gccctcggcg cttcagtgcc cgccgcaccc gcgagcggag ctgcgtcgaa ctaa         1134


<210> SEQ ID NO 4
<211> LENGTH: 377
<212> TYPE: PRT
<213> ORGANISM: Anaeromyxobacter dehalogenans 2CP-C

<400> SEQUENCE: 4

Met Glu Ala Asp Gln Lys Phe Asn Met Glu Phe Ser Glu Gln His Tyr
1               5                   10                  15

Val Pro Val Leu Lys Trp Lys Arg Gly Glu Ala Arg Ala Leu Lys Asp
            20                  25                  30

Leu Asp Pro Ala Val Lys Ala Ala Cys Thr Pro Leu Val Glu Val Val
        35                  40                  45

Pro Val Pro Thr Asp Pro Glu Thr Gly Ala Ala Lys Lys Thr Leu Ser
    50                  55                  60

Lys His Leu Asp Asp Ala Ile Ala Glu Met Lys Ser Ser Trp Gly Thr
65                  70                  75                  80

Ala His Pro Ile Phe Val Asp Ile Arg Leu Leu Pro Pro Asn Gln Ala
                85                  90                  95

Thr Gly Ala Thr Leu Thr Gly Leu Phe Asp Arg Leu Arg Ala Ala Ala
            100                 105                 110

Ile Leu Ala Ile Pro Val Ile Ser Thr Gly Ala Thr Gln Asp Ile Leu
        115                 120                 125

Gln Ala Ala Ala Gly Ile His Lys Lys Asp Arg Arg Gly Val Cys Leu
    130                 135                 140

Arg Glu Gly Leu Asp Ala Val Met Ala Pro Ala Phe Pro Val Ala Val
145                 150                 155                 160

Ser Lys Ala Leu Leu Ala Thr Gly Val Thr Gln Lys Thr Ala Asp Val
                165                 170                 175

Val Ile Asp Met Gln Asp Val Ser Ala Asn Lys Thr Thr Val Asn Ala
            180                 185                 190

Ala Leu Ala Ala Ser Ala Ile Gly Lys Val Pro Asn Leu Lys Ala Trp
        195                 200                 205

Arg Thr Phe Thr Ile Val Ala Thr Ala Phe Pro Leu Asn Leu Ser Gly
    210                 215                 220

Ile Ala Pro Gly Val His Thr Leu Pro Arg Ala Glu Trp Ala Leu Trp
225                 230                 235                 240

Lys Ala Leu Gly Ser Leu Pro Arg Arg Pro Thr Tyr Gly Asp Tyr Ala
                245                 250                 255

Val Ala His Trp Asp Leu Gln Glu Leu Asp Pro Arg Val Ile Leu Ile
            260                 265                 270

Ser Ala Ser Ile Arg Tyr Thr Ser Asp Asp Glu Trp Val Ile Phe Arg
        275                 280                 285

Gly Arg Asn Val Lys Asn Tyr Gly Phe Gly Gln Phe Thr Ala Leu Ser
    290                 295                 300

Lys Leu Val Val Lys His Pro Ala Tyr Cys Gly Ser Ala Phe Ser Ala
305                 310                 315                 320

Gly Asp Asp Tyr Ile Ala Ala Cys Ala Ser Gly Thr Val Gly Ser Gly
                325                 330                 335

Asn His Glu Thr Trp Arg Arg Val Ala Thr Asn His His Ile Thr Phe
            340                 345                 350
```

```
Val Val Asp Gln Leu Ser Lys Leu Ala Leu Gly Ala Ser Val Pro Ala
        355                 360                 365

Ala Pro Ala Ser Gly Ala Ala Ser Asn
    370                 375


<210> SEQ ID NO 5
<211> LENGTH: 204
<212> TYPE: DNA
<213> ORGANISM: Burkholderia cenocepacia AU 1054

<400> SEQUENCE: 5

atggcaactg gtatcgttaa gtggttcaac gacgcgaagg gcttcggttt catcactccc      60

gacgagggcg gtgaggatct gtttgcgcac ttctcggcta tcaccatgaa tggcttcaag     120

acgctgaagg aaggccagaa ggtgagcttt gacgtcgttc aaggaccgaa gggcaagcaa     180

gcgtcgaaca tccaggccgc ataa                                            204


<210> SEQ ID NO 6
<211> LENGTH: 67
<212> TYPE: PRT
<213> ORGANISM: Burkholderia cenocepacia AU 1054

<400> SEQUENCE: 6

Met Ala Thr Gly Ile Val Lys Trp Phe Asn Asp Ala Lys Gly Phe Gly
1               5                   10                  15

Phe Ile Thr Pro Asp Glu Gly Gly Glu Asp Leu Phe Ala His Phe Ser
            20                  25                  30

Ala Ile Thr Met Asn Gly Phe Lys Thr Leu Lys Glu Gly Gln Lys Val
        35                  40                  45

Ser Phe Asp Val Val Gln Gly Pro Lys Gly Lys Gln Ala Ser Asn Ile
    50                  55                  60

Gln Ala Ala
65


<210> SEQ ID NO 7
<211> LENGTH: 531
<212> TYPE: DNA
<213> ORGANISM: Burkholderia sp. strain 383, chromosome #2

<400> SEQUENCE: 7

atgttgacag ccctgttgat aacccgccgg acaagcacgc aagtggttga gcgcgcagca      60

ttttgcgcgc gcggaggtcg atcgtcacga aatgggcaaa tgcggtcgct ggccgcatgc     120

acgatggcga tcgcgctgct cgccggttgc gcggcaccgc cctcgcccgt cgccggcgcg     180

ccgtcggcct gcacgcaacc gggcgaaagc gccatgctgc aggccgacct gctgttcggg     240

cgcgacatca cggggcgcgg ccccgtcacc gatgcggagc gcgcggcctt cctcgccgac     300

acggtcacgc cgcggttccc cgacggcctc acctactggg acacgcacgg ccagtggcgc     360

gaccgggcaa gcggcgggat cacgcgtgaa gacagcttcg tgatccgtat catcgccgac     420

gatacgtccg acacacgtgc gcggctcgcc gcgatccggc aaacgtacat gcagcgattc     480

caccagcaat cggtcggcat gacggtcgta gcggcctgcg cgtcgttctg a              531


<210> SEQ ID NO 8
<211> LENGTH: 176
<212> TYPE: PRT
<213> ORGANISM: Burkholderia sp. strain 383

<400> SEQUENCE: 8

Met Leu Thr Ala Leu Leu Ile Thr Arg Arg Thr Ser Thr Gln Val Val
```

-continued

```
1               5                   10                  15

Glu Arg Ala Ala Phe Cys Ala Arg Gly Gly Arg Ser Ser Arg Asn Gly
            20                  25                  30

Gln Met Arg Ser Leu Ala Ala Cys Thr Met Ala Ile Ala Leu Leu Ala
        35                  40                  45

Gly Cys Ala Ala Pro Pro Ser Pro Val Ala Gly Ala Pro Ser Ala Cys
    50                  55                  60

Thr Gln Pro Gly Glu Ser Ala Met Leu Gln Ala Asp Leu Leu Phe Gly
65                  70                  75                  80

Arg Asp Ile Thr Gly Arg Gly Pro Val Thr Asp Ala Glu Arg Ala Ala
                85                  90                  95

Phe Leu Ala Asp Thr Val Thr Pro Arg Phe Pro Asp Gly Leu Thr Tyr
            100                 105                 110

Trp Asp Thr His Gly Gln Trp Arg Asp Arg Ala Ser Gly Gly Ile Thr
        115                 120                 125

Arg Glu Asp Ser Phe Val Ile Arg Ile Ile Ala Asp Asp Thr Ser Asp
    130                 135                 140

Thr Arg Ala Arg Leu Ala Ala Ile Arg Gln Thr Tyr Met Gln Arg Phe
145                 150                 155                 160

His Gln Gln Ser Val Gly Met Thr Val Val Ala Ala Cys Ala Ser Phe
                165                 170                 175


<210> SEQ ID NO 9
<211> LENGTH: 765
<212> TYPE: PRT
<213> ORGANISM: Burkholderia sp. strain 383

<400> SEQUENCE: 9

Gly Thr Gly Gly Ala Cys Cys Ala Gly Thr Cys Thr Cys Ala Gly Gly
1               5                   10                  15

Thr Cys Thr Thr Thr Cys Gly Cys Gly Cys Gly Ala Thr Gly Ala Thr
            20                  25                  30

Gly Cys Cys Cys Gly Gly Gly Thr Thr Gly Ala Cys Gly Ala Gly Cys
        35                  40                  45

Gly Cys Cys Ala Ala Cys Gly Gly Cys Gly Cys Cys Cys Gly Cys Ala
    50                  55                  60

Thr Cys Gly Cys Gly Gly Thr Cys Gly Cys Cys Thr Ala Cys Cys Cys
65                  70                  75                  80

Gly Thr Cys Gly Thr Thr Thr Cys Cys Cys Cys Gly Gly Cys Cys Gly
                85                  90                  95

Cys Thr Gly Cys Cys Gly Cys Thr Cys Gly Thr Gly Cys Gly Gly Cys
            100                 105                 110

Thr Cys Gly Ala Cys Cys Gly Thr Cys Gly Cys Gly Gly Cys Cys Thr
        115                 120                 125

Cys Gly Thr Gly Thr Thr Cys Cys Gly Cys Gly Cys Cys Gly Gly Cys
    130                 135                 140

Gly Gly Cys Gly Cys Cys Gly Cys Gly Cys Cys Gly Cys Thr Cys Gly
145                 150                 155                 160

Thr Cys Thr Gly Cys Gly Gly Gly Cys Thr Gly Cys Cys Ala Cys Gly
                165                 170                 175

Cys Gly Cys Gly Gly Cys Gly Ala Cys Gly Cys Thr Gly Cys Thr Gly
            180                 185                 190

Gly Thr Thr Gly Cys Gly Gly Ala Cys Gly Ala Gly Cys Cys Gly Cys
        195                 200                 205

Thr Cys Thr Gly Cys Thr Cys Gly Cys Thr Gly Cys Gly Cys Cys Thr
```

-continued

```
    210                 215                 220

Cys Gly Thr Gly Ala Thr Cys Cys Gly Cys Gly Ala Cys Ala Thr Cys
225                 230                 235                 240

Gly Cys Thr Cys Cys Gly Gly Cys Cys Gly Gly Cys Gly Ala Ala Gly
                245                 250                 255

Gly Cys Cys Gly Gly Thr Ala Thr Gly Ala Cys Cys Thr Gly Ala Cys
            260                 265                 270

Gly Ala Thr Gly Cys Ala Gly Cys Cys Gly Thr Cys Cys Gly Gly Cys
        275                 280                 285

Gly Cys Cys Gly Cys Thr Gly Gly Cys Gly Ala Cys Gly Ala Ala Cys
    290                 295                 300

Thr Gly Cys Thr Gly Thr Gly Gly Cys Ala Thr Gly Cys Gly Cys Thr
305                 310                 315                 320

Gly Cys Gly Cys Gly Ala Thr Cys Gly Cys Gly Ala Gly Cys Cys Cys
                325                 330                 335

Thr Ala Cys Cys Gly Cys Cys Gly Gly Ala Thr Thr Cys Gly Gly Cys
            340                 345                 350

Ala Ala Cys Cys Gly Cys Thr Cys Gly Cys Gly Cys Cys Cys Gly Thr
        355                 360                 365

Cys Gly Ala Cys Ala Cys Ala Thr Cys Cys Ala Thr Cys Gly Cys Ala
    370                 375                 380

Thr Cys Cys Gly Ala Cys Gly Gly Thr Gly Ala Ala Cys Cys Gly Cys
385                 390                 395                 400

Ala Cys Gly Cys Gly Thr Cys Gly Gly Cys Cys Gly Gly Cys Gly Ala
                405                 410                 415

Ala Gly Cys Cys Gly Gly Gly Cys Thr Gly Cys Gly Cys Cys Cys Gly
            420                 425                 430

Thr Cys Ala Cys Gly Cys Ala Gly Cys Gly Cys Gly Gly Cys Cys Thr
        435                 440                 445

Thr Cys Cys Gly Gly Cys Thr Gly Cys Cys Cys Thr Gly Cys Cys Ala
    450                 455                 460

Cys Ala Gly Cys Gly Ala Cys Gly Cys Ala Cys Thr Gly Thr Thr Cys
465                 470                 475                 480

Thr Thr Thr Gly Cys Cys Gly Ala Thr Thr Gly Gly Cys Thr Cys Gly
                485                 490                 495

Ala Ala Thr Ala Thr Cys Ala Cys Thr Thr Cys Gly Ala Cys Gly Ala
            500                 505                 510

Gly Thr Thr Gly Cys Gly Thr Gly Cys Gly Cys Thr Gly Thr Cys Gly
        515                 520                 525

Cys Ala Gly Cys Ala Ala Cys Ala Thr Gly Gly Gly Thr Cys Gly Cys
    530                 535                 540

Ala Ala Cys Thr Gly Cys Ala Gly Cys Thr Cys Ala Ala Cys Cys Ala
545                 550                 555                 560

Gly Cys Thr Cys Gly Ala Gly Cys Gly Ala Cys Ala Gly Gly Thr Gly
                565                 570                 575

Gly Cys Cys Gly Ala Cys Gly Ala Cys Gly Ala Gly Gly Thr Cys Gly
            580                 585                 590

Gly Cys Gly Thr Gly Cys Gly Cys Thr Thr Cys Gly Thr Cys Thr Ala
        595                 600                 605

Cys Gly Ala Cys Ala Thr Cys Gly Ala Cys Gly Gly Gly Cys Ala Cys
    610                 615                 620

Gly Cys Gly Ala Cys Gly Cys Gly Gly Cys Ala Cys Gly Cys Gly Cys
625                 630                 635                 640
```

```
Thr Gly Ala Cys Thr Gly Ala Cys Thr Gly Cys Gly Cys Gly Cys Gly
                645                 650                 655

Cys Gly Ala Gly Gly Cys Cys Thr Gly Thr Gly Cys Ala Thr Gly Gly
            660                 665                 670

Ala Thr Cys Gly Ala Gly Ala Cys Gly Gly Ala Gly Ala Thr Gly Cys
        675                 680                 685

Gly Cys Gly Ala Cys Ala Ala Gly Thr Ala Cys Gly Cys Gly Thr Thr
    690                 695                 700

Ala Cys Cys Gly Gly Thr Cys Gly Cys Gly Cys Ala Gly Gly Ala Gly
705                 710                 715                 720

Cys Gly Thr Thr Thr Cys Ala Gly Cys Gly Cys Gly Thr Thr Thr Gly
                725                 730                 735

Cys Gly Gly Cys Gly Cys Ala Cys Gly Cys Cys Cys Gly Gly Gly Cys
            740                 745                 750

Thr Gly Gly Cys Ala Gly Cys Ala Thr Gly Thr Gly Ala
        755                 760                 765


<210> SEQ ID NO 10
<211> LENGTH: 254
<212> TYPE: PRT
<213> ORGANISM: Burkholderia sp. strain 383

<400> SEQUENCE: 10

Met Asp Gln Ser Gln Val Phe Arg Ala Met Met Pro Gly Leu Thr Ser
1               5                   10                  15

Ala Asn Gly Ala Arg Ile Ala Val Ala Tyr Pro Ser Phe Pro Arg Pro
            20                  25                  30

Leu Pro Leu Val Arg Leu Asp Arg Arg Gly Leu Val Phe Arg Ala Gly
        35                  40                  45

Gly Ala Ala Pro Leu Val Cys Gly Leu Pro Arg Ala Ala Thr Leu Leu
    50                  55                  60

Val Ala Asp Glu Pro Leu Cys Ser Leu Arg Leu Val Ile Arg Asp Ile
65                  70                  75                  80

Ala Pro Ala Gly Glu Gly Arg Tyr Asp Leu Thr Met Gln Pro Ser Gly
                85                  90                  95

Ala Ala Gly Asp Glu Leu Leu Trp His Ala Leu Arg Asp Arg Glu Pro
            100                 105                 110

Tyr Arg Arg Ile Arg Gln Pro Leu Ala Pro Val Asp Thr Ser Ile Ala
        115                 120                 125

Ser Asp Gly Glu Pro His Ala Ser Ala Gly Glu Ala Gly Leu Arg Pro
    130                 135                 140

Ser Arg Ser Ala Ala Phe Arg Leu Pro Cys His Ser Asp Ala Leu Phe
145                 150                 155                 160

Phe Ala Asp Trp Leu Glu Tyr His Phe Asp Glu Leu Arg Ala Leu Ser
                165                 170                 175

Gln Gln His Gly Ser Gln Leu Gln Leu Asn Gln Leu Glu Arg Gln Val
            180                 185                 190

Ala Asp Asp Glu Val Gly Val Arg Phe Val Tyr Asp Ile Asp Gly His
        195                 200                 205

Ala Thr Arg His Ala Leu Thr Asp Cys Ala Arg Glu Ala Cys Ala Trp
    210                 215                 220

Ile Glu Thr Glu Met Arg Asp Lys Tyr Ala Leu Pro Val Ala Gln Glu
225                 230                 235                 240

Arg Phe Ser Ala Phe Ala Ala His Ala Arg Ala Gly Ser Met
                245                 250
```

<210> SEQ ID NO 11
<211> LENGTH: 891
<212> TYPE: DNA
<213> ORGANISM: Burkholderia cenocepacia HI2424 chromosome #2

<400> SEQUENCE: 11

```
atgacgaagc tccgccctca tcttccgctc aatgcgttgc gcgcgttcga atcgtcggcg      60
cgccacctga acttcacgcg cgccggcctc gaactgagcg tgacccaggc cgccgtcagc     120
cagcaggtgc gctcgctcga ggagcgactc ggctgcacgc tgtttacgcg tctgccgcgc     180
ggcctcgggc tgaccgacga ggggcgcgca ctgctgccgg tgctgagcga cgcgttcagc     240
cgcatcgaga cggtgctcaa gcagttcgac ggcgggcgtt tccacgaggt gctgacgctc     300
ggcgtcgtcg gcacctttgc cctaggctgg ctaatgccgc ggctgaagca gttcggcgac     360
acgcacccgt tcgtcgagct gcggctgcgg accaacaaca acgtcgtcga tctcgccgcc     420
gagggcctcg atttcgcgat ccgctttggc gttggcaact ggccggcgac gcgcaacgag     480
cggctgctcg atgcgccgct caccgcgctg tgcacgccgg acatcgcacg gcgcctcgcg     540
cagccggccg atctcgcgaa cgaaacgttg ctgcgctcgt atcgcaccga cgaatggctc     600
ggctggttcg acgccgcgca gctcgaaccg tgggccgtca acgggcccgt gttcgattcg     660
tcccggctga tggtcgaggc cgcgatgcag ggtgcgggca tcgcgctcgc ccccgcctgc     720
atgttcgcgc gcgaactgca gctcggcctg ctcgcacgac cgctcgacat cgacgtgcgc     780
gccggcggct actggctcac gtcgctgaag tcgaaaccgc tgacgcccgc gatgacgctc     840
tttcgcgact ggatcgtggc ggaagcggcg agcgccgcgc ccaccgaata g              891
```

<210> SEQ ID NO 12
<211> LENGTH: 296
<212> TYPE: PRT
<213> ORGANISM: Burkholderia cenocepacia HI2424 chromosome #2

<400> SEQUENCE: 12

```
Met Thr Lys Leu Arg Pro His Leu Pro Leu Asn Ala Leu Arg Ala Phe
1               5                   10                  15

Glu Ser Ser Ala Arg His Leu Asn Phe Thr Arg Ala Gly Leu Glu Leu
            20                  25                  30

Ser Val Thr Gln Ala Ala Val Ser Gln Gln Val Arg Ser Leu Glu Glu
        35                  40                  45

Arg Leu Gly Cys Thr Leu Phe Thr Arg Leu Pro Arg Gly Leu Gly Leu
    50                  55                  60

Thr Asp Glu Gly Arg Ala Leu Leu Pro Val Leu Ser Asp Ala Phe Ser
65                  70                  75                  80

Arg Ile Glu Thr Val Leu Lys Gln Phe Asp Gly Gly Arg Phe His Glu
                85                  90                  95

Val Leu Thr Leu Gly Val Val Gly Thr Phe Ala Leu Gly Trp Leu Met
            100                 105                 110

Pro Arg Leu Lys Gln Phe Gly Asp Thr His Pro Phe Val Glu Leu Arg
        115                 120                 125

Leu Arg Thr Asn Asn Asn Val Val Asp Leu Ala Ala Glu Gly Leu Asp
    130                 135                 140

Phe Ala Ile Arg Phe Gly Val Gly Asn Trp Pro Ala Thr Arg Asn Glu
145                 150                 155                 160

Arg Leu Leu Asp Ala Pro Leu Thr Ala Leu Cys Thr Pro Asp Ile Ala
                165                 170                 175

Arg Arg Leu Ala Gln Pro Ala Asp Leu Ala Asn Glu Thr Leu Leu Arg
```

```
            180                 185                 190

Ser Tyr Arg Thr Asp Glu Trp Leu Gly Trp Phe Asp Ala Ala Gln Leu
        195                 200                 205

Glu Pro Trp Ala Val Asn Gly Pro Val Phe Asp Ser Ser Arg Leu Met
    210                 215                 220

Val Glu Ala Ala Met Gln Gly Ala Gly Ile Ala Leu Ala Pro Ala Cys
225                 230                 235                 240

Met Phe Ala Arg Glu Leu Gln Leu Gly Leu Leu Ala Arg Pro Leu Asp
                245                 250                 255

Ile Asp Val Arg Ala Gly Gly Tyr Trp Leu Thr Ser Leu Lys Ser Lys
            260                 265                 270

Pro Leu Thr Pro Ala Met Thr Leu Phe Arg Asp Trp Ile Val Ala Glu
        275                 280                 285

Ala Ala Ser Ala Ala Pro Thr Glu
    290                 295


<210> SEQ ID NO 13
<211> LENGTH: 939
<212> TYPE: DNA
<213> ORGANISM: Burkholderia cenocepacia HI2424, chromosome #2

<400> SEQUENCE: 13

atgacctact catcgaaacg tcgaaccctg ttgctggctg ccgcgacggc gccgctcgtt      60

ctcaccgtca ccgcgtgcgc gtcgcggcag ggcgctgcac cggacgaagc cacgcgggca     120

gcggcggctg ccgcggacgc cattgcgcct gccgcggcgg cgacgacgct tgccgatctc     180

gagcgcgacg cgggcggccg tctcggcgta tgcgcgatcg acacggccag cggtcgcatc     240

atcgagcatc gcgcgggcga gcgtttcccg ttctgcagta cgttcaaggc gatgctgagt     300

gcggccgtgc tcgcgcagag cgtcgagcgg ccgggcttgc tgcaacagcg cgtgacttat     360

accaaggccg acctcgtcaa ctattcgccg gtgtcggaga agcacgtcgg ctcgggcatg     420

acggtcgccg cgctgtgcga ggccgcgatc cagtacagcg acaattcggc cgcgaacctg     480

ctgatgaagc tgatcggcgg cccgtcggcg gtaacggcct acgcgcgctc gatcggcgac     540

gacacgttcc ggctcgatcg atgggagacc gaactgaaca ccgcgctgcc gggcgacccg     600

cgcgacacga cgacgcccgc cgcgatggcc gccagcctgc gcgtgctgac gctcggcgac     660

gcattgccgg ccgcgcagcg tgcgcagctc gtcgcgtggc tgcgcggcaa caaggtcggc     720

gacaagcgga ttcgcgcggg cgtgccggcc gggtgggtgg tgggcgacaa gaccggtacc     780

ggcgactacg ggacgacgaa cgacgcgggc gtcatctggc cgacgtcgcg cgcgccgatc     840

gtgctggccg tgtactacac gcagacgcga gccgatgcgc gggcgaagga cgacgtgatc     900

gcgtcggtcg cgcgcatcgt cgcgcagacg ttcggttga                            939


<210> SEQ ID NO 14
<211> LENGTH: 312
<212> TYPE: PRT
<213> ORGANISM: Burkholderia cenocepacia HI2424, chromosome #2

<400> SEQUENCE: 14

Met Thr Tyr Ser Ser Lys Arg Arg Thr Leu Leu Leu Ala Ala Ala Thr
1               5                   10                  15

Ala Pro Leu Val Leu Thr Val Thr Ala Cys Ala Ser Arg Gln Gly Ala
            20                  25                  30

Ala Pro Asp Glu Ala Thr Arg Ala Ala Ala Ala Ala Ala Asp Ala Ile
        35                  40                  45
```

```
Ala Pro Ala Ala Ala Ala Thr Thr Leu Ala Asp Leu Glu Arg Asp Ala
    50                  55                  60

Gly Gly Arg Leu Gly Val Cys Ala Ile Asp Thr Ala Ser Gly Arg Ile
65                  70                  75                  80

Ile Glu His Arg Ala Gly Glu Arg Phe Pro Phe Cys Ser Thr Phe Lys
                85                  90                  95

Ala Met Leu Ser Ala Ala Val Leu Ala Gln Ser Val Glu Arg Pro Gly
            100                 105                 110

Leu Leu Gln Gln Arg Val Thr Tyr Thr Lys Ala Asp Leu Val Asn Tyr
        115                 120                 125

Ser Pro Val Ser Glu Lys His Val Gly Ser Gly Met Thr Val Ala Ala
    130                 135                 140

Leu Cys Glu Ala Ala Ile Gln Tyr Ser Asp Asn Ser Ala Ala Asn Leu
145                 150                 155                 160

Leu Met Lys Leu Ile Gly Gly Pro Ser Ala Val Thr Ala Tyr Ala Arg
                165                 170                 175

Ser Ile Gly Asp Asp Thr Phe Arg Leu Asp Arg Trp Glu Thr Glu Leu
            180                 185                 190

Asn Thr Ala Leu Pro Gly Asp Pro Arg Asp Thr Thr Thr Pro Ala Ala
        195                 200                 205

Met Ala Ala Ser Leu Arg Val Leu Thr Leu Gly Asp Ala Leu Pro Ala
    210                 215                 220

Ala Gln Arg Ala Gln Leu Val Ala Trp Leu Arg Gly Asn Lys Val Gly
225                 230                 235                 240

Asp Lys Arg Ile Arg Ala Gly Val Pro Ala Gly Trp Val Val Gly Asp
                245                 250                 255

Lys Thr Gly Thr Gly Asp Tyr Gly Thr Thr Asn Asp Ala Gly Val Ile
            260                 265                 270

Trp Pro Thr Ser Arg Ala Pro Ile Val Leu Ala Val Tyr Tyr Thr Gln
        275                 280                 285

Thr Arg Ala Asp Ala Arg Ala Lys Asp Asp Val Ile Ala Ser Val Ala
    290                 295                 300

Arg Ile Val Ala Gln Thr Phe Gly
305                 310
```

<210> SEQ ID NO 15
<211> LENGTH: 375
<212> TYPE: DNA
<213> ORGANISM: Dechloromonas aromatica RCB

<400> SEQUENCE: 15

```
atgaccacag aaaccaacaa tttgtcgacc atcaacccgc caatctcatg cgaaacacca      60

gatgccgagc ggattgctgg cgctaaggaa tgcgttattg ctctcgcaaa gctcgaacag     120

tcagcagaga acctgccgga atcggccaat gatggagcgg tcttcgcagc tattcagtca     180

agcgacgccg aagctcttgt tgctcagttc gggccactaa cacaaagaca ggaaggtgcg     240

ttcagaacgc tggccgaata cattcattgc ctcgccacga cgggaacacc atatctcgag     300

aaatggacgc catatgtagc acgcaccgag caacagattg ttgaatgggc tgcggcgatg     360

aacgcacaag agtaa                                                      375
```

<210> SEQ ID NO 16
<211> LENGTH: 124
<212> TYPE: PRT
<213> ORGANISM: Dechloromonas aromatica RCB

<400> SEQUENCE: 16

```
Met Thr Thr Glu Thr Asn Asn Leu Ser Thr Ile Asn Pro Pro Ile Ser
1               5                   10                  15

Cys Glu Thr Pro Asp Ala Glu Arg Ile Ala Gly Ala Lys Glu Cys Val
            20                  25                  30

Ile Ala Leu Ala Lys Leu Glu Gln Ser Ala Glu Asn Leu Pro Glu Ser
        35                  40                  45

Ala Asn Asp Gly Ala Val Phe Ala Ala Ile Gln Ser Ser Asp Ala Glu
    50                  55                  60

Ala Leu Val Ala Gln Phe Gly Pro Leu Thr Gln Arg Gln Glu Gly Ala
65                  70                  75                  80

Phe Arg Thr Leu Ala Glu Tyr Ile His Cys Leu Ala Thr Thr Gly Thr
                85                  90                  95

Pro Tyr Leu Glu Lys Trp Thr Pro Tyr Val Ala Arg Thr Glu Gln Gln
            100                 105                 110

Ile Val Glu Trp Ala Ala Ala Met Asn Ala Gln Glu
        115                 120
```

<210> SEQ ID NO 17
<211> LENGTH: 474
<212> TYPE: DNA
<213> ORGANISM: Ehrlichia canis Jake

<400> SEQUENCE: 17

```
atgagtaatg caatagacta tcaaaaactc atgcactctg ctatgtgcac tgttgtaaaa      60

aatgctttga ctgtcatagc tcattcagaa cattcaacta atgtacacat tgctatatcc     120

ttcttaacta attataaagg agtgacatta cctgatcata taaaagagaa ctatccacaa     180

gaaattactg taatattgca gcatcaattc agaagtctac aggtatttga caatagtatc     240

agtgtaatat tgagttttag aggtcaagaa gaaacagttg ttataccatt tcattctatt     300

atcaaatata tagatgttta tcaaggcttc gtacttgatc ttgaacaata tatgagcaac     360

aacattgaag aggctgataa ttatgattac gatactgatg acaagaatga agaaagtgat     420

cagcaaaaca accaagacaa tattatcttt atagatacat ttttaaaaaa ataa           474
```

<210> SEQ ID NO 18
<211> LENGTH: 157
<212> TYPE: PRT
<213> ORGANISM: Ehrlichia canis Jake

<400> SEQUENCE: 18

```
Met Ser Asn Ala Ile Asp Tyr Gln Lys Leu Met His Ser Ala Met Cys
1               5                   10                  15

Thr Val Val Lys Asn Ala Leu Thr Val Ile Ala His Ser Glu His Ser
            20                  25                  30

Thr Asn Val His Ile Ala Ile Ser Phe Leu Thr Asn Tyr Lys Gly Val
        35                  40                  45

Thr Leu Pro Asp His Ile Lys Glu Asn Tyr Pro Gln Glu Ile Thr Val
    50                  55                  60

Ile Leu Gln His Gln Phe Arg Ser Leu Gln Val Phe Asp Asn Ser Ile
65                  70                  75                  80

Ser Val Ile Leu Ser Phe Arg Gly Gln Glu Glu Thr Val Val Ile Pro
                85                  90                  95

Phe His Ser Ile Ile Lys Tyr Ile Asp Val Tyr Gln Gly Phe Val Leu
            100                 105                 110

Asp Leu Glu Gln Tyr Met Ser Asn Asn Ile Glu Glu Ala Asp Asn Tyr
        115                 120                 125
```

Asp Tyr Asp Thr Asp Asp Lys Asn Glu Glu Ser Asp Gln Gln Asn Asn
    130                 135                 140

Gln Asp Asn Ile Ile Phe Ile Asp Thr Phe Leu Lys Lys
145                 150                 155

<210> SEQ ID NO 19
<211> LENGTH: 828
<212> TYPE: DNA
<213> ORGANISM: Ehrlichia canis Jake

<400> SEQUENCE: 19
atggttatta agatgaatta caaaagattt gttgtaggtg ttacgctgag tacatttgtt 60
tttttcttat ctgatggtgc tttttctgat gcaaattttt ctgaagggag gagaggactt 120
tatataggta gtcagtataa agttggtatt cccaatttta gtaatttttc agctgaagaa 180
acaattcctg gtattacaaa aaagattttt gcgttaggtc ttgataagtc tgagataaat 240
actcacagca attttacacg atcatatgac cctacttatg caagcagttt tgcagggttt 300
agtggtatca ttggatatta tgttaatgac tttagggtag aatttgaagg ttcttatgag 360
aattttgaac ctgaaagaca atggtaccct gagaatagcc aaagctacaa atttttttgct 420 ttgtctcgaa atgctacaaa tagtgataat aagtttatag tactagagaa taacggcgtt 480
gttgacaagt ctcttaatgt aaatgtttgt tatgatattg ctagtggtag tattccttta 540
gcaccttata tgtgtgctgg tgttggtgca gattatataa agtttttagg tatatcattg 600
cctaagtttt cttatcaagt taagtttggt gtcaactacc ctctaaatgt taatactatg 660
ttgtttggtg gggttattta ccataaggtt gtaggtgata ggtatgagag agtagaaata 720
gcttaccatc ctactgcatt atctgacgtt cctagaacta cttcagcttc tgctacttta 780
aatactgatt attttggttg ggagattgga tttagatttg cgctatag 828

<210> SEQ ID NO 20
<211> LENGTH: 275
<212> TYPE: PRT
<213> ORGANISM: Ehrlichia canis Jake

<400> SEQUENCE: 20

Met Val Ile Lys Met Asn Tyr Lys Arg Phe Val Val Gly Val Thr Leu
1               5                   10                  15

Ser Thr Phe Val Phe Phe Leu Ser Asp Gly Ala Phe Ser Asp Ala Asn
            20                  25                  30

Phe Ser Glu Gly Arg Arg Gly Leu Tyr Ile Gly Ser Gln Tyr Lys Val
        35                  40                  45

Gly Ile Pro Asn Phe Ser Asn Phe Ser Ala Glu Glu Thr Ile Pro Gly
    50                  55                  60

Ile Thr Lys Lys Ile Phe Ala Leu Gly Leu Asp Lys Ser Glu Ile Asn
65                  70                  75                  80

Thr His Ser Asn Phe Thr Arg Ser Tyr Asp Pro Thr Tyr Ala Ser Ser
                85                  90                  95

Phe Ala Gly Phe Ser Gly Ile Ile Gly Tyr Tyr Val Asn Asp Phe Arg
            100                 105                 110

Val Glu Phe Glu Gly Ser Tyr Glu Asn Phe Glu Pro Glu Arg Gln Trp
        115                 120                 125

Tyr Pro Glu Asn Ser Gln Ser Tyr Lys Phe Phe Ala Leu Ser Arg Asn
    130                 135                 140

Ala Thr Asn Ser Asp Asn Lys Phe Ile Val Leu Glu Asn Asn Gly Val
145                 150                 155                 160

```
Ala Asp Lys Ser Leu Asn Val Asn Val Cys Tyr Asp Ile Ala Ser Gly
                165                 170                 175

Ser Ile Pro Leu Ala Pro Tyr Met Cys Ala Gly Val Gly Ala Asp Tyr
            180                 185                 190

Ile Lys Phe Leu Gly Ile Ser Leu Pro Lys Phe Ser Tyr Gln Val Lys
        195                 200                 205

Phe Gly Val Asn Tyr Pro Leu Asn Val Asn Thr Met Leu Phe Gly Gly
    210                 215                 220

Gly Tyr Tyr His Lys Val Val Gly Asp Arg Tyr Glu Arg Val Glu Ile
225                 230                 235                 240

Ala Tyr His Pro Thr Ala Leu Ser Asp Val Pro Arg Thr Thr Ser Ala
                245                 250                 255

Ser Ala Thr Leu Asn Thr Asp Tyr Phe Gly Trp Glu Ile Gly Phe Arg
            260                 265                 270

Phe Ala Leu
        275
```

<210> SEQ ID NO 21
<211> LENGTH: 990
<212> TYPE: DNA
<213> ORGANISM: Mesorhizobium sp. BNC1

<400> SEQUENCE: 21

```
atgttatcga ccaccatatc gaaggccatt gcgctcacac ttgcggcagt ggggttactg      60

ctgcaggtcg aatccgcagc ggcccaggga tatcctgaga ggacagtgcg cctcatcgtg     120

cccttcgctg cgggcggcgg tgtcggagtc ttcggccagc agcttgttgc ccatttgggg     180

cccgaactgg gacaggagat tgtccttgaa tatcttccgg gttcaggcgg catgatcgga     240

gctgcagcag tcgctcaggc agccccagac ggctatacgc tgttgctgtc gaccgccggg     300

ccgatcgagg tcagtcccgt tacctatgaa aacgtgcctt tcgacccgat cgaggatttc     360

gagcacatca cccggctggg cagcgttccc tacattctcg tcgcgcacaa gaagctgggt     420

gtcaaaacgc ttgaggagtt catcgaactc gcgaagaagc agccgggggc gctgagttac     480

ggctcctccg gatcaggcac gataaatttc ctggccgcag aactgctcaa gatccgtgcc     540

ggtatcgatc tggttcatat cccctatcag ggcaatggcc cccagatggt tgaccttgtg     600

gcaggacggc ttgatgtctc catgctggta cccaacgcca ttactcaata tgtcgacgac     660

ggcacgttga ttccgcttgc gaccaccggc agcgaacgct ccagcaatta tcccgatgtc     720

cccaccttca aggaactcgg ggtcgatgtc gaagtcagca gctggtatgg catctccgct     780

ccccgcggca cggatcccaa gattattgcc gctcttgacg agacctcccg caagctcatg     840

caggggggata gcctgcctgc cgagctaaag ggcctgggca tcgatgccga tgtcagcgct     900

tcgcccgagg agttcgagaa ggatatagcc gctcagcttg ccctctgggc gcaggtcatg     960

aagcaggctg gtatcgaaaa gatcaaataa                                      990
```

<210> SEQ ID NO 22
<211> LENGTH: 329
<212> TYPE: PRT
<213> ORGANISM: Mesorhizobium sp. BNC1

<400> SEQUENCE: 22

```
Met Leu Ser Thr Thr Ile Ser Lys Ala Ile Ala Leu Thr Leu Ala Ala
1               5                   10                  15

Val Gly Leu Leu Leu Gln Val Glu Ser Ala Ala Ala Gln Gly Tyr Pro
            20                  25                  30
```

```
Glu Arg Thr Val Arg Leu Ile Val Pro Phe Ala Ala Gly Gly Gly Val
        35                  40                  45

Gly Val Phe Gly Gln Gln Leu Val Ala His Leu Gly Pro Glu Leu Gly
    50                  55                  60

Gln Glu Ile Val Leu Glu Tyr Leu Pro Gly Ser Gly Gly Met Ile Gly
65                  70                  75                  80

Ala Ala Ala Val Ala Gln Ala Ala Pro Asp Gly Tyr Thr Leu Leu Leu
                85                  90                  95

Ser Thr Ala Gly Pro Ile Glu Val Ser Pro Val Thr Tyr Glu Asn Val
            100                 105                 110

Pro Phe Asp Pro Ile Glu Asp Phe Glu His Ile Thr Arg Leu Gly Ser
        115                 120                 125

Val Pro Tyr Ile Leu Val Ala His Lys Lys Leu Gly Val Lys Thr Leu
    130                 135                 140

Glu Glu Phe Ile Glu Leu Ala Lys Lys Gln Pro Gly Ala Leu Ser Tyr
145                 150                 155                 160

Gly Ser Ser Gly Ser Gly Thr Ile Asn Phe Leu Ala Ala Glu Leu Leu
                165                 170                 175

Lys Ile Arg Ala Gly Ile Asp Leu Val His Ile Pro Tyr Gln Gly Asn
            180                 185                 190

Gly Pro Gln Met Val Asp Leu Val Ala Gly Arg Leu Asp Val Ser Met
        195                 200                 205

Leu Val Pro Asn Ala Ile Thr Gln Tyr Val Asp Asp Gly Thr Leu Ile
    210                 215                 220

Pro Leu Ala Thr Thr Gly Ser Glu Arg Ser Ser Asn Tyr Pro Asp Val
225                 230                 235                 240

Pro Thr Phe Lys Glu Leu Gly Val Asp Val Glu Val Ser Ser Trp Tyr
                245                 250                 255

Gly Ile Ser Ala Pro Arg Gly Thr Asp Pro Lys Ile Ile Ala Ala Leu
            260                 265                 270

Asp Glu Thr Ser Arg Lys Leu Met Gln Gly Asp Ser Leu Pro Ala Glu
        275                 280                 285

Leu Lys Gly Leu Gly Ile Asp Ala Asp Val Ser Ala Ser Pro Glu Glu
    290                 295                 300

Phe Glu Lys Asp Ile Ala Ala Gln Leu Ala Leu Trp Ala Gln Val Met
305                 310                 315                 320

Lys Gln Ala Gly Ile Glu Lys Ile Lys
                325
```

<210> SEQ ID NO 23
<211> LENGTH: 432
<212> TYPE: DNA
<213> ORGANISM: Mesorhizobium sp. BNC1

<400> SEQUENCE: 23

```
atggagaaca ttatgggtcc tgttgctttg tttggtggtg gtggagtggt caggcatatc      60

gttggcgcgg ttgccgatgc agtcgggggc atgtccaggg gcgctttggg tgcggcaaac     120

aaggcgtctg gtgcatggtc gggaggctgt aatgcggctt ctggtgtcgc agacagcaat     180

cgtcttcagc agacgatgaa gatgttgcag gatgaccagg aaaaccagat cattcggcat     240

atgcaggtta gccatgacca agccatgttt aacaatgcca tggagcacgc gcagcagcag     300

actgcccagc agatgcagca taaccgcgcg ctgaccaaca acgccaagga gatctttacg     360

acggcgcagg aagatgcgca gagctggttg aagagctcga cgcagaaact ttctcaaacg     420
```

```
gcggcggcgt aa                                                          432


<210> SEQ ID NO 24
<211> LENGTH: 143
<212> TYPE: PRT
<213> ORGANISM: Mesorhizobium sp. BNC1

<400> SEQUENCE: 24

Met Glu Asn Ile Met Gly Pro Val Ala Leu Phe Gly Gly Gly Gly Val
1               5                   10                  15

Val Arg His Ile Val Gly Ala Val Ala Asp Ala Val Gly Gly Met Ser
            20                  25                  30

Arg Gly Ala Leu Gly Ala Ala Asn Lys Ala Ser Gly Ala Trp Ser Gly
        35                  40                  45

Gly Cys Asn Ala Ala Ser Gly Val Ala Asp Ser Asn Arg Leu Gln Gln
    50                  55                  60

Thr Met Lys Met Leu Gln Asp Asp Gln Glu Asn Gln Ile Ile Arg His
65                  70                  75                  80

Met Gln Val Ser His Asp Gln Ala Met Phe Asn Asn Ala Met Glu His
                85                  90                  95

Ala Gln Gln Gln Thr Ala Gln Gln Met Gln His Asn Arg Ala Leu Thr
            100                 105                 110

Asn Asn Ala Lys Glu Ile Phe Thr Thr Ala Gln Glu Asp Ala Gln Ser
        115                 120                 125

Trp Leu Lys Ser Ser Thr Gln Lys Leu Ser Gln Thr Ala Ala Ala
    130                 135                 140


<210> SEQ ID NO 25
<211> LENGTH: 753
<212> TYPE: DNA
<213> ORGANISM: Methanosarcina barkeri Fusaro

<400> SEQUENCE: 25

atgaataata catcaagaaa accctggact atttcactgg gaatttttac aatctggctg      60

attgttgttg tgggaggagg actgctgcag gttaaaggcc agcccactca acttgatgaa     120

ctggttaaaa gtcagcttat ttatggagta cttactgcaa tagtcttttt gtctggggca     180

attacctatt ttaactggtg ggatcaagtc gggtggaaag gtccgaatga ttcacggaat     240

ttgcgccttt tattgttacc ggccatgttc ctcttcatca tgctactgat agttttattt     300

acaggcctgc caccaacccg tgtactctta attgtaatta taaacacctt gatggtaggc     360

atcagtgaag agttgatgtt tcgaggtgta ttatttcatg gggcttcatc attatttgga     420

atctggcgtg cagtgtggat cacagcaatt gttttcggtt cggttcatac gctaaacagc     480

ttaataaccg gagactttaa tgcaagcgta ttccaggctt tttttgcagg tatgtttgga     540

gtctgggcag tagccttgcg ggtccgcctc gacacagtaa ttcctttaat tgtcattcac     600

tggctgtggg attgcctggc atttctgaca ggttcttctg aagggctggt gttgttactc     660

ttttcgttta ttctattctt atatggtatc tggctattac gaggctttcg cacaaccgct     720

gcgtcggttc acgtcaatag agttcgggaa taa                                  753


<210> SEQ ID NO 26
<211> LENGTH: 250
<212> TYPE: PRT
<213> ORGANISM: Methanosarcina barkeri Fusaro

<400> SEQUENCE: 26

Met Asn Asn Thr Ser Arg Lys Pro Trp Thr Ile Ser Leu Gly Ile Phe
```

-continued

```
1               5                   10                  15

Thr Ile Trp Leu Ile Val Val Val Gly Gly Gly Leu Leu Gln Val Lys
            20                  25                  30

Gly Gln Pro Thr Gln Leu Asp Glu Leu Val Lys Ser Gln Leu Ile Tyr
        35                  40                  45

Gly Val Leu Thr Ala Ile Val Phe Leu Ser Gly Ala Ile Thr Tyr Phe
    50                  55                  60

Asn Trp Trp Asp Gln Val Gly Trp Lys Gly Pro Asn Asp Ser Arg Asn
65                  70                  75                  80

Leu Arg Leu Leu Leu Leu Pro Ala Met Phe Leu Phe Ile Met Leu Leu
                85                  90                  95

Ile Val Leu Phe Thr Gly Leu Pro Pro Thr Arg Val Leu Leu Ile Val
            100                 105                 110

Ile Ile Asn Thr Leu Met Val Gly Ile Ser Glu Glu Leu Met Phe Arg
        115                 120                 125

Gly Val Leu Phe His Gly Ala Ser Ser Leu Phe Gly Ile Trp Arg Ala
    130                 135                 140

Val Trp Ile Thr Ala Ile Val Phe Gly Ser Val His Thr Leu Asn Ser
145                 150                 155                 160

Leu Ile Thr Gly Asp Phe Asn Ala Ser Val Phe Gln Ala Phe Phe Ala
                165                 170                 175

Gly Met Phe Gly Val Trp Ala Val Ala Leu Arg Val Arg Leu Asp Thr
            180                 185                 190

Val Ile Pro Leu Ile Val Ile His Trp Leu Trp Asp Cys Leu Ala Phe
        195                 200                 205

Leu Thr Gly Ser Ser Glu Gly Leu Val Leu Leu Leu Phe Ser Phe Ile
    210                 215                 220

Leu Phe Leu Tyr Gly Ile Trp Leu Leu Arg Gly Phe Arg Thr Thr Ala
225                 230                 235                 240

Ala Ser Val His Val Asn Arg Val Arg Glu
                245                 250
```

<210> SEQ ID NO 27
<211> LENGTH: 633
<212> TYPE: DNA
<213> ORGANISM: Methanosarcina barkeri Fusaro

<400> SEQUENCE: 27

```
atgaaaatga gatgggtatg ttctttggtt atatttttgt taattattcc aagcaccaca      60

cttgcagaat ctcaatatgg ttcaatggat gtatattata atgacaaact tttacctgga     120

aaagaaacgg ctaagcctac tttaaaaatt gaagagtcat ttaaagtaaa aattaatctg     180

acagtatatc aaaaaagtga tgtttatgtc tctttatcgt gcatggaaaa agattcattc     240

aaaattataa aaggtccaac atcaagaatc gaagaatact ccaaaccaga catcttagaa     300

gcaaattctt ctaaagaata cgaatggact gttgaaccta ctgaaaagtg gagtggtgga     360

tcattgcctc tagatatata ttatacaatt cttgctcatg gtgactctga acctcttatc     420

aatagcggtt ttacagtcgc ctactgcaca atctccaacg aacattacca aggcgaaact     480

cctacatctg agcaacctga aaccgaaaat caaccaattt ctgggcagcc atcttcagaa     540

aattcatctt cgccagcatc tgcaccagct ttcagtttag taactgcaat ttcggcactt     600

atgcttgtat tcttcagctt ctctcgccag taa                                   633
```

<210> SEQ ID NO 28
<211> LENGTH: 210

<212> TYPE: PRT
<213> ORGANISM: Methanosarcina barkeri Fusaro

<400> SEQUENCE: 28

```
Met Lys Met Arg Trp Val Cys Ser Leu Val Ile Phe Leu Leu Ile Ile
1               5                   10                  15

Pro Ser Thr Thr Leu Ala Glu Ser Gln Tyr Gly Ser Met Asp Val Tyr
            20                  25                  30

Tyr Asn Asp Lys Leu Leu Pro Gly Lys Glu Thr Ala Lys Pro Thr Leu
        35                  40                  45

Lys Ile Glu Glu Ser Phe Lys Val Lys Ile Asn Leu Thr Val Tyr Gln
    50                  55                  60

Lys Ser Asp Val Tyr Val Ser Leu Ser Cys Met Glu Lys Asp Ser Phe
65                  70                  75                  80

Lys Ile Ile Lys Gly Pro Thr Ser Arg Ile Glu Glu Tyr Ser Lys Pro
                85                  90                  95

Asp Ile Leu Glu Ala Asn Ser Ser Lys Glu Tyr Glu Trp Thr Val Glu
            100                 105                 110

Pro Thr Glu Lys Trp Ser Gly Gly Ser Leu Pro Leu Asp Ile Tyr Tyr
        115                 120                 125

Thr Ile Leu Ala His Gly Asp Ser Glu Pro Leu Ile Asn Ser Gly Phe
    130                 135                 140

Thr Val Ala Tyr Cys Thr Ile Ser Asn Glu His Tyr Gln Gly Glu Thr
145                 150                 155                 160

Pro Thr Ser Glu Gln Pro Glu Thr Glu Asn Gln Pro Ile Ser Gly Gln
                165                 170                 175

Pro Ser Ser Glu Asn Ser Ser Ser Pro Ala Ser Ala Pro Ala Phe Ser
            180                 185                 190

Leu Val Thr Ala Ile Ser Ala Leu Met Leu Val Phe Phe Ser Phe Ser
        195                 200                 205

Arg Gln
    210
```

<210> SEQ ID NO 29
<211> LENGTH: 333
<212> TYPE: DNA
<213> ORGANISM: Methanosarcina barkeri Fusaro

<400> SEQUENCE: 29

```
atgggagaac atacatttac cagaatgaaa aagactgtaa ccattttgat agcagtcttt      60

tttatagcaa cactgacagc ggtgtcagta agtgcacagc cccatccgac ttctcgcggt     120

cctgcaggtc atccgcatat gaggtgggat ggtcataaca tgtgggatga tgaccacaac     180

tggagatggg atggtcatag ctggtatgaa cgtgaacata actggagatg ggatggtcat     240

agctggtggg acgatagaca ccactggaga tgggacggaa acagatggtg ggacggaaac     300

agatggtggg acggaaacaa gtggagacac taa                                  333
```

<210> SEQ ID NO 30
<211> LENGTH: 110
<212> TYPE: PRT
<213> ORGANISM: Methanosarcina barkeri Fusaro

<400> SEQUENCE: 30

```
Met Gly Glu His Thr Phe Thr Arg Met Lys Lys Thr Val Thr Ile Leu
1               5                   10                  15

Ile Ala Val Phe Phe Ile Ala Thr Leu Thr Ala Val Ser Val Ser Ala
            20                  25                  30
```

-continued

```
Gln Pro His Pro Thr Ser Arg Gly Pro Ala Gly His Pro His Met Arg
        35                  40                  45

Trp Asp Gly His Asn Met Trp Asp Asp Asp His Asn Trp Arg Trp Asp
    50                  55                  60

Gly His Ser Trp Tyr Glu Arg Glu His Asn Trp Arg Trp Asp Gly His
65                  70                  75                  80

Ser Trp Trp Asp Asp Arg His His Trp Arg Trp Asp Gly Asn Arg Trp
                85                  90                  95

Trp Asp Gly Asn Arg Trp Trp Asp Gly Asn Lys Trp Arg His
            100                 105                 110


<210> SEQ ID NO 31
<211> LENGTH: 654
<212> TYPE: DNA
<213> ORGANISM: Methylobacillus flagellatus strain KT

<400> SEQUENCE: 31

atgatcaagt atttggtagg ttctgccgca ttggcagtga gcatgctggc gcctatcgcg      60

caggcgaatg acactgcttt gccatttgtg gatgtggcgg attccgtcga atttaatggt     120

tggaatcagc tggttggctc cgtagtgacg ggagctcaac ttgcagccgg ttatggtgcc     180

aacgtcgcgg gttcgggcga tgccgtactg actcgtatcg caggcacggc ttatcctgca     240

gggggcggtt tgtatgaatg gagcagtccg ttctccactt tcaccctgac tgacgccaca     300

gtcgcagaca acctgacttc cgtcgtattc cagagccata gtgcacctgg tggcacaggc     360

aagggtctgt atgatgtttc cctgagctat accgttgacg gtgtggatta cctggctgct     420

ctggttgatg gtaatgcaca agcgagtgct tacaagtatt tctcctggga cttgagcgat     480

gtgaccggta tcgatgccat caaggtgaca ttctctactg aagcacatgc caactccttc     540

gcattccagc ttgaccaagt ggtcgcggca gttccagagc cttcagaata tgcgctgttg     600

ctggctggtc tggctttcgt tggtttcgcc gcacgtcgta agcagcaagc ctaa           654


<210> SEQ ID NO 32
<211> LENGTH: 217
<212> TYPE: PRT
<213> ORGANISM: Methylobacillus flagellatus strain KT

<400> SEQUENCE: 32

Met Ile Lys Tyr Leu Val Gly Ser Ala Ala Leu Ala Val Ser Met Leu
1               5                   10                  15

Ala Pro Ile Ala Gln Ala Asn Asp Thr Ala Leu Pro Phe Val Asp Val
            20                  25                  30

Ala Asp Ser Val Glu Phe Asn Gly Trp Asn Gln Leu Val Gly Ser Val
        35                  40                  45

Val Thr Gly Ala Gln Leu Ala Ala Gly Tyr Gly Ala Asn Val Ala Gly
    50                  55                  60

Ser Gly Asp Ala Val Leu Thr Arg Ile Ala Gly Thr Ala Tyr Pro Ala
65                  70                  75                  80

Gly Gly Gly Leu Tyr Glu Trp Ser Ser Pro Phe Ser Thr Phe Thr Leu
                85                  90                  95

Thr Asp Ala Thr Val Ala Asp Asn Leu Thr Ser Val Val Phe Gln Ser
            100                 105                 110

His Ser Ala Pro Gly Gly Thr Gly Lys Gly Leu Tyr Asp Val Ser Leu
        115                 120                 125

Ser Tyr Thr Val Asp Gly Val Asp Tyr Leu Ala Ala Leu Val Asp Gly
    130                 135                 140
```

```
Asn Ala Gln Ala Ser Ala Tyr Lys Tyr Phe Ser Trp Asp Leu Ser Asp
145                 150                 155                 160

Val Thr Gly Ile Asp Ala Ile Lys Val Thr Phe Ser Thr Glu Ala His
                165                 170                 175

Ala Asn Ser Phe Ala Phe Gln Leu Asp Gln Val Val Ala Ala Val Pro
            180                 185                 190

Glu Pro Ser Glu Tyr Ala Leu Leu Leu Ala Gly Leu Ala Phe Val Gly
        195                 200                 205

Phe Ala Ala Arg Arg Lys Gln Gln Ala
    210                 215


<210> SEQ ID NO 33
<211> LENGTH: 747
<212> TYPE: DNA
<213> ORGANISM: Methylobacillus flagellatus strain KT

<400> SEQUENCE: 33

atgcatttca catacactaa aagcattctt gcactgagcc tgcttgcagc cacatccatc      60

gctcaggcag ccaccgaaac cagcgaatac ttcactgacg ttgcaggctc agcgtctaca     120

gacggcttca accaattgat tgccagtcgt ctcggtagtg gcgcaaccgg catagccgca     180

gtcaccacag gcgttgtcag caacgctcct gctggcgatg ccgtcctgac ccgcacatct     240

ggcacagctt atcctgcagg cttcggcctc tatgagtggc aaggcccata ctcaactttc     300

accattagcg atgaaacact gatctctgat cttggctcca tcgtattcca gagccatgtc     360

aaccctggcg gcaattatga gcttggcggc gctggcggca ttgatgctgc gatttcagaa     420

gtattcctga gcttcaacgg cggcaaccaa cttcttgcgg caacttcgtt cagcctcaca     480

aatgccattg acaaccctgg ctcgcctttc tacaaccctg acagtccaat ccttgaggca     540

gcaatcggct actttacgtg ggatttgagc gggatcagcg acccaatcac ttcctactca     600

atttctttcg gtacccatgc ccacagcagc atcatcgcct tccaggttga ccagatcgct     660

gccgctgtac ccgagccttc cgcttatgca ctgatgctcg gcggcctggc gctggtgggc     720

tttgcggctc gtcgcaaaaa ggcttaa                                         747


<210> SEQ ID NO 34
<211> LENGTH: 248
<212> TYPE: PRT
<213> ORGANISM: Methylobacillus flagellatus strain KT

<400> SEQUENCE: 34

Met His Phe Thr Tyr Thr Lys Ser Ile Leu Ala Leu Ser Leu Leu Ala
1               5                   10                  15

Ala Thr Ser Ile Ala Gln Ala Ala Thr Glu Thr Ser Glu Tyr Phe Thr
            20                  25                  30

Asp Val Ala Gly Ser Ala Ser Thr Asp Gly Phe Asn Gln Leu Ile Ala
        35                  40                  45

Ser Arg Leu Gly Ser Gly Ala Thr Gly Ile Ala Ala Val Thr Thr Gly
    50                  55                  60

Val Val Ser Asn Ala Pro Ala Gly Asp Ala Val Leu Thr Arg Thr Ser
65                  70                  75                  80

Gly Thr Ala Tyr Pro Ala Gly Phe Gly Leu Tyr Glu Trp Gln Gly Pro
                85                  90                  95

Tyr Ser Thr Phe Thr Ile Ser Asp Glu Thr Leu Ile Ser Asp Leu Gly
            100                 105                 110

Ser Ile Val Phe Gln Ser His Val Asn Pro Gly Gly Asn Tyr Glu Leu
```

-continued

```
        115                 120                 125

Gly Gly Ala Gly Gly Ile Asp Ala Ala Ile Ser Glu Val Phe Leu Ser
    130                 135                 140

Phe Asn Gly Gly Asn Gln Leu Leu Ala Ala Thr Ser Phe Ser Leu Thr
145                 150                 155                 160

Asn Ala Ile Asp Asn Pro Gly Ser Pro Phe Tyr Asn Pro Asp Ser Pro
                165                 170                 175

Ile Leu Glu Ala Ala Ile Gly Tyr Phe Thr Trp Asp Leu Ser Gly Ile
            180                 185                 190

Ser Asp Pro Ile Thr Ser Tyr Ser Ile Ser Phe Gly Thr His Ala His
        195                 200                 205

Ser Ser Ile Ile Ala Phe Gln Val Asp Gln Ile Ala Ala Ala Val Pro
    210                 215                 220

Glu Pro Ser Ala Tyr Ala Leu Met Leu Gly Gly Leu Ala Leu Val Gly
225                 230                 235                 240

Phe Ala Ala Arg Arg Lys Lys Ala
                245


<210> SEQ ID NO 35
<211> LENGTH: 2403
<212> TYPE: DNA
<213> ORGANISM: Methylobacillus flagellatus strain KT

<400> SEQUENCE: 35

atgcacctgg gccggatttt tctgcctact cgtatccacc atatggctca aactcagcat     60

tccaagcttt atctgcaagc cttgagcgcg cttacattcc tcataattca tggcggggta    120

cttgcagccg caggggcaac gccttctaac tccaacaata cctccacaac ggctactgaa    180

cgcgttaaag aaaatgacac ttccgcatcc tctccctctt ccagtaagag cagcagcact    240

gcatcgccca cagtcctgcc cgagattggc gtaagctcaa cccgcatcaa gcaagatgcg    300

atcaccatta acccaaccca gaccatcacc acaatagaag ccaaggaatt agaaagaaca    360

caacccacaa cgatatttga ggcaattcgc gatacgccag gcgtcgcgat tgaaggtggc    420

cctcgtccaa gcggcatgac attcaatgtc cggggattta acagcaatga agatgtccag    480

gtgcgtgtag acaatgtccc taaagggttt gaaaaatacc gctttggcgg caccttcata    540

gaaccagacc tgctcaagtc tattgaggtg cagcgtggtc cgcaaatcgc cagcggttcc    600

ggttcattag gcggcaccat cttggccaag accaaagatg cagccgacct gctgaaaccg    660

ggacggcgct atggcggacg catcaagcta ggctatgcaa gcaacaatga cgaggttcaa    720

cgctcctatt tggcttttgc tcgcccggta gatgctgtgg atattctgta taaccgcacc    780

tatcgcaatt ccaacgatat tactcatagc gatggcagca agttacctca gtcgaaagtc    840

aactcacggg cccagttatt gaaagtaggg atatttccaa cagactttct cgaattgata    900

acctcagtca cgttactcga ggaaagcgga ctgcagccat atgacgccct caccagcgac    960

ccaggactat cgaactttgg taatgtcctt cgtgacatag aggatttaag cattgcccat   1020

acggctcatt ggaaccctga gtaccgatgg atagatttgt ccgcaaccgt tgcctttggt   1080

cacacaaaag tactagagac atatcttcct ggcatgagca ggaatcgctc atgcggtctc   1140

caaggagtca ccttctgtgg aaatgattat cacgaccaaa aagttaaagg cattacacta   1200

gagctgacta ataccgctca actatataag caagataatt tcagcatttc cctgcttacc   1260

gggctgcagt accgttcgat ggaaaatgaa acaagaagaa caaccgatag ccaagggcct   1320

aatatcaatg aatcatttcc tgctgatggc ttctgggccg ccagcacctc aggggaaaac   1380
```

```
gcatatacgg ctgcatttat tcaatcccgc atccaatatg gtcggcttgg aattattccc   1440

ggggtcagag tggactggta cgaaatctca tcaacagaag atcgcgtcaa acgtcacttg   1500

gccgagaaag gcttatcgtc tgaaatcgat tttgatcata ccagctatag tatggggctg   1560

acttttgatg ccattgccaa tagcctgact ttctttgcaa attacggtga ggggttccgc   1620

ccccctcga tcaatgacta ttttacttac ggcgaccgcg caggcactcc gccaaaaccg   1680

gcaaactggc ttcctaacag accatggctt ggtgaggtag gactgggccc tccttatagt   1740

tcaggcgaag gaagatgcaa tactcctgat acaaattttc tttgcggtga tgtatttaaa   1800

atacaaagct cccagtctag cgaaataggc gttcattatc agacaccaaa cttatttggg   1860

aaaaatattc agttaatgag taaattcacc tatttccaca ttgaaaccaa gcatttattg   1920

cgctatttct ccattgatga cttgacaaat acttacgtac cgcaagatgg atgggaaaaa   1980

cgcaatggca cagagtttga ggggagctta ttttataaag acagttactt cagagccaat   2040

tattcgcgca cctggggatc atactttaat cctcaaacag ggaatatcag ctctattgcc   2100

tgggtaccag ccaatacgct gaatttgaca attggaactc agctcacctc tcgggtcggt   2160

atcaatgcca gttaccgcaa agtttcagag cgcccgctca tcaacggagg cactcaagat   2220

ggctatgagc ttttcagtgc aggaggcttc tggagcccga cagacaatct aacattcaga   2280

atcattggtg aaaatattac taataaagat tatcacctga atggcggtgg tgatttctcg   2340

ggtcttttag gcaatcgcgg cccaggtcgc aacattcgcc tgatcacaga gataaccttc   2400

taa                                                                 2403
```

<210> SEQ ID NO 36
<211> LENGTH: 800
<212> TYPE: PRT
<213> ORGANISM: Methylobacillus flagellatus strain KT

<400> SEQUENCE: 36

```
Met His Leu Gly Arg Ile Phe Leu Pro Thr Arg Ile His His Met Ala
1               5                   10                  15

Gln Thr Gln His Ser Lys Leu Tyr Leu Gln Ala Leu Ser Ala Leu Thr
            20                  25                  30

Phe Leu Ile Ile His Gly Gly Val Leu Ala Ala Ala Gly Ala Thr Pro
        35                  40                  45

Ser Asn Ser Asn Asn Thr Ser Thr Thr Ala Thr Glu Arg Val Lys Glu
    50                  55                  60

Asn Asp Thr Ser Ala Ser Ser Pro Ser Ser Ser Lys Ser Ser Ser Thr
65                  70                  75                  80

Ala Ser Pro Thr Val Leu Pro Glu Ile Gly Val Ser Ser Thr Arg Ile
                85                  90                  95

Lys Gln Asp Ala Ile Thr Ile Asn Pro Thr Gln Thr Ile Thr Thr Ile
            100                 105                 110

Glu Ala Lys Glu Leu Glu Arg Thr Gln Pro Thr Thr Ile Phe Glu Ala
        115                 120                 125

Ile Arg Asp Thr Pro Gly Val Ala Ile Glu Gly Gly Pro Arg Pro Ser
    130                 135                 140

Gly Met Thr Phe Asn Val Arg Gly Phe Asn Ser Asn Glu Asp Val Gln
145                 150                 155                 160

Val Arg Val Asp Asn Val Pro Lys Gly Phe Glu Lys Tyr Arg Phe Gly
                165                 170                 175

Gly Thr Phe Ile Glu Pro Asp Leu Leu Lys Ser Ile Glu Val Gln Arg
            180                 185                 190
```

```
Gly Pro Gln Ile Ala Ser Gly Ser Gly Ser Leu Gly Gly Thr Ile Leu
        195                 200                 205

Ala Lys Thr Lys Asp Ala Ala Asp Leu Leu Lys Pro Gly Arg Arg Tyr
    210                 215                 220

Gly Gly Arg Ile Lys Leu Gly Tyr Ala Ser Asn Asn Asp Glu Val Gln
225                 230                 235                 240

Arg Ser Tyr Leu Ala Phe Ala Arg Pro Val Asp Ala Val Asp Ile Leu
                245                 250                 255

Tyr Asn Arg Thr Tyr Arg Asn Ser Asn Asp Ile Thr His Ser Asp Gly
            260                 265                 270

Ser Lys Leu Pro Gln Ser Lys Val Asn Ser Arg Ala Gln Leu Leu Lys
        275                 280                 285

Val Gly Ile Phe Pro Thr Asp Phe Leu Glu Leu Ile Thr Ser Val Thr
    290                 295                 300

Leu Leu Glu Glu Ser Gly Leu Gln Pro Tyr Asp Ala Leu Thr Ser Asp
305                 310                 315                 320

Pro Gly Leu Ser Asn Phe Gly Asn Val Leu Arg Asp Ile Glu Asp Leu
                325                 330                 335

Ser Ile Ala His Thr Ala His Trp Asn Pro Glu Tyr Arg Trp Ile Asp
            340                 345                 350

Leu Ser Ala Thr Val Ala Phe Gly His Thr Lys Val Leu Glu Thr Tyr
        355                 360                 365

Leu Pro Gly Met Ser Arg Asn Arg Ser Cys Gly Leu Gln Gly Val Thr
    370                 375                 380

Phe Cys Gly Asn Asp Tyr His Asp Gln Lys Val Lys Gly Ile Thr Leu
385                 390                 395                 400

Glu Leu Thr Asn Thr Ala Gln Leu Tyr Lys Gln Asp Asn Phe Ser Ile
                405                 410                 415

Ser Leu Leu Thr Gly Leu Gln Tyr Arg Ser Met Glu Asn Glu Thr Arg
            420                 425                 430

Arg Thr Thr Asp Ser Gln Gly Pro Asn Ile Asn Glu Ser Phe Pro Ala
        435                 440                 445

Asp Gly Phe Trp Ala Ala Ser Thr Ser Gly Glu Asn Ala Tyr Thr Ala
    450                 455                 460

Ala Phe Ile Gln Ser Arg Ile Gln Tyr Gly Arg Leu Gly Ile Ile Pro
465                 470                 475                 480

Gly Val Arg Val Asp Trp Tyr Glu Ile Ser Ser Thr Glu Asp Arg Val
                485                 490                 495

Lys Arg His Leu Ala Glu Lys Gly Leu Ser Ser Glu Ile Asp Phe Asp
            500                 505                 510

His Thr Ser Tyr Ser Met Gly Leu Thr Phe Asp Ala Ile Ala Asn Ser
        515                 520                 525

Leu Thr Phe Phe Ala Asn Tyr Gly Glu Gly Phe Arg Pro Pro Ser Ile
    530                 535                 540

Asn Asp Tyr Phe Thr Tyr Gly Asp Arg Ala Gly Thr Pro Pro Lys Pro
545                 550                 555                 560

Ala Asn Trp Leu Pro Asn Arg Pro Trp Leu Gly Glu Val Gly Leu Gly
                565                 570                 575

Pro Pro Tyr Ser Ser Gly Glu Gly Arg Cys Asn Thr Pro Asp Thr Asn
            580                 585                 590

Phe Leu Cys Gly Asp Val Phe Lys Ile Gln Ser Ser Gln Ser Ser Glu
        595                 600                 605

Ile Gly Val His Tyr Gln Thr Pro Asn Leu Phe Gly Lys Asn Ile Gln
    610                 615                 620
```

```
Leu Met Ser Lys Phe Thr Tyr Phe His Ile Glu Thr Lys His Leu Leu
625                 630                 635                 640

Arg Tyr Phe Ser Ile Asp Asp Leu Thr Asn Thr Tyr Val Pro Gln Asp
                645                 650                 655

Gly Trp Glu Lys Arg Asn Gly Thr Glu Phe Glu Gly Ser Leu Phe Tyr
            660                 665                 670

Lys Asp Ser Tyr Phe Arg Ala Asn Tyr Ser Arg Thr Trp Gly Ser Tyr
        675                 680                 685

Phe Asn Pro Gln Thr Gly Asn Ile Ser Ser Ile Ala Trp Val Pro Ala
    690                 695                 700

Asn Thr Leu Asn Leu Thr Ile Gly Thr Gln Leu Thr Ser Arg Val Gly
705                 710                 715                 720

Ile Asn Ala Ser Tyr Arg Lys Val Ser Glu Arg Pro Leu Ile Asn Gly
                725                 730                 735

Gly Thr Gln Asp Gly Tyr Glu Leu Phe Ser Ala Gly Gly Phe Trp Ser
            740                 745                 750

Pro Thr Asp Asn Leu Thr Phe Arg Ile Ile Gly Glu Asn Ile Thr Asn
        755                 760                 765

Lys Asp Tyr His Leu Asn Gly Gly Gly Asp Phe Ser Gly Leu Leu Gly
    770                 775                 780

Asn Arg Gly Pro Gly Arg Asn Ile Arg Leu Ile Thr Glu Ile Thr Phe
785                 790                 795                 800


<210> SEQ ID NO 37
<211> LENGTH: 1914
<212> TYPE: DNA
<213> ORGANISM: Methylobacillus flagellatus strain KT

<400> SEQUENCE: 37

atgtccacta aagcaaaaat gccgctgaat catacggtca gcctggctgt aatttgctca      60

tccatcgcat tgatcggttg tgatggcggg ggaagcagca atgtcaggcc aaccaacact     120

tccaataacc cgcctatcgt gacaacagct gacaacacgc tgaatgatac gattgatacg     180

gtcaatgacc tcaccaacga cgtgcttcaa ccagtgacca cagccttgca acccgtcact     240

gatccactcg gcaatgcgct ggatcccgtt cttgagcctg ttgtgtctgc tttgcagcca     300

gtgctgaatc cggtagtgag tacgctgagc ccggtgacag ctgcacttgc gcctgtcacg     360

gatagtttgc tgcctgtgac cggtgtgctg ggagaggtac tagcaccttt aggcacagct     420

ctcggcccta cgtccgaagc cctttctggc gctctagagc cgctggcgac agccttgggg     480

ccggtagcgg gcggattgaa tggcacattg ctgcctgtga cgacggcgac gggcaatgcc     540

ctcacgcctg tattaactgg cgtgggaaca ttgcttgagc ctattgcggg cccgttggca     600

cctgtgatca atacggcagg cggtgtcttg cagccagtgc ttcagcctgt ggcaggcgtg     660

ctggcgcccg tggcacaaac actggcacct gtgacggata ccctggcgcc tgtcatcaat     720

accgttgcag gtattgccaa tccgctgctg gatactgtca atggcgtgac tgcgcctttg     780

gcatcgacat tggcgccaac attggaaaca gtgggcaata cagtgggttc tcttgctaac     840

gtgactggca cggttggcgg tacggtggat ggcattgtca caccattgac aacaacggtc     900

ggaggtgtag tcggccagct tggatccact ttgactggcg ctattccagg agttgagggt     960

ggactgggcc ccgtcactga cttgctgggt ggtggcaatg gcctggcagg cttggatggg    1020

cttggcaatg gcttggtcac ccaagtggcg gcgacgacga aatttactgt cgacagcgtc    1080

gctggcctgg ccaaaacagt aacaggatcc attgcaggca atggcgccct ggctccagtc    1140
```

-continued

```
accaatttat tggccggaac caatgggctg cttgacccat tgatcggcac gaatggcatt    1200

ttgcctctga cgactgacgg agatcagaca ctgcttgatc cgctggtcgg caagaacggt    1260

gtattggccc tgaccagtgg agaggccagc aatggccagc cagcgttgct tgatccgttg    1320

attggagagg gtggtgtatt gcctttgacc agtgcggagg gcaatctcac aacgcttgat    1380

ccgttgatcg ggcatgctgg tgtattgcct ttgaccagca atgtacctgc cggtggcaac    1440

ggcggcatac ttgcccctgt gctgaacttg tcctcaggca atctgggcgg cttgggtagc    1500

gtgctggcac cggtgaccaa tattctagcc ggaggcgggg cgaacgggct gaatgggtta    1560

ttggcccccg tgaccggact attgggtggc gcactgcctg ccaatggtgg tctgctcgct    1620

cctgtaacag gattattggg cgctggacag cctaatggcg gattgctggc accggtaact    1680

aatattctgg cgctgggcgg cggtagtgga ggcagtgctc ctgccaacct cctgacaccc    1740

gtcacagcat tgttgtcagg taataatggt ggtggtctac ttgcacctgt gaccaatatt    1800

ctggggggga ttactcagaa tgggggggga actgttgcaa gcccatctgc gaccgaaggt    1860

ggcaatcctg tcaatggatt gtctggcctg ctgggcgctc ttttagggct gtaa          1914
```

<210> SEQ ID NO 38
<211> LENGTH: 637
<212> TYPE: PRT
<213> ORGANISM: Methylobacillus flagellatus strain KT

<400> SEQUENCE: 38

```
Met Ser Thr Lys Ala Lys Met Pro Leu Asn His Thr Val Ser Leu Ala
1               5                   10                  15

Val Ile Cys Ser Ser Ile Ala Leu Ile Gly Cys Asp Gly Gly Gly Ser
            20                  25                  30

Ser Asn Val Arg Pro Thr Asn Thr Ser Asn Pro Pro Ile Val Thr
        35                  40                  45

Thr Ala Asp Asn Thr Leu Asn Asp Thr Ile Asp Thr Val Asn Asp Leu
    50                  55                  60

Thr Asn Asp Val Leu Gln Pro Val Thr Thr Ala Leu Gln Pro Val Thr
65                  70                  75                  80

Asp Pro Leu Gly Asn Ala Leu Asp Pro Val Leu Glu Pro Val Val Ser
                85                  90                  95

Ala Leu Gln Pro Val Leu Asn Pro Val Val Ser Thr Leu Ser Pro Val
            100                 105                 110

Thr Ala Ala Leu Ala Pro Val Thr Asp Ser Leu Leu Pro Val Thr Gly
        115                 120                 125

Val Leu Gly Glu Val Leu Ala Pro Leu Gly Thr Ala Leu Gly Pro Thr
    130                 135                 140

Ser Glu Ala Leu Ser Gly Ala Leu Glu Pro Leu Ala Thr Ala Leu Gly
145                 150                 155                 160

Pro Val Ala Gly Gly Leu Asn Gly Thr Leu Leu Pro Val Thr Thr Ala
                165                 170                 175

Thr Gly Asn Ala Leu Thr Pro Val Leu Thr Gly Val Gly Thr Leu Leu
            180                 185                 190

Glu Pro Ile Ala Gly Pro Leu Ala Pro Val Ile Asn Thr Ala Gly Gly
        195                 200                 205

Val Leu Gln Pro Val Leu Gln Pro Val Ala Gly Val Leu Ala Pro Val
    210                 215                 220

Ala Gln Thr Leu Ala Pro Val Thr Asp Thr Leu Ala Pro Val Ile Asn
225                 230                 235                 240

Thr Val Ala Gly Ile Ala Asn Pro Leu Leu Asp Thr Val Asn Gly Val
```

-continued

```
                245                 250                 255

Thr Ala Pro Leu Ala Ser Thr Leu Ala Pro Thr Leu Glu Thr Val Gly
            260                 265                 270

Asn Thr Val Gly Ser Leu Ala Asn Val Thr Gly Thr Val Gly Gly Thr
        275                 280                 285

Val Asp Gly Ile Val Thr Pro Leu Thr Thr Thr Val Gly Gly Val Val
    290                 295                 300

Gly Gln Leu Gly Ser Thr Leu Thr Gly Ala Ile Pro Gly Val Glu Gly
305                 310                 315                 320

Gly Leu Gly Pro Val Thr Asp Leu Leu Gly Gly Gly Asn Gly Leu Ala
                325                 330                 335

Gly Leu Asp Gly Leu Gly Asn Gly Leu Val Thr Gln Val Ala Ala Thr
            340                 345                 350

Thr Lys Phe Thr Val Asp Ser Val Ala Gly Leu Ala Lys Thr Val Thr
        355                 360                 365

Gly Ser Ile Ala Gly Asn Gly Ala Leu Ala Pro Val Thr Asn Leu Leu
    370                 375                 380

Ala Gly Thr Asn Gly Leu Leu Asp Pro Leu Ile Gly Thr Asn Gly Ile
385                 390                 395                 400

Leu Pro Leu Thr Thr Asp Gly Asp Gln Thr Leu Leu Asp Pro Leu Val
                405                 410                 415

Gly Lys Asn Gly Val Leu Ala Leu Thr Ser Gly Glu Ala Ser Asn Gly
            420                 425                 430

Gln Pro Ala Leu Leu Asp Pro Leu Ile Gly Glu Gly Gly Val Leu Pro
        435                 440                 445

Leu Thr Ser Ala Glu Gly Asn Leu Thr Thr Leu Asp Pro Leu Ile Gly
    450                 455                 460

His Ala Gly Val Leu Pro Leu Thr Ser Asn Val Pro Ala Gly Gly Asn
465                 470                 475                 480

Gly Gly Ile Leu Ala Pro Val Leu Asn Leu Ser Ser Gly Asn Leu Gly
                485                 490                 495

Gly Leu Gly Ser Val Leu Ala Pro Val Thr Asn Ile Leu Ala Gly Gly
            500                 505                 510

Gly Ala Asn Gly Leu Asn Gly Leu Leu Ala Pro Val Thr Gly Leu Leu
        515                 520                 525

Gly Gly Ala Leu Pro Ala Asn Gly Gly Leu Leu Ala Pro Val Thr Gly
    530                 535                 540

Leu Leu Gly Ala Gly Gln Pro Asn Gly Gly Leu Leu Ala Pro Val Thr
545                 550                 555                 560

Asn Ile Leu Ala Leu Gly Gly Gly Ser Gly Gly Ser Ala Pro Ala Asn
                565                 570                 575

Leu Leu Thr Pro Val Thr Ala Leu Leu Ser Gly Asn Asn Gly Gly Gly
            580                 585                 590

Leu Leu Ala Pro Val Thr Asn Ile Leu Gly Gly Ile Thr Gln Asn Gly
        595                 600                 605

Gly Gly Thr Val Ala Ser Pro Ser Ala Thr Glu Gly Gly Asn Pro Val
    610                 615                 620

Asn Gly Leu Ser Gly Leu Leu Gly Ala Leu Leu Gly Leu
625                 630                 635
```

<210> SEQ ID NO 39
<211> LENGTH: 684
<212> TYPE: DNA
<213> ORGANISM: Nitrobacter winogradskyi Nb-255

<400> SEQUENCE: 39

```
atgacgacat ccggcgacac atcgttcccg tcacgtctca ctaagatcga cgagctcacg     60
cgcggcgatc acaccttcct cgaagccggg gacgagtgcc tgtttttggg ggactattcg    120
gcacgcaaag gcttttccca cagcgccaca aaccagctca tcctaaactt taagaagccc    180
gttcgattcc gtggcacggc gagttggcgg tacaaggcgc tggcgattaa cgctgccgcg    240
aacgccttca cgcggaatct gggcgcggct ttgtctcagt tgacgcttgt gccggttccg    300
ccgtcaaagc tcaaaacaga cccggagtat gacgatcgcg ttatggacat gctgcgcgcc    360
ataagagcgc cggcaggagt aaatccagac gttcgagaac ttattcggca aacacatccg    420
atggcggcgg cgcacgagag cgctaatcga ccgccgccag gcgactggga aagcgtctat    480
gcaatcgacg aaacgctcgt gcaaaacgaa cccacatgga tcggcattgt tgacgatctg    540
ttggtcacag gatgtaggtt ccgcgcgatg tcaaacgtac tgaagcggcg ctttccagcg    600
gcaaggatca caggcctatt tcttgctcgc cgcgtgccag aggcaatcga cttctccgaa    660
tttttcacag acctcgacca gtag                                           684
```

<210> SEQ ID NO 40
<211> LENGTH: 227
<212> TYPE: PRT
<213> ORGANISM: Nitrobacter winogradskyi Nb-255

<400> SEQUENCE: 40

```
Met Thr Thr Ser Gly Asp Thr Ser Phe Pro Ser Arg Leu Thr Lys Ile
1               5                   10                  15

Asp Glu Leu Thr Arg Gly Asp His Thr Phe Leu Glu Ala Gly Asp Glu
            20                  25                  30

Cys Leu Phe Phe Gly Asp Tyr Ser Ala Arg Lys Gly Phe Ser His Ser
        35                  40                  45

Ala Thr Asn Gln Leu Ile Leu Asn Phe Lys Lys Pro Val Arg Phe Arg
    50                  55                  60

Gly Thr Ala Ser Trp Arg Tyr Lys Ala Leu Ala Ile Asn Ala Ala Ala
65                  70                  75                  80

Asn Ala Phe Thr Arg Asn Leu Gly Ala Ala Leu Ser Gln Leu Thr Leu
                85                  90                  95

Val Pro Val Pro Pro Ser Lys Leu Lys Thr Asp Pro Glu Tyr Asp Asp
            100                 105                 110

Arg Val Met Asp Met Leu Arg Ala Ile Arg Ala Pro Ala Gly Val Asn
        115                 120                 125

Pro Asp Val Arg Glu Leu Ile Arg Gln Thr His Pro Met Ala Ala Ala
    130                 135                 140

His Glu Ser Ala Asn Arg Pro Pro Pro Gly Asp Trp Glu Ser Val Tyr
145                 150                 155                 160

Ala Ile Asp Glu Thr Leu Val Gln Asn Glu Pro Thr Trp Ile Gly Ile
                165                 170                 175

Val Asp Asp Leu Leu Val Thr Gly Cys Arg Phe Arg Ala Met Ser Asn
            180                 185                 190

Val Leu Lys Arg Arg Phe Pro Ala Ala Arg Ile Thr Gly Leu Phe Leu
        195                 200                 205

Ala Arg Arg Val Pro Glu Ala Ile Asp Phe Ser Glu Phe Phe Thr Asp
    210                 215                 220

Leu Asp Gln
225
```

<210> SEQ ID NO 41
<211> LENGTH: 786
<212> TYPE: DNA
<213> ORGANISM: Nitrosococcus oceani ATCC 19707

<400> SEQUENCE: 41
atggctgcaa ctagtagagc tgtagcgcaa ggagtagccg agaaagaaac tgctgatctc 60
tttgcctggc gtggcatgtg gttagcggtc gcggcctttt tcgcgttcta catctgtgtg 120
cgttggtatg aaggtgttta tggatggaag tatggtttag atgccttttc gccggaattc 180
caaacatact ggatgaatct gctgtacatt gagctcgttg ttgaggcact ggcaacagca 240
gccctggttt cttacctaat taagacccgg gatcgcaata tggaagccat gactccccgc 300
gaggagctgc gccgttactg caccctttat atgtggtggg ttgtttatgg cgttgggtta 360
ttctggggcg cgagcttctt taccgagcag gatggtgctt ggcatcagac cgtagttcgg 420
gatacagact tcaccccaag ccatattatt gagttctaca tgagctaccc gatctacgta 480
atggtaggtt taggttcgtt cacgtatgct aagacccgta ttccttattt tgcaaagggc 540
tggtctgtac cctacctcat gttggtgttt ggaccettta tgatcttccc gaatgtgggt 600
ctgaatgaat ggggtcacac cttctggttt atggaggagc tgtttgtggc acctctgcac 660
tggggttttg tattctttgc ttggtttatc cttgcagtat tcggggtgtt tctgcaggtt 720
cagccccgta tgaaggaatt gatcggcaga gagctgcagc agagcgagga ctatgcccgt 780
agctga 786

<210> SEQ ID NO 42
<211> LENGTH: 261
<212> TYPE: PRT
<213> ORGANISM: Nitrosococcus oceani ATCC 19707

<400> SEQUENCE: 42

Met Ala Ala Thr Ser Arg Ala Val Ala Gln Gly Val Ala Glu Lys Glu
1               5                   10                  15

Thr Ala Asp Leu Phe Ala Trp Arg Gly Met Trp Leu Ala Val Ala Ala
            20                  25                  30

Phe Phe Ala Phe Tyr Ile Cys Val Arg Trp Tyr Glu Gly Val Tyr Gly
        35                  40                  45

Trp Lys Tyr Gly Leu Asp Ala Phe Ser Pro Glu Phe Gln Thr Tyr Trp
    50                  55                  60

Met Asn Leu Leu Tyr Ile Glu Leu Val Val Glu Ala Leu Ala Thr Ala
65                  70                  75                  80

Ala Leu Val Ser Tyr Leu Ile Lys Thr Arg Asp Arg Asn Met Glu Ala
                85                  90                  95

Met Thr Pro Arg Glu Glu Leu Arg Arg Tyr Cys Thr Leu Tyr Met Trp
            100                 105                 110

Trp Val Val Tyr Gly Val Gly Leu Phe Trp Gly Ala Ser Phe Phe Thr
        115                 120                 125

Glu Gln Asp Gly Ala Trp His Gln Thr Val Val Arg Asp Thr Asp Phe
    130                 135                 140

Thr Pro Ser His Ile Ile Glu Phe Tyr Met Ser Tyr Pro Ile Tyr Val
145                 150                 155                 160

Met Val Gly Leu Gly Ser Phe Thr Tyr Ala Lys Thr Arg Ile Pro Tyr
                165                 170                 175

Phe Ala Lys Gly Trp Ser Val Pro Tyr Leu Met Leu Val Phe Gly Pro
            180                 185                 190

Phe Met Ile Phe Pro Asn Val Gly Leu Asn Glu Trp Gly His Thr Phe

-continued

```
        195                 200                 205

Trp Phe Met Glu Glu Leu Phe Val Ala Pro Leu His Trp Gly Phe Val
    210                 215                 220

Phe Phe Ala Trp Phe Ile Leu Ala Val Phe Gly Val Phe Leu Gln Val
225                 230                 235                 240

Gln Pro Arg Met Lys Glu Leu Ile Gly Arg Glu Leu Gln Gln Ser Glu
                245                 250                 255

Asp Tyr Ala Arg Ser
            260


<210> SEQ ID NO 43
<211> LENGTH: 744
<212> TYPE: DNA
<213> ORGANISM: Nitrosococcus oceani ATCC 19707

<400> SEQUENCE: 43

atgagtgcac ttacgtctgc ggttcgtaca ccggaggaag ctgctaaagt ctctagaacg      60

ttggatttta tagcgttagg ggcttttttt atgattttgc tggcttccca ccacgttcac     120

gtcatgcttt taatgggcga ctgggatttc tgggttgact ggaaagaccg gcgtttttgg     180

gtcaccgtag ttcccattgt atcggttgct taccccgctg ctgcacaggc gtttttttgg     240

gagaagttcc gccttccctt tggtgctacc cttgtaacgc taggggtgtt agcaggtgag     300

tgggctaacc gctactttaa tttcgtaggg tttacctatt ttccgattaa tttcgtatgg     360

ccgaccattc tgctgcccat ggcgctgttc ttggatgcca tgcttgcgat ttccaagagc     420

tacggcttga cggcggtagt gggtggatta atgtacggtt tgttgatgta tcccgctaac     480

tggccgctgc tttcggcatt ccatgtgcct gctgagtaca atggagtagt aatgtctttg     540

gccgatatta tgggctacca atacgtccgg accggtactc ctgagtatat ccggatgatt     600

gagaaaggta ccttgagaac gtttggtaag gacgtggtcc cggtttcagc tttcttctcg     660

ggttttgttg ccatggtaat gtactttgtg tggcactttg ttggccgctg gttctccaag     720

gactaccata tcgaccaagt gtag                                            744


<210> SEQ ID NO 44
<211> LENGTH: 247
<212> TYPE: PRT
<213> ORGANISM: Nitrosococcus oceani ATCC 19707

<400> SEQUENCE: 44

Met Ser Ala Leu Thr Ser Ala Val Arg Thr Pro Glu Glu Ala Ala Lys
1               5                   10                  15

Val Ser Arg Thr Leu Asp Phe Ile Ala Leu Gly Ala Phe Phe Met Ile
            20                  25                  30

Leu Leu Ala Ser His His Val His Val Met Leu Leu Met Gly Asp Trp
        35                  40                  45

Asp Phe Trp Val Asp Trp Lys Asp Arg Arg Phe Trp Val Thr Val Val
    50                  55                  60

Pro Ile Val Ser Val Ala Tyr Pro Ala Ala Ala Gln Ala Phe Phe Trp
65                  70                  75                  80

Glu Lys Phe Arg Leu Pro Phe Gly Ala Thr Leu Val Thr Leu Gly Val
                85                  90                  95

Leu Ala Gly Glu Trp Ala Asn Arg Tyr Phe Asn Phe Val Gly Phe Thr
            100                 105                 110

Tyr Phe Pro Ile Asn Phe Val Trp Pro Thr Ile Leu Leu Pro Met Ala
        115                 120                 125
```

Leu Phe Leu Asp Ala Met Leu Ala Ile Ser Lys Ser Tyr Gly Leu Thr
130 135 140

Ala Val Val Gly Gly Leu Met Tyr Gly Leu Leu Met Tyr Pro Ala Asn
145 150 155 160

Trp Pro Leu Leu Ser Ala Phe His Val Pro Ala Glu Tyr Asn Gly Val
165 170 175

Val Met Ser Leu Ala Asp Ile Met Gly Tyr Gln Tyr Val Arg Thr Gly
180 185 190

Thr Pro Glu Tyr Ile Arg Met Ile Glu Lys Gly Thr Leu Arg Thr Phe
195 200 205

Gly Lys Asp Val Val Pro Val Ser Ala Phe Phe Ser Gly Phe Val Ala
210 215 220

Met Val Met Tyr Phe Val Trp His Phe Val Gly Arg Trp Phe Ser Lys
225 230 235 240

Asp Tyr His Ile Asp Gln Val
245

<210> SEQ ID NO 45
<211> LENGTH: 822
<212> TYPE: DNA
<213> ORGANISM: Nitrosococcus oceani ATCC 19707

<400> SEQUENCE: 45
atggctgatt ttttgcaaga aggtagcggt ttggtttttg gttctgaaga aaatgatgtg 60
atacggacct ctggaccctc cgtagtattt gctggtgctg gcgacgatgg cgttagaatg 120
ggttattcca atgatattgc ctatctggga gagggcaatg atgtggccta tgcggaagcg 180
ggcaatgatc taatcttcgg cgaagccggt gatgatctta tgtatggagg cagcggcaat 240
gattggcttg acgggggtga gggcaatgac ttcctgtggg gcggagaagg cagtgatcag 300
cttttcggca aggagggaga cgatacgatc tatggtgtaa ccggcaccaa tgccctctat 360
ggttctacgg gtaacgatct aattatgggg ggtgatcaat cggacgttat ctttagtggc 420
gaggacgatg acgtggtgct gggaggcgat ggcggcgact ggatttccgg cggctcgggc 480
cataaccaaa tttatggtca ggggggtgat gatattattt atggttcggg tagtaatgac 540
gatggcgacc gctccaatga aatcttttat actggtaatg atggcactga tacggtgaat 600
cgcttcaatg cggaaagcga tcagttcgtg attgccgccg acatcaatgg tacgggcatc 660
gcaagtatcg acgatctctc ctcccgcgtg agcaacttta ctgacgaagt tggcgagcct 720
ggcgccgtga ttgatttggg cgaaggtagc agcattcaac tggttggcgt tgaggccagc 780
gaagttaccg ctaatctttc cgattatttc actgtggcct ga 822

<210> SEQ ID NO 46
<211> LENGTH: 273
<212> TYPE: PRT
<213> ORGANISM: Nitrosococcus oceani ATCC 19707

<400> SEQUENCE: 46

Met Ala Asp Phe Leu Gln Glu Gly Ser Gly Leu Val Phe Gly Ser Glu
1 5 10 15

Glu Asn Asp Val Ile Arg Thr Ser Gly Pro Ser Val Val Phe Ala Gly
20 25 30

Ala Gly Asp Asp Gly Val Arg Met Gly Tyr Ser Asn Asp Ile Ala Tyr
35 40 45

Leu Gly Glu Gly Asn Asp Val Ala Tyr Ala Glu Ala Gly Asn Asp Leu
50 55 60

```
Ile Phe Gly Glu Ala Gly Asp Asp Leu Met Tyr Gly Gly Ser Gly Asn
65                  70                  75                  80

Asp Trp Leu Asp Gly Gly Glu Gly Asn Asp Phe Leu Trp Gly Gly Glu
                85                  90                  95

Gly Ser Asp Gln Leu Phe Gly Lys Glu Gly Asp Asp Thr Ile Tyr Gly
            100                 105                 110

Val Thr Gly Thr Asn Ala Leu Tyr Gly Ser Thr Gly Asn Asp Leu Ile
        115                 120                 125

Met Gly Gly Asp Gln Ser Asp Val Ile Phe Ser Gly Glu Asp Asp Asp
    130                 135                 140

Val Val Leu Gly Gly Asp Gly Gly Asp Trp Ile Ser Gly Gly Ser Gly
145                 150                 155                 160

His Asn Gln Ile Tyr Gly Gln Gly Gly Asp Asp Ile Ile Tyr Gly Ser
                165                 170                 175

Gly Ser Asn Asp Asp Gly Asp Arg Ser Asn Glu Ile Phe Tyr Thr Gly
            180                 185                 190

Asn Asp Gly Thr Asp Thr Val Asn Arg Phe Asn Ala Glu Ser Asp Gln
        195                 200                 205

Phe Val Ile Ala Ala Asp Ile Asn Gly Thr Gly Ile Ala Ser Ile Asp
    210                 215                 220

Asp Leu Ser Ser Arg Val Ser Asn Phe Thr Asp Glu Val Gly Glu Pro
225                 230                 235                 240

Gly Ala Val Ile Asp Leu Gly Glu Gly Ser Ser Ile Gln Leu Val Gly
                245                 250                 255

Val Glu Ala Ser Glu Val Thr Ala Asn Leu Ser Asp Tyr Phe Thr Val
            260                 265                 270

Ala
```

<210> SEQ ID NO 47
<211> LENGTH: 897
<212> TYPE: DNA
<213> ORGANISM: Polaromonas sp. JS666

<400> SEQUENCE: 47

```
atgaaactca aactagccgc tctgtccatc gccttgctcg caaccggcgg tgccatcgcc     60

caggcgaacg acaccatcgc caaggtcaag gcctcaggcg tggtgaccat gggggtgcgc    120

gactcgtccg gtctttcctt taccctcggt gacggcaagt acgccggtta ccacgttgac    180

gtgtgtcagc gcattctggc cagactcgaa aaaacggtag gcaagaaact ggaagtgaaa    240

tacctgccgg tgacatcgca aaaccgcatt cccctggtgc aaaacggcac ggtcgatatt    300

gagtgcggct ccaccaccaa taatgcgacg cgccaaaaag atgttgcgtt tgctgtgacc    360

acctttgttg aagaggttcg cattgcggtg aaagccgact caggcattac gtctatcgcc    420

cagctcaatg gcaaaagcgt ggccaccacc accggcacca cctccgtcca gaccttgcgc    480

aaaaacgagc gcgccaccgg cattgacttc aaggaagtct tcggcaaaga ccactccgac    540

agctttctgc tgctggagtc cggccgtgcc gatgcatttg tcatggatgg ctccatcctg    600

gccagcaaca tcgccaactc caagaacccc gccggcttca agatcgtcgg tgaagtactg    660

agcgttgagc cgattgccat catgatgcgc aaagatgacc cggcgttcaa aaaattgtcg    720

gatgacacca tcaaggacct gatcaagtcc ggcgagctgg caaaaatata tgacaagtgg    780

ctcatgcaac ctgttccacc gaaaaatgta cgcgttgggt tgccagccag cgacagcacc    840

aaggctgctt gggcaacgcc taacgacaag cccatggaag attacgccaa aaagtaa       897
```

<210> SEQ ID NO 48
<211> LENGTH: 298
<212> TYPE: PRT
<213> ORGANISM: Polaromonas sp. JS666

<400> SEQUENCE: 48

```
Met Lys Leu Lys Leu Ala Ala Leu Ser Ile Ala Leu Leu Ala Thr Gly
1               5                   10                  15

Gly Ala Ile Ala Gln Ala Asn Asp Thr Ile Ala Lys Val Lys Ala Ser
            20                  25                  30

Gly Val Val Thr Met Gly Val Arg Asp Ser Ser Gly Leu Ser Phe Thr
        35                  40                  45

Leu Gly Asp Gly Lys Tyr Ala Gly Tyr His Val Asp Val Cys Gln Arg
    50                  55                  60

Ile Leu Ala Arg Leu Glu Lys Thr Val Gly Lys Lys Leu Glu Val Lys
65                  70                  75                  80

Tyr Leu Pro Val Thr Ser Gln Asn Arg Ile Pro Leu Val Gln Asn Gly
                85                  90                  95

Thr Val Asp Ile Glu Cys Gly Ser Thr Thr Asn Asn Ala Thr Arg Gln
            100                 105                 110

Lys Asp Val Ala Phe Ala Val Thr Thr Phe Val Glu Glu Val Arg Ile
        115                 120                 125

Ala Val Lys Ala Asp Ser Gly Ile Thr Ser Ile Ala Gln Leu Asn Gly
    130                 135                 140

Lys Ser Val Ala Thr Thr Thr Gly Thr Thr Ser Val Gln Thr Leu Arg
145                 150                 155                 160

Lys Asn Glu Arg Ala Thr Gly Ile Asp Phe Lys Glu Val Phe Gly Lys
                165                 170                 175

Asp His Ser Asp Ser Phe Leu Leu Leu Glu Ser Gly Arg Ala Asp Ala
            180                 185                 190

Phe Val Met Asp Gly Ser Ile Leu Ala Ser Asn Ile Ala Asn Ser Lys
        195                 200                 205

Asn Pro Ala Gly Phe Lys Ile Val Gly Glu Val Leu Ser Val Glu Pro
    210                 215                 220

Ile Ala Ile Met Met Arg Lys Asp Asp Pro Ala Phe Lys Lys Leu Ser
225                 230                 235                 240

Asp Asp Thr Ile Lys Asp Leu Ile Lys Ser Gly Glu Leu Ala Lys Ile
                245                 250                 255

Tyr Asp Lys Trp Leu Met Gln Pro Val Pro Pro Lys Asn Val Arg Val
            260                 265                 270

Gly Leu Pro Ala Ser Asp Ser Thr Lys Ala Ala Trp Ala Thr Pro Asn
        275                 280                 285

Asp Lys Pro Met Glu Asp Tyr Ala Lys Lys
    290                 295
```

<210> SEQ ID NO 49
<211> LENGTH: 1338
<212> TYPE: DNA
<213> ORGANISM: Pseudoalteromonas atlantica T6c

<400> SEQUENCE: 49

```
atgataaaca aaaaaatatt agccgtagcc gttgctacag ccttttcagc aaacacatac      60

gcagctgtag atttagacgc ggcaggtaca actgctgacc catacggaac agcagttttc     120

gcctctgaag caattgaatc aactgatttg acagatggcc ttttggaagc ggttaataat     180

acaaacattt tagacgtatc agctagtgtt ggtttcacta tcggtaacgg tacgtcaaaa     240
```

```
tacgttcgcg tagctctagg taacggtgct aaattcgatg cagtacctac tcttactact    300

gctaatggta ctgcttcagt tgctcaaggc ggtgacgaag caacttacgt tattttcgaa    360

gttgctgctt cagctgatat cccagctgct caagcttacg tagttgcctc tgctaactac    420

ttgctaaatg cttctggtac aacgtctgta actgtttcaa cttatgagac tgctgctgat    480

gcagtgaacg aagtaaacgg tctatacact gacaccgctc ctctttcatc agttgcttca    540

atcgtaactg gcgaaatcgc tgacgctagc ttctctacag ctactgtagc gagtgacttt    600

aaagcgtttg aatttggcgc tggcgctgat ggtgatgcag tttctgctgt actaggtaac    660

cttggtgcgc ttgacgttac tggttacgtt gatggcacag cttacaaccc tgcaggtgtt    720

gcagtaactg ctgctactct acttaccgct tcacaagacg taacagttac tggtgatttc    780

agcttcggtg cttggacttt agatataaca cctgcttgtg atggcgtatc tgatatcgat    840

ttgactgtta atgctgatga agacgctgca actgcatctg ctgttactgt tgctactaaa    900

cagtacctat gtgtaactgt tgatactact gaagtaatca acaaaggttc ttacagcctt    960

gaacttgtag acgatgaagt ttctgacgta gtaggtaaaa ttgtatatga tacaactact   1020

attgaagtac cttacttgac tacatttagt gactacaacc aacgtttata catcactaac   1080

tacggttcaa ttgatgctgc atacactatt tctttcacat ctgaagacgg tgtagaagca   1140

gtagctggcg acaaagcaac tggtattgtt cctaaaggtg agatgatcgc tattaaagca   1200

actgacatcg ttactttaac tggtagaact cgtactgctg caactctaga agtagaagca   1260

gaagacgaga acgtttcagc tacgactcag actgtaaacg ttgcagacaa gtctactgat   1320

actgttgtat taaactaa                                                 1338
```

<210> SEQ ID NO 50
<211> LENGTH: 445
<212> TYPE: PRT
<213> ORGANISM: Pseudoalteromonas atlantica T6c

<400> SEQUENCE: 50

```
Met Ile Asn Lys Lys Ile Leu Ala Val Ala Val Ala Thr Ala Phe Ser
1               5                   10                  15

Ala Asn Thr Tyr Ala Ala Val Asp Leu Asp Ala Ala Gly Thr Thr Ala
            20                  25                  30

Asp Pro Tyr Gly Thr Ala Val Phe Ala Ser Glu Ala Ile Glu Ser Thr
        35                  40                  45

Asp Leu Thr Asp Gly Leu Leu Glu Ala Val Asn Asn Thr Asn Ile Leu
    50                  55                  60

Asp Val Ser Ala Ser Val Gly Phe Thr Ile Gly Asn Gly Thr Ser Lys
65                  70                  75                  80

Tyr Val Arg Val Ala Leu Gly Asn Gly Ala Lys Phe Asp Ala Val Pro
                85                  90                  95

Thr Leu Thr Thr Ala Asn Gly Thr Ala Ser Val Ala Gln Gly Gly Asp
            100                 105                 110

Glu Ala Thr Tyr Val Ile Phe Glu Val Ala Ala Ser Ala Asp Ile Pro
        115                 120                 125

Ala Ala Gln Ala Tyr Val Val Ala Ser Ala Asn Tyr Leu Leu Asn Ala
    130                 135                 140

Ser Gly Thr Thr Ser Val Thr Val Ser Thr Tyr Glu Thr Ala Ala Asp
145                 150                 155                 160

Ala Val Asn Glu Val Asn Gly Leu Tyr Thr Asp Thr Ala Pro Leu Ser
                165                 170                 175

Ser Val Ala Ser Ile Val Thr Gly Glu Ile Ala Asp Ala Ser Phe Ser
```

```
            180                 185                 190

Thr Ala Thr Val Ala Ser Asp Phe Lys Ala Phe Glu Phe Gly Ala Gly
        195                 200                 205

Ala Asp Gly Asp Ala Val Ser Ala Val Leu Gly Asn Leu Gly Ala Leu
    210                 215                 220

Asp Val Thr Gly Tyr Val Asp Gly Thr Ala Tyr Asn Pro Ala Gly Val
225                 230                 235                 240

Ala Val Thr Ala Ala Thr Leu Leu Thr Ala Ser Gln Asp Val Thr Val
                245                 250                 255

Thr Gly Asp Phe Ser Phe Gly Ala Trp Thr Leu Asp Ile Thr Pro Ala
            260                 265                 270

Cys Asp Gly Val Ser Asp Ile Asp Leu Thr Val Asn Ala Asp Glu Asp
        275                 280                 285

Ala Ala Thr Ala Ser Ala Val Thr Val Ala Thr Lys Gln Tyr Leu Cys
    290                 295                 300

Val Thr Val Asp Thr Thr Glu Val Ile Asn Lys Gly Ser Tyr Ser Leu
305                 310                 315                 320

Glu Leu Val Asp Asp Glu Val Ser Asp Val Val Gly Lys Ile Val Tyr
                325                 330                 335

Asp Thr Thr Thr Ile Glu Val Pro Tyr Leu Thr Thr Phe Ser Asp Tyr
            340                 345                 350

Asn Gln Arg Leu Tyr Ile Thr Asn Tyr Gly Ser Ile Asp Ala Ala Tyr
        355                 360                 365

Thr Ile Ser Phe Thr Ser Glu Asp Gly Val Glu Ala Val Ala Gly Asp
    370                 375                 380

Lys Ala Thr Gly Ile Val Pro Lys Gly Glu Met Ile Ala Ile Lys Ala
385                 390                 395                 400

Thr Asp Ile Val Thr Leu Thr Gly Arg Thr Arg Thr Ala Ala Thr Leu
                405                 410                 415

Glu Val Glu Ala Glu Asp Glu Asn Val Ser Ala Thr Thr Gln Thr Val
            420                 425                 430

Asn Val Ala Asp Lys Ser Thr Asp Thr Val Val Leu Asn
        435                 440                 445
```

<210> SEQ ID NO 51
<211> LENGTH: 1419
<212> TYPE: DNA
<213> ORGANISM: Pseudoalteromonas atlantica T6c

<400> SEQUENCE: 51

```
atgatgttaa aaaatagaca aacaacattc gtttcgaccg cagccaaaag cgctatcaac      60

gcatctaact caaagacctg taataaacgt tctgcatccg tatttaataa acttggagtc     120

gttgcagcag cggttatggc cgcttcaata cctgcgcaag ttaacgctgc tacatttctt     180

gatggcttag tagatgtgaa ctttttagcg atgcaaaact atcaagcgat tcaagctaaa     240

gaaggcgcat ttagaccaga agatgaagaa cagtcgtcag gttttggccg tattcgagcc     300

aacttgatgt ttaaatttca catcaacgat tacatcactg ccgatatcga catcgcagaa     360

gagccaaatg actttggtaa caatggtgat cgagactttt cattccacaa cgattacgcc     420

ggaattgaat ttgatgtatt tggtttaacg gaatacaaac gtgacaacgc cgacctgaca     480

cttcgcttag gaaacattgg cggctcgcct tttcagttta aaggctttca agacggagca     540

gacaaccaag gcaatgcact tattggtaac tggatgaccg actacgctac tgcagaaaac     600

ggcgctcagc tgcgttacaa cgaacgtttt gatagcggtg tgattcgcgc ttataacgtg     660
```

acgggtcaca ttactacttc aagctttggt gaggcttttc aagaagatcg cggttttaat 720
tacttgttac aaggtactct agaattcact ggcggcttca aagtcggttt gaacttctta 780
caagctaatc agggcgacca actgcgtttt gaaaatggtg ttgccagcct tgacggtctg 840
accactacca attatcgctt tggtgacggt gaaaactaca acttctctgc ttcccctagc 900
agtgagcgtg atactcacgt cggtattatg cctggccttg accaaaccac cattcaacta 960
aacttagctt atcaaccgaa tgcagatacc agcgttattt tgatggtagg ccaatcaagt 1020
gatgattaca cctttgctga taccgagggt aatgcagttg ctggtattac ttatttcggt 1080
actgatggtg tagctgaccc cgcgggtacc actttgatt caaaccgcgt gattaaaggc 1140
gaatcatctg tcgagtactg gacggtagaa gcacaacatt acgtaattcc cggcaaattc 1200
tatgtggctg cccgttatgg agaagccgaa aacacctcgg acttaattgc ccaaacagac 1260
aacacagtag agcgcttaca agttgcagcg ggttactggt tcaacgataa aaccctattg 1320
aaagtggaat acgttgatca agacgaaggc attaactctg gcggccaaat tggcgcaggg 1380
tttgacggta tcacgtcaga gatctcagtt aagttttaa 1419

<210> SEQ ID NO 52
<211> LENGTH: 472
<212> TYPE: PRT
<213> ORGANISM: Pseudoalteromonas atlantica T6c

<400> SEQUENCE: 52

Met Met Leu Lys Asn Arg Gln Thr Thr Phe Val Ser Thr Ala Ala Lys
1 5 10 15

Ser Ala Ile Asn Ala Ser Asn Ser Lys Thr Cys Asn Lys Arg Ser Ala
20 25 30

Ser Val Phe Asn Lys Leu Gly Val Val Ala Ala Ala Val Met Ala Ala
35 40 45

Ser Ile Pro Ala Gln Val Asn Ala Ala Thr Phe Leu Asp Gly Leu Val
50 55 60

Asp Val Asn Phe Leu Ala Met Gln Asn Tyr Gln Ala Ile Gln Ala Lys
65 70 75 80

Glu Gly Ala Phe Arg Pro Glu Asp Glu Glu Gln Ser Ser Gly Phe Gly
85 90 95

Arg Ile Arg Ala Asn Leu Met Phe Lys Phe His Ile Asn Asp Tyr Ile
100 105 110

Thr Ala Asp Ile Asp Ile Ala Glu Glu Pro Asn Asp Phe Gly Asn Asn
115 120 125

Gly Asp Arg Asp Phe Ser Phe His Asn Asp Tyr Ala Gly Ile Glu Phe
130 135 140

Asp Val Phe Gly Leu Thr Glu Tyr Lys Arg Asp Asn Ala Asp Leu Thr
145 150 155 160

Leu Arg Leu Gly Asn Ile Gly Gly Ser Pro Phe Gln Phe Lys Gly Phe
165 170 175

Gln Asp Gly Ala Asp Asn Gln Gly Asn Ala Leu Ile Gly Asn Trp Met
180 185 190

Thr Asp Tyr Ala Thr Ala Glu Asn Gly Ala Gln Leu Arg Tyr Asn Glu
195 200 205

Arg Phe Asp Ser Gly Val Ile Arg Ala Tyr Asn Val Thr Gly His Ile
210 215 220

Thr Thr Ser Ser Phe Gly Glu Ala Phe Gln Glu Asp Arg Gly Phe Asn
225 230 235 240

Tyr Leu Leu Gln Gly Thr Leu Glu Phe Thr Gly Gly Phe Lys Val Gly

-continued

```
                245                 250                 255

Leu Asn Phe Leu Gln Ala Asn Gln Gly Asp Gln Leu Arg Phe Glu Asn
            260                 265                 270

Gly Val Ala Ser Leu Asp Gly Leu Thr Thr Thr Asn Tyr Arg Phe Gly
        275                 280                 285

Asp Gly Glu Asn Tyr Asn Phe Ser Ala Ser Pro Ser Ser Glu Arg Asp
    290                 295                 300

Thr His Val Gly Ile Met Pro Gly Leu Asp Gln Thr Thr Ile Gln Leu
305                 310                 315                 320

Asn Leu Ala Tyr Gln Pro Asn Ala Asp Thr Ser Val Ile Leu Met Val
                325                 330                 335

Gly Gln Ser Ser Asp Asp Tyr Thr Phe Ala Asp Thr Glu Gly Asn Ala
            340                 345                 350

Val Ala Gly Ile Thr Tyr Phe Gly Thr Asp Gly Val Ala Asp Pro Ala
        355                 360                 365

Gly Thr Thr Phe Asp Ser Asn Arg Val Ile Lys Gly Glu Ser Ser Val
    370                 375                 380

Glu Tyr Trp Thr Val Glu Ala Gln His Tyr Val Ile Pro Gly Lys Phe
385                 390                 395                 400

Tyr Val Ala Ala Arg Tyr Gly Glu Ala Glu Asn Thr Ser Asp Leu Ile
                405                 410                 415

Ala Gln Thr Asp Asn Thr Val Glu Arg Leu Gln Val Ala Ala Gly Tyr
            420                 425                 430

Trp Phe Asn Asp Lys Thr Leu Leu Lys Val Glu Tyr Val Asp Gln Asp
        435                 440                 445

Glu Gly Ile Asn Ser Gly Gly Gln Ile Gly Ala Gly Phe Asp Gly Ile
    450                 455                 460

Thr Ser Glu Ile Ser Val Lys Phe
465                 470


<210> SEQ ID NO 53
<211> LENGTH: 1275
<212> TYPE: DNA
<213> ORGANISM: Pseudomonas syringae

<400> SEQUENCE: 53

atgaaacagc tgaaatctct tcttcccgcc gcgctgctca ccctgtctgc agggtttcct      60

gcgctgtcga acgcagccga tctgacgatc tcgtgcgggg ccgtcggcgc tgaattgcaa     120

ctgtgcaagg aggcagtcga tagctggtca aaacagaccg gcaacaacgt tcaggtggtt     180

tccacgccta actctgcgac cgagcgtctg tcgttctacc agcagatcct cagtgcccag     240

tccaccgaca tcgacatcat tcaaatcgac atggtgtggc cggggatgct cgccaaacac     300

ctgacggatc tgcgcgaact gcttccggcg aatgcgacac aaggctattt ccaggcccag     360

gtggacaacg ccaccgtcga cggccggctg gtgtcgatgc cctggtttac cgactcgggg     420

ctgctgtact accgcaagga tctgctcgac aagtaccaac agccggtccc ccagacctgg     480

gaggacatga ccgctaccgc ccaaaaagtg caaaaagccg agcgcgatgc cgggaacgcc     540

actatgtggg gctatgtgtt ccaggggcgc gcttatgaag gcctgacatg caacgctctg     600

gaatggatca gcagccagcc ggacggcgga ctggtcaacc cgcgcggaga catcgtggtc     660

aacagccagg cctcacgagt cgcgctgacc ctggccaaaa gctgggtcgg cgacatctcc     720

ccgcccggcg tcctcaatta caccgaggaa gaaggccgtg gcgtgttcca gtcgggaaat     780

gcactgttca tgcgcaactg gccttacgtg tgggccttgg tgcaaagcaa ggacagcgcg     840
```

-continued

```
ataaaagaca aggttggcgt agcgcccctg cccagcggcg gcgcgaacgg cacccatgct    900

tcaacgctcg gaggctgggg gctggcggtt tcgcgctaca gccgcaaccc caagctggcg    960

gcagaactgg ttgcctacct gaccagcgcc caacagcaaa aacagcgtgc cctggcaggt   1020

gcctacaacc cggtcatcga gtcgctgtat gccgaccccg agttgctcgc ggcaatgcct   1080

tactaccccc agttgcacag catcctcagc aatggggtca tgcgccccgc cgccatcacg   1140

gccaacggct acccacgcgt ctccaacgcc ttcttcgatc gggtgcatag cgtgctggcg   1200

ggcgatatac cggtcgatca ggcactggtc gaactggaac gcgaactgac ccgcatcaaa   1260

cgccggaact ggtaa                                                    1275


<210> SEQ ID NO 54
<211> LENGTH: 424
<212> TYPE: PRT
<213> ORGANISM: Pseudomonas syringae

<400> SEQUENCE: 54

Met Lys Gln Leu Lys Ser Leu Leu Pro Ala Ala Leu Leu Thr Leu Ser
1               5                   10                  15

Ala Gly Phe Pro Ala Leu Ser Asn Ala Ala Asp Leu Thr Ile Ser Cys
            20                  25                  30

Gly Ala Val Gly Ala Glu Leu Gln Leu Cys Lys Glu Ala Val Asp Ser
        35                  40                  45

Trp Ser Lys Gln Thr Gly Asn Asn Val Gln Val Val Ser Thr Pro Asn
    50                  55                  60

Ser Ala Thr Glu Arg Leu Ser Phe Tyr Gln Gln Ile Leu Ser Ala Gln
65                  70                  75                  80

Ser Thr Asp Ile Asp Ile Ile Gln Ile Asp Met Val Trp Pro Gly Met
                85                  90                  95

Leu Ala Lys His Leu Thr Asp Leu Arg Glu Leu Leu Pro Ala Asn Ala
            100                 105                 110

Thr Gln Gly Tyr Phe Gln Ala Gln Val Asp Asn Ala Thr Val Asp Gly
        115                 120                 125

Arg Leu Val Ser Met Pro Trp Phe Thr Asp Ser Gly Leu Leu Tyr Tyr
    130                 135                 140

Arg Lys Asp Leu Leu Asp Lys Tyr Gln Gln Pro Val Pro Gln Thr Trp
145                 150                 155                 160

Glu Asp Met Thr Ala Thr Ala Gln Lys Val Gln Lys Ala Glu Arg Asp
                165                 170                 175

Ala Gly Asn Ala Thr Met Trp Gly Tyr Val Phe Gln Gly Arg Ala Tyr
            180                 185                 190

Glu Gly Leu Thr Cys Asn Ala Leu Glu Trp Ile Ser Ser Gln Pro Asp
        195                 200                 205

Gly Gly Leu Val Asn Pro Arg Gly Asp Ile Val Val Asn Ser Gln Ala
    210                 215                 220

Ser Arg Val Ala Leu Thr Leu Ala Lys Ser Trp Val Gly Asp Ile Ser
225                 230                 235                 240

Pro Pro Gly Val Leu Asn Tyr Thr Glu Glu Glu Gly Arg Gly Val Phe
                245                 250                 255

Gln Ser Gly Asn Ala Leu Phe Met Arg Asn Trp Pro Tyr Val Trp Ala
            260                 265                 270

Leu Val Gln Ser Lys Asp Ser Ala Ile Lys Asp Lys Val Gly Val Ala
        275                 280                 285

Pro Leu Pro Ser Gly Gly Ala Asn Gly Thr His Ala Ser Thr Leu Gly
    290                 295                 300
```

```
Gly Trp Gly Leu Ala Val Ser Arg Tyr Ser Arg Asn Pro Lys Leu Ala
305                 310                 315                 320

Ala Glu Leu Val Ala Tyr Leu Thr Ser Ala Gln Gln Gln Lys Gln Arg
                325                 330                 335

Ala Leu Ala Gly Ala Tyr Asn Pro Val Ile Glu Ser Leu Tyr Ala Asp
            340                 345                 350

Pro Glu Leu Leu Ala Ala Met Pro Tyr Tyr Pro Gln Leu His Ser Ile
        355                 360                 365

Leu Ser Asn Gly Val Met Arg Pro Ala Ala Ile Thr Ala Asn Gly Tyr
    370                 375                 380

Pro Arg Val Ser Asn Ala Phe Phe Asp Arg Val His Ser Val Leu Ala
385                 390                 395                 400

Gly Asp Ile Pro Val Asp Gln Ala Leu Val Glu Leu Glu Arg Glu Leu
                405                 410                 415

Thr Arg Ile Lys Arg Arg Asn Trp
            420


<210> SEQ ID NO 55
<211> LENGTH: 273
<212> TYPE: DNA
<213> ORGANISM: Psychrobacter cryohalolentis K5

<400> SEQUENCE: 55

atgaataagt cagaattaat tgatagcatt gctgagaaaa gtggtctaaa taaaactcaa     60

gctggcgatg cattgaacgc agttatggaa agcgttggcg aagctctaga agctggcgat    120

agcatttcac tagttggttt tggtactttt agcgtaaaag accgtaaagc acgtactggc    180

cgtaacccta agactggtga agagctaagt atcccagcca gcaaagtacc aagctttaaa    240

gctggtaaaa acctaaaaga acgcttgaac tag                                 273


<210> SEQ ID NO 56
<211> LENGTH: 90
<212> TYPE: PRT
<213> ORGANISM: Psychrobacter cryohalolentis K5

<400> SEQUENCE: 56

Met Asn Lys Ser Glu Leu Ile Asp Ser Ile Ala Glu Lys Ser Gly Leu
1               5                   10                  15

Asn Lys Thr Gln Ala Gly Asp Ala Leu Asn Ala Val Met Glu Ser Val
            20                  25                  30

Gly Glu Ala Leu Glu Ala Gly Asp Ser Ile Ser Leu Val Gly Phe Gly
        35                  40                  45

Thr Phe Ser Val Lys Asp Arg Lys Ala Arg Thr Gly Arg Asn Pro Lys
    50                  55                  60

Thr Gly Glu Glu Leu Ser Ile Pro Ala Ser Lys Val Pro Ser Phe Lys
65                  70                  75                  80

Ala Gly Lys Asn Leu Lys Glu Arg Leu Asn
                85                  90


<210> SEQ ID NO 57
<211> LENGTH: 756
<212> TYPE: DNA
<213> ORGANISM: Rhodoferax ferrireducens DSM 15236

<400> SEQUENCE: 57

atgcgtgaac ctctctatgc ccagatcgct cgtgagctcg cacagggcat cgcttcagga     60

aagtttcctg agggctcctt gctgtcatcc gaatttgact tatgcaatca gtaccaggcc    120
```

```
agccgacaaa ccgttcgcgc agcgctgcgg gagttgatgg atcttgggtt ggtgtcgcgc    180

cgcaaaggtg ttggtacccg agtcgaggcg cggacgaaag cgcagggcta cgatcattcc    240

ttgggatcgc tggacgacct ggtgcaactt gcgatgacaa accctcgcgt tgtgaagcgg    300

accaatgagg ttgtggctga ccgcgaactg gcaaaggcta ttggttgtgc gcctgggtca    360

cgctggctgc atatcgccag catccgccaa gacagcgata agagcgctcc gccggtttgc    420

tggaccgata cctatgtcaa taccgcctac tcggatttga gccagcttgt gcgccaggat    480

ccgactccct tgatcagcga attgatcgaa aaacactatg gtcggcgcag cgccgaggtg    540

catcagacca tttcagctgt caccatttcc cctcttctgg ctgaagagtt acaggttgaa    600

ccggggtcgc cggcgttacg tatcgtgcgg cgctacatcg accgcgtggg cgaaaccatc    660

gaaacaacca tatccgttca tccagcagag cggtacacgt tctcaatggt attgaagcgc    720

tcaagcatcg ggcaagacgc caatctaacg acgtag                              756
```

<210> SEQ ID NO 58
<211> LENGTH: 251
<212> TYPE: PRT
<213> ORGANISM: Rhodoferax ferrireducens DSM 15236

<400> SEQUENCE: 58

```
Met Arg Glu Pro Leu Tyr Ala Gln Ile Ala Arg Glu Leu Ala Gln Gly
1               5                   10                  15

Ile Ala Ser Gly Lys Phe Pro Glu Gly Ser Leu Leu Ser Ser Glu Phe
            20                  25                  30

Asp Leu Cys Asn Gln Tyr Gln Ala Ser Arg Gln Thr Val Arg Ala Ala
        35                  40                  45

Leu Arg Glu Leu Met Asp Leu Gly Leu Val Ser Arg Arg Lys Gly Val
    50                  55                  60

Gly Thr Arg Val Glu Ala Arg Thr Lys Ala Gln Gly Tyr Asp His Ser
65                  70                  75                  80

Leu Gly Ser Leu Asp Asp Leu Val Gln Leu Ala Met Thr Asn Pro Arg
                85                  90                  95

Val Val Lys Arg Thr Asn Glu Val Val Ala Asp Arg Glu Leu Ala Lys
            100                 105                 110

Ala Ile Gly Cys Ala Pro Gly Ser Arg Trp Leu His Ile Ala Ser Ile
        115                 120                 125

Arg Gln Asp Ser Asp Lys Ser Ala Pro Pro Val Cys Trp Thr Asp Thr
    130                 135                 140

Tyr Val Asn Thr Ala Tyr Ser Asp Leu Ser Gln Leu Val Arg Gln Asp
145                 150                 155                 160

Pro Thr Pro Leu Ile Ser Glu Leu Ile Glu Lys His Tyr Gly Arg Arg
                165                 170                 175

Ser Ala Glu Val His Gln Thr Ile Ser Ala Val Thr Ile Ser Pro Leu
            180                 185                 190

Leu Ala Glu Glu Leu Gln Val Glu Pro Gly Ser Pro Ala Leu Arg Ile
        195                 200                 205

Val Arg Arg Tyr Ile Asp Arg Val Gly Glu Thr Ile Glu Thr Thr Ile
    210                 215                 220

Ser Val His Pro Ala Glu Arg Tyr Thr Phe Ser Met Val Leu Lys Arg
225                 230                 235                 240

Ser Ser Ile Gly Gln Asp Ala Asn Leu Thr Thr
                245                 250
```

<210> SEQ ID NO 59
<211> LENGTH: 843
<212> TYPE: DNA
<213> ORGANISM: Rhodoferax ferrireducens DSM 15236

<400> SEQUENCE: 59
atgaaatttc gacttttagc tttggcggca ctgtccgcga tcactgcatt gacgggtgct 60
tcagtcaatg ccgcaggtac gagcaaactc gatcaggtct tggcgcgagg taagctcatt 120
gtggggacgg gaagcacgaa tgcaccgtgg catttcaaaa gcgccgataa caaattgcag 180
gggtttgaca tcgatatcgc gaagatcatc tccaaggcgt tgtttgacaa tccggacaag 240
attgaatttg tcaaccaatc gtcggatgcc cgtattccga acatcaccac cgacaaggtt 300
gatatcacct gccagtttct gacggtcact ggcgggcgtg cacagcaagt cgcattcact 360
attccctatt ttcgggaggg cgtgggcctg atgacaaaga cagggagcaa acgtggcgat 420
tacgcggcgt tgaaggcggc gggggcttcg gttaatgtgg ctgtgctaca gaacgtctac 480
gctgagagca tggtgcatgc cgcattgccc atggctaagg tcgctcaata cgactcccca 540
gacctgatgt atcaagcctt gaattcgggt cgcgccgatg ccgcagcgac tgaccagtcg 600
tccatctctt ggttcatcaa gcagaaccca ggtaaatata aggatgccgg gtatgggtgg 660
aaccctcaga cttatgcgtg tgcggtgaag cgcggcgatc aggattggct aaatttcgtc 720
aatacagcgc tgcatgaggc catgacgggg gtggagttcg atgcctatgc tgcgtcctac 780
aagacctggt ttggtgttga tctcgcgccg ccaaagatcg gttttccggt tgagtataaa 840
tag 843

<210> SEQ ID NO 60
<211> LENGTH: 280
<212> TYPE: PRT
<213> ORGANISM: Rhodoferax ferrireducens DSM 15236

<400> SEQUENCE: 60

Met Lys Phe Arg Leu Leu Ala Leu Ala Ala Leu Ser Ala Ile Thr Ala
1 5 10 15

Leu Thr Gly Ala Ser Val Asn Ala Ala Gly Thr Ser Lys Leu Asp Gln
20 25 30

Val Leu Ala Arg Gly Lys Leu Ile Val Gly Thr Gly Ser Thr Asn Ala
35 40 45

Pro Trp His Phe Lys Ser Ala Asp Asn Lys Leu Gln Gly Phe Asp Ile
50 55 60

Asp Ile Ala Lys Ile Ile Ser Lys Ala Leu Phe Asp Asn Pro Asp Lys
65 70 75 80

Ile Glu Phe Val Asn Gln Ser Ser Asp Ala Arg Ile Pro Asn Ile Thr
85 90 95

Thr Asp Lys Val Asp Ile Thr Cys Gln Phe Leu Thr Val Thr Gly Gly
100 105 110

Arg Ala Gln Gln Val Ala Phe Thr Ile Pro Tyr Phe Arg Glu Gly Val
115 120 125

Gly Leu Met Thr Lys Thr Gly Ser Lys Arg Gly Asp Tyr Ala Ala Leu
130 135 140

Lys Ala Ala Gly Ala Ser Val Asn Val Ala Val Leu Gln Asn Val Tyr
145 150 155 160

Ala Glu Ser Met Val His Ala Ala Leu Pro Met Ala Lys Val Ala Gln
165 170 175

Tyr Asp Ser Pro Asp Leu Met Tyr Gln Ala Leu Asn Ser Gly Arg Ala
180 185 190

```
Asp Ala Ala Ala Thr Asp Gln Ser Ser Ile Ser Trp Phe Ile Lys Gln
        195                 200                 205

Asn Pro Gly Lys Tyr Lys Asp Ala Gly Tyr Gly Trp Asn Pro Gln Thr
    210                 215                 220

Tyr Ala Cys Ala Val Lys Arg Gly Asp Gln Asp Trp Leu Asn Phe Val
225                 230                 235                 240

Asn Thr Ala Leu His Glu Ala Met Thr Gly Val Glu Phe Asp Ala Tyr
                245                 250                 255

Ala Ala Ser Tyr Lys Thr Trp Phe Gly Val Asp Leu Ala Pro Pro Lys
            260                 265                 270

Ile Gly Phe Pro Val Glu Tyr Lys
        275                 280


<210> SEQ ID NO 61
<211> LENGTH: 252
<212> TYPE: DNA
<213> ORGANISM: Rhodoferax ferrireducens DSM 15236

<400> SEQUENCE: 61

atgtctgaaa caaccgtttt catcgcctcc aatctgattg gattggtttc aattgctatc      60

tcgtcctttg tgatttttca ccatgtacgg ggcgggcagc gagaggttga gttttatacg     120

aaagagcacg tggaaaagct gggtaccacg cctgattttt tcgccaaggt gtccgcatgg     180

aacgctgcac tcggtggccc agcgcctaaa tggcactgga tcaaacctgt ttcaccattc     240

cagtcgaagt ga                                                         252


<210> SEQ ID NO 62
<211> LENGTH: 83
<212> TYPE: PRT
<213> ORGANISM: Rhodoferax ferrireducens DSM 15236

<400> SEQUENCE: 62

Met Ser Glu Thr Thr Val Phe Ile Ala Ser Asn Leu Ile Gly Leu Val
1               5                   10                  15

Ser Ile Ala Ile Ser Ser Phe Val Ile Phe His His Val Arg Gly Gly
            20                  25                  30

Gln Arg Glu Val Glu Phe Tyr Thr Lys Glu His Val Glu Lys Leu Gly
        35                  40                  45

Thr Thr Pro Asp Phe Phe Ala Lys Val Ser Ala Trp Asn Ala Ala Leu
    50                  55                  60

Gly Gly Pro Ala Pro Lys Trp His Trp Ile Lys Pro Val Ser Pro Phe
65                  70                  75                  80

Gln Ser Lys


<210> SEQ ID NO 63
<211> LENGTH: 279
<212> TYPE: DNA
<213> ORGANISM: Rhodoferax ferrireducens DSM 15236

<400> SEQUENCE: 63

atgagaacca tcattttcgg cctgtgcgcc atagccattg cgctgattgc cggggtggcg      60

actccggcag agctatctgc tatcgctgaa gtgaaccagg ccaaggttct tactggaaat     120

gaggctcttg ggcgctcaa gcgggaggct acgccagtag cgctgggcca gattatcaag     180

gaccctggtg gatgcctcta cgccgttgtg tcgaagaata agcgcctgac gctgatccaa     240

gtgcgtgaca aagcaaaacg ccaggtgtgc ggcaactaa                            279
```

<210> SEQ ID NO 64
<211> LENGTH: 92
<212> TYPE: PRT
<213> ORGANISM: Rhodoferax ferrireducens DSM 15236

<400> SEQUENCE: 64

```
Met Arg Thr Ile Ile Phe Gly Leu Cys Ala Ile Ala Ile Ala Leu Ile
1               5                   10                  15

Ala Gly Val Ala Thr Pro Ala Glu Leu Ser Ala Ile Ala Glu Val Asn
            20                  25                  30

Gln Ala Lys Val Leu Thr Gly Asn Glu Ala Leu Gly Ala Leu Lys Arg
        35                  40                  45

Glu Ala Thr Pro Val Ala Leu Gly Gln Ile Ile Lys Asp Pro Gly Gly
    50                  55                  60

Cys Leu Tyr Ala Val Val Ser Lys Asn Lys Arg Leu Thr Leu Ile Gln
65                  70                  75                  80

Val Arg Asp Lys Ala Lys Arg Gln Val Cys Gly Asn
                85                  90
```

<210> SEQ ID NO 65
<211> LENGTH: 948
<212> TYPE: DNA
<213> ORGANISM: Rhodoferax ferrireducens DSM 15236

<400> SEQUENCE: 65

```
atgaaaaacc cttgggcttc cccgcaaaga aaaaaccgtc cgagtcttct cctgtcgttg      60

ggcttgagtc tggtcctcgc cgttcccagt gcgaatgccg gcttcattac caggacattg     120

accagagtgg ctgccgcggc ggccattacg tccgtcgccc acgcctatgc gaagaacaag     180

cgatcttctg accgcgaggc cgatgcccct cgcggtcaga ccaccggtga ccgcgcatcg     240

tgcacagatc agcttcctat gggcaaggcg cctacgttct ccaacccaaa gctgggcgaa     300

aacactcacc aggtttgcta ccaggagtac acggtgctgg tgtcggggaa gacgttgact     360

cccttgtggt cggcggaata catgaccaaa cagcgcgtcc tggccgcgcg tcgaatgaag     420

cgggtaaatt ccttccatga agaggactcc gttcccattg cggcacgcgc ccgtctggca     480

gacttcgttg gcgcaaaaaa tattgaccgc gggcacctcg cccctagtgg agatatgaca     540

agtccaggcg cccagtatga gagtttttca ttgggaaaca tgatcgcgca gaactcaagc     600

aataaccgcc atgtctggga agggatcgag tccggtacca gaaattttgc agtgagcaac     660

ggcaaggtct acgtgatcac cggacctctg ttcatcgggc agaacatcag gttcatgaac     720

aatcgggtgg cgatcccgac gcaaatcttc aagctgctgt acaaccccgt gaaccagacc     780

ggtggcgtgt atgttgtcga caatgttgat actgaaacaa ttggctggaa gtccattgcc     840

cagttcgagc aattcagtgg ctaccgtttt aacctgggtg cgccggcctt gatggccatg     900

cctcagcctc aacaacactt tgaaagatca aaatatgcca aaaactag                 948
```

<210> SEQ ID NO 66
<211> LENGTH: 315
<212> TYPE: PRT
<213> ORGANISM: Rhodoferax ferrireducens DSM 15236

<400> SEQUENCE: 66

```
Met Lys Asn Pro Trp Ala Ser Pro Gln Arg Lys Asn Arg Pro Ser Leu
1               5                   10                  15

Leu Leu Ser Leu Gly Leu Ser Leu Val Leu Ala Val Pro Ser Ala Asn
            20                  25                  30
```

-continued

```
Ala Gly Phe Ile Thr Arg Thr Leu Thr Arg Val Ala Ala Ala Ala Ala
        35                  40                  45

Ile Thr Ser Val Ala His Ala Tyr Ala Lys Asn Lys Arg Ser Ser Asp
    50                  55                  60

Arg Glu Ala Asp Ala Pro Arg Gly Gln Thr Thr Gly Asp Arg Ala Ser
65                  70                  75                  80

Cys Thr Asp Gln Leu Pro Met Gly Lys Ala Pro Thr Phe Ser Asn Pro
                85                  90                  95

Lys Leu Gly Glu Asn Thr His Gln Val Cys Tyr Gln Glu Tyr Thr Val
            100                 105                 110

Leu Val Ser Gly Lys Thr Leu Thr Pro Leu Trp Ser Ala Glu Tyr Met
        115                 120                 125

Thr Lys Gln Arg Val Leu Ala Ala Arg Arg Met Lys Arg Val Asn Ser
    130                 135                 140

Phe His Glu Glu Asp Ser Val Pro Ile Ala Ala Arg Ala Arg Leu Ala
145                 150                 155                 160

Asp Phe Val Gly Ala Lys Asn Ile Asp Arg Gly His Leu Ala Pro Ser
                165                 170                 175

Gly Asp Met Thr Ser Pro Gly Ala Gln Tyr Glu Ser Phe Ser Leu Gly
            180                 185                 190

Asn Met Ile Ala Gln Asn Ser Ser Asn Asn Arg His Val Trp Glu Gly
        195                 200                 205

Ile Glu Ser Gly Thr Arg Asn Phe Ala Val Ser Asn Gly Lys Val Tyr
    210                 215                 220

Val Ile Thr Gly Pro Leu Phe Ile Gly Gln Asn Ile Arg Phe Met Asn
225                 230                 235                 240

Asn Arg Val Ala Ile Pro Thr Gln Ile Phe Lys Leu Leu Tyr Asn Pro
                245                 250                 255

Val Asn Gln Thr Gly Gly Val Tyr Val Val Asp Asn Val Asp Thr Glu
            260                 265                 270

Thr Ile Gly Trp Lys Ser Ile Ala Gln Phe Glu Gln Phe Ser Gly Tyr
        275                 280                 285

Arg Phe Asn Leu Gly Ala Pro Ala Leu Met Ala Met Pro Gln Pro Gln
    290                 295                 300

Gln His Phe Glu Arg Ser Lys Tyr Ala Lys Asn
305                 310                 315
```

<210> SEQ ID NO 67
<211> LENGTH: 513
<212> TYPE: DNA
<213> ORGANISM: Rubrobacter xylanophilus DSM 9941

<400> SEQUENCE: 67

```
ttgaggaagg tagtgttgtt ggcggccatg ctggccatgg cgctgttcgc cgccgccccg     60

gtgctggcgc aggccaacgc ggtgggtggg gacgtacaga tccaggacca ggactgcgcc    120

caggtgatct cggtgctcgg ccagcaggcc cagtacggtg acgccggcgc cgtctccggc    180

gacatcggca gcgccgccgc cgcggacata gcccaggagc tcgggatctc ggtcgacgcg    240

gtgcagaact gcctgcaggc cggcgacgac ataaacctgg agcagggcgg caccgtggtt    300

gtccatccgg gacacgacga cggcggcgac gtccacggtg acgacaacgg cggcacgtcc    360

tccgaggatg gcgcgaccgc atcggccagc gcctccgccg ctgccgccac cggcggcgtt    420

ttgcccgaga cgggcggcgc ctcgctgatc gcgctcggcg ccggcgccct gctggtggcc    480

ggcggtctgc tcgctcgccg gatcatccgc tag                                 513
```

<210> SEQ ID NO 68
<211> LENGTH: 170
<212> TYPE: PRT
<213> ORGANISM: Rubrobacter xylanophilus DSM 9941

<400> SEQUENCE: 68

```
Leu Arg Lys Val Val Leu Leu Ala Ala Met Leu Ala Met Ala Leu Phe
1               5                   10                  15

Ala Ala Ala Pro Val Leu Ala Gln Ala Asn Ala Val Gly Gly Asp Val
            20                  25                  30

Gln Ile Gln Asp Gln Asp Cys Ala Gln Val Ile Ser Val Leu Gly Gln
        35                  40                  45

Gln Ala Gln Tyr Gly Asp Ala Gly Ala Val Ser Gly Asp Ile Gly Ser
    50                  55                  60

Ala Ala Ala Ala Asp Ile Ala Gln Glu Leu Gly Ile Ser Val Asp Ala
65                  70                  75                  80

Val Gln Asn Cys Leu Gln Ala Gly Asp Asp Ile Asn Leu Glu Gln Gly
                85                  90                  95

Gly Thr Val Val Val His Pro Gly His Asp Asp Gly Gly Asp Val His
            100                 105                 110

Gly Asp Asp Asn Gly Gly Thr Ser Ser Glu Asp Gly Ala Thr Ala Ser
        115                 120                 125

Ala Ser Ala Ser Ala Ala Ala Ala Thr Gly Gly Val Leu Pro Glu Thr
    130                 135                 140

Gly Gly Ala Ser Leu Ile Ala Leu Gly Ala Gly Ala Leu Leu Val Ala
145                 150                 155                 160

Gly Gly Leu Leu Ala Arg Arg Ile Ile Arg
                165                 170
```

<210> SEQ ID NO 69
<211> LENGTH: 1332
<212> TYPE: DNA
<213> ORGANISM: Shewanella denitrificans OS217

<400> SEQUENCE: 69

```
atgccgcaaa agcagtcttc agccaaagag gtcgtcactc acacaataga gataagtata     60

ataatgaata aatttaacaa gacactcctc gctactgcca tcacattagc cagcactcaa    120

gcaatgtcag ccggctttca gttaaacagt caatctgcca ccggtatcgg ccgtgctatg    180

gccggtgacg ctatcattgc tgacaacgct tcagtacttt cacgtaaccc tgctgctatg    240

gcattgtttg acaaaaaagc actatctgta gggttaacct ttgctgatat cgacgttaat    300

gtcgatgatg ttaccaagac agttcccggc cttgggacag taaactttgg tgatgtgcac    360

ggcgccgctg acagcaagat cattccaaac ttttactaca tcaatcctat cgacgacaag    420

tttgccattg gcttcgccgc ttttagtaat tatggcactg gcactgactt aaccccgtta    480

gccaatgctg gcgtcaacac gcctgtaggt tttatgcctg ctcctgtgga tctactgggt    540

aacactgaag tgcttactgt taatttcaac accagtatga gctatcgtgt taatgaagaa    600

ttcagctttg gctttggcat agatgccatt tacgccgaag gcaccttaac ccgtaaaggc    660

agcgtacctg tggctaatgt gggtgtagtg cctgtgaccc ttgtggatgt tgatgccgat    720

ggttgggcct ttggtgctat tttaggtatg agctatgaag ttaatgcgga tcacagattt    780

ggtttaagct atcgctttag cccaacctta agcgcaaaag gtgatatcag ttttaatcgt    840

caagactacg ctaagattga tatccctatg gctgatattg ctcagttcgc cggtttccat    900

cagttgaccg acaccttcgc ggtgcactac acggctcagt ggactagctg gagcgacttt    960
```

```
gaccatatca cagtcaaaaa taaccccgtt cagcaacacc taaaaacata ccactggcag   1020

gattcttggt tcttgagctt aggggcaact tataatatca gccaagactt aacggctcgt   1080

gtgggtgtgg ctagcgatca aggcgtcgtt gatcaattgt cttcattgtc tattcctgat   1140

tctgaccgtc actggtacac cactggactg agctatcagt taaatgaaca atcgagtgtc   1200

gacttgggcg tggcttatgt acgcggcgag aatgtcactg tgaaagaaaa cagtgcgatc   1260

ttaggcgaga ttacagcgca cacccgctct aacggtactt actactcagt gcagtacaac   1320

tacagtttct aa                                                       1332


<210> SEQ ID NO 70
<211> LENGTH: 443
<212> TYPE: PRT
<213> ORGANISM: Shewanella denitrificans OS217

<400> SEQUENCE: 70

Met Pro Gln Lys Gln Ser Ser Ala Lys Glu Val Val Thr His Thr Ile
1               5                   10                  15

Glu Ile Ser Ile Ile Met Asn Lys Phe Asn Lys Thr Leu Leu Ala Thr
            20                  25                  30

Ala Ile Thr Leu Ala Ser Thr Gln Ala Met Ser Ala Gly Phe Gln Leu
        35                  40                  45

Asn Ser Gln Ser Ala Thr Gly Ile Gly Arg Ala Met Ala Gly Asp Ala
    50                  55                  60

Ile Ile Ala Asp Asn Ala Ser Val Leu Ser Arg Asn Pro Ala Ala Met
65                  70                  75                  80

Ala Leu Phe Asp Lys Lys Ala Leu Ser Val Gly Leu Thr Phe Ala Asp
                85                  90                  95

Ile Asp Val Asn Val Asp Asp Val Thr Lys Thr Val Pro Gly Leu Gly
            100                 105                 110

Thr Val Asn Phe Gly Asp Val His Gly Ala Ala Asp Ser Lys Ile Ile
        115                 120                 125

Pro Asn Phe Tyr Tyr Ile Asn Pro Ile Asp Asp Lys Phe Ala Ile Gly
    130                 135                 140

Phe Ala Ala Phe Ser Asn Tyr Gly Thr Gly Thr Asp Leu Thr Pro Leu
145                 150                 155                 160

Ala Asn Ala Gly Val Asn Thr Pro Val Gly Phe Met Pro Ala Pro Val
                165                 170                 175

Asp Leu Leu Gly Asn Thr Glu Val Leu Thr Val Asn Phe Asn Thr Ser
            180                 185                 190

Met Ser Tyr Arg Val Asn Glu Glu Phe Ser Phe Gly Phe Gly Ile Asp
        195                 200                 205

Ala Ile Tyr Ala Glu Gly Thr Leu Thr Arg Lys Gly Ser Val Pro Val
    210                 215                 220

Ala Asn Val Gly Val Val Pro Val Thr Leu Val Asp Val Asp Ala Asp
225                 230                 235                 240

Gly Trp Ala Phe Gly Ala Ile Leu Gly Met Ser Tyr Glu Val Asn Ala
                245                 250                 255

Asp His Arg Phe Gly Leu Ser Tyr Arg Phe Ser Pro Thr Leu Ser Ala
            260                 265                 270

Lys Gly Asp Ile Ser Phe Asn Arg Gln Asp Tyr Ala Lys Ile Asp Ile
        275                 280                 285

Pro Met Ala Asp Ile Ala Gln Phe Ala Gly Phe His Gln Leu Thr Asp
    290                 295                 300
```

```
Thr Phe Ala Val His Tyr Thr Ala Gln Trp Thr Ser Trp Ser Asp Phe
305                 310                 315                 320

Asp His Ile Thr Val Lys Asn Asn Pro Val Gln Gln His Leu Lys Thr
                325                 330                 335

Tyr His Trp Gln Asp Ser Trp Phe Leu Ser Leu Gly Ala Thr Tyr Asn
            340                 345                 350

Ile Ser Gln Asp Leu Thr Ala Arg Val Gly Val Ala Ser Asp Gln Gly
        355                 360                 365

Val Val Asp Gln Leu Ser Ser Leu Ser Ile Pro Asp Ser Asp Arg His
    370                 375                 380

Trp Tyr Thr Thr Gly Leu Ser Tyr Gln Leu Asn Glu Gln Ser Ser Val
385                 390                 395                 400

Asp Leu Gly Val Ala Tyr Val Arg Gly Glu Asn Val Thr Val Lys Glu
                405                 410                 415

Asn Ser Ala Ile Leu Gly Glu Ile Thr Ala His Thr Arg Ser Asn Gly
            420                 425                 430

Thr Tyr Tyr Ser Val Gln Tyr Asn Tyr Ser Phe
        435                 440
```

<210> SEQ ID NO 71
<211> LENGTH: 840
<212> TYPE: DNA
<213> ORGANISM: Shewanella frigidimarina NCMB400

<400> SEQUENCE: 71

```
atgaaaaatg taaaaatgtt agctttagcg ggtgcaacag tcgctgctat ttctggtaat      60

gctttcgctg cagatcgtac cgatcttcac gctactgatt acaaatggtt gcagtttaat     120

gctatgtact ctattggcga aaagccagat aacccagctt ctggtgatca acataactac     180

ttagaaatgg agtttggtgg tcgttctggt gttgttgatc tttatggtta tgttgatgtg     240

ttcaacttag caaatgaatc tactgacaat ggtgacaaaa atcctggttc aggcactagt     300

aaattgttca tgaaatttgc tccacgtttc tctatcgatg cgattactgg taaagattta     360

tcttttggtc caatccaaga agtatatttc tcaaccttgt tcaactggga tggtcttaac     420

ggcgaaggcg ttaactctac attctggggt gttggtgctg atgtaaacgt accttggtta     480

ggcaaaactg gtatgaacct ttatggttac tacgacatga acgctaaaga gtggaacgga     540

tatcagttct cagctaactg gttcaagcct ttctacttct tcgacaacaa gagcttctta     600

tcattccaag gttatatcga ttaccaattt ggtgctgatg aagacgacaa catgttcgtt     660

cctaagactt caagcggtgg taacatcttc tttggtctat actggcactc agatcgttac     720

gcgcttggtt atggcttaaa aggcttcaaa gacgtatacc tacttgaaga tgaaggcggt     780

ttggttggcc tagaatctac tggttggtca cattacctat ctgcaactta caagttctaa     840
```

<210> SEQ ID NO 72
<211> LENGTH: 279
<212> TYPE: PRT
<213> ORGANISM: Shewanella frigidimarina NCMB400

<400> SEQUENCE: 72

```
Met Lys Asn Val Lys Met Leu Ala Leu Ala Gly Ala Thr Val Ala Ala
1               5                   10                  15

Ile Ser Gly Asn Ala Phe Ala Ala Asp Arg Thr Asp Leu His Ala Thr
            20                  25                  30

Asp Tyr Lys Trp Leu Gln Phe Asn Ala Met Tyr Ser Ile Gly Glu Lys
        35                  40                  45
```

```
Pro Asp Asn Pro Ala Ser Gly Asp Gln His Asn Tyr Leu Glu Met Glu
    50                  55                  60

Phe Gly Gly Arg Ser Gly Val Val Asp Leu Tyr Gly Tyr Val Asp Val
65                  70                  75                  80

Phe Asn Leu Ala Asn Glu Ser Thr Asp Asn Gly Asp Lys Asn Pro Gly
                85                  90                  95

Ser Gly Thr Ser Lys Leu Phe Met Lys Phe Ala Pro Arg Phe Ser Ile
            100                 105                 110

Asp Ala Ile Thr Gly Lys Asp Leu Ser Phe Gly Pro Ile Gln Glu Val
        115                 120                 125

Tyr Phe Ser Thr Leu Phe Asn Trp Asp Gly Leu Asn Gly Glu Gly Val
    130                 135                 140

Asn Ser Thr Phe Trp Gly Val Gly Ala Asp Val Asn Val Pro Trp Leu
145                 150                 155                 160

Gly Lys Thr Gly Met Asn Leu Tyr Gly Tyr Tyr Asp Met Asn Ala Lys
                165                 170                 175

Glu Trp Asn Gly Tyr Gln Phe Ser Ala Asn Trp Phe Lys Pro Phe Tyr
            180                 185                 190

Phe Phe Asp Asn Lys Ser Phe Leu Ser Phe Gln Gly Tyr Ile Asp Tyr
        195                 200                 205

Gln Phe Gly Ala Asp Glu Asp Asp Asn Met Phe Val Pro Lys Thr Ser
    210                 215                 220

Ser Gly Gly Asn Ile Phe Phe Gly Leu Tyr Trp His Ser Asp Arg Tyr
225                 230                 235                 240

Ala Leu Gly Tyr Gly Leu Lys Gly Phe Lys Asp Val Tyr Leu Leu Glu
                245                 250                 255

Asp Glu Gly Gly Leu Val Gly Leu Glu Ser Thr Gly Trp Ser His Tyr
            260                 265                 270

Leu Ser Ala Thr Tyr Lys Phe
        275
```

<210> SEQ ID NO 73
<211> LENGTH: 1659
<212> TYPE: DNA
<213> ORGANISM: Shewanella frigidimarina NCMB400

<400> SEQUENCE: 73

```
atgaaacgat tgtttccttt ttgcgccatt gccttactgt cagcatgtaa cggcgatgat      60

gctaaacaca ctgcaaccga cgatattatt ccggctaaag tgactgcggt aacctttgat     120

gaacaacgct ttagaactga tatcgaaaca ttatcgtcag ataaatttga aggtcgcgcg     180

ccgacaaccc aaggcgaaaa gcttacccta gaatatttgt ctgccgcctt cacccaaatg     240

gggcttaaag gcgcttataa aggaagtttt ttgcaaccgg ttccaatggt gagctacacc     300

gcaagcgagc aacaacaagt tactttagct gggatggatt tacagtatcg ccaagatatc     360

gtgttaggca gtcgtcacga tagcaatcaa gtgagtatta aagatgcgcc attagtgttt     420

gttggttacg gtattaatgc acctgaatat ggctggaatg attaccaaga cctcaacatg     480

aaaggcaaaa ttgccatcat tttggtcaac gatccaggct ttgcacatcc tgaaggtgcc     540

aagttcaatg gtaaggcgat gacttactat ggtcgttgga gctataagtt tgaagaagcc     600

agtcgccaag gcgcgttagg cgcaattatc attcatgata cagaaccggc ctcttaccct     660

tggtcggtag ttgaaaacag ctggactggt gctcaacaag atttagttca aagcaaagca     720

gaacaagatc agcgggtcca agttgaaggt tggttaacct tagacagtgc tacagcctta     780

ttcgataaag cgggcctgtc attaacgtca ttaatggatc gcgccgcaac caattcactc     840
```

```
aatgtcgatt tggcccaaac agccagcatt gaatttgcca ataaagccga atatgccgac    900

agttataatg tggttgcaac attagctggc agcaaacaag ctgatgagca gattttattt    960

actgcccatt gggatcatat cggtacagat gacactaaag acggcgacca aatttataat   1020

ggcgcgttag ataatgccac tggtaccgcc ggtattttag aaattgcccg tcagtttgcc   1080

cagcaagcta aacaagggca tggcttagcc cgttcattaa cctttattgc tactactggt   1140

gaagaacaag gcttattagg ttcacgttat tatgccgcta acccaattta tccaattgat   1200

aaaaccgtgg cagtatttaa cctcgacagc actaatattt atggcaaaac caaagattac   1260

acgattgtcg gtaaaggcca gtctgagtta gaaaactatt tagaccgcgc tgtcgctaaa   1320

caaaatcgca ccagccaagg cgagctaaac cctgcatcgg gcggtttttt ccgttcagac   1380

cacttcagct ttgctaaatt aggcgtgcca gcagtatttg ccggtggtgg taacgaacca   1440

cttgatgaag ctaccgcaca atacaaaacg gcaatgttgg tcaaaatgaa gggctgttac   1500

cataacgttt gcgatcatta tcgtcctgaa tgggatttat ccggttcatt acaagattta   1560

ggcgtgtact accaagccgc tgctgagtta ggtaataatc aagattggcc aggatacttt   1620

gccggttctg aatttaatca attacgtcct gcagattag                          1659
```

<210> SEQ ID NO 74
<211> LENGTH: 552
<212> TYPE: PRT
<213> ORGANISM: Shewanella frigidimarina NCMB400

<400> SEQUENCE: 74

```
Met Lys Arg Leu Phe Pro Phe Cys Ala Ile Ala Leu Leu Ser Ala Cys
1               5                   10                  15

Asn Gly Asp Asp Ala Lys His Thr Ala Thr Asp Asp Ile Ile Pro Ala
            20                  25                  30

Lys Val Thr Ala Val Thr Phe Asp Glu Gln Arg Phe Arg Thr Asp Ile
        35                  40                  45

Glu Thr Leu Ser Ser Asp Lys Phe Glu Gly Arg Ala Pro Thr Thr Gln
    50                  55                  60

Gly Glu Lys Leu Thr Leu Glu Tyr Leu Ser Ala Ala Phe Thr Gln Met
65                  70                  75                  80

Gly Leu Lys Gly Ala Tyr Lys Gly Ser Phe Leu Gln Pro Val Pro Met
                85                  90                  95

Val Ser Tyr Thr Ala Ser Glu Gln Gln Gln Val Thr Leu Ala Gly Met
            100                 105                 110

Asp Leu Gln Tyr Arg Gln Asp Ile Val Leu Gly Ser Arg His Asp Ser
        115                 120                 125

Asn Gln Val Ser Ile Lys Asp Ala Pro Leu Val Phe Val Gly Tyr Gly
    130                 135                 140

Ile Asn Ala Pro Glu Tyr Gly Trp Asn Asp Tyr Gln Asp Leu Asn Met
145                 150                 155                 160

Lys Gly Lys Ile Ala Ile Ile Leu Val Asn Asp Pro Gly Phe Ala His
                165                 170                 175

Pro Glu Gly Ala Lys Phe Asn Gly Lys Ala Met Thr Tyr Tyr Gly Arg
            180                 185                 190

Trp Ser Tyr Lys Phe Glu Glu Ala Ser Arg Gln Gly Ala Leu Gly Ala
        195                 200                 205

Ile Ile Ile His Asp Thr Glu Pro Ala Ser Tyr Pro Trp Ser Val Val
    210                 215                 220

Glu Asn Ser Trp Thr Gly Ala Gln Gln Asp Leu Val Gln Ser Lys Ala
```

```
225                 230                 235                 240

Glu Gln Asp Gln Arg Val Gln Val Glu Gly Trp Leu Thr Leu Asp Ser
                245                 250                 255

Ala Thr Ala Leu Phe Asp Lys Ala Gly Leu Ser Leu Thr Ser Leu Met
            260                 265                 270

Asp Arg Ala Ala Thr Asn Ser Leu Asn Val Asp Leu Ala Gln Thr Ala
        275                 280                 285

Ser Ile Glu Phe Ala Asn Lys Ala Glu Tyr Ala Asp Ser Tyr Asn Val
    290                 295                 300

Val Ala Thr Leu Ala Gly Ser Lys Gln Ala Asp Glu Gln Ile Leu Phe
305                 310                 315                 320

Thr Ala His Trp Asp His Ile Gly Thr Asp Asp Thr Lys Asp Gly Asp
                325                 330                 335

Gln Ile Tyr Asn Gly Ala Leu Asp Asn Ala Thr Gly Thr Ala Gly Ile
            340                 345                 350

Leu Glu Ile Ala Arg Gln Phe Ala Gln Gln Ala Lys Gln Gly His Gly
        355                 360                 365

Leu Ala Arg Ser Leu Thr Phe Ile Ala Thr Thr Gly Glu Glu Gln Gly
    370                 375                 380

Leu Leu Gly Ser Arg Tyr Tyr Ala Ala Asn Pro Ile Tyr Pro Ile Asp
385                 390                 395                 400

Lys Thr Val Ala Val Phe Asn Leu Asp Ser Thr Asn Ile Tyr Gly Lys
                405                 410                 415

Thr Lys Asp Tyr Thr Ile Val Gly Lys Gly Gln Ser Glu Leu Glu Asn
            420                 425                 430

Tyr Leu Asp Arg Ala Val Ala Lys Gln Asn Arg Thr Ser Gln Gly Glu
        435                 440                 445

Leu Asn Pro Ala Ser Gly Gly Phe Phe Arg Ser Asp His Phe Ser Phe
    450                 455                 460

Ala Lys Leu Gly Val Pro Ala Val Phe Ala Gly Gly Gly Asn Glu Pro
465                 470                 475                 480

Leu Asp Glu Ala Thr Ala Gln Tyr Lys Thr Ala Met Leu Val Lys Met
                485                 490                 495

Lys Gly Cys Tyr His Asn Val Cys Asp His Tyr Arg Pro Glu Trp Asp
            500                 505                 510

Leu Ser Gly Ser Leu Gln Asp Leu Gly Val Tyr Tyr Gln Ala Ala Ala
        515                 520                 525

Glu Leu Gly Asn Asn Gln Asp Trp Pro Gly Tyr Phe Ala Gly Ser Glu
    530                 535                 540

Phe Asn Gln Leu Arg Pro Ala Asp
545                 550
```

<210> SEQ ID NO 75
<211> LENGTH: 570
<212> TYPE: DNA
<213> ORGANISM: Silicibacter sp. TM1040

<400> SEQUENCE: 75

```
atgttttaca aagacgaacg gcttgcgctg ttcatagatg gctcgaattt atatgcctcc      60

gccaaggcat tgggatttga catcgactac aagcttctgc gtcaggaatt catgcgtcgc     120

ggcaaacttg tacgggcttt ctattacacg gcgctgcttg aaaacgacga atactctccg     180

attcgccccc ttgtagattg gttgcattac aatggatttt ccatggtgac caaacctgcc     240

aaggaataca ccgacagcat gggccgtcgg aaggtgaagg gcaacatgga catcgaactc     300
```

acggttgatg ctatggagct tgcgccgcgc gtcgatcata tcgtgctgtt ctcgggcgac 360
ggtgacttcc gtccgctgat cgccagcctg cagcgtcagg gtgtgcgcgt gtcggtcgtt 420
tcgacgatcc gcagccagcc accaatgatt tcggacgagt tgcgccgaca ggccgacaat 480
ttcatcgagc ttgaagagct gcgcgatgtc attggccgcc cccctcgcga agtcccgagc 540
gaaccccgcg cggttccggc cgaggattga 570

<210> SEQ ID NO 76
<211> LENGTH: 189
<212> TYPE: PRT
<213> ORGANISM: Silicibacter sp. TM1040

<400> SEQUENCE: 76

Met Phe Tyr Lys Asp Glu Arg Leu Ala Leu Phe Ile Asp Gly Ser Asn
1 5 10 15

Leu Tyr Ala Ser Ala Lys Ala Leu Gly Phe Asp Ile Asp Tyr Lys Leu
20 25 30

Leu Arg Gln Glu Phe Met Arg Arg Gly Lys Leu Val Arg Ala Phe Tyr
35 40 45

Tyr Thr Ala Leu Leu Glu Asn Asp Glu Tyr Ser Pro Ile Arg Pro Leu
50 55 60

Val Asp Trp Leu His Tyr Asn Gly Phe Ser Met Val Thr Lys Pro Ala
65 70 75 80

Lys Glu Tyr Thr Asp Ser Met Gly Arg Arg Lys Val Lys Gly Asn Met
85 90 95

Asp Ile Glu Leu Thr Val Asp Ala Met Glu Leu Ala Pro Arg Val Asp
100 105 110

His Ile Val Leu Phe Ser Gly Asp Gly Asp Phe Arg Pro Leu Ile Ala
115 120 125

Ser Leu Gln Arg Gln Gly Val Arg Val Ser Val Val Ser Thr Ile Arg
130 135 140

Ser Gln Pro Pro Met Ile Ser Asp Glu Leu Arg Arg Gln Ala Asp Asn
145 150 155 160

Phe Ile Glu Leu Glu Glu Leu Arg Asp Val Ile Gly Arg Pro Pro Arg
165 170 175

Glu Val Pro Ser Glu Pro Arg Ala Val Pro Ala Glu Asp
180 185

<210> SEQ ID NO 77
<211> LENGTH: 490
<212> TYPE: DNA
<213> ORGANISM: Synechococcus sp. PCC 7942 (elongatus)

<400> SEQUENCE: 77
atgccttaca tcaccagcat tgaacgcatt ggcagacagg aaggccggag ggaacaagct 60
gatactttag ttctccggca gcttacccga cgttgtggca cgctctcacc tgctttgctg 120
acgcagatac aagccctatc gctcgaacag atggagaatc tagcagatga cttgttggat 180
ttctctggca ttcaagattt agaggactgg ctcaatcagc agttgtaggc aggagtaacc 240
gatgccttac atcaccagcg ttgaacgcat tgctcggaaa gaaggctttg cacagggttt 300
tcaagaaggc cggctagagg tggcaacggc ttttgttctt cgtttgctac caaagcgatg 360
tggggtgctg tcaccagagt tactggagca agttcaagcc ctatctcttg agcaactaga 420
agatctatgt gaggcgttgt tggattttgc cgatgttcaa gatttagaag attggctgaa 480
tcagcagtaa 490

<210> SEQ ID NO 78
<211> LENGTH: 75
<212> TYPE: PRT
<213> ORGANISM: Synechococcus sp. PCC 7942 (elongatus)

<400> SEQUENCE: 78

Met Pro Tyr Ile Thr Ser Ile Glu Arg Ile Gly Arg Gln Glu Gly Arg
1               5                   10                  15

Arg Glu Gln Ala Asp Thr Leu Val Leu Arg Gln Leu Thr Arg Arg Cys
            20                  25                  30

Gly Thr Leu Ser Pro Ala Leu Leu Thr Gln Ile Gln Ala Leu Ser Leu
        35                  40                  45

Glu Gln Met Glu Asn Leu Ala Asp Asp Leu Leu Asp Phe Ser Gly Ile
    50                  55                  60

Gln Asp Leu Glu Asp Trp Leu Asn Gln Gln Leu
65                  70                  75

<210> SEQ ID NO 79
<211> LENGTH: 82
<212> TYPE: PRT
<213> ORGANISM: Synechococcus sp. PCC 7942 (elongatus)

<400> SEQUENCE: 79

Met Pro Tyr Ile Thr Ser Val Glu Arg Ile Ala Arg Lys Glu Gly Phe
1               5                   10                  15

Ala Gln Gly Phe Gln Glu Gly Arg Leu Glu Val Ala Thr Ala Phe Val
            20                  25                  30

Leu Arg Leu Leu Pro Lys Arg Cys Gly Val Leu Ser Pro Glu Leu Leu
        35                  40                  45

Glu Gln Val Gln Ala Leu Ser Leu Glu Gln Leu Glu Asp Leu Cys Glu
    50                  55                  60

Ala Leu Leu Asp Phe Ala Asp Val Gln Asp Leu Glu Asp Trp Leu Asn
65                  70                  75                  80

Gln Gln

<210> SEQ ID NO 80
<211> LENGTH: 2391
<212> TYPE: DNA
<213> ORGANISM: Novosphingobium aromaticivorans DSM 12444 (F199)

<400> SEQUENCE: 80
atggcacaag ccaatcgtac cacgtcgttc attcgacttt tcgctgcggg tagcactgct 60
gcgctcgcgc tcggcattgc cacgccgtcg ttcgcgcaag acgcccaggc ccaggccgac 120
caggcgccga ccaccggcga gatcgtcgtc accgcacagt tccgcgagca gcgcctgcag 180
gataccccgc tgtcgatcac cgcggtcgat gccagcctgc tcgcctcgcg caaccagacc 240
gacatctcgc agatcgcggc tcaggcgccg aacgtgcagc tcacccagat gggcggcgcc 300
ttcggttcgt cgatggcggc ctatatccgc ggcatcggcc agtacgactt caacccggcc 360
tacgaaccgg gcgtgggtat ctatgtcgac gacgtctact acgcgacgct gaccggctcg 420
gtcatggacc tgctcgacct cgaccgcgtc gaagtgctgc gcggtccgca aggcacgctg 480
actggccgca actcgatcgg cggcgcgatc aagctgttct cggccaagcc taccgaaggc 540
aacagcggca ccgtcgaggc gacctatggc tcgcgccagc gcgtcgacct gcgcgccacg 600
gccaacttcg agctgaccga cggcctctat gcgcgcatct cgggcgtgtt caagcgccag 660
gacggctatg tcgaccagat cgactatggc tgcgccaacc cggacaacga actcggcatc 720

```
ggcggcaatg cctcgacgcc cgcggactgc gtcgtcgcca agctgggcga gaagaactac    780

tcgggtatcc gcggttcgct gcgctacaat ccgtcggata cgatcgactg gattgtcacc    840

ggcgactaca cctatgaaaa tcgcaccaac gccgccggcg tgatgagcgc gactgacccg    900

tccaagaccg gcggcgtcga tttcacctgc ggcaagttct gcacctatgc cagctggtac    960

atgccggagg gcggtcaggc gacccaggcc tactacaacc ccaacaccac caagttcgaa   1020

ggctggggcg tttcgagcaa cctgacggtc ggaatctcgg actcgctgaa gctccaggcg   1080

atcactgcct atcgcaagta caaccagatc ttcggcacgg atgatgacta caccccctac   1140

agcctgatcg gcggttcggg cttcaacgac ctcgacttca agttcttcag ccaggaactg   1200

cgcctcaacg gccaggtcgg cgacaatatc gactggacca tcggcgggtt ctacaacaac   1260

cagacctcgg tctacttcac ccgccaggac atccgctaca tcgtgccgat cggcgtgccc   1320

tcgctgttcc tgcagttcca gggtaacgac ccgatcaagg ccaacagcaa ggccgcgttc   1380

ggtacggtga tcttccaccc gaccgaagcg atgaccgtga ccggcggcat ccgctacacc   1440

aaggagcaca aggactatac cttcgtgcgc caggcatggg atggcggtac gctgaccgat   1500

ccgttcggcg tcggtgcgct cgatggttcc aaggcggtct acgacggcga caaggtcgac   1560

tggcgccttt cgctcgacta ccgcttcagc cccgaagtcc tggcctatgc gacggtcagc   1620

acgggcttca agggcggcgg cgtcacggcg cgtccgttca ccaagaacca ggcgatcaac   1680

ggcacgttcg atccggaaac gctccatgcc tatgaagtgg gcctgaagac cgacctgttc   1740

gaccgcaggc tgcgcctgaa cctgtcgggc ttctacaacg actacaagaa catccagctt   1800

ccgatcggag actgctcggc gctcgacggg ttcgaacccg gcaccgatcc gttcccctgc   1860

gcggcgatcc agaacgccgg tgacggcgag atgtacggcc tcgaggcgga actctcggcc   1920

cacccggtcg aaggtctcga catcgatgct tcgctgagct ggatcgacgg caagtggaag   1980

cggatcgaca ccgcggcgca gggcgcgctg cgcgtgaccg acccgatcac cacgccggcc   2040

tggcgcggaa gcttcggcat ccagtacaag gcgctgctgg gcaacaacgc gggttcgatc   2100

acgccccgct tcgacctgtc ctacaccggc aagcagacga tcggccgtct gatcaactcc   2160

ggcgagttcg gcccgctgca gtacaatccg tcgatcacgc tggcgaacgc ccgcgtcacc   2220

tggaagaacg aggacgagaa ccttgcggtc tcgttcgagg tccagaacct gttcgacaag   2280

tactactacc tgccgctgcg cttcgctgcg gtctatgcct tcgtcggcac ggcctactcc   2340

aacgtcggtc gcccgcgcga atgggcggtc acggttcaga agaagttctg a            2391
```

<210> SEQ ID NO 81
<211> LENGTH: 796
<212> TYPE: PRT
<213> ORGANISM: Novosphingobium aromaticivorans DSM 12444 (F199)

<400> SEQUENCE: 81

```
Met Ala Gln Ala Asn Arg Thr Thr Ser Phe Ile Arg Leu Phe Ala Ala
1               5                   10                  15

Gly Ser Thr Ala Ala Leu Ala Leu Gly Ile Ala Thr Pro Ser Phe Ala
            20                  25                  30

Gln Asp Ala Gln Ala Gln Ala Asp Gln Ala Pro Thr Thr Gly Glu Ile
        35                  40                  45

Val Val Thr Ala Gln Phe Arg Glu Gln Arg Leu Gln Asp Thr Pro Leu
    50                  55                  60

Ser Ile Thr Ala Val Asp Ala Ser Leu Leu Ala Ser Arg Asn Gln Thr
65                  70                  75                  80

Asp Ile Ser Gln Ile Ala Ala Gln Ala Pro Asn Val Gln Leu Thr Gln
```

```
                85                  90                  95

Met Gly Gly Ala Phe Gly Ser Ser Met Ala Ala Tyr Ile Arg Gly Ile
            100                 105                 110

Gly Gln Tyr Asp Phe Asn Pro Ala Tyr Glu Pro Gly Val Gly Ile Tyr
        115                 120                 125

Val Asp Asp Val Tyr Tyr Ala Thr Leu Thr Gly Ser Val Met Asp Leu
    130                 135                 140

Leu Asp Leu Asp Arg Val Glu Val Leu Arg Gly Pro Gln Gly Thr Leu
145                 150                 155                 160

Thr Gly Arg Asn Ser Ile Gly Gly Ala Ile Lys Leu Phe Ser Ala Lys
            165                 170                 175

Pro Thr Glu Gly Asn Ser Gly Thr Val Glu Ala Thr Tyr Gly Ser Arg
            180                 185                 190

Gln Arg Val Asp Leu Arg Ala Thr Ala Asn Phe Glu Leu Thr Asp Gly
        195                 200                 205

Leu Tyr Ala Arg Ile Ser Gly Val Phe Lys Arg Gln Asp Gly Tyr Val
    210                 215                 220

Asp Gln Ile Asp Tyr Gly Cys Ala Asn Pro Asp Asn Glu Leu Gly Ile
225                 230                 235                 240

Gly Gly Asn Ala Ser Thr Pro Ala Asp Cys Val Val Ala Lys Leu Gly
                245                 250                 255

Glu Lys Asn Tyr Ser Gly Ile Arg Gly Ser Leu Arg Tyr Asn Pro Ser
            260                 265                 270

Asp Thr Ile Asp Trp Ile Val Thr Gly Asp Tyr Thr Tyr Glu Asn Arg
        275                 280                 285

Thr Asn Ala Ala Gly Val Met Ser Ala Thr Asp Pro Ser Lys Thr Gly
    290                 295                 300

Gly Val Asp Phe Thr Cys Gly Lys Phe Cys Thr Tyr Ala Ser Trp Tyr
305                 310                 315                 320

Met Pro Glu Gly Gly Gln Ala Thr Gln Ala Tyr Tyr Asn Pro Asn Thr
                325                 330                 335

Thr Lys Phe Glu Gly Trp Gly Val Ser Ser Asn Leu Thr Val Gly Ile
            340                 345                 350

Ser Asp Ser Leu Lys Leu Gln Ala Ile Thr Ala Tyr Arg Lys Tyr Asn
        355                 360                 365

Gln Ile Phe Gly Thr Asp Asp Asp Tyr Thr Pro Tyr Ser Leu Ile Gly
    370                 375                 380

Gly Ser Gly Phe Asn Asp Leu Asp Phe Lys Phe Phe Ser Gln Glu Leu
385                 390                 395                 400

Arg Leu Asn Gly Gln Val Gly Asp Asn Ile Asp Trp Thr Ile Gly Gly
                405                 410                 415

Phe Tyr Asn Asn Gln Thr Ser Val Tyr Phe Thr Arg Gln Asp Ile Arg
            420                 425                 430

Tyr Ile Val Pro Ile Gly Val Pro Ser Leu Phe Leu Gln Phe Gln Gly
        435                 440                 445

Asn Asp Pro Ile Lys Ala Asn Ser Lys Ala Ala Phe Gly Thr Val Ile
    450                 455                 460

Phe His Pro Thr Glu Ala Met Thr Val Thr Gly Gly Ile Arg Tyr Thr
465                 470                 475                 480

Lys Glu His Lys Asp Tyr Thr Phe Val Arg Gln Ala Trp Asp Gly Gly
                485                 490                 495

Thr Leu Thr Asp Pro Phe Gly Val Gly Ala Leu Asp Gly Ser Lys Ala
            500                 505                 510
```

```
Val Tyr Asp Gly Asp Lys Val Asp Trp Arg Leu Ser Leu Asp Tyr Arg
        515                 520                 525

Phe Ser Pro Glu Val Leu Ala Tyr Ala Thr Val Ser Thr Gly Phe Lys
    530                 535                 540

Gly Gly Gly Val Thr Ala Arg Pro Phe Thr Lys Asn Gln Ala Ile Asn
545                 550                 555                 560

Gly Thr Phe Asp Pro Glu Thr Leu His Ala Tyr Glu Val Gly Leu Lys
                565                 570                 575

Thr Asp Leu Phe Asp Arg Arg Leu Arg Leu Asn Leu Ser Gly Phe Tyr
            580                 585                 590

Asn Asp Tyr Lys Asn Ile Gln Leu Pro Ile Gly Asp Cys Ser Ala Leu
        595                 600                 605

Asp Gly Phe Glu Pro Gly Thr Asp Pro Phe Pro Cys Ala Ala Ile Gln
    610                 615                 620

Asn Ala Gly Asp Gly Glu Met Tyr Gly Leu Glu Ala Glu Leu Ser Ala
625                 630                 635                 640

His Pro Val Glu Gly Leu Asp Ile Asp Ala Ser Leu Ser Trp Ile Asp
                645                 650                 655

Gly Lys Trp Lys Arg Ile Asp Thr Ala Ala Gln Gly Ala Leu Arg Val
            660                 665                 670

Thr Asp Pro Ile Thr Thr Pro Ala Trp Arg Gly Ser Phe Gly Ile Gln
        675                 680                 685

Tyr Lys Ala Leu Leu Gly Asn Asn Ala Gly Ser Ile Thr Pro Arg Phe
    690                 695                 700

Asp Leu Ser Tyr Thr Gly Lys Gln Thr Ile Gly Arg Leu Ile Asn Ser
705                 710                 715                 720

Gly Glu Phe Gly Pro Leu Gln Tyr Asn Pro Ser Ile Thr Leu Ala Asn
                725                 730                 735

Ala Arg Val Thr Trp Lys Asn Glu Asp Glu Asn Leu Ala Val Ser Phe
            740                 745                 750

Glu Val Gln Asn Leu Phe Asp Lys Tyr Tyr Tyr Leu Pro Leu Arg Phe
        755                 760                 765

Ala Ala Val Tyr Ala Phe Val Gly Thr Ala Tyr Ser Asn Val Gly Arg
    770                 775                 780

Pro Arg Glu Trp Ala Val Thr Val Gln Lys Lys Phe
785                 790                 795
```

<210> SEQ ID NO 82
<211> LENGTH: 1248
<212> TYPE: DNA
<213> ORGANISM: Novosphingobium aromaticivorans DSM 12444 (F199)

<400> SEQUENCE: 82

```
gtgctcaagg gggcgatctt ttcgctgcac gatgtgctcg tgaccaaggg cacgatcaac      60

gcgccgctgt ttgaggaaac gctgcggctg ctgcgctatc tcaaggcgcg gggtgtcgaa     120

ccggttttca ttggcaacca tgactggacg gtcaccagtc ccggccagtc gaagccgttc     180

cggaccctgc tcgaagagcg gctcggtccg atcagctatt atatcggcgg ccaaaacggg     240

atgccttata agccacgcgc cgattccacc gcgcatatcc tctccgacaa gggctggcag     300

cggaatgagg tcctttatgt cggcaacaca accgacgata tgaagaccgc tgccaatggc     360

ggcctgatgt ttgtgaacgt catgtggcac ggagtggcga gcccctacgg ctttcaattc     420

gactctccac gcgacgtcgc gcgcttcgtc gattgcctct gtctgggcct cgacggctgg     480

ttctgggcgc tcgaacagag cgatctgcgg gtctatgcgc tcgcgccttt cacaacgctc     540
```

```
tcgccgcgct acgcacaagc gcatgcctat tctgaaaacg ccaaggcgac ctcgaaacac    600

ggtgccggtg atgcgaattt ctggggccgt ctgctcgcgg cgcgcatcta tttttcaggt    660

ctcgctgacg agatcgacta tatcaccgcc tatcccgggc acgcgcctac ttccaacgcg    720

acggtgatca gtgaggcgct taacatcctg ggcagtcac tgcgcaagag ctatctgccc    780

gacctcattc tccgtcacac caaagcggtg aaatcgcaga ccgcgcgggc ctcaggggga    840

agcgtgggcc tcgacaatca gctcaacacg atccggctca acccggcacc cgtccgcggc    900

gtgggcggca aaccctataa gtcgccgccc gcgcgcggcg gcaagcgtgt cctcgttatc    960

gatgatatct gcaccgaggg taacagcttc gagggtgcgc gggcctatct gagggccgca   1020

ggagcgcaaa cggtctgcgt gagctggctc aagacgatca ataaggacta tcgcgccgtg   1080

tcaccagcct tcggcccgtt caatccctac atcgcgcaaa ccttcccgac accgatcgcg   1140

accacaacgc actggtattc gagcgcgatc agctcgcatg ctgcgccgac tgacctcgcc   1200

gacgtctata atcgctactt cagctgggct tggcccgccg atatatga                  1248
```

```
<210> SEQ ID NO 83
<211> LENGTH: 415
<212> TYPE: PRT
<213> ORGANISM: Novosphingobium aromaticivorans DSM 12444 (F199)

<400> SEQUENCE: 83

Met Leu Lys Gly Ala Ile Phe Ser Leu His Asp Val Leu Val Thr Lys
1               5                   10                  15

Gly Thr Ile Asn Ala Pro Leu Phe Glu Glu Thr Leu Arg Leu Leu Arg
            20                  25                  30

Tyr Leu Lys Ala Arg Gly Val Glu Pro Val Phe Ile Gly Asn His Asp
        35                  40                  45

Trp Thr Val Thr Ser Pro Gly Gln Ser Lys Pro Phe Arg Thr Leu Leu
    50                  55                  60

Glu Glu Arg Leu Gly Pro Ile Ser Tyr Tyr Ile Gly Gly Gln Asn Gly
65                  70                  75                  80

Met Pro Tyr Lys Pro Arg Ala Asp Ser Thr Ala His Ile Leu Ser Asp
                85                  90                  95

Lys Gly Trp Gln Arg Asn Glu Val Leu Tyr Val Gly Asn Thr Thr Asp
            100                 105                 110

Asp Met Lys Thr Ala Ala Asn Gly Gly Leu Met Phe Val Asn Val Met
        115                 120                 125

Trp His Gly Val Ala Ser Pro Tyr Gly Phe Gln Phe Asp Ser Pro Arg
    130                 135                 140

Asp Val Ala Arg Phe Val Asp Cys Leu Cys Leu Gly Leu Asp Gly Trp
145                 150                 155                 160

Phe Trp Ala Leu Glu Gln Ser Asp Leu Arg Val Tyr Ala Leu Ala Pro
                165                 170                 175

Phe Thr Thr Leu Ser Pro Arg Tyr Ala Gln Ala His Ala Tyr Ser Glu
            180                 185                 190

Asn Ala Lys Ala Thr Ser Lys His Gly Ala Gly Asp Ala Asn Phe Trp
        195                 200                 205

Gly Arg Leu Leu Ala Ala Arg Ile Tyr Phe Ser Gly Leu Ala Asp Glu
    210                 215                 220

Ile Asp Tyr Ile Thr Ala Tyr Pro Gly His Ala Pro Thr Ser Asn Ala
225                 230                 235                 240

Thr Val Ile Ser Glu Ala Leu Asn Ile Leu Gly Gln Ser Leu Arg Lys
                245                 250                 255
```

-continued

```
Ser Tyr Leu Pro Asp Leu Ile Leu Arg His Thr Lys Ala Val Lys Ser
            260                 265                 270

Gln Thr Ala Arg Ala Ser Gly Gly Ser Val Gly Leu Asp Asn Gln Leu
        275                 280                 285

Asn Thr Ile Arg Leu Asn Pro Ala Pro Val Arg Gly Val Gly Gly Lys
    290                 295                 300

Pro Tyr Lys Ser Pro Pro Ala Arg Gly Gly Lys Arg Val Leu Val Ile
305                 310                 315                 320

Asp Asp Ile Cys Thr Glu Gly Asn Ser Phe Glu Gly Ala Arg Ala Tyr
                325                 330                 335

Leu Arg Ala Ala Gly Ala Gln Thr Val Cys Val Ser Trp Leu Lys Thr
            340                 345                 350

Ile Asn Lys Asp Tyr Arg Ala Val Ser Pro Ala Phe Gly Pro Phe Asn
        355                 360                 365

Pro Tyr Ile Ala Gln Thr Phe Pro Thr Pro Ile Ala Thr Thr Thr His
    370                 375                 380

Trp Tyr Ser Ser Ala Ile Ser Ser His Ala Ala Pro Thr Asp Leu Ala
385                 390                 395                 400

Asp Val Tyr Asn Arg Tyr Phe Ser Trp Ala Trp Pro Ala Asp Ile
                405                 410                 415
```

<210> SEQ ID NO 84
<211> LENGTH: 546
<212> TYPE: DNA
<213> ORGANISM: Thiomicrospira denitrificans ATCC 33889

<400> SEQUENCE: 84

```
atggacaata ataactttga aataattaaa caagcattag gtaatgtgat ttacacacaa      60

aaaacacatg aaatggcaat cacaaggaaa agtaattatg ttacttgtat taaatggtta     120

aatataatct tggtgggtat tgtatttttt gtactttttt tacaaatttt caatcaagat     180

gataaagatt atttgtatgc tggaattttt tttactgtta ttgaagctct tttttaatt      240

tttcaattaa gctttaatcc tgaaaaagag gtattagaac atagaaatac ggcaaataga     300

ttatggttaa tgagggaaaa gcatttaaat ttattaactg atataaaaaa tgagattttt     360

gattttaatc aaaatgctat taaaagagat gagctaacta atgaattaaa tgaaatttat     420

aaaaatgctc ctagaacaaa tagtgatgat tatgaaaaag cttctaaagc attaaatgga     480

aatcaaaaac caaaagccga tgaagatgaa atgattaatt ttcttcctaa aaatcttcaa     540

agttaa                                                                546
```

<210> SEQ ID NO 85
<211> LENGTH: 181
<212> TYPE: PRT
<213> ORGANISM: Thiomicrospira denitrificans ATCC 33889

<400> SEQUENCE: 85

```
Met Asp Asn Asn Asn Phe Glu Ile Ile Lys Gln Ala Leu Gly Asn Val
1               5                   10                  15

Ile Tyr Thr Gln Lys Thr His Glu Met Ala Ile Thr Arg Lys Ser Asn
            20                  25                  30

Tyr Val Thr Cys Ile Lys Trp Leu Asn Ile Ile Leu Val Gly Ile Val
        35                  40                  45

Phe Phe Val Leu Phe Leu Gln Ile Phe Asn Gln Asp Asp Lys Asp Tyr
    50                  55                  60

Leu Tyr Ala Gly Ile Phe Phe Thr Val Ile Glu Ala Leu Phe Leu Ile
65                  70                  75                  80
```

```
Phe Gln Leu Ser Phe Asn Pro Glu Lys Glu Val Leu Glu His Arg Asn
                85                  90                  95

Thr Ala Asn Arg Leu Trp Leu Met Arg Glu Lys His Leu Asn Leu Leu
            100                 105                 110

Thr Asp Ile Lys Asn Glu Ile Phe Asp Phe Asn Gln Asn Ala Ile Lys
        115                 120                 125

Arg Asp Glu Leu Thr Asn Glu Leu Asn Glu Ile Tyr Lys Asn Ala Pro
    130                 135                 140

Arg Thr Asn Ser Asp Asp Tyr Glu Lys Ala Ser Lys Ala Leu Asn Gly
145                 150                 155                 160

Asn Gln Lys Pro Lys Ala Asp Glu Asp Glu Met Ile Asn Phe Leu Pro
               165                 170                 175

Lys Asn Leu Gln Ser
            180
```

<210> SEQ ID NO 86
<211> LENGTH: 261
<212> TYPE: DNA
<213> ORGANISM: Thiomicrospira denitrificans ATCC 33889

<400> SEQUENCE: 86

```
gtgtacaaaa taattcttca taaaaaagtt attaaattta tcaacagtag aaatccaaaa      60

gacaagcaaa aaattaaaga aaaatttgag cttttacaaa ataaccctta tccgtcaaac     120

tataatatag atgtcaaaaa gatgcgaaat gccaatggat ttagattaag aatcagcgat     180

tatagatttt tatatgatgt tgtcgaagat gaattgataa tatatatgga aaacggtgat     240

aacagaggcg atatatatta a                                               261
```

<210> SEQ ID NO 87
<211> LENGTH: 86
<212> TYPE: PRT
<213> ORGANISM: Thiomicrospira denitrificans ATCC 33889

<400> SEQUENCE: 87

```
Met Tyr Lys Ile Ile Leu His Lys Lys Val Ile Lys Phe Ile Asn Ser
1               5                   10                  15

Arg Asn Pro Lys Asp Lys Gln Lys Ile Lys Glu Lys Phe Glu Leu Leu
            20                  25                  30

Gln Asn Asn Pro Tyr Pro Ser Asn Tyr Asn Ile Asp Val Lys Lys Met
        35                  40                  45

Arg Asn Ala Asn Gly Phe Arg Leu Arg Ile Ser Asp Tyr Arg Phe Leu
    50                  55                  60

Tyr Asp Val Val Glu Asp Glu Leu Ile Ile Tyr Met Glu Asn Gly Asp
65                  70                  75                  80

Asn Arg Gly Asp Ile Tyr
                85
```

<210> SEQ ID NO 88
<211> LENGTH: 213
<212> TYPE: DNA
<213> ORGANISM: Thiomicrospira denitrificans ATCC 33889

<400> SEQUENCE: 88

```
ttgattgatg ataaagttat taaagattta aaacaaattg ataagttgtg gcaaaagaaa      60

attatagaag tcattaaaac aaagcttgta gaaaatctct cccattatta tcgcttacta     120

gttgctgatt atagggtaat ttatgagata aaggatgatg aagtagttat aatcgtcatc     180
```

aaaattgggc atcgtaaaga tatttataaa tag 213

<210> SEQ ID NO 89
<211> LENGTH: 70
<212> TYPE: PRT
<213> ORGANISM: Thiomicrospira denitrificans ATCC 33889

<400> SEQUENCE: 89

Met Ile Asp Asp Lys Val Ile Lys Asp Leu Lys Gln Ile Asp Lys Leu
1 5 10 15

Trp Gln Lys Lys Ile Ile Glu Val Ile Lys Thr Lys Leu Val Glu Asn
20 25 30

Leu Ser His Tyr Tyr Arg Leu Leu Val Ala Asp Tyr Arg Val Ile Tyr
35 40 45

Glu Ile Lys Asp Asp Glu Val Val Ile Ile Val Ile Lys Ile Gly His
50 55 60

Arg Lys Asp Ile Tyr Lys
65 70

<210> SEQ ID NO 90
<211> LENGTH: 168
<212> TYPE: DNA
<213> ORGANISM: Thiomicrospira denitrificans ATCC 33889

<400> SEQUENCE: 90
atggtgcctg tcaccccttt tcaaacgacc aaagagtttt ttgttaaaga agctttgaga 60
aattatcttg atgatacgca agagtattat gaagtgcaaa aacgctcaaa tgcagaagat 120
agaaatctta taactcttga ggagttggag agagcgcttg agttataa 168

<210> SEQ ID NO 91
<211> LENGTH: 55
<212> TYPE: PRT
<213> ORGANISM: Thiomicrospira denitrificans ATCC 33889

<400> SEQUENCE: 91

Met Val Pro Val Thr Pro Phe Gln Thr Thr Lys Glu Phe Phe Val Lys
1 5 10 15

Glu Ala Leu Arg Asn Tyr Leu Asp Asp Thr Gln Glu Tyr Tyr Glu Val
20 25 30

Gln Lys Arg Ser Asn Ala Glu Asp Arg Asn Leu Ile Thr Leu Glu Glu
35 40 45

Leu Glu Arg Ala Leu Glu Leu
50 55

<210> SEQ ID NO 92
<211> LENGTH: 243
<212> TYPE: DNA
<213> ORGANISM: Thiomicrospira denitrificans ATCC 33889

<400> SEQUENCE: 92
atgaatactt caattacaag agttgatttc ggtgataaaa tttatatata tttaaaaagt 60
aatgatattt taactattcc ttatagttat actaaaaaaa ttcaatatgc aaaaaaagag 120
cagcttttaa actaccgtat aattggtggt gggattggag tgcattttga agaaatagat 180
gaagatattt cacttaacgg tattatcaca tataaaatca atcacgaact aaaagcttct 240
tga 243

<210> SEQ ID NO 93
<211> LENGTH: 80

<212> TYPE: PRT
<213> ORGANISM: Thiomicrospira denitrificans ATCC 33889

<400> SEQUENCE: 93

```
Met Asn Thr Ser Ile Thr Arg Val Asp Phe Gly Asp Lys Ile Tyr Ile
1               5                   10                  15

Tyr Leu Lys Ser Asn Asp Ile Leu Thr Ile Pro Tyr Ser Tyr Thr Lys
            20                  25                  30

Lys Ile Gln Tyr Ala Lys Lys Glu Gln Leu Leu Asn Tyr Arg Ile Ile
        35                  40                  45

Gly Gly Gly Ile Gly Val His Phe Glu Glu Ile Asp Glu Asp Ile Ser
    50                  55                  60

Leu Asn Gly Ile Ile Thr Tyr Lys Ile Asn His Glu Leu Lys Ala Ser
65                  70                  75                  80
```

<210> SEQ ID NO 94
<211> LENGTH: 201
<212> TYPE: DNA
<213> ORGANISM: Geobacter metallireducens GS-15

<400> SEQUENCE: 94

```
atggcaaacg gtacagtaaa gtggttcaac gacagcaagg ggtttggttt tctggagcag      60

gagaacggcg aggacgtatt tgtccacttc tcggccatca acggcgacgg tttcaaatcc     120

cttactgaag gtgatagggt aacgttcgac gtcgtcaagg gcccgaaagg cctgcaggcg     180

gccaacgtaa ccagggtgta a                                               201
```

<210> SEQ ID NO 95
<211> LENGTH: 66
<212> TYPE: PRT
<213> ORGANISM: Geobacter metallireducens GS-15

<400> SEQUENCE: 95

```
Met Ala Asn Gly Thr Val Lys Trp Phe Asn Asp Ser Lys Gly Phe Gly
1               5                   10                  15

Phe Leu Glu Gln Glu Asn Gly Glu Asp Val Phe Val His Phe Ser Ala
            20                  25                  30

Ile Asn Gly Asp Gly Phe Lys Ser Leu Thr Glu Gly Asp Arg Val Thr
        35                  40                  45

Phe Asp Val Val Lys Gly Pro Lys Gly Leu Gln Ala Ala Asn Val Thr
    50                  55                  60

Arg Val
65
```

<210> SEQ ID NO 96
<211> LENGTH: 282
<212> TYPE: DNA
<213> ORGANISM: Geobacter metallireducens GS-15

<400> SEQUENCE: 96

```
atgaagaaga tggctgtatt gttgatggcg gcatttatga tgtcggctac cgtaccggtt      60

ttcgctgctg agatgaccaa ggaagagaag gaccagtgcc tcctggcttc caagaactgc     120

ggtatggagg tcgacactct gcagaagaag atcaagaagc tcaactccga gatcaagaag     180

gggaagaaag tctactccgc cgacgagatc aagaagctcc agcagaagct tgacgaggcc     240

aacgccctgc tcgacgacat cctcaagggt ggcggcaatt aa                        282
```

<210> SEQ ID NO 97
<211> LENGTH: 93

<212> TYPE: PRT
<213> ORGANISM: Geobacter metallireducens GS-15

<400> SEQUENCE: 97

```
Met Lys Lys Met Ala Val Leu Leu Met Ala Ala Phe Met Met Ser Ala
1               5                   10                  15

Thr Val Pro Val Phe Ala Ala Glu Met Thr Lys Glu Glu Lys Asp Gln
            20                  25                  30

Cys Leu Leu Ala Ser Lys Asn Cys Gly Met Glu Val Asp Thr Leu Gln
        35                  40                  45

Lys Lys Ile Lys Lys Leu Asn Ser Glu Ile Lys Lys Gly Lys Lys Val
    50                  55                  60

Tyr Ser Ala Asp Glu Ile Lys Lys Leu Gln Gln Lys Leu Asp Glu Ala
65                  70                  75                  80

Asn Ala Leu Leu Asp Asp Ile Leu Lys Gly Gly Gly Asn
                85                  90
```

<210> SEQ ID NO 98
<211> LENGTH: 1419
<212> TYPE: DNA
<213> ORGANISM: Geobacter metallireducens GS-15

<400> SEQUENCE: 98

```
atgaaaaaga aagtattggc agtatccgca gcctgtgcgc tgaccgctgc gacggcagtt     60

ccggccctgg cgctggaaaa cgagttccac gggatgttcc gggtgttcgg gacgatgtca    120

aacttcaacg acggtggttc cgggcgcctt ctgcctacag acgcaaccac gggaagagac    180

cccaagacca ggagcttcgt cgagcagcgg gcccgcctca tgtacatcgc caaggccaac    240

gacgatctca aactggttac ccacttcgag atcgactccc gctggggtga caactcctat    300

gccaacggcc gcaactccgg cggcgccatc ggcgccgaca ccgtgaacct ggaaaccaag    360

aacgtctacc tcgacttcaa catcccctcc acccccatga acttcaaggt cggtatccag    420

ccgctcgtcg actcctacaa gggggtcttc ttcaacaccg acgtggccgc agcccttgcc    480

accgccaagc tcggcaacgg ttccgtggtg gtcggcttcg cccggttgga cgacgccgac    540

acctttaccc ttggttcagc agctggcaga tcaacgtcca cccccggtaa ggccaagcgc    600

gacctctaca tcgtggacgg caagtacaac atcaccaagg acgtgaaggt tggggcctcc    660

tactacctcc tcaacgtcga tcagaaggcc ggggataact tcgtccccac atcaaccacc    720

caaacttatg actacatgcg ccacaccttc ggcgtgaacg ctgaagcaaa gttcgcacct    780

ctcaccctgg acggcttcct cctctatcag accgcccgca ccaacgggcc ggacaagatc    840

gaccagaagg gctgggccgc caaccttacc ggcaagggga agctgggccc tggcaccctg    900

aaggcgtcgt tcctctatgc ctccggcgac agcaagagag gcacggtaag agatgacaac    960

acctattacg ggatcaccaa cgagacctct ggagccaacg gcgagcacag cttctatgag   1020

tccgacatga tgatcctgtt ccggaacaag tacaacatta ccggcgaccg ggccatcgtg   1080

tacaacgtga ccaacgtcat cggcggcttt gtgggctaca acgccaacat tactcccaag   1140

gccttcgcca acgtcaatgc cggtttcgtg gctgccgcca cggggaacga cgacttcggt   1200

tccgcgcgcg tcacgattgg cggccacaag agtgattacc tcggcaccga gatcaacggc   1260

gaaatcggct ataaggtgtt cgacaacctg accgccagcc tccagggcgc ctatgtgttc   1320

cttggcgact actacaagga tactgtcggc acggcagcca atcctcaaac cccgcgcgac   1380

ccgtacgagg gccgcatcat gctgaactac gcattctaa                          1419
```

<210> SEQ ID NO 99
<211> LENGTH: 472
<212> TYPE: PRT
<213> ORGANISM: Geobacter metallireducens GS-15

<400> SEQUENCE: 99

```
Met Lys Lys Lys Val Leu Ala Val Ser Ala Ala Cys Ala Leu Thr Ala
1               5                   10                  15

Ala Thr Ala Val Pro Ala Leu Ala Leu Glu Asn Glu Phe His Gly Met
            20                  25                  30

Phe Arg Val Phe Gly Thr Met Ser Asn Phe Asn Asp Gly Gly Ser Gly
        35                  40                  45

Arg Leu Leu Pro Thr Asp Ala Thr Thr Gly Arg Asp Pro Lys Thr Arg
    50                  55                  60

Ser Phe Val Glu Gln Arg Ala Arg Leu Met Tyr Ile Ala Lys Ala Asn
65                  70                  75                  80

Asp Asp Leu Lys Leu Val Thr His Phe Glu Ile Asp Ser Arg Trp Gly
                85                  90                  95

Asp Asn Ser Tyr Ala Asn Gly Arg Asn Ser Gly Gly Ala Ile Gly Ala
            100                 105                 110

Asp Thr Val Asn Leu Glu Thr Lys Asn Val Tyr Leu Asp Phe Asn Ile
        115                 120                 125

Pro Ser Thr Pro Met Asn Phe Lys Val Gly Ile Gln Pro Leu Val Asp
    130                 135                 140

Ser Tyr Lys Gly Val Phe Phe Asn Thr Asp Val Ala Ala Ala Leu Ala
145                 150                 155                 160

Thr Ala Lys Leu Gly Asn Gly Ser Val Val Val Gly Phe Ala Arg Leu
                165                 170                 175

Asp Asp Ala Asp Thr Phe Thr Leu Gly Ser Ala Ala Gly Arg Ser Thr
            180                 185                 190

Ser Thr Pro Gly Lys Ala Lys Arg Asp Leu Tyr Ile Val Asp Gly Lys
        195                 200                 205

Tyr Asn Ile Thr Lys Asp Val Lys Val Gly Ala Ser Tyr Tyr Leu Leu
    210                 215                 220

Asn Val Asp Gln Lys Ala Gly Asp Asn Phe Val Pro Thr Ser Thr Thr
225                 230                 235                 240

Gln Thr Tyr Asp Tyr Met Arg His Thr Phe Gly Val Asn Ala Glu Ala
                245                 250                 255

Lys Phe Ala Pro Leu Thr Leu Asp Gly Phe Leu Leu Tyr Gln Thr Ala
            260                 265                 270

Arg Thr Asn Gly Pro Asp Lys Ile Asp Gln Lys Gly Trp Ala Ala Asn
        275                 280                 285

Leu Thr Gly Lys Gly Lys Leu Gly Pro Gly Thr Leu Lys Ala Ser Phe
    290                 295                 300

Leu Tyr Ala Ser Gly Asp Ser Lys Arg Gly Thr Val Arg Asp Asp Asn
305                 310                 315                 320

Thr Tyr Tyr Gly Ile Thr Asn Glu Thr Ser Gly Ala Asn Gly Glu His
                325                 330                 335

Ser Phe Tyr Glu Ser Asp Met Met Ile Leu Phe Arg Asn Lys Tyr Asn
            340                 345                 350

Ile Thr Gly Asp Arg Ala Ile Val Tyr Asn Val Thr Asn Val Ile Gly
        355                 360                 365

Gly Phe Val Gly Tyr Asn Ala Asn Ile Thr Pro Lys Ala Phe Ala Asn
    370                 375                 380

Val Asn Ala Gly Phe Val Ala Ala Ala Thr Gly Asn Asp Asp Phe Gly
```

```
385                 390                 395                 400

Ser Ala Arg Val Thr Ile Gly Gly His Lys Ser Asp Tyr Leu Gly Thr
                405                 410                 415

Glu Ile Asn Gly Glu Ile Gly Tyr Lys Val Phe Asp Asn Leu Thr Ala
            420                 425                 430

Ser Leu Gln Gly Ala Tyr Val Phe Leu Gly Asp Tyr Tyr Lys Asp Thr
        435                 440                 445

Val Gly Thr Ala Ala Asn Pro Gln Thr Pro Arg Asp Pro Tyr Glu Gly
    450                 455                 460

Arg Ile Met Leu Asn Tyr Ala Phe
465                 470


<210> SEQ ID NO 100
<211> LENGTH: 246
<212> TYPE: DNA
<213> ORGANISM: Rubrobacter xylanophilus DSM 9941

<400> SEQUENCE: 100

atgcacaggg atttcatgta cgagatggcg cgggagcgga tggccgagta ccaccgggag      60

gcggagcgcc ggaggaggtc ggggccttcg gggaggggcg tctggaggcg ctgggtcgcc     120

cggcgcctct tcgaggcggc cttctcggtc gacgccgagg agggctggag ggcgatgtgg     180

gacaggatgt ccgctcccgg gcgccggggc aggaggtcgt ccggcgcccg gaaggttgcg     240

gggtga                                                                246


<210> SEQ ID NO 101
<211> LENGTH: 81
<212> TYPE: PRT
<213> ORGANISM: Rubrobacter xylanophilus DSM 9941

<400> SEQUENCE: 101

Met His Arg Asp Phe Met Tyr Glu Met Ala Arg Glu Arg Met Ala Glu
1               5                   10                  15

Tyr His Arg Glu Ala Glu Arg Arg Arg Arg Ser Gly Pro Ser Gly Arg
            20                  25                  30

Gly Val Trp Arg Arg Trp Val Ala Arg Arg Leu Phe Glu Ala Ala Phe
        35                  40                  45

Ser Val Asp Ala Glu Glu Gly Trp Arg Ala Met Trp Asp Arg Met Ser
    50                  55                  60

Ala Pro Gly Arg Arg Gly Arg Arg Ser Ser Gly Ala Arg Lys Val Ala
65                  70                  75                  80

Gly


<210> SEQ ID NO 102
<211> LENGTH: 1086
<212> TYPE: DNA
<213> ORGANISM: Burkholderia sp. strain 383

<400> SEQUENCE: 102

ttgaaaacgg tcatcaagcg gatttgcgag cttcagccaa tgtattcgtc atcgaatacg      60

cccgaaatgc aggagcgcgg caatctcatt cgatccgagc tagcgcaaga actacgtcgg     120

cgccttccgg agctgagtcg agcgttcgat ccgctgttcg atgatttagc cgtggagggt     180

tcagacggca tcggcaggaa gacggaagcg ccgtgggtcc gactctactc gaaggcaatg     240

tctccgactc cacggcaggg gttctatgtc gtcattcact tctctgctga tggttcggcc     300

tgctttttca ccgtcggttg cggcagtacg gtttggagcg gcggtgatct gcgccccgta     360
```

-continued

```
tctgatgcgc agctaactgc aaaaacgtcg tgggctcgct ccgttgttga gcagcgttgg    420

aaaacgctgg cgccgtttac cgacaccatc tcgctaggcg cacgcgcatc acttcctagg    480

acatttgaaa aggcgacggc attggcccga cgggtacccg tcgaaagcgt cgacgcatcc    540

gatttggatg agctactctt ttctgcagca gaaagactct ccgcgatata tcttgcgcag    600

cttgatcaac gagatgtggc tccgggtgat caagacgctc gcgatctcga agcaatcgta    660

aggccgttac gccagcgaac acgtgcacaa ggcattggac tcactgcatc cgagcgaaag    720

gctgtcgaac tgcgtgcaat gctcttggca atccaatttc tccaatccga aggcttcacg    780

tgcgacgaca aatcggcggc tgagccattt gacattctgg ctcggcgaga cggccaagca    840

ttgaagattg aggtgaaggg aacgactagc gaactatgcg actcgattct gatgacccga    900

aacgaagtcg agcttcatag gcgcgaaaaa ggcacaactg gtcttgtgat tgtttctcga    960

attcagctca atcgaagcgg tgcagcaccg agcgcttcgg gcggagtggt agaggccaaa   1020

atgcaatggg acatcgacca gtggatactt gaatccatag cctttaaagt gcgccgacct   1080

acatag                                                              1086
```

<210> SEQ ID NO 103
<211> LENGTH: 361
<212> TYPE: PRT
<213> ORGANISM: Burkholderia sp. strain 383

<400> SEQUENCE: 103

```
Met Lys Thr Val Ile Lys Arg Ile Cys Glu Leu Gln Pro Met Tyr Ser
1               5                   10                  15

Ser Ser Asn Thr Pro Glu Met Gln Glu Arg Gly Asn Leu Ile Arg Ser
            20                  25                  30

Glu Leu Ala Gln Glu Leu Arg Arg Arg Leu Pro Glu Leu Ser Arg Ala
        35                  40                  45

Phe Asp Pro Leu Phe Asp Asp Leu Ala Val Glu Gly Ser Asp Gly Ile
    50                  55                  60

Gly Arg Lys Thr Glu Ala Pro Trp Val Arg Leu Tyr Ser Lys Ala Met
65                  70                  75                  80

Ser Pro Thr Pro Arg Gln Gly Phe Tyr Val Val Ile His Phe Ser Ala
                85                  90                  95

Asp Gly Ser Ala Cys Phe Phe Thr Val Gly Cys Gly Ser Thr Val Trp
            100                 105                 110

Ser Gly Gly Asp Leu Arg Pro Val Ser Asp Ala Gln Leu Thr Ala Lys
        115                 120                 125

Thr Ser Trp Ala Arg Ser Val Val Glu Gln Arg Trp Lys Thr Leu Ala
    130                 135                 140

Pro Phe Thr Asp Thr Ile Ser Leu Gly Ala Arg Ala Ser Leu Pro Arg
145                 150                 155                 160

Thr Phe Glu Lys Ala Thr Ala Leu Ala Arg Arg Val Pro Val Glu Ser
                165                 170                 175

Val Asp Ala Ser Asp Leu Asp Glu Leu Leu Phe Ser Ala Ala Glu Arg
            180                 185                 190

Leu Ser Ala Ile Tyr Leu Ala Gln Leu Asp Gln Arg Asp Val Ala Pro
        195                 200                 205

Gly Asp Gln Asp Ala Arg Asp Leu Glu Ala Ile Val Arg Pro Leu Arg
    210                 215                 220

Gln Arg Thr Arg Ala Gln Gly Ile Gly Leu Thr Ala Ser Glu Arg Lys
225                 230                 235                 240

Ala Val Glu Leu Arg Ala Met Leu Leu Ala Ile Gln Phe Leu Gln Ser
```

-continued

```
                245                 250                 255

Glu Gly Phe Thr Cys Asp Asp Lys Ser Ala Ala Glu Pro Phe Asp Ile
            260                 265                 270

Leu Ala Arg Arg Asp Gly Gln Ala Leu Lys Ile Glu Val Lys Gly Thr
        275                 280                 285

Thr Ser Glu Leu Cys Asp Ser Ile Leu Met Thr Arg Asn Glu Val Glu
    290                 295                 300

Leu His Arg Arg Glu Lys Gly Thr Thr Gly Leu Val Ile Val Ser Arg
305                 310                 315                 320

Ile Gln Leu Asn Arg Ser Gly Ala Ala Pro Ser Ala Ser Gly Gly Val
                325                 330                 335

Val Glu Ala Lys Met Gln Trp Asp Ile Asp Gln Trp Ile Leu Glu Ser
            340                 345                 350

Ile Ala Phe Lys Val Arg Arg Pro Thr
        355                 360


<210> SEQ ID NO 104
<211> LENGTH: 595
<212> TYPE: DNA
<213> ORGANISM: Cupriavidus necator (Ralstonia eutropha) JMP134,
     chromosome #1

<400> SEQUENCE: 104

atgcccaacg cccttccacc cgcagccacg tatcagcacg ccttcgaggc gcagcgcgcg      60

gccggcggcc aggtggtttc cacccgcacc ctggtgcgtg agacgaccac ccgtatccac     120

ggccgcgacc atttcgagtt ccgcggcacc gacgaggact cggtctacgc cgccgcgctc     180

gaccgcaaaa attccatcga catctaccgc tcgcccgccg tggcctaccg ctactgggaa     240

ggcgatgagt acgtggtgat ggttcgttgc ttcggtctgg actgaggggc gcgaaatggc     300

tacggcaacc accattcgca aagtcatcct ggccgacggc gaagagatcg tcctggatgg     360

tcctcgcacg atcgaccaaa tccgcgaccg catcggcgcc gactatctgg acaccgtccg     420

cctgcgggac cgacggcacg tgatgctcgt cgacgacgac ggtcacccca agggcttgcg     480

tgtcaacgag aaggagacgc ggctctactg ggatgtctgc attcccggca ccacgcacca     540

gattcgcggc gccgtggtca tcgttcccga cagcgacttc gggcgctccc tgtga          595


<210> SEQ ID NO 105
<211> LENGTH: 94
<212> TYPE: PRT
<213> ORGANISM: Cupriavidus necator (Ralstonia eutropha) JMP134,
      chromosome #1

<400> SEQUENCE: 105

Met Pro Asn Ala Leu Pro Pro Ala Ala Thr Tyr Gln His Ala Phe Glu
1               5                   10                  15

Ala Gln Arg Ala Ala Gly Gly Gln Val Val Ser Thr Arg Thr Leu Val
            20                  25                  30

Arg Glu Thr Thr Thr Arg Ile His Gly Arg Asp His Phe Glu Phe Arg
        35                  40                  45

Gly Thr Asp Glu Asp Ser Val Tyr Ala Ala Ala Leu Asp Arg Lys Asn
    50                  55                  60

Ser Ile Asp Ile Tyr Arg Ser Pro Ala Val Ala Tyr Arg Tyr Trp Glu
65                  70                  75                  80

Gly Asp Glu Tyr Val Val Met Val Arg Cys Phe Gly Leu Asp
                85                  90
```

<210> SEQ ID NO 106
<211> LENGTH: 99
<212> TYPE: PRT
<213> ORGANISM: Cupriavidus necator (Ralstonia eutropha) JMP134, chromosome #1

<400> SEQUENCE: 106

```
Met Ala Thr Ala Thr Thr Ile Arg Lys Val Ile Leu Ala Asp Gly Glu
1               5                   10                  15

Glu Ile Val Leu Asp Gly Pro Arg Thr Ile Asp Gln Ile Arg Asp Arg
            20                  25                  30

Ile Gly Ala Asp Tyr Leu Asp Thr Val Arg Leu Arg Asp Arg Arg His
        35                  40                  45

Val Met Leu Val Asp Asp Asp Gly His Pro Lys Gly Leu Arg Val Asn
    50                  55                  60

Glu Lys Glu Thr Arg Leu Tyr Trp Asp Val Cys Ile Pro Gly Thr Thr
65                  70                  75                  80

His Gln Ile Arg Gly Ala Val Val Ile Val Pro Asp Ser Asp Phe Gly
                85                  90                  95

Arg Ser Leu
```

<210> SEQ ID NO 107
<211> LENGTH: 1101
<212> TYPE: DNA
<213> ORGANISM: Dechloromonas aromatica RCB

<400> SEQUENCE: 107

```
atgaacggag tgattgggcg cgaggagttg ttggtctcga ctaaggccga aaagaagaga     60

cgtggccggg tttccagcct gatggtgtca ggacttccct gggtgattat cggtgggttg    120

ctctgggctg gcctgtttat aaagccacag ccggttgggg caacagtaaa gccgccaatc    180

atggagcgca gggatcatta ctacggcctt gccattgttc ctgggcaagg tcgctggctg    240

gccggttcaa gcggaaaaat cgtcagaatc gatgctgatg gccatattga gagactggct    300

tcggtgacgg agcagactct tcaagatatt gcagtttggg atggtgaaca tggcctggcg    360

gttggcaacg agggagttgt tcttcgtacc gccgatggtg gcaaaacctg gcaagaggtt    420

cgtgatgtgc cgaaatctca ggttgctaac aagctgagcc gcgtccgagt tgcacccggt    480

ggggtcgccg tggtgagtgg agagatgggg gcgttgcttg gcactcagga ttttggtgag    540

cactggaagc gtttgcgccc agaagaggat caagcctgga atgacgtggc tttgctgcct    600

gatgggcgcc gtgtcgctgt tggtgagttt ggcagaatca ctttgagtga cgatttcggc    660

gcgacgtggg tcgatatcaa gacacccgtt gaggtgtcgc tgatgtcggt ttccttcggc    720

gatgccctga atggcctagc agtcggtctt gagggaactg ttctgataac gcgggatggc    780

ggcaagaatt ggaagtcact cgatgtcgat ctgcacgatc acctctatga catcgcctgg    840

gatgcggctg gcaagcgctg gattggcgca ggtaatttgg ggcgctggct cgtggtggcg    900

gttgatggca aagcagagac cggtcggctc gacgagcggg atctttcgtg gcacgtccgg    960

gcggttcccg agggcgatgc agtctggttc gctggtgcga atgttgggca atggaatggc   1020

aaatcatgga agcccttggg tgagtcctgg ctgcccaaaa cattgatcgg acttcctgtc   1080

acttcggaga aaagcaaatg a                                              1101
```

<210> SEQ ID NO 108
<211> LENGTH: 366
<212> TYPE: PRT
<213> ORGANISM: Dechloromonas aromatica RCB

<400> SEQUENCE: 108

```
Met Asn Gly Val Ile Gly Arg Glu Glu Leu Leu Val Ser Thr Lys Ala
1               5                   10                  15

Glu Lys Lys Arg Arg Gly Arg Val Ser Ser Leu Met Val Ser Gly Leu
            20                  25                  30

Pro Trp Val Ile Ile Gly Gly Leu Leu Trp Ala Gly Leu Phe Ile Lys
        35                  40                  45

Pro Gln Pro Val Gly Ala Thr Val Lys Pro Pro Ile Met Glu Arg Arg
    50                  55                  60

Asp His Tyr Tyr Gly Leu Ala Ile Val Pro Gly Gln Gly Arg Trp Leu
65                  70                  75                  80

Ala Gly Ser Ser Gly Lys Ile Val Arg Ile Asp Ala Asp Gly His Ile
                85                  90                  95

Glu Arg Leu Ala Ser Val Thr Glu Gln Thr Leu Gln Asp Ile Ala Val
            100                 105                 110

Trp Asp Gly Glu His Gly Leu Ala Val Gly Asn Glu Gly Val Val Leu
        115                 120                 125

Arg Thr Ala Asp Gly Gly Lys Thr Trp Gln Glu Val Arg Asp Val Pro
    130                 135                 140

Lys Ser Gln Val Ala Asn Lys Leu Ser Arg Val Arg Val Ala Pro Gly
145                 150                 155                 160

Gly Val Ala Val Val Ser Gly Glu Met Gly Ala Leu Leu Gly Thr Gln
                165                 170                 175

Asp Phe Gly Glu His Trp Lys Arg Leu Arg Pro Glu Glu Asp Gln Ala
            180                 185                 190

Trp Asn Asp Val Ala Leu Leu Pro Asp Gly Arg Arg Val Ala Val Gly
        195                 200                 205

Glu Phe Gly Arg Ile Thr Leu Ser Asp Asp Phe Gly Ala Thr Trp Val
    210                 215                 220

Asp Ile Lys Thr Pro Val Glu Val Ser Leu Met Ser Val Ser Phe Gly
225                 230                 235                 240

Asp Ala Leu Asn Gly Leu Ala Val Gly Leu Glu Gly Thr Val Leu Ile
                245                 250                 255

Thr Arg Asp Gly Gly Lys Asn Trp Lys Ser Leu Asp Val Asp Leu His
            260                 265                 270

Asp His Leu Tyr Asp Ile Ala Trp Asp Ala Ala Gly Lys Arg Trp Ile
        275                 280                 285

Gly Ala Gly Asn Leu Gly Arg Trp Leu Val Val Ala Val Asp Gly Lys
    290                 295                 300

Ala Glu Thr Gly Arg Leu Asp Glu Arg Asp Leu Ser Trp His Val Arg
305                 310                 315                 320

Ala Val Pro Glu Gly Asp Ala Val Trp Phe Ala Gly Ala Asn Val Gly
                325                 330                 335

Gln Trp Asn Gly Lys Ser Trp Lys Pro Leu Gly Glu Ser Trp Leu Pro
            340                 345                 350

Lys Thr Leu Ile Gly Leu Pro Val Thr Ser Glu Lys Ser Lys
        355                 360                 365
```

<210> SEQ ID NO 109
<211> LENGTH: 681
<212> TYPE: DNA
<213> ORGANISM: Deinococcus geothermalis, DSM11300

<400> SEQUENCE: 109

```
gtgcctacga ttcctttgtt ccctggattt actccggttc gctataccga ggcggatttc     60
```

```
cgccgtgatg tggagacttt cgggtttctt gccattcgtc gactcaccga gagggtttat    120

caggaagccc ccggtgaagt tcggcgaatc ttctctgaac tgccagaagt acggcggatg    180

atcggtcaag tgcggcattc acttatggag caagagatgc gtgctttggg acgccgcgga    240

gatatctcgc agcttagtgc caaggacgaa cagctacgtt cacgtcgtgg ctgtattaag    300

ccaggcagtt acgttgctat tcactacggc aatgttctta ttactcaatc ccatacggat    360

gtggctgagc aactgccgcc ggaagcgcta ttccgaaaaa acaacgctcg tctgaaccaa    420

tggactcttg aggagagtat tgagggaagc ggcccgcaac gatacatcgt cgttacgcat    480

gggccaacta aggagaatcc tgaagaactt ggcttcattc aggcaggttt tctgcacccg    540

aacggacata agtacgttta tcagtatgat cttctcaaac tacctgtcag ccagattatc    600

ggtgtaatcg aaactaccga tgatatcgaa atcaagctcg atatcatcga ggaagcaaag    660

gaagaaggcg aggagggcta a                                                681
```

```
<210> SEQ ID NO 110
<211> LENGTH: 226
<212> TYPE: PRT
<213> ORGANISM: Deinococcus geothermalis, DSM11300

<400> SEQUENCE: 110

Met Pro Thr Ile Pro Leu Phe Pro Gly Phe Thr Pro Val Arg Tyr Thr
1               5                   10                  15

Glu Ala Asp Phe Arg Arg Asp Val Glu Thr Phe Gly Phe Leu Ala Ile
            20                  25                  30

Arg Arg Leu Thr Glu Arg Val Tyr Gln Glu Ala Pro Gly Glu Val Arg
        35                  40                  45

Arg Ile Phe Ser Glu Leu Pro Glu Val Arg Arg Met Ile Gly Gln Val
    50                  55                  60

Arg His Ser Leu Met Glu Gln Glu Met Arg Ala Leu Gly Arg Arg Gly
65                  70                  75                  80

Asp Ile Ser Gln Leu Ser Ala Lys Asp Glu Gln Leu Arg Ser Arg Arg
                85                  90                  95

Gly Cys Ile Lys Pro Gly Ser Tyr Val Ala Ile His Tyr Gly Asn Val
            100                 105                 110

Leu Ile Thr Gln Ser His Thr Asp Val Ala Glu Gln Leu Pro Pro Glu
        115                 120                 125

Ala Leu Phe Arg Lys Asn Asn Ala Arg Leu Asn Gln Trp Thr Leu Glu
    130                 135                 140

Glu Ser Ile Glu Gly Ser Gly Pro Gln Arg Tyr Ile Val Val Thr His
145                 150                 155                 160

Gly Pro Thr Lys Glu Asn Pro Glu Glu Leu Gly Phe Ile Gln Ala Gly
                165                 170                 175

Phe Leu His Pro Asn Gly His Lys Tyr Val Tyr Gln Tyr Asp Leu Leu
            180                 185                 190

Lys Leu Pro Val Ser Gln Ile Ile Gly Val Ile Glu Thr Thr Asp Asp
        195                 200                 205

Ile Glu Ile Lys Leu Asp Ile Ile Glu Glu Ala Lys Glu Glu Gly Glu
    210                 215                 220

Glu Gly
225

<210> SEQ ID NO 111
<211> LENGTH: 987
<212> TYPE: DNA
```

<213> ORGANISM: Ehrlichia canis Jake

<400> SEQUENCE: 111
atggtattac aaaacgacaa cattactgat gatacacaga ataataaaga tgaagtgcac 60
gatacacaac aatctacaga aatagtcaaa gaatcctctg tggtcacatc agaaacacag 120
ccaacacatg ataaaaaatt agataaaata gactttaaca cattgttttt agcaatctct 180
tttgctgggc tattaataga agctgcatct gctatattta atttagtttc aacctatgtt 240
tatgtacccg aacgtattaa gcacatagta gctactgcat tttatgccat atctataatt 300
gtttcattat ccatgatggc aagttcaata cttgcaatca agcagtcgtt aaacagtaag 360
aaaaagcttc aagaaacatc aacaggtcca aacaaggaag cagaaagaag cataaatgaa 420
gggttgttag gatatgataa attaaaacaa aaacaagcta atattcaaat ttccgaaaat 480
actataacta ttatctcaga aatcttatgg ataatagttt ctgctgcatc attagtaatg 540
attactgtag gtactggtac tccagcgctt gaacttgcaa gtttatgtct tgcagttatt 600
gcaccttttt tagcttttat ttcttgcgct ttaagattat cagatgcaaa tatatcaaga 660
aaaacagcta cttctaacaa agaaaaaaga cacgctagta atttcacagt tttatgcact 720
attattttac tatttgaagc aatccattgc ggttgccatg tagctgaagc agttatgctt 780
ggtggaaaga tgcaaaatat ctatgatttt caagatgcta ttgtacttgg cctagagctg 840
gcagcagtag ttatgtttat tgcagcattt tttatagaaa agtaccttga caaaaaagct 900
gaaaaatctg atcctcaagc taccccctagt agcctactag atgataaagc tatagataga 960
atgttccgtg aagctcaaat atcttaa 987

<210> SEQ ID NO 112
<211> LENGTH: 328
<212> TYPE: PRT
<213> ORGANISM: Ehrlichia canis Jake

<400> SEQUENCE: 112

Met Val Leu Gln Asn Asp Asn Ile Thr Asp Asp Thr Gln Asn Asn Lys
1               5                   10                  15

Asp Glu Val His Asp Thr Gln Gln Ser Thr Glu Ile Val Lys Glu Ser
            20                  25                  30

Ser Val Val Thr Ser Glu Thr Gln Pro Thr His Asp Lys Lys Leu Asp
        35                  40                  45

Lys Ile Asp Phe Asn Thr Leu Phe Leu Ala Ile Ser Phe Ala Gly Leu
    50                  55                  60

Leu Ile Glu Ala Ala Ser Ala Ile Phe Asn Leu Val Ser Thr Tyr Val
65                  70                  75                  80

Tyr Val Pro Glu Arg Ile Lys His Ile Val Ala Thr Ala Phe Tyr Ala
                85                  90                  95

Ile Ser Ile Ile Val Ser Leu Ser Met Met Ala Ser Ser Ile Leu Ala
            100                 105                 110

Ile Lys Gln Ser Leu Asn Ser Lys Lys Lys Leu Gln Glu Thr Ser Thr
        115                 120                 125

Gly Pro Asn Lys Glu Ala Glu Arg Ser Ile Asn Glu Gly Leu Leu Gly
    130                 135                 140

Tyr Asp Lys Leu Lys Gln Lys Gln Ala Asn Ile Gln Ile Ser Glu Asn
145                 150                 155                 160

Thr Ile Thr Ile Ile Ser Glu Ile Leu Trp Ile Ile Val Ser Ala Ala
                165                 170                 175

Ser Leu Val Met Ile Thr Val Gly Thr Gly Thr Pro Ala Leu Glu Leu

```
            180                 185                 190

Ala Ser Leu Cys Leu Ala Val Ile Ala Pro Phe Leu Ala Phe Ile Ser
        195                 200                 205

Cys Ala Leu Arg Leu Ser Asp Ala Asn Ile Ser Arg Lys Thr Ala Thr
    210                 215                 220

Ser Asn Lys Glu Lys Arg His Ala Ser Asn Phe Thr Val Leu Cys Thr
225                 230                 235                 240

Ile Ile Leu Leu Phe Glu Ala Ile His Cys Gly Cys His Val Ala Glu
                245                 250                 255

Ala Val Met Leu Gly Gly Lys Met Gln Asn Ile Tyr Asp Phe Gln Asp
            260                 265                 270

Ala Ile Val Leu Gly Leu Glu Leu Ala Ala Val Val Met Phe Ile Ala
        275                 280                 285

Ala Phe Phe Ile Glu Lys Tyr Leu Asp Lys Lys Ala Glu Lys Ser Asp
    290                 295                 300

Pro Gln Ala Thr Pro Ser Ser Leu Leu Asp Asp Lys Ala Ile Asp Arg
305                 310                 315                 320

Met Phe Arg Glu Ala Gln Ile Ser
                325


<210> SEQ ID NO 113
<211> LENGTH: 1218
<212> TYPE: DNA
<213> ORGANISM: Methanosarcina barkeri Fusaro

<400> SEQUENCE: 113

atgctcaaaa aaatagcagt actcatgacc atatttctca tatcgttaca agctgcatct     60

gcagcagata tcgggattgg agtcagtccc ggaaagatga gtttcgagct taatcccggg    120

gctcaggaag aacaactgtt atacgtgatt aatactggca gtgaaactgc aagttatgag    180

atcaatatcg ataattctac atatgaaagc tggttctcta tgccctcctc ttctttcagc    240

ctgcagtcag gggaaaacaa ggaggtaaaa gtaacagtta ctgtaccttc ttctgcagaa    300

accgatgtgg actgtaaaat tttggttcag ccaacgtccg gaaccgaagt gatgacagga    360

ataagagttc cggtccatat aaatgtggtt agtttcactt ccaacgattc ttccgggagc    420

tctggtgtct ctggtgtctc tgatggctct gatggttctg acggctctga cggctctgac    480

ggctctgacg gctctgatga ctctggtgtc tctggtggct cttcccatgg ctcgtcttct    540

ggtggaggtg gaggttctcc cgaacctgct agtaatgtta agaacaagga actttcccaa    600

cagttcgtta caaatggaaa tcatattgaa tttaagtttc ctgaggaagc tactccagtt    660

acttatgtag aatttgatgc taaaaagagt gcaggaaaaa tcaccactat tgttgaagaa    720

ctgaaagaaa aatcaacgct aactacaacc gaacctgaag gaaatattta tcattacctg    780

aatatttggg taggaaacgg aggttttgca acccaggaaa atattgacaa ttcagttgta    840

ggtttcaggg taagtaaatc atgggtcaaa gaaaacaaca ttgatgtgga ttcaatcgct    900

cttcaacact ttgtagatga tacatggaac tcactttcaa gcgccagagt acgtgaagga    960

gatgaatatt tttattttga agcaaaaacc tccggtttct cttcatttgc gataaccggg   1020

gagactatcg aatcttcaac caaaatcaac aaagcagatg atgtggaatc caattctcaa   1080

gacatacaga ctaagtcttc tcctgaaagt gaaaacgaag aagataaaga tgcaaaagcc   1140

agtcccggat tttgcacttt ttttgtcggt gtaggattta cagtttctgc taccatttta   1200

aaaaggagag ggatttga                                                1218
```

<210> SEQ ID NO 114
<211> LENGTH: 405
<212> TYPE: PRT
<213> ORGANISM: Methanosarcina barkeri Fusaro

<400> SEQUENCE: 114

```
Met Leu Lys Lys Ile Ala Val Leu Met Thr Ile Phe Leu Ile Ser Leu
1               5                   10                  15

Gln Ala Ala Ser Ala Ala Asp Ile Gly Ile Gly Val Ser Pro Gly Lys
            20                  25                  30

Met Ser Phe Glu Leu Asn Pro Gly Ala Gln Glu Glu Gln Leu Leu Tyr
        35                  40                  45

Val Ile Asn Thr Gly Ser Glu Thr Ala Ser Tyr Glu Ile Asn Ile Asp
    50                  55                  60

Asn Ser Thr Tyr Glu Ser Trp Phe Ser Met Pro Ser Ser Ser Phe Ser
65                  70                  75                  80

Leu Gln Ser Gly Glu Asn Lys Glu Val Lys Val Thr Val Thr Val Pro
                85                  90                  95

Ser Ser Ala Glu Thr Asp Val Asp Cys Lys Ile Leu Val Gln Pro Thr
            100                 105                 110

Ser Gly Thr Glu Val Met Thr Gly Ile Arg Val Pro Val His Ile Asn
        115                 120                 125

Val Val Ser Phe Thr Ser Asn Asp Ser Ser Gly Ser Ser Gly Val Ser
    130                 135                 140

Gly Val Ser Asp Gly Ser Asp Gly Ser Asp Gly Ser Asp Gly Ser Asp
145                 150                 155                 160

Gly Ser Asp Gly Ser Asp Asp Ser Gly Val Ser Gly Gly Ser Ser His
                165                 170                 175

Gly Ser Ser Ser Gly Gly Gly Gly Gly Ser Pro Glu Pro Ala Ser Asn
            180                 185                 190

Val Lys Asn Lys Glu Leu Ser Gln Gln Phe Val Thr Asn Gly Asn His
        195                 200                 205

Ile Glu Phe Lys Phe Pro Glu Glu Ala Thr Pro Val Thr Tyr Val Glu
    210                 215                 220

Phe Asp Ala Lys Lys Ser Ala Gly Lys Ile Thr Thr Ile Val Glu Glu
225                 230                 235                 240

Leu Lys Glu Lys Ser Thr Leu Thr Thr Thr Glu Pro Glu Gly Asn Ile
                245                 250                 255

Tyr His Tyr Leu Asn Ile Trp Val Gly Asn Gly Gly Phe Ala Thr Gln
            260                 265                 270

Glu Asn Ile Asp Asn Ser Val Val Gly Phe Arg Val Ser Lys Ser Trp
        275                 280                 285

Val Lys Glu Asn Asn Ile Asp Val Asp Ser Ile Ala Leu Gln His Phe
    290                 295                 300

Val Asp Asp Thr Trp Asn Ser Leu Ser Ser Ala Arg Val Arg Glu Gly
305                 310                 315                 320

Asp Glu Tyr Phe Tyr Phe Glu Ala Lys Thr Ser Gly Phe Ser Ser Phe
                325                 330                 335

Ala Ile Thr Gly Glu Thr Ile Glu Ser Ser Thr Lys Ile Asn Lys Ala
            340                 345                 350

Asp Asp Val Glu Ser Asn Ser Gln Asp Ile Gln Thr Lys Ser Ser Pro
        355                 360                 365

Glu Ser Glu Asn Glu Glu Asp Lys Asp Ala Lys Ala Ser Pro Gly Phe
    370                 375                 380

Cys Thr Phe Phe Val Gly Val Gly Phe Thr Val Ser Ala Thr Ile Leu
```

385 390 395 400

Lys Arg Arg Gly Ile
405

<210> SEQ ID NO 115
<211> LENGTH: 534
<212> TYPE: DNA
<213> ORGANISM: Methylobacillus flagellatus strain KT

<400> SEQUENCE: 115
atgaagttca tcaagactct gctggcctct gtagcgttca ttgctgtggc taccagtgca 60
aatgctgctc ctgaagtaaa gggtgatttt ggtcttatca ctgaccttac atttactgag 120
ttgcctgtaa ccgtaggcgc tgcttctact tttgatcata ttttcaagtt tgaattgaat 180
tcgccagctg ctgatttttc agttagcaaa ttgattttaa cgcatggccc agcaacaatc 240
tgggattttt ctacaattac atttaatgtt tttgctggtg aatttgtttc tgatgtgaca 300
gatggcgcat tgttgaatgt ggctcctgtt gtgactgctg atactgttga gttcactttg 360
aatggtttgg acgttggtca ttatttcatt caagttgcag gtaattccag tggcatcgct 420
ggtggcgcat atactttgc cattactcca gtaccagaac caagcagcgt tgccatgttg 480
ctgatcggtt ttgctgcgct gggtgctgtt gctcggcgtc gcaagacact gtaa 534

<210> SEQ ID NO 116
<211> LENGTH: 177
<212> TYPE: PRT
<213> ORGANISM: Methylobacillus flagellatus strain KT

<400> SEQUENCE: 116

Met Lys Phe Ile Lys Thr Leu Leu Ala Ser Val Ala Phe Ile Ala Val
1 5 10 15

Ala Thr Ser Ala Asn Ala Ala Pro Glu Val Lys Gly Asp Phe Gly Leu
20 25 30

Ile Thr Asp Leu Thr Phe Thr Glu Leu Pro Val Thr Val Gly Ala Ala
35 40 45

Ser Thr Phe Asp His Ile Phe Lys Phe Glu Leu Asn Ser Pro Ala Ala
50 55 60

Asp Phe Ser Val Ser Lys Leu Ile Leu Thr His Gly Pro Ala Thr Ile
65 70 75 80

Trp Asp Phe Ser Thr Ile Thr Phe Asn Val Phe Ala Gly Glu Phe Val
85 90 95

Ser Asp Val Thr Asp Gly Ala Leu Leu Asn Val Ala Pro Val Val Thr
100 105 110

Ala Asp Thr Val Glu Phe Thr Leu Asn Gly Leu Asp Val Gly His Tyr
115 120 125

Phe Ile Gln Val Ala Gly Asn Ser Ser Gly Ile Ala Gly Gly Ala Tyr
130 135 140

Thr Phe Ala Ile Thr Pro Val Pro Glu Pro Ser Ser Val Ala Met Leu
145 150 155 160

Leu Ile Gly Phe Ala Ala Leu Gly Ala Val Ala Arg Arg Arg Lys Thr
165 170 175

Leu

<210> SEQ ID NO 117
<211> LENGTH: 681
<212> TYPE: DNA
<213> ORGANISM: Methylobacillus flagellatus strain KT

<400> SEQUENCE: 117

```
atgaacatga catccgttcg tgccatcatt ggtgccagcc ttcttgccgt agcaagcctt     60
gctcaagcga atgcaaccca tgagagtttt attgacgttg cagggtccgt gtcctttgac    120
ggctggaacc aactgaatcg caaccgcacc gatgccaagg gcaaccccga cccattgacc    180
tccgcacaac tggaagccgg taccgctggc aatgtagcag gttcaggcga tgcactactg    240
acactgattt ccggctccta ctatcctgca ggtgcgggcc tgtatggtaa tgcttccatc    300
acctttagcg acaacaccgt tgccagcaac atctcctccc tcgcattcca aggcatcatc    360
aatgactttg atggatcctt tggcggcacc ccattctcct tgagcctgag ctacaatggt    420
ggcgatcagg ccattgccgg cacattggtc aacttcgttg ataccggcac cgctgccgac    480
tattactatt tcacctggga tctgagcggt atttccacgc ccatcacttc ctacaccctc    540
aatttcgaca tcggcttctc ccagtcgctg gctttccaga ttgaccaagt agccgcagta    600
cctgaaccat ccacctatgc catgctcatg ctgggcctgg gtgcagtagg cttcgcagca    660
cgtcgtcgca agcaagccta a                                              681
```

<210> SEQ ID NO 118
<211> LENGTH: 226
<212> TYPE: PRT
<213> ORGANISM: Methylobacillus flagellatus strain KT

<400> SEQUENCE: 118

```
Met Asn Met Thr Ser Val Arg Ala Ile Ile Gly Ala Ser Leu Leu Ala
1               5                   10                  15

Val Ala Ser Leu Ala Gln Ala Asn Ala Thr His Glu Ser Phe Ile Asp
            20                  25                  30

Val Ala Gly Ser Val Ser Phe Asp Gly Trp Asn Gln Leu Asn Arg Asn
        35                  40                  45

Arg Thr Asp Ala Lys Gly Asn Pro Asp Pro Leu Thr Ser Ala Gln Leu
    50                  55                  60

Glu Ala Gly Thr Ala Gly Asn Val Ala Gly Ser Gly Asp Ala Leu Leu
65                  70                  75                  80

Thr Leu Ile Ser Gly Ser Tyr Tyr Pro Ala Gly Ala Gly Leu Tyr Gly
                85                  90                  95

Asn Ala Ser Ile Thr Phe Ser Asp Asn Thr Val Ala Ser Asn Ile Ser
            100                 105                 110

Ser Leu Ala Phe Gln Gly Ile Ile Asn Asp Phe Asp Gly Ser Phe Gly
        115                 120                 125

Gly Thr Pro Phe Ser Leu Ser Leu Ser Tyr Asn Gly Gly Asp Gln Ala
    130                 135                 140

Ile Ala Gly Thr Leu Val Asn Phe Val Asp Thr Gly Thr Ala Ala Asp
145                 150                 155                 160

Tyr Tyr Tyr Phe Thr Trp Asp Leu Ser Gly Ile Ser Thr Pro Ile Thr
                165                 170                 175

Ser Tyr Thr Leu Asn Phe Asp Ile Gly Phe Ser Gln Ser Leu Ala Phe
            180                 185                 190

Gln Ile Asp Gln Val Ala Ala Val Pro Glu Pro Ser Thr Tyr Ala Met
        195                 200                 205

Leu Met Leu Gly Leu Gly Ala Val Gly Phe Ala Ala Arg Arg Arg Lys
    210                 215                 220

Gln Ala
225
```

-continued

<210> SEQ ID NO 119
<211> LENGTH: 498
<212> TYPE: DNA
<213> ORGANISM: Nitrobacter winogradskyi Nb-255

<400> SEQUENCE: 119
atgggattcg gggggatcat gtctcgagga ttgtccgccg cgtgcgcgtt aggcgccgtg 60
gtgatgctgt cgatgtcgac cagcctggcg ggggctggcc cgtttgaagg tttggcgggg 120
atctggaccg gacgtggcac gatacagctc gaggacggat cgaccgaaaa gattcgatgc 180
aaagccactt atgcggtcag cggcgatgct cagggcctca atcagaccct gctctgcgcc 240
agcgacagct acaagttcga gctcaaaagc aacgtgctcg ctcgcaacgg cgttctgtct 300
ggagactggc gcgagaccag ccgcaatgtt ggcggcaccc tcgaaggccg tgccggtaat 360
ggccagttca acgtcgacgt cagcgctccc gcatttaccg cgaagctcaa actgaagacg 420
aacggcaacc ggcaggacgt ggtcatcagt tccgacgggc agttcaaggg cgccagtatt 480
tctctgtcgc gttcctga 498

<210> SEQ ID NO 120
<211> LENGTH: 165
<212> TYPE: PRT
<213> ORGANISM: Nitrobacter winogradskyi Nb-255

<400> SEQUENCE: 120

Met Gly Phe Gly Gly Ile Met Ser Arg Gly Leu Ser Ala Ala Cys Ala
1 5 10 15

Leu Gly Ala Val Val Met Leu Ser Met Ser Thr Ser Leu Ala Gly Ala
20 25 30

Gly Pro Phe Glu Gly Leu Ala Gly Ile Trp Thr Gly Arg Gly Thr Ile
35 40 45

Gln Leu Glu Asp Gly Ser Thr Glu Lys Ile Arg Cys Lys Ala Thr Tyr
50 55 60

Ala Val Ser Gly Asp Ala Gln Gly Leu Asn Gln Thr Leu Leu Cys Ala
65 70 75 80

Ser Asp Ser Tyr Lys Phe Glu Leu Lys Ser Asn Val Leu Ala Arg Asn
85 90 95

Gly Val Leu Ser Gly Asp Trp Arg Glu Thr Ser Arg Asn Val Gly Gly
100 105 110

Thr Leu Glu Gly Arg Ala Gly Asn Gly Gln Phe Asn Val Asp Val Ser
115 120 125

Ala Pro Ala Phe Thr Ala Lys Leu Lys Leu Lys Thr Asn Gly Asn Arg
130 135 140

Gln Asp Val Val Ile Ser Ser Asp Gly Gln Phe Lys Gly Ala Ser Ile
145 150 155 160

Ser Leu Ser Arg Ser
165

<210> SEQ ID NO 121
<211> LENGTH: 960
<212> TYPE: DNA
<213> ORGANISM: Nitrosococcus oceani ATCC 19707

<400> SEQUENCE: 121
atgactttta gagataaagt ccaagttagg gaggaagata tgaagaataa aaaaaccatg 60
gcaatcatgg caatatttac gccattattg ctagctgttt atacatccgc gctagcggag 120
gacgatcatc ccctgtatgc gccctataag ggctggccgc catgcgctgt tatgacgggg 180

-continued

```
gaaggagata tggcacctga tggcagatca gtcacgggag tcatttgccg ttcgactctc    240

tttattccag atagcgataa agacggagtc ccggacgata aggatcaatg ccctaataca    300

cctccaggcg ttgaagtgga cgaagtcggc tgccccctgg acagtgacaa cgatggcgtg    360

ccggactacc ttgatcaatg ccccgatacg cctatgggag tagaggtagg agaagatggc    420

tgccccctgg atagcgacgg cgatggcgtg ccggattatc tcgatcaatg tcccgataca    480

cccatgggag tagaggtaaa cagccaaggc tgccccctaa gcgtggacag tgatggcgac    540

ggagtgcccg atgatatcga tgagtgcccc gatacagcgt atggggttga cgtggacgag    600

gtgggttgtc ccaagcctgt cgtgcttgaa gacggtgttc attttggatt tgattccgcc    660

aagctgtctc ccaatgccca taccatccta gataaggtcg tggaaaatat gcgcacttat    720

cctgatttag aaatcaccat tgctggtcat acagatagca ccggtaacgc ggattacaac    780

caacgccttt cccagcttcg cgccgaggcg gccatgaact atctggcctc caagggtatt    840

gatccatcga ggatggaagc aataggctat ggagaagaac gcccgattgc ctccaattcc    900

accaaggaag gccgggccaa aaatcgccgg gttgaacttc aaacccacga cgaggattaa    960
```

```
<210> SEQ ID NO 122
<211> LENGTH: 319
<212> TYPE: PRT
<213> ORGANISM: Nitrosococcus oceani ATCC 19707

<400> SEQUENCE: 122

Met Thr Phe Arg Asp Lys Val Gln Val Arg Glu Glu Asp Met Lys Asn
1               5                   10                  15

Lys Lys Thr Met Ala Ile Met Ala Ile Phe Thr Pro Leu Leu Leu Ala
            20                  25                  30

Val Tyr Thr Ser Ala Leu Ala Glu Asp Asp His Pro Leu Tyr Ala Pro
        35                  40                  45

Tyr Lys Gly Trp Pro Pro Cys Ala Val Met Thr Gly Glu Gly Asp Met
    50                  55                  60

Ala Pro Asp Gly Arg Ser Val Thr Gly Val Ile Cys Arg Ser Thr Leu
65                  70                  75                  80

Phe Ile Pro Asp Ser Asp Lys Asp Gly Val Pro Asp Asp Lys Asp Gln
                85                  90                  95

Cys Pro Asn Thr Pro Pro Gly Val Glu Val Asp Glu Val Gly Cys Pro
            100                 105                 110

Leu Asp Ser Asp Asn Asp Gly Val Pro Asp Tyr Leu Asp Gln Cys Pro
        115                 120                 125

Asp Thr Pro Met Gly Val Glu Val Gly Glu Asp Gly Cys Pro Leu Asp
    130                 135                 140

Ser Asp Gly Asp Gly Val Pro Asp Tyr Leu Asp Gln Cys Pro Asp Thr
145                 150                 155                 160

Pro Met Gly Val Glu Val Asn Ser Gln Gly Cys Pro Leu Ser Val Asp
                165                 170                 175

Ser Asp Gly Asp Gly Val Pro Asp Asp Ile Asp Glu Cys Pro Asp Thr
            180                 185                 190

Ala Tyr Gly Val Asp Val Asp Glu Val Gly Cys Pro Lys Pro Val Val
        195                 200                 205

Leu Glu Asp Gly Val His Phe Gly Phe Asp Ser Ala Lys Leu Ser Pro
    210                 215                 220

Asn Ala His Thr Ile Leu Asp Lys Val Val Glu Asn Met Arg Thr Tyr
225                 230                 235                 240

Pro Asp Leu Glu Ile Thr Ile Ala Gly His Thr Asp Ser Thr Gly Asn
```

-continued 245 250 255

Ala Asp Tyr Asn Gln Arg Leu Ser Gln Leu Arg Ala Glu Ala Ala Met
260 265 270

Asn Tyr Leu Ala Ser Lys Gly Ile Asp Pro Ser Arg Met Glu Ala Ile
275 280 285

Gly Tyr Gly Glu Glu Arg Pro Ile Ala Ser Asn Ser Thr Lys Glu Gly
290 295 300

Arg Ala Lys Asn Arg Arg Val Glu Leu Gln Thr His Asp Glu Asp
305 310 315

<210> SEQ ID NO 123
<211> LENGTH: 216
<212> TYPE: DNA
<213> ORGANISM: Polaromonas sp. JS666

<400> SEQUENCE: 123
ttgattaagt gccacttgtc caagttgatg ggggagcgaa agctcaagat cagcgatgtg 60
gcgcgcgata caggattgca tcggaacacc gtcacgctgc tctaccagga gacagccacc 120
cggatcgata tcgaagcaat ggatgccctg tgcagatact tcagtgttcg cgtgggggat 180
ctctttgagt tcattgacaa ctcaacccca gcatag 216

<210> SEQ ID NO 124
<211> LENGTH: 71
<212> TYPE: PRT
<213> ORGANISM: Polaromonas sp. JS666

<400> SEQUENCE: 124

Met Ile Lys Cys His Leu Ser Lys Leu Met Gly Glu Arg Lys Leu Lys
1 5 10 15

Ile Ser Asp Val Ala Arg Asp Thr Gly Leu His Arg Asn Thr Val Thr
20 25 30

Leu Leu Tyr Gln Glu Thr Ala Thr Arg Ile Asp Ile Glu Ala Met Asp
35 40 45

Ala Leu Cys Arg Tyr Phe Ser Val Arg Val Gly Asp Leu Phe Glu Phe
50 55 60

Ile Asp Asn Ser Thr Pro Ala
65 70

<210> SEQ ID NO 125
<211> LENGTH: 2067
<212> TYPE: DNA
<213> ORGANISM: Pseudoalteromonas atlantica T6c

<400> SEQUENCE: 125
atgagtcgtg aattcttcgg gtttaaaaag tcgcctatag cgttaggtgt gatggggctt 60
atgggcgcag caatgatgcc agcgcaagcc gccagttgga gtgatggcga ttggtcagtt 120
acctttgact cgaacttttc tttgggtacc agcattcgtg ttgaagagcg cgatttctca 180
cgcgtgggta atagtaacgg tgtacagttt gattggacag gttataaccc tgctaccaat 240
cctatttaca gctcagctga cgtgtgggca ttaggtacag gtggttactc gacaaatggt 300
gacttaagca ccctgaacta cgaaaaagga aacccatttt cgacgctgtt caaaggcgtg 360
catgaacttg atatccaata caaaaacatg ggcgttttca tgcgtggaat gtatttctac 420
gactttgaaa tgaaagatag ttcgcgggat tggcagaatc cgattacagg taaaacacaa 480
gacccttgtg cttcgtctac cgctaatgat gaactatgtt cagatgtacg tttgttagac 540
gcctacttct actctgattt ctatatcggc gatatgccgg tcacattccg agtgggtgac 600

-continued

```
caagtggtga gctggggtga aagtacgttc attcagcatg gtattaactc aaccaaccct    660

gtggatgtct ctcgtgctca agcaccaggt gctgagctta aagaagtctt tattccagtg    720

gggatggtat tcgctcagtt tggtttgacc gaaaatttaa gcttgtctat gtactaccag    780

tatcagtggg agcgtagccg attaccacaa gcaggtagtt acttcgctac caatgacttt    840

gctggcgaag gcggtcaagc gcagaatatc cagttaggtt ttagtggtaa ccctgatatc    900

gatttggatt tcttgttatc aagtttgaac gggcttggag atttactacg aagtggtgct    960

gatgcagctc aaataggtca ggcctattta gcttatccaa ctaaagtggc tgtgcgtggt   1020

tatagtgatt ccgcacatga agatgcagac gaccaaggtc agtatgggat aaaaattggt   1080

tactacgcag aagacttgaa cgaaactgag ttcaatttct atatgcttaa ctaccacagc   1140

caacgcccat taatctctgg gttaacgtct gattttactt ctgcaagtat tgccgctgat   1200

cttggtatgt tggccacaac tgaaatcact aaagacaatg taacagacct taaagctttc   1260

acgaaaacag gctttgttta tcctgaagac ttgaaactgt atggctttag ttttaacacc   1320

aatgtaggta caacagctct tgcgggggaa atcgcgtacc gtgttgatga acctctgcag   1380

atagatgacg ttgaactgtt gtatgctgcg atgccacagc aattagcgat tgcgggttta   1440

cgtcctgatt tagcgggtat ttctcaacta gacggatatc aaggatttac aacggggcct   1500

ggggaaacgg caacgggcta cattgagtct gatacattgc aaatgcaagt cacagcaaca   1560

catatttttg gccctgcttt gggtacggat aatttagtgg tgttgggcga agttgggtat   1620

gtcagcattc aagacttccc ggatccaaat gttattcgac taaatggtcc tggttctgtg   1680

cgtacgcctt cgcttgagcc aacagcggat ggtaacaccc gagaaggttt gcatattggt   1740

ctgtctgatg gcccagaaac aaacccattc ccaacgtcga gtgcttgggg ataccgctta   1800

ctggctaatg cgtcatttaa caacgttttc gctggtatta atctgcaagc acgtggcacc   1860

tttgcacatg atgtaaatgg tattacgcct gatccattat tcttatttat cgaagataga   1920

aaatcagcta gcgcgtcatt aacgtttgat tatttaagca aatggtcagc aacggcttct   1980

tataacacgt tctggggcgg tcaaggcacc accaaccagc tgtcggatcg tgattatgtc   2040

tcttttaaca tcaagtattc tatctag                                       2067
```

```
<210> SEQ ID NO 126
<211> LENGTH: 688
<212> TYPE: PRT
<213> ORGANISM: Pseudoalteromonas atlantica T6c

<400> SEQUENCE: 126

Met Ser Arg Glu Phe Phe Gly Phe Lys Lys Ser Pro Ile Ala Leu Gly
1               5                   10                  15

Val Met Gly Leu Met Gly Ala Ala Met Met Pro Ala Gln Ala Ala Ser
            20                  25                  30

Trp Ser Asp Gly Asp Trp Ser Val Thr Phe Asp Ser Asn Phe Ser Leu
        35                  40                  45

Gly Thr Ser Ile Arg Val Glu Glu Arg Asp Phe Ser Arg Val Gly Asn
    50                  55                  60

Ser Asn Gly Val Gln Phe Asp Trp Thr Gly Tyr Asn Pro Ala Thr Asn
65                  70                  75                  80

Pro Ile Tyr Ser Ser Ala Asp Val Trp Ala Leu Gly Thr Gly Gly Tyr
                85                  90                  95

Ser Thr Asn Gly Asp Leu Ser Thr Leu Asn Tyr Glu Lys Gly Asn Pro
            100                 105                 110
```

```
Phe Ser Thr Leu Phe Lys Gly Val His Glu Leu Asp Ile Gln Tyr Lys
        115                 120                 125

Asn Met Gly Val Phe Met Arg Gly Met Tyr Phe Tyr Asp Phe Glu Met
    130                 135                 140

Lys Asp Ser Ser Arg Asp Trp Gln Asn Pro Ile Thr Gly Lys Thr Gln
145                 150                 155                 160

Asp Pro Cys Ala Ser Ser Thr Ala Asn Asp Glu Leu Cys Ser Asp Val
                165                 170                 175

Arg Leu Leu Asp Ala Tyr Phe Tyr Ser Asp Phe Tyr Ile Gly Asp Met
            180                 185                 190

Pro Val Thr Phe Arg Val Gly Asp Gln Val Val Ser Trp Gly Glu Ser
        195                 200                 205

Thr Phe Ile Gln His Gly Ile Asn Ser Thr Asn Pro Val Asp Val Ser
    210                 215                 220

Arg Ala Gln Ala Pro Gly Ala Glu Leu Lys Glu Val Phe Ile Pro Val
225                 230                 235                 240

Gly Met Val Phe Ala Gln Phe Gly Leu Thr Glu Asn Leu Ser Leu Ser
                245                 250                 255

Met Tyr Tyr Gln Tyr Gln Trp Glu Arg Ser Arg Leu Pro Gln Ala Gly
            260                 265                 270

Ser Tyr Phe Ala Thr Asn Asp Phe Ala Gly Glu Gly Gly Gln Ala Gln
        275                 280                 285

Asn Ile Gln Leu Gly Phe Ser Gly Asn Pro Asp Ile Asp Leu Asp Phe
    290                 295                 300

Leu Leu Ser Ser Leu Asn Gly Leu Gly Asp Leu Leu Arg Ser Gly Ala
305                 310                 315                 320

Asp Ala Ala Gln Ile Gly Gln Ala Tyr Leu Ala Tyr Pro Thr Lys Val
                325                 330                 335

Ala Val Arg Gly Tyr Ser Asp Ser Ala His Glu Asp Ala Asp Asp Gln
            340                 345                 350

Gly Gln Tyr Gly Ile Lys Ile Gly Tyr Tyr Ala Glu Asp Leu Asn Glu
        355                 360                 365

Thr Glu Phe Asn Phe Tyr Met Leu Asn Tyr His Ser Gln Arg Pro Leu
    370                 375                 380

Ile Ser Gly Leu Thr Ser Asp Phe Thr Ser Ala Ser Ile Ala Ala Asp
385                 390                 395                 400

Leu Gly Met Leu Ala Thr Thr Glu Ile Thr Lys Asp Asn Val Thr Asp
                405                 410                 415

Leu Lys Ala Phe Thr Lys Thr Gly Phe Val Tyr Pro Glu Asp Leu Lys
            420                 425                 430

Leu Tyr Gly Phe Ser Phe Asn Thr Asn Val Gly Thr Thr Ala Leu Ala
        435                 440                 445

Gly Glu Ile Ala Tyr Arg Val Asp Glu Pro Leu Gln Ile Asp Asp Val
    450                 455                 460

Glu Leu Leu Tyr Ala Ala Met Pro Gln Gln Leu Ala Ile Ala Gly Leu
465                 470                 475                 480

Arg Pro Asp Leu Ala Gly Ile Ser Gln Leu Asp Gly Tyr Gln Gly Phe
                485                 490                 495

Thr Thr Gly Pro Gly Glu Thr Ala Thr Gly Tyr Ile Glu Ser Asp Thr
            500                 505                 510

Leu Gln Met Gln Val Thr Ala Thr His Ile Phe Gly Pro Ala Leu Gly
        515                 520                 525

Thr Asp Asn Leu Val Val Leu Gly Glu Val Gly Tyr Val Ser Ile Gln
    530                 535                 540
```

```
Asp Phe Pro Asp Pro Asn Val Ile Arg Leu Asn Gly Pro Gly Ser Val
545                 550                 555                 560

Arg Thr Pro Ser Leu Glu Pro Thr Ala Asp Gly Asn Thr Arg Glu Gly
                565                 570                 575

Leu His Ile Gly Leu Ser Asp Gly Pro Glu Thr Asn Pro Phe Pro Thr
            580                 585                 590

Ser Ser Ala Trp Gly Tyr Arg Leu Leu Ala Asn Ala Ser Phe Asn Asn
        595                 600                 605

Val Phe Ala Gly Ile Asn Leu Gln Ala Arg Gly Thr Phe Ala His Asp
    610                 615                 620

Val Asn Gly Ile Thr Pro Asp Pro Leu Phe Leu Phe Ile Glu Asp Arg
625                 630                 635                 640

Lys Ser Ala Ser Ala Ser Leu Thr Phe Asp Tyr Leu Ser Lys Trp Ser
                645                 650                 655

Ala Thr Ala Ser Tyr Asn Thr Phe Trp Gly Gly Gln Gly Thr Thr Asn
            660                 665                 670

Gln Leu Ser Asp Arg Asp Tyr Val Ser Phe Asn Ile Lys Tyr Ser Ile
        675                 680                 685
```

<210> SEQ ID NO 127
<211> LENGTH: 1587
<212> TYPE: DNA
<213> ORGANISM: Pseudoalteromonas atlantica T6c

<400> SEQUENCE: 127

```
atgatagatg aaacctttgt ggatctatcg aggttacagt ttgcgatcac cgcactgttt     60

cattttttat ttgtgcctct aacactgggt atgacgtgga ttttggtcat catggagtcg    120

gtttttgtta tgaccggccg acaaatttat cgcgacatga ctaagttttg gggcaagcta    180

ttcggaatca actttgccat aggggttgcc actgggctaa ctatggagtt tgagttcggc    240

accaattggt cgtactactc acactatgta ggtgacgtgt ttggtgcgcc attggcgata    300

gagggcttaa tggctttctt tttagaatcg acctttgtag gtatgttctt tttaggctgg    360

gacagactaa cgcgccgtca acacttaggc gtaacgttct taatggcggt aggcactaat    420

ctatctgcat tgtggatttt gattgccaac ggttggatgc aaaaccccgt cggcgcggaa    480

tttaactatc aaaccatgcg tatggaaatg actagctttg ctgagctggt gtttaatccc    540

gtggcgcagg ttaagtttat tcatactgtt tccgccggtt atgttgctgc gtcaatgttt    600

gtgcttggga tcagcagtta ttatattcta aaaggacgtg atgtttcttt tgccaaacgt    660

tcattctcgg tggcaagtgg cttcggcttg gcgtcaatat tgtgtgttat tttactaggt    720

gatgagtctg gttacgaagt gggtgaagta caaaaagtga aactggcgac tatcgaagct    780

gagtggcaca cagaagaagc accagcggcg tttaccatgt ttggcttccc tgattcagaa    840

gagcaagtaa ctcatgctgc tattaaaata ccctatgcgt taggcatcat tgctacgcgc    900

tcattagatg aagaagtgga ggggataagc gatttagaga aaaaccatga aaaacgtatt    960

cgtaacggca tgttggctta tgcgtacctc gataaactta gaaatggtca agacacacct   1020

gaaaacatcg ccacgtttga tgagctaaaa gccgatttgg gttatggctt attgctcaag   1080

cgttacacgc caaatgtggt tgatgccacg gaagaaaata ttcaacaagc ggtgaaagac   1140

tccttcccta aagtgggccc gatgttttgg tcatttagga tcatggtggc ctgtggtgtg   1200

gctatgctcg tcgtatttgt actggctttt tactataacg cgcaccgggt tatcgaacag   1260

aaacgttggt tattgtgggc ggcggtattc agtattccac tgccatggat agccattgaa   1320
```

-continued

```
ttcggctggg tggtcgcaga atacggcaga caaccttggg caatttcaga gattttaccc   1380

acgttcttgg caacctcgtc attgaccaca aacgacttga tcatgagtat tgctgggttt   1440

gtcatctttt ataccggctt ggcaatcgtc gaaggttggt taatgctgag atttgttaag   1500

caagggccga gctcattgca caccaataaa tatcattttg aaaagattta ccaagaaccg   1560

gctgaagaac aaggagcgca atcatga                                        1587
```

```
<210> SEQ ID NO 128
<211> LENGTH: 528
<212> TYPE: PRT
<213> ORGANISM: Pseudoalteromonas atlantica T6c

<400> SEQUENCE: 128

Met Ile Asp Glu Thr Phe Val Asp Leu Ser Arg Leu Gln Phe Ala Ile
1               5                   10                  15

Thr Ala Leu Phe His Phe Leu Phe Val Pro Leu Thr Leu Gly Met Thr
            20                  25                  30

Trp Ile Leu Val Ile Met Glu Ser Val Phe Val Met Thr Gly Arg Gln
        35                  40                  45

Ile Tyr Arg Asp Met Thr Lys Phe Trp Gly Lys Leu Phe Gly Ile Asn
    50                  55                  60

Phe Ala Ile Gly Val Ala Thr Gly Leu Thr Met Glu Phe Glu Phe Gly
65                  70                  75                  80

Thr Asn Trp Ser Tyr Tyr Ser His Tyr Val Gly Asp Val Phe Gly Ala
                85                  90                  95

Pro Leu Ala Ile Glu Gly Leu Met Ala Phe Phe Leu Glu Ser Thr Phe
            100                 105                 110

Val Gly Met Phe Phe Leu Gly Trp Asp Arg Leu Thr Arg Arg Gln His
        115                 120                 125

Leu Gly Val Thr Phe Leu Met Ala Val Gly Thr Asn Leu Ser Ala Leu
    130                 135                 140

Trp Ile Leu Ile Ala Asn Gly Trp Met Gln Asn Pro Val Gly Ala Glu
145                 150                 155                 160

Phe Asn Tyr Gln Thr Met Arg Met Glu Met Thr Ser Phe Ala Glu Leu
                165                 170                 175

Val Phe Asn Pro Val Ala Gln Val Lys Phe Ile His Thr Val Ser Ala
            180                 185                 190

Gly Tyr Val Ala Ala Ser Met Phe Val Leu Gly Ile Ser Ser Tyr Tyr
        195                 200                 205

Ile Leu Lys Gly Arg Asp Val Ser Phe Ala Lys Arg Ser Phe Ser Val
    210                 215                 220

Ala Ser Gly Phe Gly Leu Ala Ser Ile Leu Cys Val Ile Leu Leu Gly
225                 230                 235                 240

Asp Glu Ser Gly Tyr Glu Val Gly Glu Val Gln Lys Val Lys Leu Ala
                245                 250                 255

Thr Ile Glu Ala Glu Trp His Thr Glu Glu Ala Pro Ala Ala Phe Thr
            260                 265                 270

Met Phe Gly Phe Pro Asp Ser Glu Glu Gln Val Thr His Ala Ala Ile
        275                 280                 285

Lys Ile Pro Tyr Ala Leu Gly Ile Ile Ala Thr Arg Ser Leu Asp Glu
    290                 295                 300

Glu Val Glu Gly Ile Ser Asp Leu Glu Lys Asn His Glu Lys Arg Ile
305                 310                 315                 320

Arg Asn Gly Met Leu Ala Tyr Ala Tyr Leu Asp Lys Leu Arg Asn Gly
                325                 330                 335
```

```
Gln Asp Thr Pro Glu Asn Ile Ala Thr Phe Asp Glu Leu Lys Ala Asp
            340                 345                 350

Leu Gly Tyr Gly Leu Leu Leu Lys Arg Tyr Thr Pro Asn Val Val Asp
        355                 360                 365

Ala Thr Glu Glu Asn Ile Gln Gln Ala Val Lys Asp Ser Phe Pro Lys
    370                 375                 380

Val Gly Pro Met Phe Trp Ser Phe Arg Ile Met Val Ala Cys Gly Val
385                 390                 395                 400

Ala Met Leu Val Val Phe Val Leu Ala Phe Tyr Tyr Asn Ala His Arg
                405                 410                 415

Val Ile Glu Gln Lys Arg Trp Leu Leu Trp Ala Ala Val Phe Ser Ile
            420                 425                 430

Pro Leu Pro Trp Ile Ala Ile Glu Phe Gly Trp Val Val Ala Glu Tyr
        435                 440                 445

Gly Arg Gln Pro Trp Ala Ile Ser Glu Ile Leu Pro Thr Phe Leu Ala
    450                 455                 460

Thr Ser Ser Leu Thr Thr Asn Asp Leu Ile Met Ser Ile Ala Gly Phe
465                 470                 475                 480

Val Ile Phe Tyr Thr Gly Leu Ala Ile Val Glu Gly Trp Leu Met Leu
                485                 490                 495

Arg Phe Val Lys Gln Gly Pro Ser Ser Leu His Thr Asn Lys Tyr His
            500                 505                 510

Phe Glu Lys Ile Tyr Gln Glu Pro Ala Glu Glu Gln Gly Ala Gln Ser
        515                 520                 525
```

<210> SEQ ID NO 129
<211> LENGTH: 381
<212> TYPE: DNA
<213> ORGANISM: Pseudomonas syringae

<400> SEQUENCE: 129

```
atgtccctga tcaacgaata ccgcgctaca gaagaagcca tcaaagaact gcaagcccgt      60

ttgaagaacc tgtcgcaaga cgacaaactg caaaccgagc tggaattcga aggcaaactg     120

cgcacgctga tgggcgaata ccaaaagtcg ctgcgtgaca tcattgccct gctggatccg     180

gatgccaagg taaacaaggc ccctcgtggc ggcgctgtta aacctgccgg caccaagcgc     240

gcccgtaagg tcaagcaata caagaacccg cacaacggtg aagtcatcga aaccaaaggc     300

ggcaaccaca agacgctgaa agagtggaaa gccaagtggg gcagcgacga cgttgaaagc     360

tgggccactt tgctgggcta a                                               381
```

<210> SEQ ID NO 130
<211> LENGTH: 126
<212> TYPE: PRT
<213> ORGANISM: Pseudomonas syringae

<400> SEQUENCE: 130

```
Met Ser Leu Ile Asn Glu Tyr Arg Ala Thr Glu Glu Ala Ile Lys Glu
1               5                   10                  15

Leu Gln Ala Arg Leu Lys Asn Leu Ser Gln Asp Asp Lys Leu Gln Thr
            20                  25                  30

Glu Leu Glu Phe Glu Gly Lys Leu Arg Thr Leu Met Gly Glu Tyr Gln
        35                  40                  45

Lys Ser Leu Arg Asp Ile Ile Ala Leu Leu Asp Pro Asp Ala Lys Val
    50                  55                  60

Asn Lys Ala Pro Arg Gly Gly Ala Val Lys Pro Ala Gly Thr Lys Arg
```

```
65                  70                  75                  80

Ala Arg Lys Val Lys Gln Tyr Lys Asn Pro His Asn Gly Glu Val Ile
                85                  90                  95

Glu Thr Lys Gly Gly Asn His Lys Thr Leu Lys Glu Trp Lys Ala Lys
            100                 105                 110

Trp Gly Ser Asp Asp Val Glu Ser Trp Ala Thr Leu Leu Gly
        115                 120                 125


<210> SEQ ID NO 131
<211> LENGTH: 339
<212> TYPE: DNA
<213> ORGANISM: Psychrobacter cryohalolentis K5

<400> SEQUENCE: 131

atggcaactt tatatcaatt acatagcagt atggatacgc tcagacgcac tacggaacaa      60

atggcgttgt catggcaggc aggcgatagc atccttttat ttggtacaac cgtcgcattt     120

atagattggt tcaatgcgta tttgggcgat atcgagaata tggaaataga aaccattgct     180

ggtatttacg cgcttgccga cgatgtggca aagttgcatg aaaacaccgc agcgaagctt     240

aatctagcgg caaagctcac tggtatttta agcgatgcag aatgggtagc aatgacccaa     300

gacagccgct ttgataaagt cgtgacgatt gccttatga                            339


<210> SEQ ID NO 132
<211> LENGTH: 112
<212> TYPE: PRT
<213> ORGANISM: Psychrobacter cryohalolentis K5

<400> SEQUENCE: 132

Met Ala Thr Leu Tyr Gln Leu His Ser Ser Met Asp Thr Leu Arg Arg
1               5                   10                  15

Thr Thr Glu Gln Met Ala Leu Ser Trp Gln Ala Gly Asp Ser Ile Leu
            20                  25                  30

Leu Phe Gly Thr Thr Val Ala Phe Ile Asp Trp Phe Asn Ala Tyr Leu
        35                  40                  45

Gly Asp Ile Glu Asn Met Glu Ile Glu Thr Ile Ala Gly Ile Tyr Ala
    50                  55                  60

Leu Ala Asp Asp Val Ala Lys Leu His Glu Asn Thr Ala Ala Lys Leu
65                  70                  75                  80

Asn Leu Ala Ala Lys Leu Thr Gly Ile Leu Ser Asp Ala Glu Trp Val
                85                  90                  95

Ala Met Thr Gln Asp Ser Arg Phe Asp Lys Val Val Thr Ile Ala Leu
            100                 105                 110


<210> SEQ ID NO 133
<211> LENGTH: 849
<212> TYPE: DNA
<213> ORGANISM: Psychrobacter cryohalolentis K5

<400> SEQUENCE: 133

gtgtttgaaa taggagaaat ttataaccgt cgttctgata tacacggtat atataaaggg      60

caacaatatg gtggtatagc aacgcctgcc gagcatccat atatatttat tttcaccggc     120

gatgctggtg gtgagtatgg ttatattgat gattttgatc ctaacggcac gtttaaatat     180

actggtgaag ggcaagaagg tgacatgaaa atgaccaaag gtaatttggc aattcatgac     240

catcaaagaa acaataaaga aatcctactt ttcgaatcaa catcacgagg atttgtacga     300

tttttagggt attgcaatta catttttcat catattgaag aacggccaga tagaaatagc     360
```

-continued

```
gagcttcgtg acgctatcgt ttttcatcta gatatagtta atactaaaaa tattgataaa    420

gctcaaactc tgacttctaa actagttgaa gcccctaaag ccgtttatgt cactaagcct    480

agtaaaggta agtcattaca gcaactacga gagattgcct taagttcaac accaacccac    540

gcaagcactc aagaaaaaat tcaatctatt caaaaccgta gtacagcaat taaactgtat    600

gccaaaaaaa gagctaatgg tatatgcgag ggatgtaatg agatagctcc atttgaaact    660

aaatctggac cttatctcga agtccatcat ctaactaggt tggcagatgg tggtgcggac    720

ttacctcaaa acgtcatcgc attgtgccct acctgtcatc gaaaagctca ctactcttta    780

aatcatttag aatttaataa tcagttaata aacaaagttg ctgctatcga agcagaattt    840

agtgagtaa                                                            849


<210> SEQ ID NO 134
<211> LENGTH: 282
<212> TYPE: PRT
<213> ORGANISM: Psychrobacter cryohalolentis K5

<400> SEQUENCE: 134

Met Phe Glu Ile Gly Glu Ile Tyr Asn Arg Arg Ser Asp Ile His Gly
1               5                   10                  15

Ile Tyr Lys Gly Gln Gln Tyr Gly Gly Ile Ala Thr Pro Ala Glu His
            20                  25                  30

Pro Tyr Ile Phe Ile Phe Thr Gly Asp Ala Gly Gly Glu Tyr Gly Tyr
        35                  40                  45

Ile Asp Asp Phe Asp Pro Asn Gly Thr Phe Lys Tyr Thr Gly Glu Gly
    50                  55                  60

Gln Glu Gly Asp Met Lys Met Thr Lys Gly Asn Leu Ala Ile His Asp
65                  70                  75                  80

His Gln Arg Asn Asn Lys Glu Ile Leu Leu Phe Glu Ser Thr Ser Arg
                85                  90                  95

Gly Phe Val Arg Phe Leu Gly Tyr Cys Asn Tyr Ile Phe His His Ile
            100                 105                 110

Glu Glu Arg Pro Asp Arg Asn Ser Glu Leu Arg Asp Ala Ile Val Phe
        115                 120                 125

His Leu Asp Ile Val Asn Thr Lys Asn Ile Asp Lys Ala Gln Thr Leu
    130                 135                 140

Thr Ser Lys Leu Val Glu Ala Pro Lys Ala Val Tyr Val Thr Lys Pro
145                 150                 155                 160

Ser Lys Gly Lys Ser Leu Gln Gln Leu Arg Glu Ile Ala Leu Ser Ser
                165                 170                 175

Thr Pro Thr His Ala Ser Thr Gln Glu Lys Ile Gln Ser Ile Gln Asn
            180                 185                 190

Arg Ser Thr Ala Ile Lys Leu Tyr Ala Lys Lys Arg Ala Asn Gly Ile
        195                 200                 205

Cys Glu Gly Cys Asn Glu Ile Ala Pro Phe Glu Thr Lys Ser Gly Pro
    210                 215                 220

Tyr Leu Glu Val His His Leu Thr Arg Leu Ala Asp Gly Gly Ala Asp
225                 230                 235                 240

Leu Pro Gln Asn Val Ile Ala Leu Cys Pro Thr Cys His Arg Lys Ala
                245                 250                 255

His Tyr Ser Leu Asn His Leu Glu Phe Asn Asn Gln Leu Ile Asn Lys
            260                 265                 270

Val Ala Ala Ile Glu Ala Glu Phe Ser Glu
        275                 280
```

<210> SEQ ID NO 135
<211> LENGTH: 663
<212> TYPE: DNA
<213> ORGANISM: Rhodoferax ferrireducens DSM 15236

<400> SEQUENCE: 135
atgcgaattt ccgacaaatt acgtgaaaaa attgaagagc aaattgccac aggcgagttg 60
ccgccgggtt gcgccctgga tgaagcgatg ctggtggaag cgcacggtgt gtcacgcacc 120
cctgtgcgtg aggccctgat tcagttggcg tctgatggct tgattgaaat ccggccacgc 180
cgaggggcag tggttgccag cattggccct gcgcgcctga ttgagatgtt cgaagtcatg 240
gcggaactcg aagccatgtg cggacgactg gccgcaagac ggatgacaga ggatgaaaga 300
agcaatttgc gggcagcgta taaggcgtgc gaggtcgcac gtgcagcgca ggacactgac 360
agttattttt actgcaacga gcaatttcac gcggccattt acgcgggcag ccataacaaa 420
tttttgtgtg aacaagcctt tcagctgcaa cgcagattgc gcccttaccg gcgcttgcag 480
ttgcgggtgc gaaagcgtat gggtgtgtca ctcaaagagc ataaatccat tttgcgtttt 540
atcaccgctg ctgatgcaga ttcggcagcc attgcattgc gtgagcatgt cgtggtgcag 600
ggtgagcgct ttggtgactt gcttgcctcc ttggcagagc tggcgccagt ggccactaac 660
taa 663

<210> SEQ ID NO 136
<211> LENGTH: 220
<212> TYPE: PRT
<213> ORGANISM: Rhodoferax ferrireducens DSM 15236

<400> SEQUENCE: 136

Met Arg Ile Ser Asp Lys Leu Arg Glu Lys Ile Glu Glu Gln Ile Ala
1 5 10 15

Thr Gly Glu Leu Pro Pro Gly Cys Ala Leu Asp Glu Ala Met Leu Val
20 25 30

Glu Ala His Gly Val Ser Arg Thr Pro Val Arg Glu Ala Leu Ile Gln
35 40 45

Leu Ala Ser Asp Gly Leu Ile Glu Ile Arg Pro Arg Arg Gly Ala Val
50 55 60

Val Ala Ser Ile Gly Pro Ala Arg Leu Ile Glu Met Phe Glu Val Met
65 70 75 80

Ala Glu Leu Glu Ala Met Cys Gly Arg Leu Ala Ala Arg Arg Met Thr
85 90 95

Glu Asp Glu Arg Ser Asn Leu Arg Ala Ala Tyr Lys Ala Cys Glu Val
100 105 110

Ala Arg Ala Ala Gln Asp Thr Asp Ser Tyr Phe Tyr Cys Asn Glu Gln
115 120 125

Phe His Ala Ala Ile Tyr Ala Gly Ser His Asn Lys Phe Leu Cys Glu
130 135 140

Gln Ala Phe Gln Leu Gln Arg Arg Leu Arg Pro Tyr Arg Arg Leu Gln
145 150 155 160

Leu Arg Val Arg Lys Arg Met Gly Val Ser Leu Lys Glu His Lys Ser
165 170 175

Ile Leu Arg Phe Ile Thr Ala Ala Asp Ala Asp Ser Ala Ala Ile Ala
180 185 190

Leu Arg Glu His Val Val Val Gln Gly Glu Arg Phe Gly Asp Leu Leu
195 200 205

Ala Ser Leu Ala Glu Leu Ala Pro Val Ala Thr Asn 210 215 220

<210> SEQ ID NO 137
<211> LENGTH: 693
<212> TYPE: DNA
<213> ORGANISM: Rubrobacter xylanophilus DSM 9941

<400> SEQUENCE: 137
atggatgccg tctcgcgcgg gccgaagggg agcgacccga tccgggtgga ctccgtggtg 60
gatcttgcgt accgcaggat ccgggacctc gtcctgagcg gggagctcgc gccgggggcg 120
cggctcgggc aggtggagct tgcggagcgg ttcgggatct cgcgcacccc cgtgcgggag 180
gcgctgcggc ggctagcggg cgaggggctc gtggaccaga tctcaaaccg cggcttccgg 240
gtcgccgacc tcggcctcga cgccgtgctg cggcgcctgg aggtgcgggc catcctcgag 300
cccggcatcg cggggctcgc cgcggagcgg cggagcgggc gcgacctgga ggccatgcgg 360
gcggccatcg agcgcgagga gcgggcctca agcggcatcg aggcgcacga cgccagccgc 420
gacttccacc tcgcgctcgc gcgcgccacc ggcaacgagg agctcgtgcg ggtgctcgag 480
tcgctgtggc tcgtcgaggt cgggaggagg ctgctctccc gccggtacgc cgtctccgac 540
tggcaggccg aggacgtcgc cgagcaccgc gagatcctgg ccgccgtaga cgaggggcgc 600
gccccggacg ccgagcggct catggccgag cacgtccgcc gggcggtcca gcactgggag 660
cccgagcgcc ggggcgcccg ggagaccggc tga 693

<210> SEQ ID NO 138
<211> LENGTH: 230
<212> TYPE: PRT
<213> ORGANISM: Rubrobacter xylanophilus DSM 9941

<400> SEQUENCE: 138

Met Asp Ala Val Ser Arg Gly Pro Lys Gly Ser Asp Pro Ile Arg Val
1 5 10 15

Asp Ser Val Val Asp Leu Ala Tyr Arg Arg Ile Arg Asp Leu Val Leu
20 25 30

Ser Gly Glu Leu Ala Pro Gly Ala Arg Leu Gly Gln Val Glu Leu Ala
35 40 45

Glu Arg Phe Gly Ile Ser Arg Thr Pro Val Arg Glu Ala Leu Arg Arg
50 55 60

Leu Ala Gly Glu Gly Leu Val Asp Gln Ile Ser Asn Arg Gly Phe Arg
65 70 75 80

Val Ala Asp Leu Gly Leu Asp Ala Val Leu Arg Arg Leu Glu Val Arg
85 90 95

Ala Ile Leu Glu Pro Gly Ile Ala Gly Leu Ala Ala Glu Arg Arg Ser
100 105 110

Gly Arg Asp Leu Glu Ala Met Arg Ala Ala Ile Glu Arg Glu Glu Arg
115 120 125

Ala Ser Ser Gly Ile Glu Ala His Asp Ala Ser Arg Asp Phe His Leu
130 135 140

Ala Leu Ala Arg Ala Thr Gly Asn Glu Glu Leu Val Arg Val Leu Glu
145 150 155 160

Ser Leu Trp Leu Val Glu Val Gly Arg Arg Leu Leu Ser Arg Arg Tyr
165 170 175

Ala Val Ser Asp Trp Gln Ala Glu Asp Val Ala Glu His Arg Glu Ile
180 185 190

Leu Ala Ala Val Asp Glu Gly Arg Ala Pro Asp Ala Glu Arg Leu Met
195 200 205

Ala Glu His Val Arg Arg Ala Val Gln His Trp Glu Pro Glu Arg Arg
    210                 215                 220

Gly Ala Arg Glu Thr Gly
225                 230

<210> SEQ ID NO 139
<211> LENGTH: 1656
<212> TYPE: DNA
<213> ORGANISM: Rubrobacter xylanophilus DSM 9941

<400> SEQUENCE: 139
atgcaccgat cgtggatcgc cacccctctt ctggccctct tttgttcgc gggggcgtgc 60 gccgggtcgc gggaggatgc cccggacccc ggccggggcg gcgaccgcgg ggacccgggc 120
ggccgggacg ccgccgtctc gagcatagag gacgtgcgga aggccacggt gtacatcgag 180
gcgcggggcg gtgcctacga cgaggggcgg ggcttcgggg aggtcagcta cggcagcggc 240
tcggggttta tcgtgggcga cggcggcggg agcggcaagc tcgtcatcac caacaaccac 300
gtggtgaccg gggcgggctt tctgcaggtg tacctggacg gccaggacga gccggtcgac 360
gccagggtgc tcggcgcctc cgagtgctcg gacctcgcgc tgctggagct cgagggcggc 420
gggtacccct acctctcctg gcggaccggc gacatagacg ccggcctcgg cgtgcgcgcc 480
gccggctacc cggcggacga cgtggagacc ggcgagcggc cagactacac cataaccagc 540
gggagcataa actccaccga ggccgacggc gagacgccct gggcctcggt ggactctgtg 600
ctggagcacg acgtcctgat ccggcccggc aactccggcg ggccgctcgt cgacgagaac 660
gggcgggtgg tgggggtcaa ctacgcctcg cgggtggacg acgaggggcg cccgaccggc 720
ccgcagctgg ccatcgcccg ggacgaggcc cgcaccatcg tggacaagct gcgccagggg 780
gacgtggagt ccatcggggt gaacggcgag gcgttcagcc tcccggagca ggagatctcc 840
ggcatccggg tgacctcggt gaagaccgac tccccggcgg gccgggtggg gctgcgcaac 900
gccgttatcg acccgcagag cggcgagttc gcggccttcg acgtgatcac ggagatcgaa 960
ggcacccggc tcggcgaggg agggacgatg gaggagtatt gcaacatcct ccgccagcac 1020
gagccggacg acaggctcag catccaggcg gtgcgggtgg aggagaacgg cgacgtctcc 1080
ctgatggagg gcgccctgaa cggcgaggag ctggcggtcg tcgagaccat cccggcgcag 1140
accgacgccg gcggagagcc gcaggggggc tttgtctcgc tgaccgacga taccggcacg 1200
ctcaccatgg aggtcccggc cgcctggagc gacgtccgga ccggcgggag cctaaagctg 1260
gacggcgaga gcctggggcc ggccatgctg gcctccaccg acgcccagcg ctggatcgac 1320
accttcgagg tgcctggcgt gtacttcgcg gcctcgagcc gcctcgccga acgcttcccg 1380
gagaaccccg ttgaacagat cctggacctg ccggagtacg atttctccgg cacctgccgg 1440
tacgaggggc gggagggcta ccaggacagc aagttcaccg gcgccgtaga cacctacacc 1500
ggctgcgacg gtacggacaa cgccttccag atctacgccg caacgccccc ggacggctcc 1560
tacgtcgtgg tgctgcaggc cgtcataacc agcgaggccg acctcgacgg gctccagagg 1620
accctcgcca ccttcgacgt cctgcagcag ccctga 1656

<210> SEQ ID NO 140
<211> LENGTH: 551
<212> TYPE: PRT
<213> ORGANISM: Rubrobacter xylanophilus DSM 9941

<400> SEQUENCE: 140

Met His Arg Ser Trp Ile Ala Thr Pro Leu Leu Ala Leu Phe Leu Phe

-continued

```
1               5                   10                  15

Ala Gly Ala Cys Ala Gly Ser Arg Glu Asp Ala Pro Asp Pro Gly Arg
            20                  25                  30

Gly Gly Asp Arg Gly Asp Pro Gly Gly Arg Asp Ala Ala Val Ser Ser
        35                  40                  45

Ile Glu Asp Val Arg Lys Ala Thr Val Tyr Ile Glu Ala Arg Gly Gly
    50                  55                  60

Ala Tyr Asp Glu Gly Arg Gly Phe Gly Glu Val Ser Tyr Gly Ser Gly
65                  70                  75                  80

Ser Gly Phe Ile Val Gly Asp Gly Gly Gly Ser Gly Lys Leu Val Ile
                85                  90                  95

Thr Asn Asn His Val Val Thr Gly Ala Gly Phe Leu Gln Val Tyr Leu
            100                 105                 110

Asp Gly Gln Asp Glu Pro Val Asp Ala Arg Val Leu Gly Ala Ser Glu
        115                 120                 125

Cys Ser Asp Leu Ala Leu Leu Glu Leu Glu Gly Gly Gly Tyr Pro Tyr
    130                 135                 140

Leu Ser Trp Arg Thr Gly Asp Ile Asp Ala Gly Leu Gly Val Arg Ala
145                 150                 155                 160

Ala Gly Tyr Pro Ala Asp Asp Val Glu Thr Gly Glu Arg Pro Asp Tyr
                165                 170                 175

Thr Ile Thr Ser Gly Ser Ile Asn Ser Thr Glu Ala Asp Gly Glu Thr
            180                 185                 190

Pro Trp Ala Ser Val Asp Ser Val Leu Glu His Asp Val Leu Ile Arg
        195                 200                 205

Pro Gly Asn Ser Gly Gly Pro Leu Val Asp Glu Asn Gly Arg Val Val
    210                 215                 220

Gly Val Asn Tyr Ala Ser Arg Val Asp Asp Glu Gly Arg Pro Thr Gly
225                 230                 235                 240

Pro Gln Leu Ala Ile Ala Arg Asp Glu Ala Arg Thr Ile Val Asp Lys
                245                 250                 255

Leu Arg Gln Gly Asp Val Glu Ser Ile Gly Val Asn Gly Glu Ala Phe
            260                 265                 270

Ser Leu Pro Glu Gln Glu Ile Ser Gly Ile Arg Val Thr Ser Val Lys
        275                 280                 285

Thr Asp Ser Pro Ala Gly Arg Val Gly Leu Arg Asn Ala Val Ile Asp
    290                 295                 300

Pro Gln Ser Gly Glu Phe Ala Ala Phe Asp Val Ile Thr Glu Ile Glu
305                 310                 315                 320

Gly Thr Arg Leu Gly Glu Gly Gly Thr Met Glu Glu Tyr Cys Asn Ile
                325                 330                 335

Leu Arg Gln His Glu Pro Asp Asp Arg Leu Ser Ile Gln Ala Val Arg
            340                 345                 350

Val Glu Glu Asn Gly Asp Val Ser Leu Met Glu Gly Ala Leu Asn Gly
        355                 360                 365

Glu Glu Leu Ala Val Val Glu Thr Ile Pro Ala Gln Thr Asp Ala Gly
    370                 375                 380

Gly Glu Pro Gln Gly Gly Phe Val Ser Leu Thr Asp Asp Thr Gly Thr
385                 390                 395                 400

Leu Thr Met Glu Val Pro Ala Ala Trp Ser Asp Val Arg Thr Gly Gly
                405                 410                 415

Ser Leu Lys Leu Asp Gly Glu Ser Leu Gly Pro Ala Met Leu Ala Ser
            420                 425                 430
```

-continued

```
Thr Asp Ala Gln Arg Trp Ile Asp Thr Phe Glu Val Pro Gly Val Tyr
        435                 440                 445

Phe Ala Ala Ser Ser Arg Leu Ala Glu Arg Phe Pro Glu Asn Pro Val
    450                 455                 460

Glu Gln Ile Leu Asp Leu Pro Glu Tyr Asp Phe Ser Gly Thr Cys Arg
465                 470                 475                 480

Tyr Glu Gly Arg Glu Gly Tyr Gln Asp Ser Lys Phe Thr Gly Ala Val
                485                 490                 495

Asp Thr Tyr Thr Gly Cys Asp Gly Thr Asp Asn Ala Phe Gln Ile Tyr
            500                 505                 510

Ala Ala Thr Pro Pro Asp Gly Ser Tyr Val Val Val Leu Gln Ala Val
        515                 520                 525

Ile Thr Ser Glu Ala Asp Leu Asp Gly Leu Gln Arg Thr Leu Ala Thr
    530                 535                 540

Phe Asp Val Leu Gln Gln Pro
545                 550


<210> SEQ ID NO 141
<211> LENGTH: 951
<212> TYPE: DNA
<213> ORGANISM: Shewanella denitrificans OS217

<400> SEQUENCE: 141

atgagtgagt tatcaaatac attgcccaag tgcatttcac ttgggcctat ttttttcgtt      60

atagggttag tcatgtttaa aagcgtgttg attagtacgg ttttatttgc gttttccttt     120

gtctcacttg caggagataa agtcatttta cgccaatctg agatgatgac cattgaaccc     180

aagggcctga gttatcatgc tcgtatggac actggcgcgg aaaattcatc cttgcatgcc     240

acagagttag agattattgg tggcagcgcc aagaaaatga aaaaaaacat agggaaaact     300

atcgccttca ccactgagaa cgaacagggt gaaaagaagc gcatggaagc caaaattgtt     360

gatacctcca cagtgagcaa ctcccaaggc acagaaaccc gttacatagt tcaattgcct     420

attcgttttg aaggcaagac ccacaaggtg gatgtcaatt tacgcgaccg cagtgcgatg     480

gagtataaat tactcattgg cagaagcttt ttaaagaaag gctatgttat tgacgtttcg     540

aagaaaaagc tgattggtga acaggctaaa atcaatgtga aagaagccgg tttagtgttt     600

aacacccgta ttgattctgg tgcagtacag acctcactac atgccataga tattcacatc     660

gaagatgaag ataaggtcaa tatgaaaaat aatattggca aaaaaatcac cttcaccaca     720

gtgaatgaaa aaaataagcg caagacgatt aaaacctatg tctatggcac ttcatatatc     780

cgcaacgccc aaggggatga aacccgctat acggttatgt taaatctagg ccaaaagggc     840

agtgagcatt tggtcagggt caacctaaga gacagaacta aaatgggtta taaattgctt     900

attgggcgga attggcttca gggtcgttat ttagtggatg tcactaaata g              951


<210> SEQ ID NO 142
<211> LENGTH: 316
<212> TYPE: PRT
<213> ORGANISM: Shewanella denitrificans OS217

<400> SEQUENCE: 142

Met Ser Glu Leu Ser Asn Thr Leu Pro Lys Cys Ile Ser Leu Gly Pro
1               5                   10                  15

Ile Phe Phe Val Ile Gly Leu Val Met Phe Lys Ser Val Leu Ile Ser
            20                  25                  30

Thr Val Leu Phe Ala Phe Ser Phe Val Ser Leu Ala Gly Asp Lys Val
        35                  40                  45
```

```
Ile Leu Arg Gln Ser Glu Met Met Thr Ile Glu Pro Lys Gly Leu Ser
    50                  55                  60

Tyr His Ala Arg Met Asp Thr Gly Ala Glu Asn Ser Ser Leu His Ala
65                  70                  75                  80

Thr Glu Leu Glu Ile Ile Gly Gly Ser Ala Lys Lys Met Lys Lys Asn
                85                  90                  95

Ile Gly Lys Thr Ile Ala Phe Thr Thr Glu Asn Glu Gln Gly Glu Lys
            100                 105                 110

Lys Arg Met Glu Ala Lys Ile Val Asp Thr Ser Thr Val Ser Asn Ser
        115                 120                 125

Gln Gly Thr Glu Thr Arg Tyr Ile Val Gln Leu Pro Ile Arg Phe Glu
    130                 135                 140

Gly Lys Thr His Lys Val Asp Val Asn Leu Arg Asp Arg Ser Ala Met
145                 150                 155                 160

Glu Tyr Lys Leu Leu Ile Gly Arg Ser Phe Leu Lys Lys Gly Tyr Val
                165                 170                 175

Ile Asp Val Ser Lys Lys Lys Leu Ile Gly Glu Gln Ala Lys Ile Asn
            180                 185                 190

Val Lys Glu Ala Gly Leu Val Phe Asn Thr Arg Ile Asp Ser Gly Ala
        195                 200                 205

Val Gln Thr Ser Leu His Ala Ile Asp Ile His Ile Glu Asp Glu Asp
    210                 215                 220

Lys Val Asn Met Lys Asn Asn Ile Gly Lys Lys Ile Thr Phe Thr Thr
225                 230                 235                 240

Val Asn Glu Lys Asn Lys Arg Lys Thr Ile Lys Thr Tyr Val Tyr Gly
                245                 250                 255

Thr Ser Tyr Ile Arg Asn Ala Gln Gly Asp Glu Thr Arg Tyr Thr Val
            260                 265                 270

Met Leu Asn Leu Gly Gln Lys Gly Ser Glu His Leu Val Arg Val Asn
        275                 280                 285

Leu Arg Asp Arg Thr Lys Met Gly Tyr Lys Leu Leu Ile Gly Arg Asn
    290                 295                 300

Trp Leu Gln Gly Arg Tyr Leu Val Asp Val Thr Lys
305                 310                 315
```

<210> SEQ ID NO 143
<211> LENGTH: 528
<212> TYPE: DNA
<213> ORGANISM: Shewanella denitrificans OS217

<400> SEQUENCE: 143

```
atggcaactg taggtctttt tttcggtagc gacactggca acaccgaagc catcgccaaa      60

atgatccaga aaaaactggg taagcagatg gtagatgtta aagacatcgc taagagcact     120

aaagagcaaa tcgccgagtt cgatatgata ctgtttggca tcccaacttg gtattatggc     180

gaagctcagt gtgattggga tgacttcttc cctgaacttg agcaaattga ttttactgat     240

aagctagtgg ctattttcgg ctgtggcgat caagaagact attcagaata cttcctcgat     300

gccatgggca tggtgggtga catagtccaa gcccgcggcg gcattattgt cggtcactgg     360

cccattgaag gctatgattt tgaagcctct aaaggccaag tggatgacaa gcatttcatc     420

ggcttaggca tagatgaaga ccgtcagcca gagctaaccg aaggccgcgt cgatgcttgg     480

gttaagcaaa tttatgaaga aatgtgctta gcagaattag ctgactag                  528
```

<210> SEQ ID NO 144

<211> LENGTH: 175
<212> TYPE: PRT
<213> ORGANISM: Shewanella denitrificans OS217

<400> SEQUENCE: 144

Met Ala Thr Val Gly Leu Phe Phe Gly Ser Asp Thr Gly Asn Thr Glu
1               5                   10                  15

Ala Ile Ala Lys Met Ile Gln Lys Lys Leu Gly Lys Gln Met Val Asp
            20                  25                  30

Val Lys Asp Ile Ala Lys Ser Thr Lys Glu Gln Ile Ala Glu Phe Asp
        35                  40                  45

Met Ile Leu Phe Gly Ile Pro Thr Trp Tyr Tyr Gly Glu Ala Gln Cys
    50                  55                  60

Asp Trp Asp Asp Phe Phe Pro Glu Leu Glu Gln Ile Asp Phe Thr Asp
65                  70                  75                  80

Lys Leu Val Ala Ile Phe Gly Cys Gly Asp Gln Glu Asp Tyr Ser Glu
                85                  90                  95

Tyr Phe Leu Asp Ala Met Gly Met Val Gly Asp Ile Val Gln Ala Arg
            100                 105                 110

Gly Gly Ile Ile Val Gly His Trp Pro Ile Glu Gly Tyr Asp Phe Glu
        115                 120                 125

Ala Ser Lys Gly Gln Val Asp Asp Lys His Phe Ile Gly Leu Gly Ile
    130                 135                 140

Asp Glu Asp Arg Gln Pro Glu Leu Thr Glu Gly Arg Val Asp Ala Trp
145                 150                 155                 160

Val Lys Gln Ile Tyr Glu Glu Met Cys Leu Ala Glu Leu Ala Asp
                165                 170                 175

<210> SEQ ID NO 145
<211> LENGTH: 1152
<212> TYPE: DNA
<213> ORGANISM: Shewanella denitrificans OS217

<400> SEQUENCE: 145
atgtcaatta ataaaattac cgataatcta accaccagcg ctgaacatag cgaaaatcat 60
catgataata accaagtgac ggcgggtaaa aacatgtcta gccgcagttt gctttacgtt 120
gccgtggcac taggcttgtt tacctgtgtg gccgctcaag ctgaaaccca ggctgcatta 180
acccaagaat taaaagatga agaggggctt agccttgaaa gaagccaatt tagtgtgagc 240
cttgaaagtt ctagcacgac aaagggtacg gccacaccaa gcggtgccga aagcacagcg 300
ttgaccacag gattgcaata taacgagtta gcttctgagc ttaaacaatt gcatcaaggt 360
gcgagcctta gccgcctctg gagtcaaaaa aaaccggcat cagtggattc ggtgaattca 420
gtcgcttcga tgaataaggg cgatgctgcg ggcagtaatc ttgccacaaa ggcttcagtc 480
ttgagcgatc ctgcagtgaa agcctcacca gcaaacctaa gaactgttaa caccctagat 540
caagggctgc ttggcatgac ccgcgagcaa aaaatggcaa ttaaaagcgc tgaaaactcc 600
gccagtgttc aggcattaca gtcaagtggt ctgtttcaca gctttaacat ctatgatgcc 660
aacacgcatt tgctggaaga tttcgacggt gacagttttt attcgacctt tagtgtgacc 720
tttgatgccg atgtcgatgg gattggctac aacgaatacg ccgatgtgta tgccgagctc 780
tatgtcagcc aagagggcgg gccttggctg cattactact ccaccgaagt atttagcatt 840
gcgggtaact caagttatga tgattatcga gtgctaacaa cactgcagtc aggttatcag 900
actgcccatt atgatgtgct tatcgacttg tacgaagtgg gcgttagcaa ccctgtggcc 960
accttaagct caaatgacac caatgcactt tatgcattgc cacttgaaag tagagacaga 1020

-continued

```
gaccctattt atgttgaacc ccatgtggat acttacattg aagtggaagc gggaggggct   1080

ttatcttggt gggaactgct agtgttggtc agtcttggct tactggcaat ccggaaaagt   1140

ccgcagtgct aa                                                       1152


<210> SEQ ID NO 146
<211> LENGTH: 383
<212> TYPE: PRT
<213> ORGANISM: Shewanella denitrificans OS217

<400> SEQUENCE: 146

Met Ser Ile Asn Lys Ile Thr Asp Asn Leu Thr Thr Ser Ala Glu His
1               5                   10                  15

Ser Glu Asn His His Asp Asn Asn Gln Val Thr Ala Gly Lys Asn Met
            20                  25                  30

Ser Ser Arg Ser Leu Leu Tyr Val Ala Val Ala Leu Gly Leu Phe Thr
        35                  40                  45

Cys Val Ala Ala Gln Ala Glu Thr Gln Ala Ala Leu Thr Gln Glu Leu
    50                  55                  60

Lys Asp Glu Glu Gly Leu Ser Leu Glu Arg Ser Gln Phe Ser Val Ser
65                  70                  75                  80

Leu Glu Ser Ser Ser Thr Thr Lys Gly Thr Ala Thr Pro Ser Gly Ala
                85                  90                  95

Glu Ser Thr Ala Leu Thr Thr Gly Leu Gln Tyr Asn Glu Leu Ala Ser
            100                 105                 110

Glu Leu Lys Gln Leu His Gln Gly Ala Ser Leu Ser Arg Leu Trp Ser
        115                 120                 125

Gln Lys Lys Pro Ala Ser Val Asp Ser Val Asn Ser Val Ala Ser Met
    130                 135                 140

Asn Lys Gly Asp Ala Ala Gly Ser Asn Leu Ala Thr Lys Ala Ser Val
145                 150                 155                 160

Leu Ser Asp Pro Ala Val Lys Ala Ser Pro Ala Asn Leu Arg Thr Val
                165                 170                 175

Asn Thr Leu Asp Gln Gly Leu Leu Gly Met Thr Arg Glu Gln Lys Met
            180                 185                 190

Ala Ile Lys Ser Ala Glu Asn Ser Ala Ser Val Gln Ala Leu Gln Ser
        195                 200                 205

Ser Gly Leu Phe His Ser Phe Asn Ile Tyr Asp Ala Asn Thr His Leu
    210                 215                 220

Leu Glu Asp Phe Asp Gly Asp Ser Phe Tyr Ser Thr Phe Ser Val Thr
225                 230                 235                 240

Phe Asp Ala Asp Val Asp Gly Ile Gly Tyr Asn Glu Tyr Ala Asp Val
                245                 250                 255

Tyr Ala Glu Leu Tyr Val Ser Gln Glu Gly Gly Pro Trp Leu His Tyr
            260                 265                 270

Tyr Ser Thr Glu Val Phe Ser Ile Ala Gly Asn Ser Ser Tyr Asp Asp
        275                 280                 285

Tyr Arg Val Leu Thr Thr Leu Gln Ser Gly Tyr Gln Thr Ala His Tyr
    290                 295                 300

Asp Val Leu Ile Asp Leu Tyr Glu Val Gly Val Ser Asn Pro Val Ala
305                 310                 315                 320

Thr Leu Ser Ser Asn Asp Thr Asn Ala Leu Tyr Ala Leu Pro Leu Glu
                325                 330                 335

Ser Arg Asp Arg Asp Pro Ile Tyr Val Glu Pro His Val Asp Thr Tyr
            340                 345                 350
```

Ile Glu Val Glu Ala Gly Gly Ala Leu Ser Trp Trp Glu Leu Leu Val
        355                 360                 365

Leu Val Ser Leu Gly Leu Leu Ala Ile Arg Lys Ser Pro Gln Cys
    370                 375                 380

<210> SEQ ID NO 147
<211> LENGTH: 1263
<212> TYPE: DNA
<213> ORGANISM: Shewanella denitrificans OS217

<400> SEQUENCE: 147
atggaaatag taatgagttt agtaggggtg gtaaccctgc ttgcgatagg tttcctccta 60
tcaactaaca aaaaagcgat caatgttcgc actgtgggtg gcgcattagc tattcaagcg 120
gcattcggtg gttttgtttt atacgtgcca gtgggcaaag atattctgaa gggtgcttca 180
gatgctgtat ctagcgttat tggttatgca cagaatggta ttagtttctt attcggcgat 240
ttagctaact ttaaagttgg tttcatcttc gcaattaacg tattgccaat tatcattttc 300
ttctcttctt taattgccgt gctttactac ctaggcatca tgcagtggat catccgtatt 360
atcggtggtg gcctgcaaaa agcactaggt acaagccgta ctgagtcaat gtcagcaact 420
gctaacatct tcgttggtca aactgaagcg ccattagttg tgcgtccgtt tatcccaact 480
atgactcaat ctgaattatt cgccatcatg gtgggtggtt tagcgtctat tgcaggttct 540
gttcttgcag gttacgcgca gatgggtgta cctatcgaat acttagttgc cgcatcattc 600
atggcagcac caggtggtct attaatggct aaactgatgc accctgaaac tgaaactgct 660
aagaacgata tggatgaatt accagaagat ccagacaagc cagctaacgt attagacgca 720
gctgctgctg gtgcttcttc aggtatgaac ctagcgctta acgttggcgc tatgctaatc 780
gcattcgtag gcttaatcgc tatgatcaac ggcatcatag gtggtgttac tggttggttc 840
ggtctagaag gtatcaccct agagcttatc ctaggttaca tcttcatgcc tttagcattc 900
ctaatcggtg tgccttggag cgaagcctta gtcgctggtt ctttcattgg tcaaaagatc 960
gtagtaaacg aattcgtagc ctaccttaac tttgctcctt acttacttga tgcgtctgca 1020
gaaggtttca aagtagttgc tgagacaggt gtcatgatga ctgatagaac taaagctatc 1080
atttcgtttg cactgtgtgg attcgctaac ctttcttcta ttgcgattct acttggtggt 1140
ttaggtgcta tggcgccaaa ccgtcgccat gatttagcta acttaggtat ccgtgcggtt 1200
atcgctggtt ctttagctaa cttaatgagc gcaacacttg ctggtttatt cttagccatc 1260
taa 1263

<210> SEQ ID NO 148
<211> LENGTH: 420
<212> TYPE: PRT
<213> ORGANISM: Shewanella denitrificans OS217

<400> SEQUENCE: 148

Met Glu Ile Val Met Ser Leu Val Gly Val Val Thr Leu Leu Ala Ile
1               5                   10                  15

Gly Phe Leu Leu Ser Thr Asn Lys Lys Ala Ile Asn Val Arg Thr Val
            20                  25                  30

Gly Gly Ala Leu Ala Ile Gln Ala Ala Phe Gly Gly Phe Val Leu Tyr
        35                  40                  45

Val Pro Val Gly Lys Asp Ile Leu Lys Gly Ala Ser Asp Ala Val Ser
    50                  55                  60

Ser Val Ile Gly Tyr Ala Gln Asn Gly Ile Ser Phe Leu Phe Gly Asp

```
65                  70                  75                  80

Leu Ala Asn Phe Lys Val Gly Phe Ile Phe Ala Ile Asn Val Leu Pro
                85                  90                  95

Ile Ile Ile Phe Phe Ser Ser Leu Ile Ala Val Leu Tyr Tyr Leu Gly
            100                 105                 110

Ile Met Gln Trp Ile Ile Arg Ile Ile Gly Gly Gly Leu Gln Lys Ala
        115                 120                 125

Leu Gly Thr Ser Arg Thr Glu Ser Met Ser Ala Thr Ala Asn Ile Phe
    130                 135                 140

Val Gly Gln Thr Glu Ala Pro Leu Val Val Arg Pro Phe Ile Pro Thr
145                 150                 155                 160

Met Thr Gln Ser Glu Leu Phe Ala Ile Met Val Gly Gly Leu Ala Ser
                165                 170                 175

Ile Ala Gly Ser Val Leu Ala Gly Tyr Ala Gln Met Gly Val Pro Ile
            180                 185                 190

Glu Tyr Leu Val Ala Ala Ser Phe Met Ala Ala Pro Gly Gly Leu Leu
        195                 200                 205

Met Ala Lys Leu Met His Pro Glu Thr Glu Thr Ala Lys Asn Asp Met
    210                 215                 220

Asp Glu Leu Pro Glu Asp Pro Asp Lys Pro Ala Asn Val Leu Asp Ala
225                 230                 235                 240

Ala Ala Ala Gly Ala Ser Ser Gly Met Asn Leu Ala Leu Asn Val Gly
                245                 250                 255

Ala Met Leu Ile Ala Phe Val Gly Leu Ile Ala Met Ile Asn Gly Ile
            260                 265                 270

Ile Gly Gly Val Thr Gly Trp Phe Gly Leu Glu Gly Ile Thr Leu Glu
        275                 280                 285

Leu Ile Leu Gly Tyr Ile Phe Met Pro Leu Ala Phe Leu Ile Gly Val
    290                 295                 300

Pro Trp Ser Glu Ala Leu Val Ala Gly Ser Phe Ile Gly Gln Lys Ile
305                 310                 315                 320

Val Val Asn Glu Phe Val Ala Tyr Leu Asn Phe Ala Pro Tyr Leu Leu
                325                 330                 335

Asp Ala Ser Ala Glu Gly Phe Lys Val Val Ala Glu Thr Gly Val Met
            340                 345                 350

Met Thr Asp Arg Thr Lys Ala Ile Ile Ser Phe Ala Leu Cys Gly Phe
        355                 360                 365

Ala Asn Leu Ser Ser Ile Ala Ile Leu Leu Gly Gly Leu Gly Ala Met
    370                 375                 380

Ala Pro Asn Arg Arg His Asp Leu Ala Asn Leu Gly Ile Arg Ala Val
385                 390                 395                 400

Ile Ala Gly Ser Leu Ala Asn Leu Met Ser Ala Thr Leu Ala Gly Leu
                405                 410                 415

Phe Leu Ala Ile
            420
```

<210> SEQ ID NO 149
<211> LENGTH: 510
<212> TYPE: DNA
<213> ORGANISM: Silicibacter sp. TM1040

<400> SEQUENCE: 149

```
atgaccaaat cgaagaagct cgaattccgc cccaatgatt tcattgtata cccagcccat     60

ggcgttgggc agatcatttc gatcgaggag caggaagtgg ccggctacaa gctggagctt    120
```

ttcgtaatca cctttgaaaa agacaagatg accctgcgcg tgccgacgca taaggccatc 180
gacatcggca tgcgttcgct gtcttcccct gatgtgatca atcaggcgat gaagacgctg 240
aaaggcaagg ccaaggtcaa gcgcgccatg tggtcgcgtc gggcacagga atacgaacag 300
aagatcaatt ccggcgatct gatctccatt gccgaagtgg tgcgcgacct gcaccgtacc 360
gatgatcagc gcgagcagag ctattccgag cgtcagttgt atgaagccgc gctcgagcgt 420
ctgacccgcg aagttgcggc cgtgtccggt ggcgacgaaa tcgcggcggc caagcaggtt 480
gatgaggtcc tgacctcccg cgctgcctga 510

<210> SEQ ID NO 150
<211> LENGTH: 169
<212> TYPE: PRT
<213> ORGANISM: Silicibacter sp. TM1040

<400> SEQUENCE: 150

Met Thr Lys Ser Lys Lys Leu Glu Phe Arg Pro Asn Asp Tyr Val Val
1 5 10 15

Tyr Pro Ala His Gly Val Gly Gln Ile Leu Ser Ile Glu Glu Gln Glu
20 25 30

Val Ala Gly Phe Lys Leu Glu Leu Phe Val Ile Ser Phe Glu Lys Asp
35 40 45

Lys Met Thr Leu Arg Val Pro Thr Asn Lys Ala Thr Glu Ser Gly Leu
50 55 60

Arg Ser Leu Ser Ser Pro Asp Val Ile Ser Gln Ala Met Lys Thr Leu
65 70 75 80

Lys Gly Lys Ala Lys Val Lys Arg Ala Met Trp Ser Arg Arg Ala Gln
85 90 95

Glu Tyr Glu Gln Lys Ile Asn Ser Gly Asp Leu Ile Ser Ile Ala Glu
100 105 110

Val Val Arg Asp Leu His Arg Thr Asp Asp Gln Arg Glu Gln Ser Tyr
115 120 125

Ser Glu Arg Gln Leu Tyr Glu Ala Ala Leu Glu Arg Leu Thr Arg Glu
130 135 140

Val Ala Ala Val Ser Gly Ala Asp Glu Met Ala Ala Ala Lys Gln Val
145 150 155 160

Asp Glu Val Leu Thr Ser Arg Ala Ala
165

<210> SEQ ID NO 151
<211> LENGTH: 1089
<212> TYPE: DNA
<213> ORGANISM: Synechococcus sp. PCC 7942 (elongatus)

<400> SEQUENCE: 151
atgtctagaa ctcgttatga ctatgcacaa aaaattgcca cgtttctaag aacacatgat 60
gaacctgttc atgctaagga tatctatgaa ctttttaatg tcagccaagg aacagtaagg 120
aagcatctaa agaactatct cgatgcgaat ccgaatgcaa aagccaaagt gactggagta 180
tatccagtta attattctga ggaaatttct agctttttag cggaaaatat tggagcaata 240
gatgtcgagg atatctataa cctcttcaag gtaacgcctg gaacagttga taattatcta 300
agagaacacc ttcaccaata tcctaatgat attcctagga taattggctt ttatcctaaa 360
gcagagacag tcgttgcttt ggcagagaca gaaattggtt tggtgaccgg agaaaactta 420
ttcgaaatca atgctcattg taagcggact atagatgcta ttacgaagcc gaagcactat 480
aagtttatcg aggggcttct tcagagttat cttgaagaag atgggcaaac gattagggtt 540

```
tccaaaaatc aactaatcaa ttccctctac gagaattatg tcgactttgt acatgagtct    600

gacaatggca ttatctccag agctggaggg ataaacgaaa aaatactcat tcgcggtcta    660

gaaaacgctg ggatggttct gggtcagaat ttcaaaaaga caggaaataa cagtgaaggt    720

gacctccaag tagaatgtcg agcacaaaat tctacaaaaa ttctttactg cgaagtgaaa    780

agttatgcgg ctcgagaaag actgctaaga ggtattcagg acattcccca tccagataag    840

gttgcagtcg gctttttctt ggatcccgat gagtttaatc cagatcgaac acagacactt    900

ctagcagctg gtccgctggc aatatacatg ccagatgtaa cttatgaagc attatctgct    960

aacagcataa tacagacaac acggaggcaa gatatgcttt atcgtccttt atctagattc   1020

attgacgaca tgtgtaactt ctctcgcagt ggaaatctac ctaggtacct acaacgtcat   1080

gagaattag                                                           1089


<210> SEQ ID NO 152
<211> LENGTH: 362
<212> TYPE: PRT
<213> ORGANISM: Synechococcus sp. PCC 7942 (elongatus)

<400> SEQUENCE: 152

Met Ser Arg Thr Arg Tyr Asp Tyr Ala Gln Lys Ile Ala Thr Phe Leu
1               5                   10                  15

Arg Thr His Asp Glu Pro Val His Ala Lys Asp Ile Tyr Glu Leu Phe
            20                  25                  30

Asn Val Ser Gln Gly Thr Val Arg Lys His Leu Lys Asn Tyr Leu Asp
        35                  40                  45

Ala Asn Pro Asn Ala Lys Ala Lys Val Thr Gly Val Tyr Pro Val Asn
    50                  55                  60

Tyr Ser Glu Glu Ile Ser Ser Phe Leu Ala Glu Asn Ile Gly Ala Ile
65                  70                  75                  80

Asp Val Glu Asp Ile Tyr Asn Leu Phe Lys Val Thr Pro Gly Thr Val
                85                  90                  95

Asp Asn Tyr Leu Arg Glu His Leu His Gln Tyr Pro Asn Asp Ile Pro
            100                 105                 110

Arg Ile Ile Gly Phe Tyr Pro Lys Ala Glu Thr Val Val Ala Leu Ala
        115                 120                 125

Glu Thr Glu Ile Gly Leu Val Thr Gly Glu Asn Leu Phe Glu Ile Asn
    130                 135                 140

Ala His Cys Lys Arg Thr Ile Asp Ala Ile Thr Lys Pro Lys His Tyr
145                 150                 155                 160

Lys Phe Ile Glu Gly Leu Leu Gln Ser Tyr Leu Glu Glu Asp Gly Gln
                165                 170                 175

Thr Ile Arg Val Ser Lys Asn Gln Leu Ile Asn Ser Leu Tyr Glu Asn
            180                 185                 190

Tyr Val Asp Phe Val His Glu Ser Asp Asn Gly Ile Ile Ser Arg Ala
        195                 200                 205

Gly Gly Ile Asn Glu Lys Ile Leu Ile Arg Gly Leu Glu Asn Ala Gly
    210                 215                 220

Met Val Leu Gly Gln Asn Phe Lys Lys Thr Gly Asn Asn Ser Glu Gly
225                 230                 235                 240

Asp Leu Gln Val Glu Cys Arg Ala Gln Asn Ser Thr Lys Ile Leu Tyr
                245                 250                 255

Cys Glu Val Lys Ser Tyr Ala Ala Arg Glu Arg Leu Leu Arg Gly Ile
            260                 265                 270
```

Gln Asp Ile Pro His Pro Asp Lys Val Ala Val Gly Phe Phe Leu Asp
275 280 285

Pro Asp Glu Phe Asn Pro Asp Arg Thr Gln Thr Leu Leu Ala Ala Gly
290 295 300

Pro Leu Ala Ile Tyr Met Pro Asp Val Thr Tyr Glu Ala Leu Ser Ala
305 310 315 320

Asn Ser Ile Ile Gln Thr Thr Arg Arg Gln Asp Met Leu Tyr Arg Pro
325 330 335

Leu Ser Arg Phe Ile Asp Asp Met Cys Asn Phe Ser Arg Ser Gly Asn
340 345 350

Leu Pro Arg Tyr Leu Gln Arg His Glu Asn
355 360

<210> SEQ ID NO 153
<211> LENGTH: 378
<212> TYPE: DNA
<213> ORGANISM: Thiomicrospira crunogena, XCL-2

<400> SEQUENCE: 153
atgagaaaga caatcgcaat gagtgtgtta ctttcgttat taagtgtgat tacgcttcct 60
gtgcaggccg cgatgttaag cacccaacag ctggttcaag aatcctcgat gacatctgaa 120
cgcgctaagt tgaacgctat gatgcaacgt gaagatatac agtcgcaatt tgttgaaatg 180
ggtgtttcgc cagaagacgt tcaacagcgt gtggctgctt taacggatgc agaagttgct 240
gagttgaatc accagatgga gcaggttcct gccggtggtg acgttttggg tgtgttagta 300
ttaatttttc tcgtctttat tattacggat attattggtg cgacggatgt cttcccgttt 360
gtgcaccctg ttaaataa 378

<210> SEQ ID NO 154
<211> LENGTH: 125
<212> TYPE: PRT
<213> ORGANISM: Thiomicrospira crunogena, XCL-2

<400> SEQUENCE: 154

Met Arg Lys Thr Ile Ala Met Ser Val Leu Leu Ser Leu Leu Ser Val
1 5 10 15

Ile Thr Leu Pro Val Gln Ala Ala Met Leu Ser Thr Gln Gln Leu Val
20 25 30

Gln Glu Ser Ser Met Thr Ser Glu Arg Ala Lys Leu Asn Ala Met Met
35 40 45

Gln Arg Glu Asp Ile Gln Ser Gln Phe Val Glu Met Gly Val Ser Pro
50 55 60

Glu Asp Val Gln Gln Arg Val Ala Ala Leu Thr Asp Ala Glu Val Ala
65 70 75 80

Glu Leu Asn His Gln Met Glu Gln Val Pro Ala Gly Gly Asp Val Leu
85 90 95

Gly Val Leu Val Leu Ile Phe Leu Val Phe Ile Ile Thr Asp Ile Ile
100 105 110

Gly Ala Thr Asp Val Phe Pro Phe Val His Pro Val Lys
115 120 125

<210> SEQ ID NO 155
<211> LENGTH: 1119
<212> TYPE: DNA
<213> ORGANISM: Thiomicrospira crunogena, XCL-2

<400> SEQUENCE: 155

```
atgaaactta aaaaaatctc atttttagtc ggcgccctac tcgcttcaca aacagcaatg      60

gctgcaagca accctgaaat tgaagaattg cgccagcaaa ttaatgcttt agcacaacaa     120

gtcgaagact ctaaagcctc atccaaatcg aatacgacca ttggcggtta tggtgagttg     180

cactacaaca actggaaaac aacccagcca ggacaagccg atacagagaa aaaagaaatc     240

gacttccacc gttttgttat gtttcttggg catgaattta acgacaaaat tcgttttttc     300

tctgaagttg aaatcgaaca tggtattgcc ggtgaaagtc aaaatggtga agtcgaagtt     360

gaacaggctt atgttgaact ggatttaaac aagcaactga gcaccaaagc tggtatggtt     420

ttagtacccg tcgggatttt gaatgaaacc cacgaaccac caactttta tggcgttgag      480

cgtaacccag ttgaaaaaaa catcatcccg gccacttggt ggaatggtgg tttaaccctt     540

aacggacgct cacaatctgg tttcagttac gacgtaatga tctctgaagg gctttttca      600

gccgacggtt acagcatccg taatgggcgc caaaaaacca gtaacgccaa agccaatgac     660

ctggcgtata ccgggcgtat caaatataca ggtgtcccgg gactggaatt agcggccact     720

gcacgttatg aatcagattt aggtcaaggc acattagcca gcaaagcgcc tgcgacttta     780

ctggaaacac atgcaattta cacggttgat caattcacaa tcaaagggct atatgcacaa     840

tgggatattt ccggagatgc cgccaaagcg gcaaatgctg atcaacaatc tggttactac     900

atcgagccaa gctataaact aaccgaaaaa tggggagttt tcacgcgtta taacaactgg     960

aaaaaagcat ccggttcagc aaatgatgaa acgcaaaccg acattggtgt aaactactgg    1020

ccacatcctg acgtagtatt taaagcagat tatcagtggt ataccaaaga cgacaagaaa    1080

accaacggct tcaaccttgg tgtaggttat caattttaa                           1119
```

```
<210> SEQ ID NO 156
<211> LENGTH: 372
<212> TYPE: PRT
<213> ORGANISM: Thiomicrospira crunogena, XCL-2

<400> SEQUENCE: 156

Met Lys Leu Lys Lys Ile Ser Phe Leu Val Gly Ala Leu Leu Ala Ser
1               5                   10                  15

Gln Thr Ala Met Ala Ala Ser Asn Pro Glu Ile Glu Glu Leu Arg Gln
            20                  25                  30

Gln Ile Asn Ala Leu Ala Gln Gln Val Glu Asp Ser Lys Ala Ser Ser
        35                  40                  45

Lys Ser Asn Thr Thr Ile Gly Gly Tyr Gly Glu Leu His Tyr Asn Asn
    50                  55                  60

Trp Lys Thr Thr Gln Pro Gly Gln Ala Asp Thr Glu Lys Lys Glu Ile
65                  70                  75                  80

Asp Phe His Arg Phe Val Met Phe Leu Gly His Glu Phe Asn Asp Lys
                85                  90                  95

Ile Arg Phe Phe Ser Glu Val Glu Ile Glu His Gly Ile Ala Gly Glu
            100                 105                 110

Ser Gln Asn Gly Glu Val Glu Val Glu Gln Ala Tyr Val Glu Leu Asp
        115                 120                 125

Leu Asn Lys Gln Leu Ser Thr Lys Ala Gly Met Val Leu Val Pro Val
    130                 135                 140

Gly Ile Leu Asn Glu Thr His Glu Pro Pro Thr Phe Tyr Gly Val Glu
145                 150                 155                 160

Arg Asn Pro Val Glu Lys Asn Ile Ile Pro Ala Thr Trp Trp Asn Gly
                165                 170                 175

Gly Leu Thr Leu Asn Gly Arg Ser Gln Ser Gly Phe Ser Tyr Asp Val
```

```
            180                 185                 190

Met Ile Ser Glu Gly Leu Phe Ser Ala Asp Gly Tyr Ser Ile Arg Asn
        195                 200                 205

Gly Arg Gln Lys Thr Ser Asn Ala Lys Ala Asn Asp Leu Ala Tyr Thr
    210                 215                 220

Gly Arg Ile Lys Tyr Thr Gly Val Pro Gly Leu Glu Leu Ala Ala Thr
225                 230                 235                 240

Ala Arg Tyr Glu Ser Asp Leu Gly Gln Gly Thr Leu Ala Ser Lys Ala
                245                 250                 255

Pro Ala Thr Leu Leu Glu Thr His Ala Ile Tyr Thr Val Asp Gln Phe
            260                 265                 270

Thr Ile Lys Gly Leu Tyr Ala Gln Trp Asp Ile Ser Gly Asp Ala Ala
        275                 280                 285

Lys Ala Ala Asn Ala Asp Gln Gln Ser Gly Tyr Tyr Ile Glu Pro Ser
    290                 295                 300

Tyr Lys Leu Thr Glu Lys Trp Gly Val Phe Thr Arg Tyr Asn Asn Trp
305                 310                 315                 320

Lys Lys Ala Ser Gly Ser Ala Asn Asp Glu Thr Gln Thr Asp Ile Gly
                325                 330                 335

Val Asn Tyr Trp Pro His Pro Asp Val Val Phe Lys Ala Asp Tyr Gln
            340                 345                 350

Trp Tyr Thr Lys Asp Asp Lys Lys Thr Asn Gly Phe Asn Leu Gly Val
        355                 360                 365

Gly Tyr Gln Phe
    370


<210> SEQ ID NO 157
<211> LENGTH: 2424
<212> TYPE: DNA
<213> ORGANISM: Novosphingobium aromaticivorans DSM 12444 (F199)

<400> SEQUENCE: 157

atgccgaagt caacctacac tcgtgctttg ctggcaggcg cctgcgcgct cgccttcgcg      60

ctgcccgcgc atgcgcagga cgcagcccag gccaccgagg cagaagacac caaccccaac     120

gtcatcatcg tgaccgcgca gaaccgcgcg cagaacctca acgacgttcc gatcaagatc     180

gacgtcgtct ccggcgagga gctgcagaag gctggctttg ccagcatgaa cgacgtcggc     240

cagatcgcgc cggtcgtgca ggtcaaccag gaccagggca ccgtgaaggt ttcggtccgc     300

ggcgtcggca ccacctcgaa tgacgaagcg caggatactt cggtcgtcat caatatcgac     360

ggtgagtaca tcaaccgccc gaacgtgatg ggcatggccc tgttcgacat cgaccgggtc     420

gaagtgctgc gcggtcccca gggtacgctc tacggccgca actcgaccgg cggtgcaatc     480

aacttcatca cccgcaagcc cggcaaggaa ttcggggtca acggctcgat cagctacggc     540

aactacaacg cgatccgtgc cgatgccggt attgatctgc cgctgggcga gatcgccggc     600

cttcgcgtcg ccggcttcta cgatgagcgc gatggctaca gcaagcaccc cgcaggcggt     660

ggcttcttcg tgttcccggc ctacgccgct ggccgttctg acgacaacaa gtcgtacgga     720

ggccgcgcct cgctccgcct cgagccgacc gatcgtctct cgatcaacct ggcggccgag     780

tattcgcacc gtagcttcac ccccggcatc tttgccgccg gcgacctgaa cggtgccggc     840

aacggtccca ccggcggtgc ctgcaacaac ggcttcaccc aggttgcacc ggaatatgcg     900

caagtgctct gcgttcccag caacaccaac ctgctctcga aggtcgaccg cagcaattat     960

gcagcgccgc tcttcggcat cggccatgtc agcgatcaca cctgggccgc acgcggacgt    1020
```

```
atcgaatatg agctgagcga cgcggcaacg atcacctaca ttggcggcta tcgcaagtac   1080

tcgggcgatc ccggtcgcct gactctgccg acgatctatc agtcgttcgg ctaccaggat   1140

gaagccaaga cgcagagcca cgaactgcgc atcaacggca cggtcggcgg cgtggtctat   1200

caggtcggcg gcttctactt caaggaagac ctggcccgcg aaagcggctt catgctgccc   1260

agcttcgtct tcgccgaccc gctcaatgat cccagcctgt tcggcaagcc gggcacgttc   1320

ctcagctact tcggccgcta cgtcaaaagc gacagcaaat cggtcttcgg tcaggtcgag   1380

gttccgctgg gcgacaagct gaccgcgatc ggtggcctgc gctataccga caacaagcgc   1440

aacgcgacct atctcaacgt cgaccccttc cgcttcagcc ttgagacctt ctcgctcgta   1500

ccggacccgt acatcgtcgg cgccggtcca ggccggaagg acttcagcaa ggtgatgtat   1560

ctcaccacca ttccgctcaa gagcagcgac agcaaggtca cgtggctggc tggcctgaac   1620

ttcaagccga acagcgacac cctgatcttc gtcaaggcgt cgaccggctt caaagctggc   1680

ggtttcgact cggtcggcac ctacaagccc gagaccaaca ccgctttcga aggcggctgg   1740

aagcagacct tcggtgatca tgggcagcac cagttcaacc ttggcgcgtt ctactacgac   1800

tacaaggacc tgcaggtttc cgtactgctt gataccgcca tcggcggcca gatcttcaat   1860

gccggcaagg cgaagatctg gggcatcgaa gcctcggccg acattgccct ggacgatcgc   1920

accaacttcc atgcctcggc caactacctg aatgccgaat acaaggagct gctcgcgcag   1980

ttcaacgtgt tcgacaccac cggcgagatc aacggcgttg gcgatctcga tcccaacacc   2040

gacggcatcc agcagccgaa ctttgccggc aaccgcccgc cgttctctcc ggaatgggtg   2100

ctgaccgcct cgctcgacca cactttcccg ctgggcgata tgggtggcct gacggcgcgg   2160

gtgaacacca ccttcaagag caagtacttc accgacttct acaactatcg cgacggcacg   2220

cagagcgcgc tcagccagac cgacgcgagc ctcgaataca agcccgagaa cgagaagttc   2280

tcgatcacgg cgttcgtcaa gaacatcgaa ggcacgcgcc cgctgaccta cggcagcttc   2340

gtttcggccg gaccggacga catcttcaac tggcagttcg gcacgccgcg cacctacggc   2400

gtccgcctcg cggtcgactt ctaa                                          2424
```

<210> SEQ ID NO 158
<211> LENGTH: 807
<212> TYPE: PRT
<213> ORGANISM: Novosphingobium aromaticivorans DSM 12444 (F199)

<400> SEQUENCE: 158

```
Met Pro Lys Ser Thr Tyr Thr Arg Ala Leu Leu Ala Gly Ala Cys Ala
1               5                   10                  15

Leu Ala Phe Ala Leu Pro Ala His Ala Gln Asp Ala Ala Gln Ala Thr
            20                  25                  30

Glu Ala Glu Asp Thr Asn Pro Asn Val Ile Ile Val Thr Ala Gln Asn
        35                  40                  45

Arg Ala Gln Asn Leu Asn Asp Val Pro Ile Lys Ile Asp Val Val Ser
    50                  55                  60

Gly Glu Glu Leu Gln Lys Ala Gly Phe Ala Ser Met Asn Asp Val Gly
65                  70                  75                  80

Gln Ile Ala Pro Val Val Gln Val Asn Gln Asp Gln Gly Thr Val Lys
                85                  90                  95

Val Ser Val Arg Gly Val Gly Thr Thr Ser Asn Asp Glu Ala Gln Asp
            100                 105                 110

Thr Ser Val Val Ile Asn Ile Asp Gly Glu Tyr Ile Asn Arg Pro Asn
        115                 120                 125
```

-continued

```
Val Met Gly Met Ala Leu Phe Asp Ile Asp Arg Val Glu Val Leu Arg
    130                 135                 140

Gly Pro Gln Gly Thr Leu Tyr Gly Arg Asn Ser Thr Gly Gly Ala Ile
145                 150                 155                 160

Asn Phe Ile Thr Arg Lys Pro Gly Lys Glu Phe Gly Val Asn Gly Ser
                165                 170                 175

Ile Ser Tyr Gly Asn Tyr Asn Ala Ile Arg Ala Asp Ala Gly Ile Asp
            180                 185                 190

Leu Pro Leu Gly Glu Ile Ala Gly Leu Arg Val Ala Gly Phe Tyr Asp
        195                 200                 205

Glu Arg Asp Gly Tyr Ser Lys His Pro Ala Gly Gly Gly Phe Phe Val
    210                 215                 220

Phe Pro Ala Tyr Ala Ala Gly Arg Ser Asp Asp Asn Lys Ser Tyr Gly
225                 230                 235                 240

Gly Arg Ala Ser Leu Arg Leu Glu Pro Thr Asp Arg Leu Ser Ile Asn
                245                 250                 255

Leu Ala Ala Glu Tyr Ser His Arg Ser Phe Thr Pro Gly Ile Phe Ala
            260                 265                 270

Ala Gly Asp Leu Asn Gly Ala Gly Asn Gly Pro Thr Gly Gly Ala Cys
        275                 280                 285

Asn Asn Gly Phe Thr Gln Val Ala Pro Glu Tyr Ala Gln Val Leu Cys
    290                 295                 300

Val Pro Ser Asn Thr Asn Leu Leu Ser Lys Val Asp Arg Ser Asn Tyr
305                 310                 315                 320

Ala Ala Pro Leu Phe Gly Ile Gly His Val Ser Asp His Thr Trp Ala
                325                 330                 335

Ala Arg Gly Arg Ile Glu Tyr Glu Leu Ser Asp Ala Ala Thr Ile Thr
            340                 345                 350

Tyr Ile Gly Gly Tyr Arg Lys Tyr Ser Gly Asp Pro Gly Arg Leu Thr
        355                 360                 365

Leu Pro Thr Ile Tyr Gln Ser Phe Gly Tyr Gln Asp Glu Ala Lys Thr
    370                 375                 380

Gln Ser His Glu Leu Arg Ile Asn Gly Thr Val Gly Gly Val Val Tyr
385                 390                 395                 400

Gln Val Gly Gly Phe Tyr Phe Lys Glu Asp Leu Ala Arg Glu Ser Gly
                405                 410                 415

Phe Met Leu Pro Ser Phe Val Phe Ala Asp Pro Leu Asn Asp Pro Ser
            420                 425                 430

Leu Phe Gly Lys Pro Gly Thr Phe Leu Ser Tyr Phe Gly Arg Tyr Val
        435                 440                 445

Lys Ser Asp Ser Lys Ser Val Phe Gly Gln Val Glu Val Pro Leu Gly
    450                 455                 460

Asp Lys Leu Thr Ala Ile Gly Gly Leu Arg Tyr Thr Asp Asn Lys Arg
465                 470                 475                 480

Asn Ala Thr Tyr Leu Asn Val Asp Pro Phe Arg Phe Ser Leu Glu Thr
                485                 490                 495

Phe Ser Leu Val Pro Asp Pro Tyr Ile Val Gly Ala Gly Pro Gly Arg
            500                 505                 510

Lys Asp Phe Ser Lys Val Met Tyr Leu Thr Thr Ile Pro Leu Lys Ser
        515                 520                 525

Ser Asp Ser Lys Val Thr Trp Leu Ala Gly Leu Asn Phe Lys Pro Asn
    530                 535                 540

Ser Asp Thr Leu Ile Phe Val Lys Ala Ser Thr Gly Phe Lys Ala Gly
545                 550                 555                 560
```

```
Gly Phe Asp Ser Val Gly Thr Tyr Lys Pro Glu Thr Asn Thr Ala Phe
                565                 570                 575

Glu Gly Gly Trp Lys Gln Thr Phe Gly Asp His Gly Gln His Gln Phe
            580                 585                 590

Asn Leu Gly Ala Phe Tyr Tyr Asp Tyr Lys Asp Leu Gln Val Ser Val
        595                 600                 605

Leu Leu Asp Thr Ala Ile Gly Gly Gln Ile Phe Asn Ala Gly Lys Ala
    610                 615                 620

Lys Ile Trp Gly Ile Glu Ala Ser Ala Asp Ile Ala Leu Asp Asp Arg
625                 630                 635                 640

Thr Asn Phe His Ala Ser Ala Asn Tyr Leu Asn Ala Glu Tyr Lys Glu
                645                 650                 655

Leu Leu Ala Gln Phe Asn Val Phe Asp Thr Thr Gly Glu Ile Asn Gly
            660                 665                 670

Val Gly Asp Leu Asp Pro Asn Thr Asp Gly Ile Gln Gln Pro Asn Phe
        675                 680                 685

Ala Gly Asn Arg Pro Pro Phe Ser Pro Glu Trp Val Leu Thr Ala Ser
    690                 695                 700

Leu Asp His Thr Phe Pro Leu Gly Asp Met Gly Gly Leu Thr Ala Arg
705                 710                 715                 720

Val Asn Thr Thr Phe Lys Ser Lys Tyr Phe Thr Asp Phe Tyr Asn Tyr
                725                 730                 735

Arg Asp Gly Thr Gln Ser Ala Leu Ser Gln Thr Asp Ala Ser Leu Glu
            740                 745                 750

Tyr Lys Pro Glu Asn Glu Lys Phe Ser Ile Thr Ala Phe Val Lys Asn
        755                 760                 765

Ile Glu Gly Thr Arg Pro Leu Thr Tyr Gly Ser Phe Val Ser Ala Gly
    770                 775                 780

Pro Asp Asp Ile Phe Asn Trp Gln Phe Gly Thr Pro Arg Thr Tyr Gly
785                 790                 795                 800

Val Arg Leu Ala Val Asp Phe
                805
```

<210> SEQ ID NO 159
<211> LENGTH: 147
<212> TYPE: DNA
<213> ORGANISM: Burkholderia_cenocepacia_AU_1054

<400> SEQUENCE: 159

```
ttttcttgtg aagtcggcgg ggcattcgta taatgatcct cattggttgc cgcgctgcgg     60

caacctccgc atgtctcctc caccctcctc ctaaggtgga ttaagcccga accagccgtt    120

cgggcttttt ttcgtcccat gcaaaca                                         147
```

<210> SEQ ID NO 160
<211> LENGTH: 147
<212> TYPE: DNA
<213> ORGANISM: Burkholderia_cenocepacia_HI2424

<400> SEQUENCE: 160

```
ttttcttgtg aagtcggcgg ggcattcgta taatgatcct cattggttgc cgcgctgcgg     60

caacctccgc atgtctcctc caccctcctc ctaaggtgga ttaagcccga accagccgtt    120

cgggcttttt ttcgtcccat gcaaaca                                         147
```

<210> SEQ ID NO 161
<211> LENGTH: 147

<212> TYPE: DNA
<213> ORGANISM: Burkholderia sp 383

<400> SEQUENCE: 161
ttttcttgtg gagtcggcga cgcgttcgta taatgagcct cattggttgt cgcgctgcgg 60
caacctccga atgtctcctc caccctcctc ctatggtgga ttaagcccga accagccgtt 120
cgggcttttt ttcgtcccat gcaaaca 147

<210> SEQ ID NO 162
<211> LENGTH: 147
<212> TYPE: DNA
<213> ORGANISM: Burkholderia_ambifaria_AMMD

<400> SEQUENCE: 162
ttttcttgtg aagtcgacgc cccattcgta taatgagcct cattggttgt cgcggtgcga 60
caatctccgc atgtctcctc caccctcctc ctgaggtgga ttaagcccga accagccgtt 120
cgggcttttt ttcgtcccat gcaatga 147

<210> SEQ ID NO 163
<211> LENGTH: 144
<212> TYPE: DNA
<213> ORGANISM: Ralstonia_metallidurans

<400> SEQUENCE: 163
agtcggtaac gtacccaaat cgctcgtcgc accgcccgcc aagaccggcc ccgtcgatcg 60
cccggtgtct cctccaccct cctcctttgg tggattcgaa cccaagtcca accgacttgg 120 gtttttttc gtcttttgca aggg 144

<210> SEQ ID NO 164
<211> LENGTH: 124
<212> TYPE: DNA
<213> ORGANISM: Ralstonia_necator

<400> SEQUENCE: 164
accgtcggtc tcccagtgtc tcctccaccc tcctcctttg gtggagcccc cggccaagct 60
ctccgcaccg cccgcaagaa cttcaaaccc aggctaaacc gcctgggttt tttttcgccc 120
ctgt 124

<210> SEQ ID NO 165
<211> LENGTH: 196
<212> TYPE: DNA
<213> ORGANISM: Ralstonia_metallidurans

<400> SEQUENCE: 165
gccgatatgt ataattcaat ccatcgaacg acggcgcatg agagcgcgcc agagtgcgaa 60
agcgaaagtc ggtaacgtac ccaaatcgct cgtcgcaccg cccgccaaga ccggccccgt 120
cgatcgcccg gtgtctcctc caccctcctc ctttggtgga ttcgaaccca agtccaaccg 180
acttgggttt tttttc 196

<210> SEQ ID NO 166
<211> LENGTH: 182
<212> TYPE: DNA
<213> ORGANISM: Ralstonia_necator

<400> SEQUENCE: 166
taccccatgt ataattccaa tcattgaacg acggcgcaga cagcgcgcca gagtgcgaaa 60
gcgaagcccc cggccaagct ctccgcaccg cccgcaagaa caccgtcggt ctcccagtgt 120
ctcctccacc ctcctccttt ggtggattca aacccaggct aaaccgcctg ggtttttttt 180
cg 182

<210> SEQ ID NO 167
<211> LENGTH: 115
<212> TYPE: DNA
<213> ORGANISM: Burkholderia_cenocepacia_AU_1054

<400> SEQUENCE: 167
gggcattcgt ataatgatcc tcattggttg ccgcgctgcg gcaacctccg catgtctcct 60
ccaccctcct cctaaggtgg attaagcccg aaccagccgt tcgggctttt tttcg 115

<210> SEQ ID NO 168
<211> LENGTH: 115
<212> TYPE: DNA
<213> ORGANISM: Burkholderia_cenocepacia_HI2424

<400> SEQUENCE: 168
gggcattcgt ataatgatcc tcattggttg ccgcgctgcg gcaacctccg catgtctcct 60
ccaccctcct cctaaggtgg attaagcccg aaccagccgt tcgggctttt tttcg 115

<210> SEQ ID NO 169
<211> LENGTH: 115
<212> TYPE: DNA
<213> ORGANISM: Burkholderia_ambifaria_AMMD

<400> SEQUENCE: 169
ccccattcgt ataatgagcc tcattggttg tcgcggtgcg acaatctccg catgtctcct 60
ccaccctcct cctgaggtgg attaagcccg aaccagccgt tcgggctttt tttcg 115

<210> SEQ ID NO 170
<211> LENGTH: 115
<212> TYPE: DNA
<213> ORGANISM: Burkholderia sp 383

<400> SEQUENCE: 170
acgcgttcgt ataatgagcc tcattggttg tcgcgctgcg gcaacctccg aatgtctcct 60
ccaccctcct cctatggtgg attaagcccg aaccagccgt tcgggctttt tttcg 115

<210> SEQ ID NO 171
<211> LENGTH: 62
<212> TYPE: DNA
<213> ORGANISM: Burkholderia cenocepacia HI2424

<400> SEQUENCE: 171
tgtctcctcc atgtctcctc tgatatggat tcagcccgcc acttaggcgg gctttttttt 60
gc 62

<210> SEQ ID NO 172
<211> LENGTH: 69
<212> TYPE: DNA
<213> ORGANISM: Burkholderia cenocepacia HI2424

<400> SEQUENCE: 172
tgtctcctcc atgtctcctc ctgatatgga ttaagcccgt tccgctctgc gtgaacgggc 60
tttttttcg 69

<210> SEQ ID NO 173
<211> LENGTH: 196

<212> TYPE: DNA
<213> ORGANISM: Ralstonia metallidurans

<400> SEQUENCE: 173
gccgatatgt ataattcaat ccaucgaacg acggcgcaug agagcgcgcc agagugcgaa 60
agcgaaaguc gguaacguac ccaaaucgcu cgucgcaccg cccgccaaga ccggccccgu 120
cgaucgcccg gugucuccuc cacccuccuc cuuuggugga uucgaaccca aguccaaccg 180
acuuggguuu uuuuuc 196

<210> SEQ ID NO 174
<211> LENGTH: 182
<212> TYPE: DNA
<213> ORGANISM: Ralstonia necator

<400> SEQUENCE: 174
taccccatgt ataattccaa tcauugaacg acggcgcaga cagcgcgcca gagugcgaaa 60
gcgaagcccc cggccaagcu cuccgcaccg cccgcaagaa caccgucggu cucccagugu 120
cuccuccacc cuccuccuuu gguggauuca aacccaggcu aaaccgccug gguuuuuuuu 180
cg 182

<210> SEQ ID NO 175
<211> LENGTH: 115
<212> TYPE: DNA
<213> ORGANISM: Burkholderia_cenocepacia_AU_1054

<400> SEQUENCE: 175
gggcattcgt ataatgatcc tcauugguug ccgcgcugcg gcaaccuccg caugucuccu 60
ccacccuccu ccuaaggugg auuaagcccg aaccagccgu ucgggcuuuu uuucg 115

<210> SEQ ID NO 176
<211> LENGTH: 115
<212> TYPE: DNA
<213> ORGANISM: Burkholderia_cenocepacia_HI2424

<400> SEQUENCE: 176
gggcattcgt ataatgatcc tcauugguug ccgcgcugcg gcaaccuccg caugucuccu 60
ccacccuccu ccuaaggugg auuaagcccg aaccagccgu ucgggcuuuu uuucg 115

<210> SEQ ID NO 177
<211> LENGTH: 115
<212> TYPE: DNA
<213> ORGANISM: Burkholderia_ambifaria_AMMD

<400> SEQUENCE: 177
ccccattcgt ataatgagcc tcauugguug ucgcggugcg acaaucuccg caugucuccu 60
ccacccuccu ccuaaggugg auuaagcccg aaccagccgu ucgggcuuuu uuucg 115

<210> SEQ ID NO 178
<211> LENGTH: 115
<212> TYPE: DNA
<213> ORGANISM: Burkholderia sp 383

<400> SEQUENCE: 178
acgcgttcgt ataatgagcc tcauugguug ucgcgcugcg gcaaccuccg aaugucuccu 60
ccacccuccu ccuauggugg auuaagcccg aaccagccgu ucgggcuuuu uuucg 115

<210> SEQ ID NO 179
<211> LENGTH: 173

<212> TYPE: RNA
<213> ORGANISM: Ralstonia metallidurans

<400> SEQUENCE: 179
ucgaacgacg gcgcaugaga gcgcgccaga gugcgaaagc gaaagucggu aacguaccca 60
aaucgcucgu cgcaccgccc gccaagaccg gccccgucga ucgcccggug ucuccuccac 120
ccuccuccuu ugguggauuc gaacccaagu ccaaccgacu uggguuuuuu uuc 173

<210> SEQ ID NO 180
<211> LENGTH: 159
<212> TYPE: RNA
<213> ORGANISM: Ralstonia necator

<400> SEQUENCE: 180
uugaacgacg gcgcagacag cgcgccagag ugcgaaagcg aagcccccgg ccaagcucuc 60
cgcaccgccc gcaagaacac cgucggucuc ccagugucuc cuccacccuc cuccuuuggu 120
ggauucaaac ccaggcuaaa ccgccugggu uuuuuuucg 159

<210> SEQ ID NO 181
<211> LENGTH: 92
<212> TYPE: RNA
<213> ORGANISM: Burkholderia_cenocepacia_AU_1054

<400> SEQUENCE: 181
uugguugccg cgcugcggca accuccgcau gucuccucca cccuccuccu aagguggauu 60
aagcccgaac cagccguucg ggcuuuuuuu cg 92

<210> SEQ ID NO 182
<211> LENGTH: 92
<212> TYPE: RNA
<213> ORGANISM: Burkholderia_cenocepacia_HI2424

<400> SEQUENCE: 182
uugguugccg cgcugcggca accuccgcau gucuccucca cccuccuccu aagguggauu 60
aagcccgaac cagccguucg ggcuuuuuuu cg 92

<210> SEQ ID NO 183
<211> LENGTH: 92
<212> TYPE: RNA
<213> ORGANISM: Burkholderia_ambifaria_AMMD

<400> SEQUENCE: 183
uugguugucg cggugcgaca aucuccgcau gucuccucca cccuccuccu aagguggauu 60
aagcccgaac cagccguucg ggcuuuuuuu cg 92

<210> SEQ ID NO 184
<211> LENGTH: 92
<212> TYPE: RNA
<213> ORGANISM: Burkholderia sp 383

<400> SEQUENCE: 184
uugguugucg cgcugcggca accuccgaau gucuccucca cccuccuccu augguggauu 60
aagcccgaac cagccguucg ggcuuuuuuu cg 92

<210> SEQ ID NO 185
<211> LENGTH: 62
<212> TYPE: RNA
<213> ORGANISM: Burkholderia cenocepacia HI2424

<400> SEQUENCE: 185
ugucuccucc augucuccuc ugauauggau ucagcccgcc acuuaggcgg gcuuuuuuuu 60
gc 62

<210> SEQ ID NO 186
<211> LENGTH: 69
<212> TYPE: RNA
<213> ORGANISM: Burkholderia cenocepacia HI2424

<400> SEQUENCE: 186
ugucuccucc augucuccuc cugauaugga uuaagcccgu uccgcucugc gugaacgggc 60
uuuuuuucg 69

<210> SEQ ID NO 187
<211> LENGTH: 93
<212> TYPE: PRT
<213> ORGANISM: Geobacter metallireducens GS-15

<400> SEQUENCE: 187

Met Lys Lys Met Ala Val Leu Leu Met Ala Ala Phe Met Met Ser Ala
1 5 10 15

Thr Val Pro Val Phe Ala Ala Glu Met Thr Lys Glu Glu Lys Asp Gln
20 25 30

Cys Leu Leu Ala Ser Lys Asn Cys Gly Met Glu Val Asp Thr Leu Gln
35 40 45

Lys Lys Ile Lys Lys Leu Asn Ser Glu Ile Lys Lys Gly Lys Lys Val
50 55 60

Tyr Ser Ala Asp Glu Ile Lys Lys Leu Gln Gln Lys Leu Asp Glu Ala
65 70 75 80

Asn Ala Leu Leu Asp Asp Ile Leu Lys Gly Gly Gly Asn
85 90

<210> SEQ ID NO 188
<211> LENGTH: 93
<212> TYPE: PRT
<213> ORGANISM: Geobacter sulfurreducens PCA: NC_002939

<400> SEQUENCE: 188

Met Lys Lys Met Ala Ile Met Val Met Ala Ala Phe Met Met Ser Ala
1 5 10 15

Thr Val Pro Ala Leu Ala Ala Glu Met Thr Lys Glu Glu Lys Asp Met
20 25 30

Cys Leu Leu Ala Ser Lys Asn Cys Ala Thr Glu Val Asp Ser Leu Gln
35 40 45

Lys Lys Ile Lys Lys Leu Asn Ala Glu Ile Lys Lys Gly Lys Lys Val
50 55 60

Tyr Ser Ala Asp Glu Ile Lys Lys Leu Gln Gln Lys Leu Asp Glu Ala
65 70 75 80

Asn Asp Leu Leu Asp Ser Ile Leu Lys Gly Gly Gly Asn
85 90

<210> SEQ ID NO 189
<211> LENGTH: 95
<212> TYPE: PRT
<213> ORGANISM: Geobacter sulfurreducens PCA: NC_002939

<400> SEQUENCE: 189

Met Lys Lys Met Ala Val Leu Met Leu Thr Ala Phe Ala Phe Ser Ala
1 5 10 15

-continued

```
Thr Val Pro Thr Phe Ala Ala Glu Met Ser Lys Glu Glu Lys Asp Met
            20                  25                  30

Cys Leu Leu Ala Ser Lys Asn Cys Ala Gly Glu Val Asp Ser Leu Gln
        35                  40                  45

Lys Lys Val Lys Lys Leu Gln Ala Glu Ile Lys Lys Gly Lys Lys Val
    50                  55                  60

Tyr Thr Ala Glu Glu Leu Lys Lys Leu Glu Gln Lys Leu Lys Glu Ala
65                  70                  75                  80

Asn Glu Met Val Asp Val Leu Leu Lys Gln Gly Gly Gly Gly Lys
                85                  90                  95


<210> SEQ ID NO 190
<211> LENGTH: 92
<212> TYPE: PRT
<213> ORGANISM: Geobacter uraniumreducens Rf4

<400> SEQUENCE: 190

Met Lys Arg Ile Gly Ile Ala Ile Met Ala Ala Phe Val Met Ser Ala
1               5                   10                  15

Ala Leu Pro Ala Phe Ala Ala Asp Met Thr Lys Glu Glu Lys Asn Gln
            20                  25                  30

Cys Leu Leu Ala Ser Lys Gly Cys Thr Asp Glu Val Asp Ser Ile Gln
        35                  40                  45

Gln Lys Ile Gly Lys Leu Asn Lys Glu Ile Lys Lys Gly Lys Arg Val
    50                  55                  60

Tyr Thr Asp Glu Glu Ile Arg Lys Leu Glu Gln Lys Leu Lys Glu Ala
65                  70                  75                  80

Asn Asp Leu Leu Asp Asp Leu Leu Lys Gly His Lys
                85                  90


<210> SEQ ID NO 191
<211> LENGTH: 91
<212> TYPE: PRT
<213> ORGANISM: Geobacter uraniumreducens Rf4, unfinished sequence:
      NZ_AAON01000002

<400> SEQUENCE: 191

Met Lys Lys Ser Ala Ile Val Leu Ile Thr Ala Leu Leu Leu Ser Pro
1               5                   10                  15

Ala Gly Tyr Ile Phe Ala Gln Gln Thr His Glu Glu Lys Val Ile Cys
            20                  25                  30

Glu Leu Ala Ala Lys Asn Cys Leu Asn Arg Ile Glu Ile Ile Gln Lys
        35                  40                  45

Lys Val Lys Lys Leu Asn Asp Gln Ile Lys Lys Gly Ser Lys Thr Tyr
    50                  55                  60

Ser Ala Glu Glu Leu Lys Lys Leu Glu Gln Lys Leu Gln Glu Thr Lys
65                  70                  75                  80

Asp Leu Leu Asp Lys Leu Glu Asp Ala Gly Lys
                85                  90


<210> SEQ ID NO 192
<211> LENGTH: 92
<212> TYPE: PRT
<213> ORGANISM: Geobacter uraniumreducens Rf4, unfinished sequence:
      NZ_AAON01000044]

<400> SEQUENCE: 192

Met Lys Arg Met Thr Leu Leu Phe Leu Thr Val Leu Val Val Phe Ala
1               5                   10                  15
```

Thr Val Pro Ala Val Ser Gln Val Thr Lys Glu Glu Lys Asp Met Cys
20 25 30

Leu Leu Ala Ser Lys Asn Cys Leu Asn Asp Val Asp Thr Ile Gln Lys
35 40 45

Arg Ile Arg Lys Ile Arg Asn Glu Ile Lys Lys Gly Lys Lys Val Tyr
50 55 60

Ser Ala Glu Glu Leu Lys Lys Leu Glu Leu Lys Leu Gln Glu Ala Lys
65 70 75 80

Ser Ile Leu Asp Ser Leu Glu Asn Glu Asn Arg Pro
85 90

<210> SEQ ID NO 193
<211> LENGTH: 91
<212> TYPE: PRT
<213> ORGANISM: Pelobacter carbinolicus DSM 2380

<400> SEQUENCE: 193

Met Lys Lys Thr Ala Leu Leu Leu Leu Ala Thr Ser Cys Leu Val Phe
1 5 10 15

Cys Thr Pro Val Phe Ser Gln Thr Arg Gln Asp Gln Lys Asp Met Cys
20 25 30

Leu Leu Ser Met Lys Tyr Cys Ala Asn Gln Ala Asp Thr Ile Gln Gln
35 40 45

Thr Ile Lys Lys Leu Glu Lys Glu Ile Gly Lys Gly Glu Lys Val Tyr
50 55 60

Ser Glu Gln Glu Leu Lys Gln Leu Glu Gln Lys Leu Asn Glu Val Asn
65 70 75 80

Asp Ile Leu Lys Ser Leu Val Gly Gly Ser Lys
85 90

<210> SEQ ID NO 194
<211> LENGTH: 91
<212> TYPE: PRT
<213> ORGANISM: Geobacter sulfurreducens PCA: NC_002939

<400> SEQUENCE: 194

Met Lys Lys Ile Ile Val Ser Val Cys Ala Ala Ala Leu Ala Leu Ala
1 5 10 15

Ala Ile Pro Ala Phe Ala Ser Val Pro Pro Glu Gly Lys Asp Asp Cys
20 25 30

Leu Leu Tyr Gly Lys Asn Cys Pro Asn Val Leu Asp Ser Leu Pro Glu
35 40 45

Arg Ile Ala Lys Leu Asn Lys Glu Ile Ala Lys Gly Glu Lys Val Tyr
50 55 60

Thr Ser Glu Glu Leu Asn Leu Leu Glu Arg Lys Leu Lys Glu Asp Asn
65 70 75 80

Arg Thr Met Arg Val Leu Asn Lys Pro Gly Lys
85 90

<210> SEQ ID NO 195
<211> LENGTH: 95
<212> TYPE: PRT
<213> ORGANISM: Geobacter sulfurreducens PCA: NC_002939

<400> SEQUENCE: 195

Met Ser Tyr Lys Lys Val Val Gly Leu Ala Leu Leu Leu Leu Met Ser
1 5 10 15

Ala Ala Pro Ala Arg Pro Ala Asp Gly Pro Ala Pro Ala Gln Gly Lys
20 25 30

-continued

```
Asp Thr Cys Leu Leu Tyr His Asp Asn Cys Pro Asp Arg Lys Asp Asp
        35                  40                  45

Ile Tyr Gln Arg Ile Ala Arg Leu Arg Arg Glu Ile Ala Lys Gly Pro
    50                  55                  60

Ala Val Tyr Thr Pro Glu Glu Leu Arg Thr Leu Gln Gln Met Leu Asp
65                  70                  75                  80

Glu Tyr Glu Gln Leu Leu Asp Arg Leu Leu Tyr His Asn Thr Asp
                85                  90                  95


<210> SEQ ID NO 196
<211> LENGTH: 97
<212> TYPE: PRT
<213> ORGANISM: Geobacter uraniumreducens Rf4

<400> SEQUENCE: 196

Met Asn Leu Thr Glu Lys Gly Arg Lys Gly Gly Trp Leu Val Cys Gly
1               5                   10                  15

Val Cys Phe Val Leu Ser Ala Ala Leu Pro Ala Tyr Gly Gly Met Gly
            20                  25                  30

Ala Ser Glu Gly Lys Asp Leu Cys Leu Leu Tyr Gly Glu Asn Cys Pro
        35                  40                  45

Asp Arg Lys Glu Thr Ile Ile Glu Ile Ile Ala Arg Leu Lys Tyr Glu
    50                  55                  60

Ile Ala Arg Gly Glu Ala Val Tyr Thr Arg Lys Glu Leu Glu Arg Leu
65                  70                  75                  80

Gln Arg Lys Leu Asp Asp Tyr Glu Trp Leu Leu Phe Val Ile Leu Tyr
                85                  90                  95

Gly


<210> SEQ ID NO 197
<211> LENGTH: 70
<212> TYPE: PRT
<213> ORGANISM: Geobacter metallireducens GS-15

<400> SEQUENCE: 197

Glu Met Thr Lys Glu Glu Lys Asp Gln Cys Leu Leu Ala Ser Lys Asn
1               5                   10                  15

Cys Gly Met Glu Val Asp Thr Leu Gln Lys Lys Ile Lys Lys Leu Asn
            20                  25                  30

Ser Glu Ile Lys Lys Gly Lys Lys Val Tyr Ser Ala Asp Glu Ile Lys
        35                  40                  45

Lys Leu Gln Gln Lys Leu Asp Glu Ala Asn Ala Leu Leu Asp Asp Ile
    50                  55                  60

Leu Lys Gly Gly Gly Asn
65                  70
```

USES OF ANTIMICROBIAL GENES FROM MICROBIAL GENOME

CROSS-REFERENCE TO RELATED APPLICATIONS

This application is a national stage application under 35 U.S.C. 371 of International Patent Application No. PCT/US2007/087691, filed on Dec. 15, 2007, which claims priority to U.S. Provisional patent application Ser. No. 60/870,322, filed on Dec. 15, 2006, the contents of both of which is are hereby incorporated by reference in its entirety for all purposes

STATEMENT OF GOVERNMENTAL SUPPORT

This invention was made with government support under Contract No. DE-AC02-05CH11231 awarded by U.S. Department of Energy. The government has certain rights in this invention.

REFERENCE TO SEQUENCE LISTING AND TABLE APPENDIX

The attached sequence listing found in paper form is hereby incorporated by reference. The Sequence Listing describes the sequences of SEQ ID NOS: 1-197, antimicrobial genes and their expression products.

The attached Table 2, hereby incorporated by reference, describes the sequences in greater detail. For each gene, the following details were provided: a) The genome of origin; b) Coordinates on that genome; c) Annotation, with Genbank Accession number if one exists; d) An indication whether the gene is predicted to have a signal sequence for secretion; e) The number of covering small clones and fosmids, and an indication whether this number is regarded as statistically significant low coverage; f) Indication whether this gene was found to have low coverage in other genomes as well—for each comparison genome, the following details are given: (1) BLAST e-value between the gene described and the gene in the comparison genome; (2) GC-content of the other genome; (3) Number of small clones covering the gene in the other genome; (4) Number of fosmid clones covering the gene in the other genome; g) Nucleotide sequence of the gene; and h) Polypeptide sequence of the gene.

BACKGROUND OF THE INVENTION

1. Field of the Invention

The present invention relates to a method for mining microbial genomes for genes that kill, or inhibit the growth of, various bacteria. The present invention also relates to genes and gene products that can be used as antibiotics or as tools for molecular biology.

2. Related Art

Microbes (bacteria, archaea, fungi and viruses) frequently produce and secrete compounds aimed at killing other microbes which help them in their continuous struggle for survival in their ecological niche. Such compounds can be small molecule antibiotics, such as the ones produced by various *Streptomyces* species [Watve, Arch Microbiol. 2001 November; 176(5):386-90], or proteinacious antibiotics, often known as bacteriocins [Riley & Wertz, Annu Rev Microbiol. 2002; 56: 117-37]. Microbes also produce non-secreted defense molecules that help them escape predation by viruses. For example, "abortive infection" genes are suicidal genes that are activated in some bacteria once they sensed they were infected by a virus. These genes lead to the death of the infected bacterium and, hence, to the survival of the surrounding bacterial community [Chopin, Curr Opin Microbiol. 2005 August; 8(4):473-9]. Viruses also frequently produce molecules that inhibit the growth of, or kill, microbial cells by various mechanisms such as degradation of RNA [Sanson, FEMS Microbiol Rev. 1995 August; 17(1-2):141-50], cell lysis [Schuch, Nature. 2002 Aug. 22; 418(6900):884-9] etc.

Proteins that target bacteria have a broad medical and biotechnological application spectrum. They can be used as direct antibiotics for human and veterinary medicine [Gillor 2005, Curr Pharm Des. 2005; 11(8):1067-75], as growth enhancers in livestock [Brashears, 2003. J. Food Prot. 66, 748-754], as food preservatives [Delves-Broughton, Antonie Van Leeuwenhoek. 1996 February; 69(2): 193-202], as genes engineered into probiotic bacteria [Gillor 2005, Curr Pharm Des. 2005; 11(8):1067-75], as killers of phytopathogenic bacteria for crop management [Penyalver 2000, Eur. J. Plant Pathol. 106, 801-810], etc.

One of the popular methods to study the function of a given gene is to clone it into a model bacterial species (with *Escherichia coli* (*E. coli*) being the most popularly used model) and to study the expressed product. However, gene products that are toxic to bacteria will usually be unclonable in *E. coli* due to their negative effect on the bacterial growth. As described below, the present invention provides a method for identifying regions from microbial genomes that are unclonable into *E. coli*, retrieve antimicrobial genes that reside in these regions, and demonstrate their toxicity to *E. coli* and other pathogenic microbes. The method relies on an improvement of the microbial genome sequencing process described in URL:<http://www.jgi.doe.gov/sequencing/strategy.html> and links therein.

One aspect of the present invention involves mapping of sequencing clones onto a "finished" (fully sequenced) microbial genomic sequence. Such mapping was noted to be beneficial for detection of toxic proteins also by Roberts (U.S. Patent Application Publication No. US 2006/0014179 A1), who searched for gaps in clone start sites on either sides of open reading frames, and inferred that such open reading frames can encode for toxic genes or endonucleases.

BRIEF SUMMARY OF THE INVENTION

The present invention provides a method for identifying antimicrobial genes in a genome comprising the steps of: (a) Read mapping, wherein sequence reads are mapped back on the genomic sequence and clone positions are identified; (b) Clone coverage calculation, wherein, for each position of the analyzed genome sequence, the number of covering clones (clones that span this position) is calculated; (c) Genomic regions identification, wherein regions having no clone coverage ("uncaptured gaps"), and regions having a statistically significant reduction in coverage, are identified; (d) Toxicity level determination, wherein regions having a statistically significant reduction in fosmid-only coverage (in addition to overall reduction on small [2-4 kb] clone coverage) are marked as containing highly toxic genes; and (e) Gene selection and experimental validation, wherein genes residing in each low- or zero-covered region are identified as antimicrobial. The gene products are then experimentally tested for antimicrobial, more specifically bactericidal or bacteriostatic, effect on the growth of various microorganisms.

Antimicrobial genes were found using the present method. The compositions are nucleotide and amino acid sequences for antimicrobial polypeptides and proteins, the uses of which are further described. Specifically, the present invention provides antimicrobial nucleic acids and polypeptides having a sequence set forth in SEQ ID NOs: 1-172 and 179-197, and variants and fragments thereof. The present invention further provides compositions and methods directed to inducing plant pathogen resistance, particularly bacterial resistance.

In one aspect of the invention, an isolated nucleic acid molecule isolated using the prescribed method for identifying antimicrobial genes in a genome, wherein the nucleic acid molecule encodes a protein or RNA molecule having antimicrobial activity.

In one embodiment, the antimicrobial gene isolated from a microbe and found in Table 1. The isolated nucleic acid, wherein the sequence is selected from the group consisting of sequences, SEQ ID NOs:1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 80, 82, 84, 86, 88, 90, 92, 94, 96, 98, 100, 102, 104, 107, 109, 111, 113, 115, 117, 119, 121, 123, 125, 127, 129, 131, 133, 135, 137, 139, 141, 143, 145, 147, 149, 151, 153, 155, 157, and 159-172.

In another aspect, the encoded protein or RNA molecule having antimicrobial activity. In one embodiment, an antimicrobial protein expressed in vitro from the isolated gene of claim 2 and found in Table 1. In another embodiment, the isolated protein or RNA molecule having antimicrobial activity, comprising a sequence selected from SEQ ID NOS: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 79, 81, 83, 85, 87, 89, 91, 93, 95, 97, 99, 101, 103, 105, 106, 108, 110, 112, 114, 116, 118, 120, 122, 124, 126, 128, 130, 132, 134, 136, 138, 140, 142, 144, 146, 148, 150, 152, 154, 156, 158, and 179-197.

The isolated protein or RNA molecule having antimicrobial activity, wherein the protein or RNA molecule has antimicrobial activity against a microbe selected from the group consisting of *Staphylococcus aureus*, microorganisms of the genus *Staphylococcus, Escherichia coli*, microorganisms of the genus *Escherichia*, microorganisms of the genus *Aspergillus*, microorganisms of the genus *Candida*, microorganisms of the genus *Mucor*, microorganisms of the genus *Absidia*, microorganisms of the genus *Cryptococcus*, microorganisms of the genus *Blastomyces*, microorganisms of the genus *Paracoccidioides*, microorganisms of the genus *Coccidioides*, microorganisms of the genus *Sporothrix*, microorganisms of the genus *Phialophora*, microorganisms of the genus *Histoplasma*, microorganisms of the genus *Trichophyton*, microorganisms of the genus *Microsporum*, microorganisms of the genus *Epidermophyton*, microorganisms of the genus *Bacillus*, and microorganisms of the genus *Yersinia*, microorganisms of the genus *Salmonella*, and microorganisms of the genus *Francisella.*

In another aspect, the nucleic acid molecule encoding antimicrobial expression products, and isolated according to the prescribed method for identifying antimicrobial genes in a genome, wherein said nucleotide sequence is optimized for expression in a plant. An expression cassette comprising the nucleotide sequence operably linked to a promoter that drives expression in a plant. The expression cassette further comprising an operably linked polynucleotide encoding a signal peptide.

In another aspect, a plant comprising in its genome at least one stably incorporated expression cassette, said expression cassette comprising a heterologous nucleotide sequence isolated according to the method of identifying antimicrobial genes from a genome, operably linked to a promoter that drives expression in the plant, wherein the plant displays increased resistance to a plant pathogen. The plant is resistant to a microbe, such as *Agrobacterium tumefaciens, Burkholderia cenocepacia, Clavibacter michiganensis, Erwinia carotovora, Erwinia chrysanthemi, Leifsonia xyli, Pseudomonas syringae, Ralstonia solanacearum, Xanthomonas axonopodis, Xanthomonas campestris, Xylella fastidiosa, Spiroplasma kunkelii*, and Onion yellows phytoplasma. The promoter is preferably a pathogen-inducible promoter. In another embodiment, a transformed seed of the plant displaying increased resistance to a plant pathogen.

In another aspect, a cell comprising in its genome at least one stably incorporated expression cassette, said expression cassette comprising a heterologous nucleotide sequence isolated according to the method of identifying antimicrobial genes from a genome, operably linked to a promoter that drives expression in the cell.

In another aspect, a method for inducing pathogen resistance in an organism, said method comprising introducing into an organism at least one expression cassette, said expression cassette comprising a heterologous nucleotide sequence isolated according to the method of identifying antimicrobial genes from a genome operably linked to a promoter that drives expression in the organism. In one embodiment, an expression cassette comprising a nucleotide sequence sequence isolated according to the method of identifying antimicrobial genes from a genome operably linked to a promoter that drives expression in a microorganism. In another embodiment, transformed microorganism comprising at least one expression cassette.

It is an object of the invention to provide an antipathogenic composition comprising at least one protein or RNA molecule isolated according to the method of identifying antimicrobial genes from a genome. The composition further comprising a carrier.

Thus, it is provided a method for protecting a vertebrate from a pathogen comprising applying the antipathogenic composition to the environment of a pathogen. In one embodiment, the antipathogenic composition comprising at least one transformed microorganism, comprising at least one expression cassette comprising a nucleotide sequence isolated according to the method of identifying antimicrobial genes from a genome.

It is further provided, a method for preventing infection in a patient comprising applying the antipathogenic composition in a topical preparation to the patient. The antimicrobial composition can be prepared as in an ointment, cream or lotion for topical application.

In another embodiment, a method for preventing food spoilage comprising applying the antipathogenic composition to a food surface. In one embodiment, the antipathogenic composition is in a preparation form for surface administration such as injections, sprays, liquid solutions, liquid coating agents, gel, ointments, or aerosol.

In yet another embodiment, a method for protecting a plant from a pathogen comprising applying the antipathogenic composition to the environment of a plant pathogen. The method wherein the carrier is a surface-active agent, an inert carrier, a preservative, a humectant, a feeding stimulant, an attractant, an encapsulating agent, a binder, an emulsifier, a dye, a UV protective, a buffer, a flow agent or fertilizers, micronutrient donors, or other preparations that may be used to inhibit or control microbial or bacterial infection or growth. The antipathogenic composition further comprising one or more agrochemicals including, but not limited to, herbicides, insecticides, fungicides, bactericides, nematicides, molluscicides, acaracides, plant growth regulators, harvest aids, and fertilizers, can be combined with carriers, surfactants or adjuvants customarily employed in the art of formulation. The antimicrobial agent for preparations according to the present invention useful in exhibiting an antimicrobial effect on plant pathogenic microorganisms such as microorganisms of the genus *Agrobacterium*, microorganisms of the genus *Burkholderia*, microorganisms of the genus *Clavibacter*, microorganisms of the genus *Erwinia*, microorganisms of the genus *Ralstonia*, microorganisms of the genus *Xanthomonas*, microorganisms of the genus *Pseudomonas*, and microorganisms of the genus *Leifsonia*, microorganisms of the genus *Xylella*, microorganisms of the genus *Spiroplasma.*

BRIEF DESCRIPTION OF THE DRAWINGS

FIG. 10 shows photographs of induction of three different genes and the effect on growth of bacteria. Shown are plating results of bacteria containing each gene on plates containing no IPTG, 250 uM IPTG and 800 uM IPTG. Experiment was performed in a 48-well plate format, with each well containing LB-agar-amp+IPTG in the concentration indicated; pictures of individual wells are shown.

FIG. 12: Antimicrobial genes inhibit bacterial growth when present in the growth media. In-vitro transcription/translation system (Roche RTS100 *E. coli* HY) was used to produce cell-free protein products of toxic genes. Candidate toxic proteins were mixed with *E. coli* BL21 bacteria growing in liquid LB medium, and growth was monitored for 5.5 hours by measuring Optical Density (OD) in wavelength 600 nm every 10 minutes. Dark-blue curve shows growth of control bacteria without toxic protein addition (average and standard deviation of 9 repetitions presented); yellow, cyan and pink curves represent 3 repetitions of this growth kinetics experiment for a single toxic protein mixed with the medium.

FIG. 14: Multiple sequence alignment of DNA found in homologous low covered intergenic regions from 4 *Burkholderia* and 2 *Cupriavidus* (also herein referred to as *Ralstonia*) species. Red circle marks the conserved sequence core. Blue circle marks a conserved secondary structure predicted to be a rho independent transcriptional terminator. Compensatory mutations in the stem, where a G:C pair is changed to an A:T pair to maintain the stem are marked by blue arrows. An illustration of a typical a rho independent terminator is shown in the lower right side for comparison.

FIG. 15: Structural alignment of the toxic small RNA from 4 *Burkholderia* and 2 *Cupriavidus* (*Ralstonia*) species (SEQ ID NOS:173-178). Multiple sequence alignment of predicted small RNAs is presented. The last row in each alignment block represent the conserved RNA secondary structure in the Infernal format [URL:<http://selabjanelia.org/software.html>], where concentric "<" and ">" signs represent base-pairing within a stem, '_' signs represent loops, "," represent unstructured parts of the RNA and "." signs represent gaps. An insertion within the first stem is apparent in the *Cupriavidus* sequences. The conserved −10 TATA box of the predicted promoter is highlighted in red.

DETAILED DESCRIPTION OF THE PREFERRED EMBODIMENT

Introduction

In one embodiment, the present invention provides a method for identifying regions from microbial genomes that are unclonable into *E. coli*, wherein the method relies on a derivative of the microbial genome sequencing process.

Typically, the process of microbial genome sequencing is comprised of the following components: First, the genome of the microbe to be sequenced is isolated in multiple copies. Then, the genome is sheared into fragments typically sized 2-4 kb. These fragments are inserted into a carrying plasmid (vector) and each insert-containing vector is transformed into an *E. coli* bacterium. In some genome sequencing projects fragments of larger size, typically 30-40 kb, are also included in larger vectors called "fosmids". Vectors carrying small inserts (2-4 kb) are usually found in multiple copies (100-500) in each *E. coli* host, while fosmids are typically found in a single copy.

Each vector-containing *E. coli* bacterium is allowed to replicate into a clone, thus creating multiple copies of each insert. Inserts are then sequenced from both their ends using primers matching each end of the vector. Sequence reads that correspond to both ends of the same insert ("clone") are often called "sister-reads", "clone-mates", or "mate-pair". In the next stage, called genome-assembly, overlaps between resulting reads are used to assemble longer contiguous sequences, called "contigs". These overlaps are enabled because the amount of DNA to be sequenced is taken such that, on average, each base in the assembled genome is covered by multiple reads (typically at least 8 reads). Despite this fact, genome sequencing projects often need a final stage called "finishing", in which gaps between assembled contigs are filled [Carraro, Biotechniques. 2003 March; 34(3):626-8, 630-2].

Gaps in the assembly can be classified into two categories: "captured" and "uncaptured". Captured gaps are gaps for which there is evidence that the missing DNA was successfully cloned but was not successfully sequenced. For example, two sister reads of the same clone can exist at the edges of two different contigs, indicating that the missing DNA lies in the clone from which the sister reads originated. Self-folding, or low complexity, DNA is often the cause for such gaps, and they are typically filled by using different sequencing chemistry that allows the melting of folded DNA.

Uncaptured gaps, on the other hand, are gaps in which the missing DNA was not successfully cloned at all. Cloning independent methods, such as PCR and 454 sequencing can be used to sequence the missing DNA in these gaps [Carraro, Biotechniques. 2003 March; 34(3):626-8, 630-2].

Figure 1:
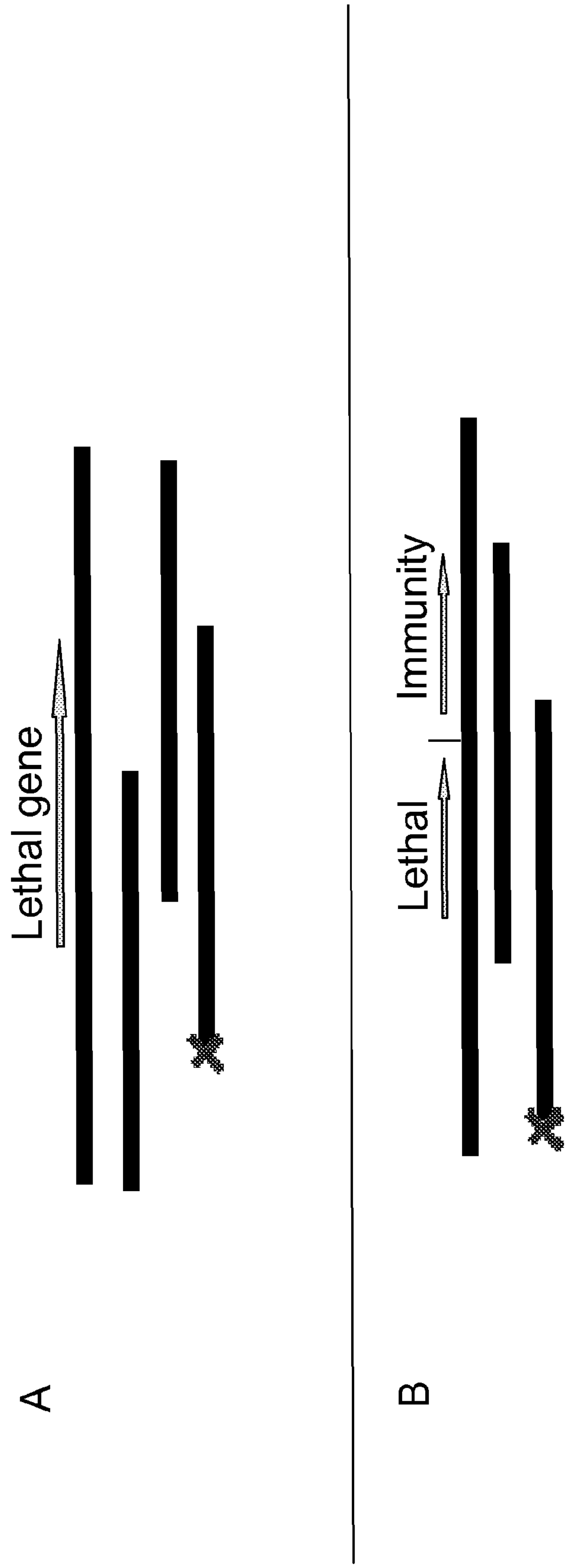
FIG. 1: Growth inhibiting genes will have lower clone coverage. Genomic DNA is in black; Clones are in grey. Genes are marked as arrows. Clones spanning the full length of a growth inhibiting gene (marked by red 'X') will cause death or growth inhibition and will therefore be eliminated, leading to lower coverage of the gene.

Gaps in or areas of low clone coverage were investigated to determine that genes that target bacteria or inhibit its growth likely exist in these regions, making them an unclonable. In some cases, growth inhibiting genes will not cause uncaptured gaps. This would happen if two (or more) overlapping clones contain parts of the gene but none of them contain the full gene sequence (FIG. 1A). Another possibility is that an immunity gene lies in the genomic vicinity of the growth inhibiting gene. Such immunity genes often protect toxin-producing bacteria from being affected by their own toxins [Sablon, Adv Biochem Eng Biotechnol. 2000; 68:21-60]. In this case, DNA fragments containing the toxic gene will be clonable if they contain the immunity gene as well (FIG. 1B). However, in both these cases the overall clonability of the region will be lower, as some clones will be lethal to the host *E coli* (for example, clones that contain the lethal gene without the full immunity gene; see FIG. 1).

Thus, the present invention provides a method to discover these unclonable regions in sequenced (and "finished") microbial genomes, retrieve the killer genes residing in these regions, and demonstrate their toxicity to *E. coli* and other pathogenic bacteria. The present method also detects genes lying in genomic regions that have a statistically significant reduction in clone coverage.

The present invention also provides the identity and characterizes several genes in microbial genomes investigated and describes the use of the genes and gene products as antimicrobial agents.

DEFINITIONS

As used herein, the term, "host cell," refers to any cell that can be transformed by foreign DNA where the foreign DNA may be a plasmid or vector containing a gene and the gene can be expressed in the cell. The host cell can be a cell from an organism, for example, microbial, including bacterial, fungal, and viral, plant, animal, or mammalian.

As used herein, the term, "library," "clone library" or "genomic library" refers to a set of clones containing DNA fragments randomly generated by fragmentation of a genome or large DNA fragment, inserted into a suitable plasmid vector and cloned into a suitable host organism, such as *E. coli*. Sequencing of clones in a library involves carrying out sequence reactions to sequence the beginning and the end of the DNA fragment inserted into each sequenced clone, also referred to as "end sequences", or "reads". The genome or large DNA fragments may be from any eukaryote, including human, mammal, plant or fungus, or prokaryote, including bacteria, virus or archaea.

As used herein, the term, "read," refers to a sequence corresponding to stretches of nucleotide sequence of on average 200-1000 bp in length, acquired from a single end-sequencing event of a clone in a genomic library.

As used herein, the term "sister reads" or "clone mates" refers to two reads that come from the beginning (forward read) and the end (reverse read) of the same cloned DNA fragment.

As used herein, the term, "mapping," refers to finding the correct position of a read on an already assembled genomic sequence. The term "clone mapping" refers to finding the correct position of two sister reads on an already assembled genomic sequence.

As used herein, the term, "shotgun sequencing" or "sequencing," refers the sequencing strategy whereby an entire genomic library is sequenced and assembled as described by the methods found at URL:<http://wwwjgi.doe-.gov/sequencing/strategy.html>. The advantage of shotgun sequencing is that a majority, if not all, of the genomic sequence will be represented by random clones about 5-20 times, depending on the number and the sizes of clones in the library.

Figure 2:
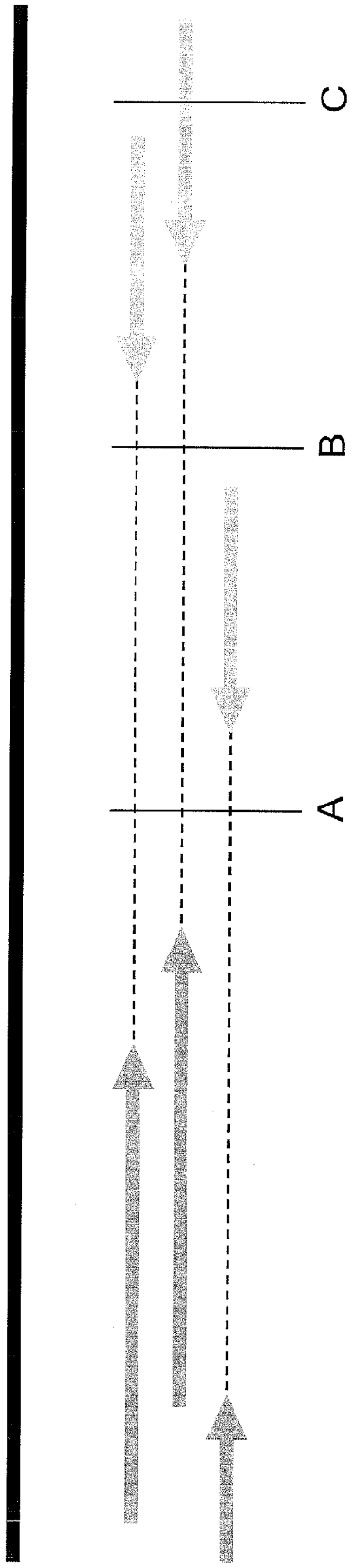
FIG. 2: Measuring clone coverage. For each clone, forward (dark gray) and reverse (light gray) clone mates are aligned to the genomic sequence (black). Coverage of the clone is measured as the genomic coordinates between the beginning of the forward clone mate to the end of the reverse clone mate (including the space in between, marked by dotted line). Therefore, the coverage in position A is 3; the coverage in position B is 2; and the coverage in position C is 1.

As used herein, the term, "clone coverage" refers to the number of clones in a library that span a particular position in a genome. A position in the genome is considered as covered by a clone if it is found between the first position of the forward-strand clone mate and the last position of the reverse strand clone mate (see FIG. 2). "Low clone coverage" refers to a particular position or a region having statistically significant under-representation of clones than expected by chance.

As used herein, the term, "gap" refers to a region of the genome or the large DNA fragment where there is an absence or low coverage.

As used herein, the term, "finished" when used referring to a genome, or large DNA fragment, refers to when all or most gaps in the sequence have been closed following additional specific sequencing reactions, and assembly of the final consensus sequence is completed.

As used herein, the term "toxic" when used to define a gene, refers to a gene whose expression product inhibits the growth of a microorganisms, such as bacteria and archae. For example, a toxic gene can be a gene which when expressed in a host cell, causes the host cell to become nonviable or causes cell death, and is thus "toxic" to the cell.

As used herein, the terms, "antipathogenic" and "antimicrobial," are used interchangeably, e.g., as used in "antipathogenic compositions," "antimicrobial agents" or "antimicrobial genes or proteins," and are intended to mean that the compositions have antimicrobial activity and thus are capable of suppressing, controlling, inhibiting and/or killing microorganisms, such as bacteria and archae. An antimicrobial polypeptide of the invention will, for example, reduce the disease symptoms resulting from microbial invasion or challenge by at least about 5% to about 50%, at least about 10% to about 60%, at least about 30% to about 70%, at least about 40% to about 80%, or at least about 50% to about 90% or greater.

As used herein, the term "nucleic acid" includes reference to a deoxyribonucleotide or ribonucleotide polymer in either single- or double-stranded form, and unless otherwise limited, encompasses known analogues (e.g., peptide nucleic acids) having the essential nature of natural nucleotides in that they hybridize to single-stranded nucleic acids in a manner similar to naturally occurring nucleotides.

As used herein, the terms "polypeptide" and "protein" are used interchangeably and are intended to refer to a polymer of amino acid residues. The terms apply to amino acid polymers in which one or more amino acid residues is an artificial chemical analogue of a corresponding naturally occurring amino acid, as well as to naturally occurring amino acid polymers. Polypeptides of the invention can be produced either from a nucleic acid disclosed herein, or by the use of standard molecular biology techniques. For example, a truncated protein of the invention can be produced by expression of a recombinant nucleic acid of the invention in an appropriate host cell, or alternatively by a combination of ex vivo procedures, such as protease digestion and purification, or in-vitro peptide synthesis.

As used herein, "variants" is intended to mean substantially similar sequences. For polynucleotides, a variant comprises a deletion and/or addition of one or more nucleotides at one or more internal sites within the native polynucleotide and/or a substitution of one or more nucleotides at one or more sites in the native polynucleotide. As used herein, a "native" polynucleotide or polypeptide comprises a naturally occurring nucleotide sequence or amino acid sequence, respectively. One of skill in the art will recognize that variants of the nucleic acids of the invention will be constructed such that the open reading frame is maintained. For polynucleotides, conservative variants include those sequences that, because of the degeneracy of the genetic code, encode the amino acid sequence of one of the antimicrobial polypeptides of the invention. Naturally occurring allelic variants such as these can be identified with the use of well-known molecular biology techniques, as, for example, with polymerase chain reaction (PCR) and hybridization techniques as outlined below. Variant polynucleotides also include synthetically derived polynucleotide, such as those generated, for example, by using site-directed mutagenesis but which still encode an antimicrobial protein of the invention. Generally, variants of a particular polynucleotide of the invention will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular polynucleotide as determined by sequence alignment programs.

Variants of a particular polynucleotide of the invention (i.e., the reference polynucleotide) can also be evaluated by comparison of the percent sequence identity between the polypeptide encoded by a variant polynucleotide and the polypeptide encoded by the reference polynucleotide. Thus, for example, an isolated polynucleotide that encodes a polypeptide with a given percent sequence identity to the polypeptide of SEQ ID NO: 97 is disclosed. Percent sequence identity between any two polypeptides can be calculated using sequence alignment programs. Where any given pair of polynucleotides of the invention is evaluated by comparison of the percent sequence identity shared by the two polypeptides they encode, the percent sequence identity between the two encoded polypeptides is at least about 40%, 45%, 50%, 55%, 60%, 65%, 70%, 75%, 80%, 85%, 90%, 91%, 92%, 93%, 94%, 95%, 96%, 97%, 98%, 99% or more sequence identity.

"Variant" protein is intended to mean a protein derived from the native protein by deletion or addition of one or more amino acids at one or more internal sites in the native protein and/or substitution of one or more amino acids at one or more sites in the native protein. Variant proteins encompassed by the present invention are biologically active, that is they continue to possess the desired biological activity of the native protein, that is, antimicrobial activity as described herein. Such variants may result from, for example, genetic polymorphism or from human manipulation. Biologically active variants of a native antimicrobial protein of the invention will have at least about 40%, 45%, 50%, 55%, 60%, 65%, 70%, 75%, 80%, 85%, more preferably 90%, 91%, 92%, 93%, 94%, 95%, 96%, 97%, 98%, 99% or more sequence identity to the amino acid sequence for the native protein as determined by sequence alignment programs. A biologically active variant of a protein of the invention may differ from that protein by as few as 1-15 amino acid residues, as few as 1-10, such as 6-10, as few as 5, as few as 4, 3, 2, or even 1 amino acid residue.

The proteins of the invention may be altered in various ways including amino acid substitutions, deletions, truncations, and insertions. Methods for such manipulations are generally known in the art. For example, amino acid sequence variants and fragments of the antimicrobial proteins can be prepared by mutations in the DNA. Methods for mutagenesis and polynucleotide alterations are well known in the art. See, for example, Kunkel (1985) *Proc. Natl. Acad. Sci. USA* 82:488-492; Kunkel et al. (1987) *Methods in Enzymol.* 154: 367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be optimal.

Thus, the genes and polynucleotides of the invention include both the naturally occurring sequences and their variants as well as mutant forms. Likewise, the proteins of the invention encompass naturally occurring proteins as well as variations and modified forms thereof. Such variants will continue to possess the desired antimicrobial activity.

In nature, some polypeptides are produced as complex precursors which, in addition to targeting labels such as the signal peptides discussed elsewhere in this application, also contain other fragments of peptides which are removed (processed) at some point during protein maturation, resulting in a mature form of the polypeptide that is different from the primary translation product (aside from the removal of the signal peptide). "Mature protein" refers to a post-translationally processed polypeptide; i.e., one from which any pre- or propeptides present in the primary translation product have been removed. "Precursor protein" or "prepropeptide" or "preproprotein" all refer to the primary product of translation of mRNA; i.e., with pre- and propeptides still present. Pre- and propeptides may include, but are not limited to, intracellular or extracellular localization signals. "Pre" in this nomenclature generally refers to the signal peptide. The form of the translation product with only the signal peptide removed but no further processing yet is called a "propeptide" or "proprotein." The fragments or segments to be removed may themselves also be referred to as "propeptides." A proprotein or propeptide thus has had the signal peptide removed, but contains propeptides (here referring to propeptide segments) and the portions that will make up the mature protein. The skilled artisan is able to determine, depending on the species in which the proteins are being expressed and the desired intracellular location, if higher expression levels or higher antimicrobial activity might be obtained by using a gene construct encoding just the mature form of the protein, the mature form with a signal peptide, or the proprotein (i.e., a form including propeptides) with a signal peptide. For optimal expression in plants or fungi, the pre- and propeptide sequences may be needed. The propeptide segments may play a role in aiding correct peptide folding.

Method for Investigation of Gaps or Areas of Low Clone Coverage

For each finished genome, the present method to select for antipathogenic and antimicrobial genes is applied comprising the following steps: (a) Read mapping, wherein sequence reads are mapped back on the genomic sequence and clone positions are identified; (b) Clone coverage calculation, wherein, for each position of the analyzed genome sequence, the number of covering clones (clones that span this position) is calculated; (c) Genomic regions identification, wherein regions having no clone coverage ("uncaptured gaps"), and regions having a statistically significant reduction in coverage, are identified; (d) Toxicity level determination, wherein regions having a statistically significant reduction in fosmid-only coverage (in addition to overall reduction on small [2-4 kb] clone coverage) are marked as containing highly toxic genes; and (e) Gene selection and experimental validation, wherein genes residing in each low- or zero-covered region are identified, and their products are experimentally tested for a bactericidal or bacteriostatic effect on the growth of various bacteria.

In Read mapping, for each microbial genome that was sequenced and finished, map the original reads back on the finished, assembled genomic sequence. This mapping could be done by a sequence alignment tool, such as BLAST [Altschul, J Mol. Biol. 1990 Oct. 5; 215(3):403-10] or mummer [Delcher, Nucleic Acids Res. 2002 Jun. 1; 30(11):2478-83]. In case that a read aligns to several positions on the genomic sequence, take the region where the alignment has the highest score or a score above a certain threshold.

For each read, identify the position of its clone mate. In case a read has two or more similarly scored positions on the genomic sequence, resolve the correct position by the location of its mate. The two mates should be positioned such that the distance between them is approximately the relevant insert size (usually 2-4 kb or 30-40 kb in case of fosmid-carried inserts). The two mates should also be positioned such that one of them lies on the forward strand and the other on the reverse strand. Clones for which both mates have unambiguous positioning on the genomic sequence are deemed "mapped clones" and taken into further analysis.

In Clone coverage calculation, for each position in the genomic sequence, the number of covering clones is counted. A position in the genome is considered as covered by a clone if it is found between the first position of the forward-strand clone mate and the last position of the reverse strand mate (see FIG. 2). It is possible to calculate, for each genomic position, also fosmid-only- and small-clones-only-coverage parameter. This is useful for determining the level of toxicity of a protein in a low-coverage region (described below).

In Genomic regions identification, for each analyzed genome, the average clone coverage per genomic position and standard deviation are calculated. Regions not covered by any clone, or regions covered by statistically significant less clones than expected by chance, are further analyzed. Genomic regions identification could be done for fosmid-only-clones and small-clones-only-clones, such that regions in which only small-clones have low coverage, regions in which only fosmids have low coverage, and regions in which both library types have low coverage, could be identified.

Regions that are mapped to repetitive genomic sequences (i.e., long sequence stretches that occur two or more times in the genome with high similarity between occurrences) are excluded from the analysis. This is because repetitive genomic regions frequently cause false read-mapping, and hence can appear low covered even though they are not. The identification of repetitive genomic sequences can be done by aligning the genome to itself (using standard alignment software such as Blast), or by following reads that map to two or more regions in the genome, or by other means.

In Gene selection and experimental validation, for each selected genomic region, genes (protein coding and non-protein coding) are identified. If the region is large enough to cover several genes, multiple genes can be selected from a single region.

An optional Toxicity level determination stage could be added, in which genes are predicted to have high or low toxicity according to their fosmid-clones-only coverage. The small clones (2-4 kb) exist in the cell in high-copy number (100-500 copies), and thus the toxicity of genes that are only mildly toxic is enhanced 100-500 fold if cloned into a small-clone library. Large (fosmid) clones, on the other hand, appear only in a single-copy per cell, and thus, if a region has a statistically significant low (or zero) fosmid coverage (as well as low (or zero) small-clone coverage), it means that the gene is highly toxic, because it confers growth inhibition even when introduced into *E coli* in a single copy.

To test if the protein products of the selected genes inhibit bacterial growth, cell-free protein synthesis could be used to translate the DNA sequence of each gene into protein. Proteins can be applied on various pathogenic and non-pathogenic bacteria to determine the spectrum of activity and whether they have a bactericidal or bacteristatic effect. Minimal inhibitory concentration (MIC) can be determined by testing the growth inhibition activity of serial dilutions of the protein.

To test if the products of the selected genes inhibit bacterial growth when introduced from inside the cell, selected genes can be cloned into a vector that contains a tightly regulated inducible promoter, such that the expression of the gene is induced only after a specific molecule ("inducer") was added to the growth media. Such vectors could be inserted into *E coli* without killing it, as the gene product will only be expressed in the cell following induction. Growth of *E. coli* can be tested before and after induction to determine if the gene has a growth inhibition effect.

Detection of Candidate Genes

Figure 3:
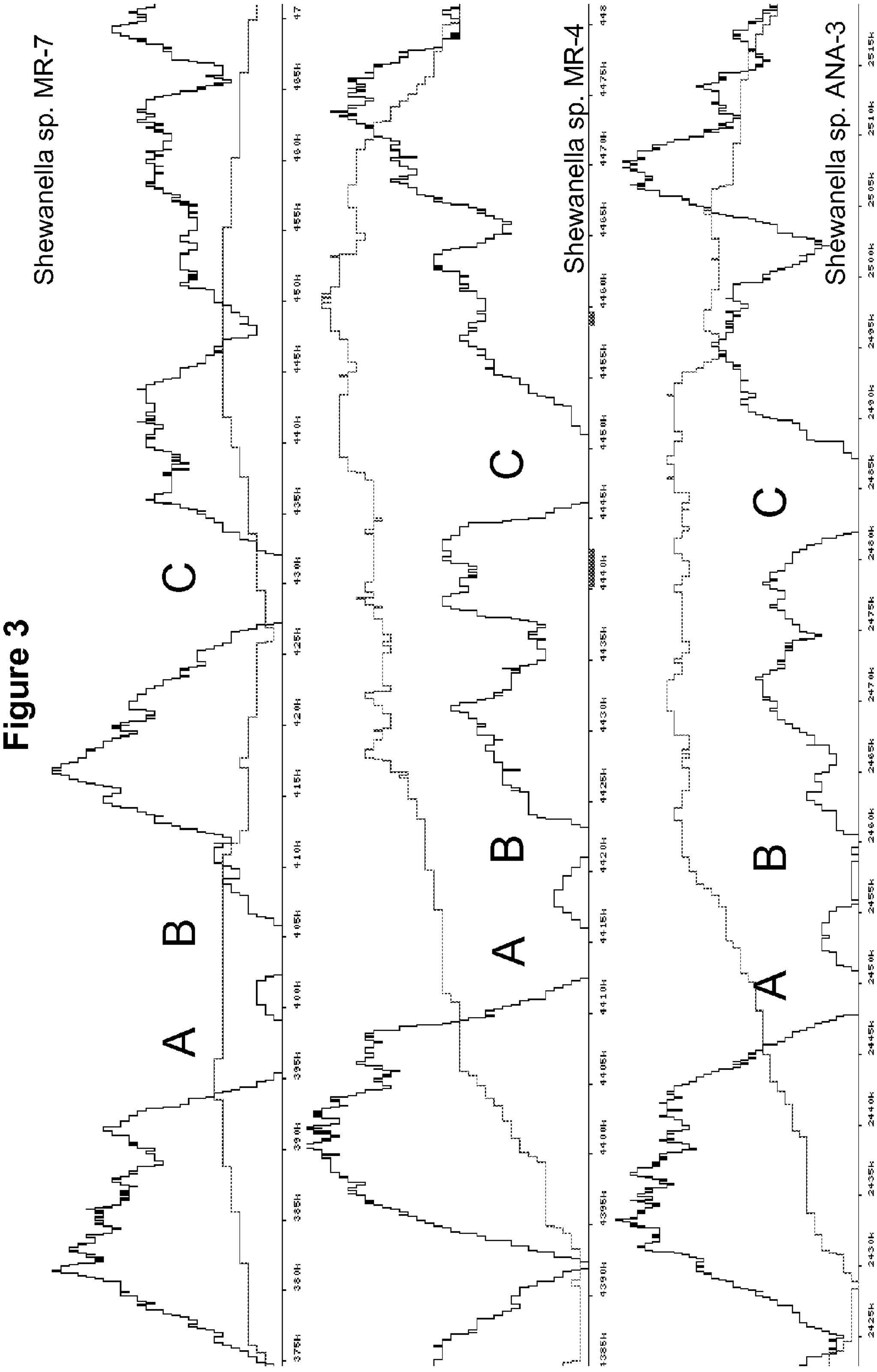
FIG. 3: Recurrence of low coverage in homologous regions in different genomes. Shown is the coverage profile of a ~95 kb region in three closely related *Shewanella* genomes. X-axis, genomic position in each genome (in kilobase). Y-axis, clone coverage. Black curve represents coverage of small clones (sized up to 10 kb); red curve represents coverage of fosmids (sized 10 kb-50 kb). Zero coverage of small clones is observed in three homologous regions (A,B and C).

The present method was applied to over 30 microbial genomes. To exclude the possibility that the observed low coverage is the result of random fluctuations in clone distribution, we examined the coverage in the genomes of three closely related *Shewanella* species. As exemplified in FIG. 3, we found that similar (homologous) sequences have a similar coverage profile across all three genomes. This shows that low clone coverage is caused by specific sequences and not by chance.

We then collected the proteins found in the zero- and low-covered regions. For each of the proteins, we looked for homologs in the genomes we analyzed, and tested the coverage of the homologs in those genomes. We prioritized genes according to the following parameters:

a) Genes that had zero- or low-coverage in more than one genome.

b) Genes that displayed coverage deficiency of both small clones and fosmid clones. As vectors carrying small inserts are usually found in a high copy number (100-500) in each *E coli* cell, the effect of a toxic gene carried on a small insert vector is amplified 100-500 fold. However, if a gene also has low fosmid coverage it is probably highly toxic, because fosmids are maintained in a single copy per cell only.

c) Genes that had homologs in only few (or zero) other genomes, as genes generating antimicrobial agents are known to evolve very fast [Riley, Annu Rev Microbiol. 2002; 56:117-37].

A list of 125 selected genes was compiled as Set 1. The 125 potentially antimicrobial genes discovered using the present invention were detailed.

dWe noted that among the proteins predicted by the present method to be toxic to *E. coli*, ribosomal proteins are frequently found. This is probably due to the fact that these proteins are parts in the large complex of the ribosome, and their expression should be strictly coordinated to maintain their relative concentrations. An ectopic addition of another copy of a ribosomal protein disrupts this balance and may cause ribosomal misassembly. Indeed, ribosomal proteins are found in a single copy in nearly every microbial genome sequenced so far. Massive ribosomal misassembly or malfunction would reduce translation of cellular proteins leading to overall growth inhibition.

Once compiled, we tested the 125 proteins from Set 1 using an inducible expression system. It was found that 78 of these proteins are indeed toxic when expressed in *E. coli*. These 78 genes and proteins are described in the attached Sequence Listing and have sequence identifiers of SEQ ID NOS: 1-158.

Table 2 is also attached and provides details for each gene and its expression products. For each gene, the following details were provided: a) The genome of origin; b) Coordinates on that genome; c) Annotation, with Genbank Accession number if one exists; d) An indication whether the gene is predicted to have a signal sequence for secretion; e) The number of covering small clones and fosmids, and an indication whether this number is regarded as statistically significant low coverage; f) Indication whether this gene was found to have low coverage in other genomes as well—for each comparison genome, the following details are given: (1) BLAST e-value between the gene described and the gene in the comparison genome; (2) GC-content of the other genome; (3) Number of small clones covering the gene in the other genome; (4) Number of fosmid clones covering the gene in the other genome; g) Nucleotide sequence of the gene; and h) Polypeptide sequence of the gene.

Figure 10:
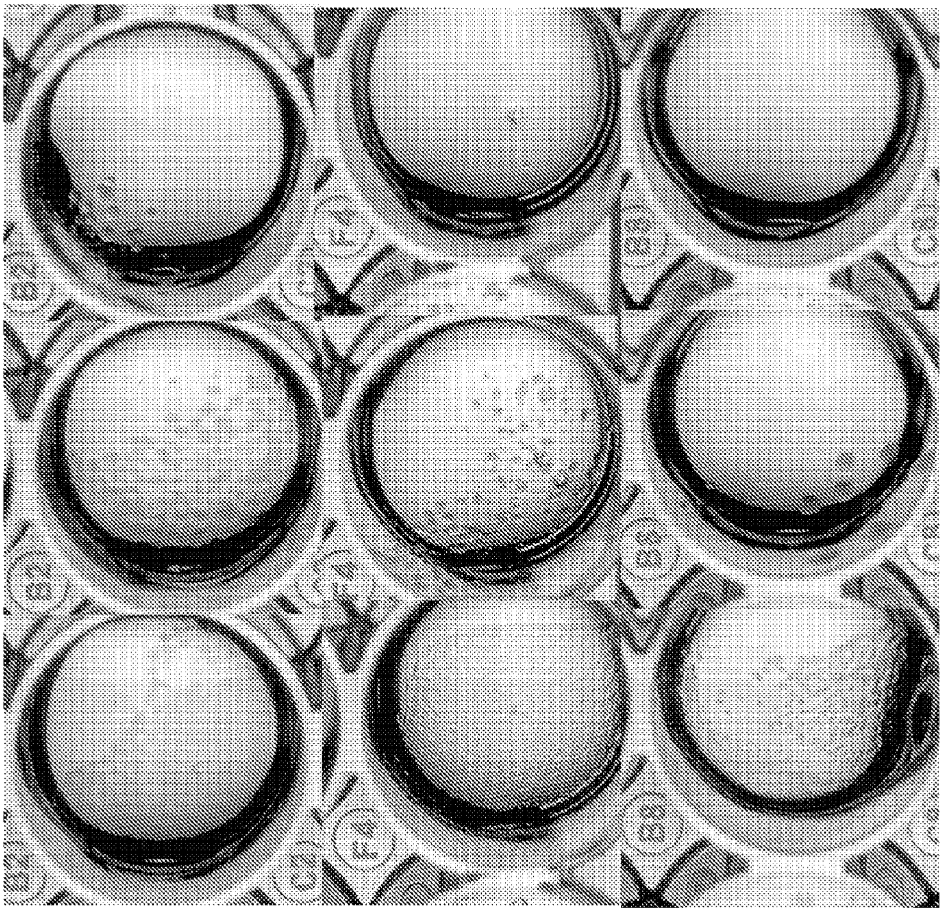
FIG. 10: Experimental results on additional genes. Seventy-eight genes that were predicted using the method described in the present invention were tested using the same system described in FIGS. 7 and 8, and found to be toxic to *E. coli* upon expression induction.
Figure 11:
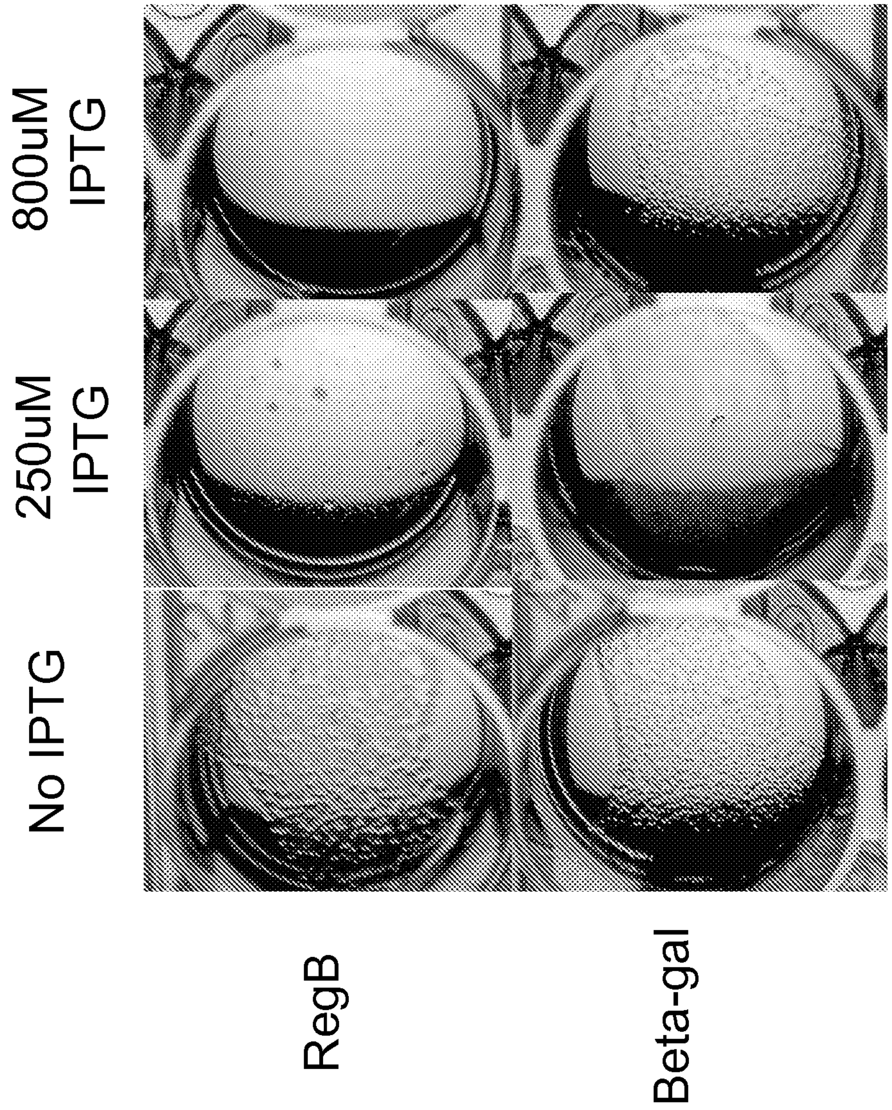
FIG. 11: Positive and negative controls to the experiment presented in FIG. 10. RegB (positive control; see FIG. 7) and beta-galactosidase (negative control; see FIG. 7) were cloned and tested in the same system described for FIG. 10 and the experiments in Example 1 (data not shown). RegB causes growth-reduction (toxic) upon expression induction; beta-galactosidase expression does not affect bacterial growth.

Exemplary data from several examples are shown in FIG. 10. Table 1 below shows the gene number, internal reference number and the corresponding sequence identifier for the nucleotide and protein sequences in the first four columns. Results are shown below in Table 1 for each protein found to have antimicrobial activity, showing the lowest concentration (uM) of IPTG needed to induce gene expression and inhibition of bacterial growth was observed. "Inhibition of growth" is defined as no more than 10 colonies observed in a well of a 48-well growth plate.

TABLE 1

The gene, Internal Reference number, sequence identifiers of antimicrobial genes and proteins in the Sequence Listing which were tested and shown to have antimicrobial activity and the lowest IPTG concentration needed for antimicrobial activity.

| Gene No. | Internal Reference | Nucleotide | Protein | Concentration of IPTG resulting in growth elimination (μM) |
|---|---|---|---|---|
| Gene No. 1 | ABB44040 | SEQ ID NO: 1 | SEQ ID NO: 2 | 250 |
| Gene No. 2 | ABB44032 | SEQ ID NO: 3 | SEQ ID NO: 4 | 250 |
| Gene No. 3 | ABB44015 | SEQ ID NO: 5 | SEQ ID NO: 6 | 800 |
| Gene No. 4 | ABB44001 | SEQ ID NO: 7 | SEQ ID NO: 8 | 800 |
| Gene No. 5 | ABB43993 | SEQ ID NO: 9 | SEQ ID NO: 10 | 800 |
| Gene No. 6 | ABB43996 | SEQ ID NO: 11 | SEQ ID NO: 12 | 800 |
| Gene No. 7 | ABB43996_1 | SEQ ID NO: 13 | SEQ ID NO: 14 | 800 |
| Gene No. 8 | ABB43899 | SEQ ID NO: 15 | SEQ ID NO: 16 | 250 |
| Gene No. 9 | ABB43889 | SEQ ID NO: 17 | SEQ ID NO: 18 | 100 |
| Gene No. 10 | ABB43891 | SEQ ID NO: 19 | SEQ ID NO: 20 | 250 |
| Gene No. 11 | ABB43856 | SEQ ID NO: 21 | SEQ ID NO: 22 | 800 |
| Gene No. 12 | ABB43853 | SEQ ID NO: 23 | SEQ ID NO: 24 | 600 |
| Gene No. 13 | ABB43839 | SEQ ID NO: 25 | SEQ ID NO: 26 | 600 |
| Gene No. 14 | ABB43838 | SEQ ID NO: 27 | SEQ ID NO: 28 | 400 |
| Gene No. 15 | ABB43836 | SEQ ID NO: 29 | SEQ ID NO: 30 | 600 |
| Gene No. 16 | ABB43820 | SEQ ID NO: 31 | SEQ ID NO: 32 | 250 |
| Gene No. 17 | ABB43819 | SEQ ID NO: 33 | SEQ ID NO: 34 | 250 |
| Gene No. 18 | ABB43823 | SEQ ID NO: 35 | SEQ ID NO: 36 | 600 |
| Gene No. 19 | ABB43822 | SEQ ID NO: 37 | SEQ ID NO: 38 | 600 |
| Gene No. 20 | 3634490_gene_1 | SEQ ID NO: 39 | SEQ ID NO: 40 | 100 |
| Gene No. 21 | ABB43761 | SEQ ID NO: 41 | SEQ ID NO: 42 | 600 |
| Gene No. 22 | ABB43760 | SEQ ID NO: 43 | SEQ ID NO: 44 | 800 |
| Gene No. 23 | ABB43762 | SEQ ID NO: 45 | SEQ ID NO: 46 | 800 |
| Gene No. 24 | ABB43749 | SEQ ID NO: 47 | SEQ ID NO: 48 | 400 |
| Gene No. 25 | ABB43724 | SEQ ID NO: 49 | SEQ ID NO: 50 | 600 |
| Gene No. 26 | ABB43725 | SEQ ID NO: 51 | SEQ ID NO: 52 | 600 |
| Gene No. 27 | ABB43718 | SEQ ID NO: 53 | SEQ ID NO: 54 | 600 |
| Gene No. 28 | ABB43700 | SEQ ID NO: 55 | SEQ ID NO: 56 | 800 |
| Gene No. 29 | ABB43688 | SEQ ID NO: 57 | SEQ ID NO: 58 | 600 |
| Gene No. 30 | ABB43689 | SEQ ID NO: 59 | SEQ ID NO: 60 | 250 |
| Gene No. 31 | ABB43694 | SEQ ID NO: 61 | SEQ ID NO: 62 | 400 |
| Gene No. 32 | ABB43693 | SEQ ID NO: 63 | SEQ ID NO: 64 | 800 |
| Gene No. 33 | YP_516003 | SEQ ID NO: 65 | SEQ ID NO: 66 | 250 |
| Gene No. 34 | ABB43675_1 | SEQ ID NO: 67 | SEQ ID NO: 68 | 400 |
| Gene No. 35 | ABB43641 | SEQ ID NO: 69 | SEQ ID NO: 70 | 800 |
| Gene No. 36 | ABB43625 | SEQ ID NO: 71 | SEQ ID NO: 72 | 400 |
| Gene No. 37 | ABB43630 | SEQ ID NO: 73 | SEQ ID NO: 74 | 800 |
| Gene No. 38 | ABB43475 | SEQ ID NO: 75 | SEQ ID NO: 76 | 600 |
| Gene No. 39 | ABB43462_1 | SEQ ID NO: 77 | SEQ ID NOs: 78, 79 | 400 |
| Gene No. 40 | ABB43753 | SEQ ID NO: 80 | SEQ ID NO: 81 | 600 |
| Gene No. 41 | ABB43755 | SEQ ID NO: 82 | SEQ ID NO: 83 | 800 |
| Gene No. 42 | ABB44224 | SEQ ID NO: 84 | SEQ ID NO: 85 | 400 |
| Gene No. 43 | ABB45229 | SEQ ID NO: 86 | SEQ ID NO: 87 | 100 |
| Gene No. 44 | ABB45230 | SEQ ID NO: 88 | SEQ ID NO: 89 | 600 |
| Gene No. 45 | ABB45231 | SEQ ID NO: 90 | SEQ ID NO: 91 | 400 |
| Gene No. 46 | ABB45232 | SEQ ID NO: 92 | SEQ ID NO: 93 | 400 |
| Gene No. 47 | ABB43866 | SEQ ID NO: 94 | SEQ ID NO: 95 | 600 |
| Gene No. 48 | ABB43867 | SEQ ID NO: 96 | SEQ ID NO: 97 | 400 |
| Gene No. 49 | ABB43869 | SEQ ID NO: 98 | SEQ ID NO: 99 | 400 |
| Gene No. 50 | ABB43678_1 | SEQ ID NO: 100 | SEQ ID NO: 101 | 800 |

TABLE 1-continued

The gene, Internal Reference number, sequence identifiers of antimicrobial genes and proteins in the Sequence Listing which were tested and shown to have antimicrobial activity and the lowest IPTG concentration needed for antimicrobial activity.

| Gene No. | Internal Reference | Nucleotide | Protein | Concentration of IPTG resulting in growth elimination (μM) |
|---|---|---|---|---|
| Gene No. 51 | ABB43998 | SEQ ID NO: 102 | SEQ ID NO: 103 | 100 |
| Gene No. 52 | ABB43913 | SEQ ID NO: 104 | SEQ ID NOs: 105, 106 | 600 |
| Gene No. 53 | ABB43902 | SEQ ID NO: 107 | SEQ ID NO: 108 | 600 |
| Gene No. 54 | ABB43892 | SEQ ID NO: 109 | SEQ ID NO: 110 | 100 |
| Gene No. 55 | ABB43890 | SEQ ID NO: 111 | SEQ ID NO: 112 | 400 |
| Gene No. 56 | ABB43841 | SEQ ID NO: 113 | SEQ ID NO: 114 | 400 |
| Gene No. 57 | ABB43827 | SEQ ID NO: 115 | SEQ ID NO: 116 | 400 |
| Gene No. 58 | ABB43821 | SEQ ID NO: 117 | SEQ ID NO: 118 | 400 |
| Gene No. 59 | ABB43768 | SEQ ID NO: 119 | SEQ ID NO: 120 | 400 |
| Gene No. 60 | ABB43764 | SEQ ID NO: 121 | SEQ ID NO: 122 | 400 |
| Gene No. 61 | ABB43748 | SEQ ID NO: 123 | SEQ ID NO: 124 | 400 |
| Gene No. 62 | ABB43726 | SEQ ID NO: 125 | SEQ ID NO: 126 | 400 |
| Gene No. 63 | ABB43722 | SEQ ID NO: 127 | SEQ ID NO: 128 | 600 |
| Gene No. 64 | ABB43712 | SEQ ID NO: 129 | SEQ ID NO: 130 | 400 |
| Gene No. 65 | ABB43702 | SEQ ID NO: 131 | SEQ ID NO: 132 | 800 |
| Gene No. 66 | ABB43704 | SEQ ID NO: 133 | SEQ ID NO: 134 | 100 |
| Gene No. 67 | ABB43690 | SEQ ID NO: 135 | SEQ ID NO: 136 | 250 |
| Gene No. 68 | ABB43674 | SEQ ID NO: 137 | SEQ ID NO: 138 | 400 |
| Gene No. 69 | ABB43678 | SEQ ID NO: 139 | SEQ ID NO: 140 | 800 |
| Gene No. 70 | ABB43658 | SEQ ID NO: 141 | SEQ ID NO: 142 | 400 |
| Gene No. 71 | ABB43659 | SEQ ID NO: 143 | SEQ ID NO: 144 | 600 |
| Gene No. 72 | ABB43655 | SEQ ID NO: 145 | SEQ ID NO: 146 | 250 |
| Gene No. 73 | ABB43638 | SEQ ID NO: 147 | SEQ ID NO: 148 | 800 |
| Gene No. 74 | ABB43474 | SEQ ID NO: 149 | SEQ ID NO: 150 | 800 |
| Gene No. 75 | ABB43461_1 | SEQ ID NO: 151 | SEQ ID NO: 152 | 600 |
| Gene No. 76 | ABB43457 | SEQ ID NO: 153 | SEQ ID NO: 154 | 800 |
| Gene No. 77 | ABB43446 | SEQ ID NO: 155 | SEQ ID NO: 156 | 600 |
| Gene No. 78 | ABB43750 | SEQ ID NO: 157 | SEQ ID NO: 158 | 600 |

To verify that the 78 proteins identified by our method are bona fide antimicrobial proteins, antimicrobial activity can be determined in various ways. In one embodiment, as also described in Example 2, an in-vitro transcription/translation system (e.g., Roche RTS 100 *E. coli* HY) can be used to produce cell-free protein products of the 78 toxic genes. Candidate toxic proteins are mixed with *E. coli* strain BL21 bacteria growing in liquid LB medium, and growth is then monitored for several hours by measuring Optical Density (OD) in wavelength 600 nm every 10 minutes. For each protein tested, the OD is measured for growth of control bacteria without toxic protein addition to the medium containing an in-vitro transcription/translation system and compared with growth curves after toxic protein addition. An empirical determination can be made for each protein to determine that they are antimicrobial, such as if the endpoint is at least 0.1 OD lower than the control, or that there is an obvious decrease in the slope of the three curves showing growth is inhibited, then it is concluded that the protein has antimicrobial activity.

Figure 12A:
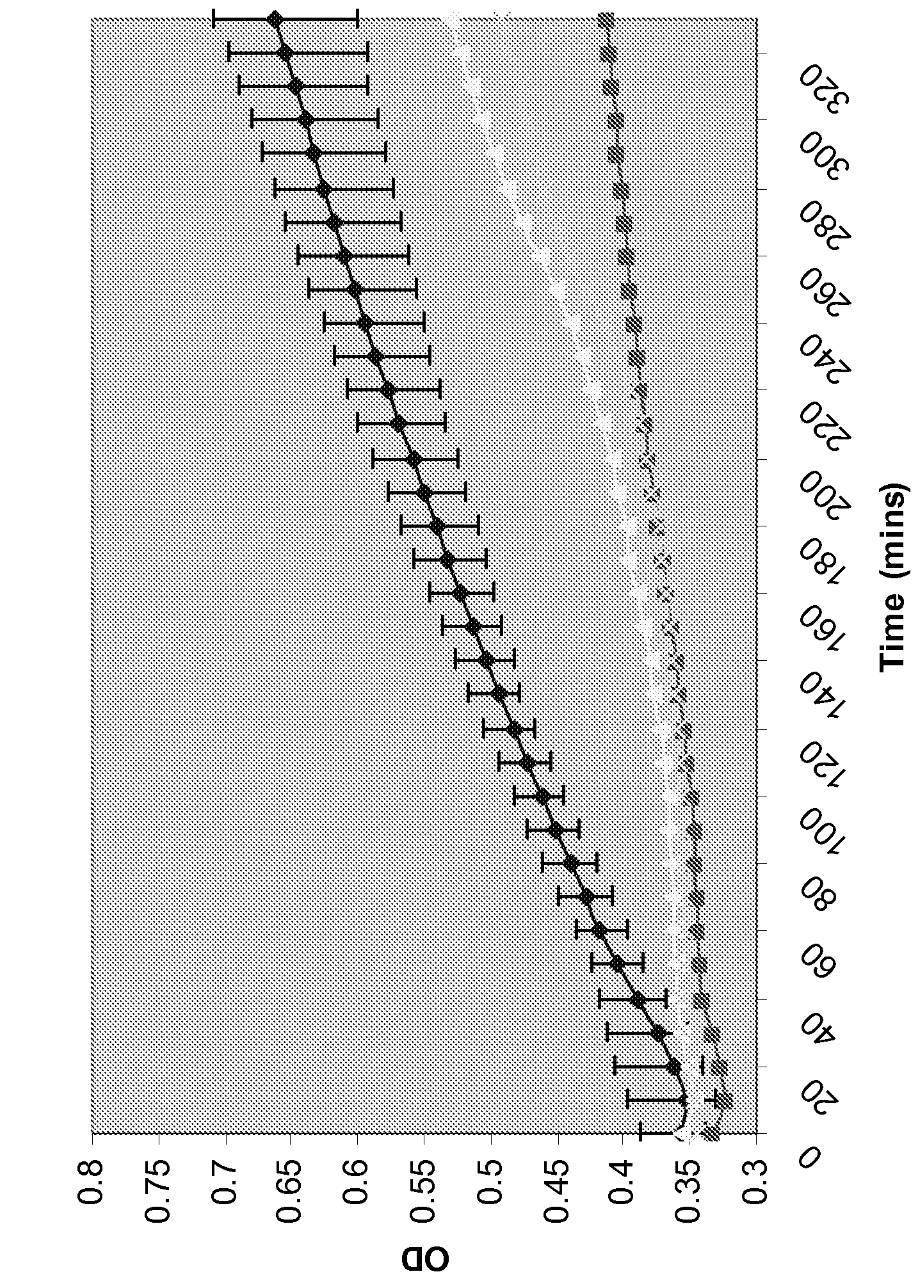
FIG. 12(A) shows antimicrobial activity of protein ABB43836 (SEQ ID NO: 30)
Figure 12B:
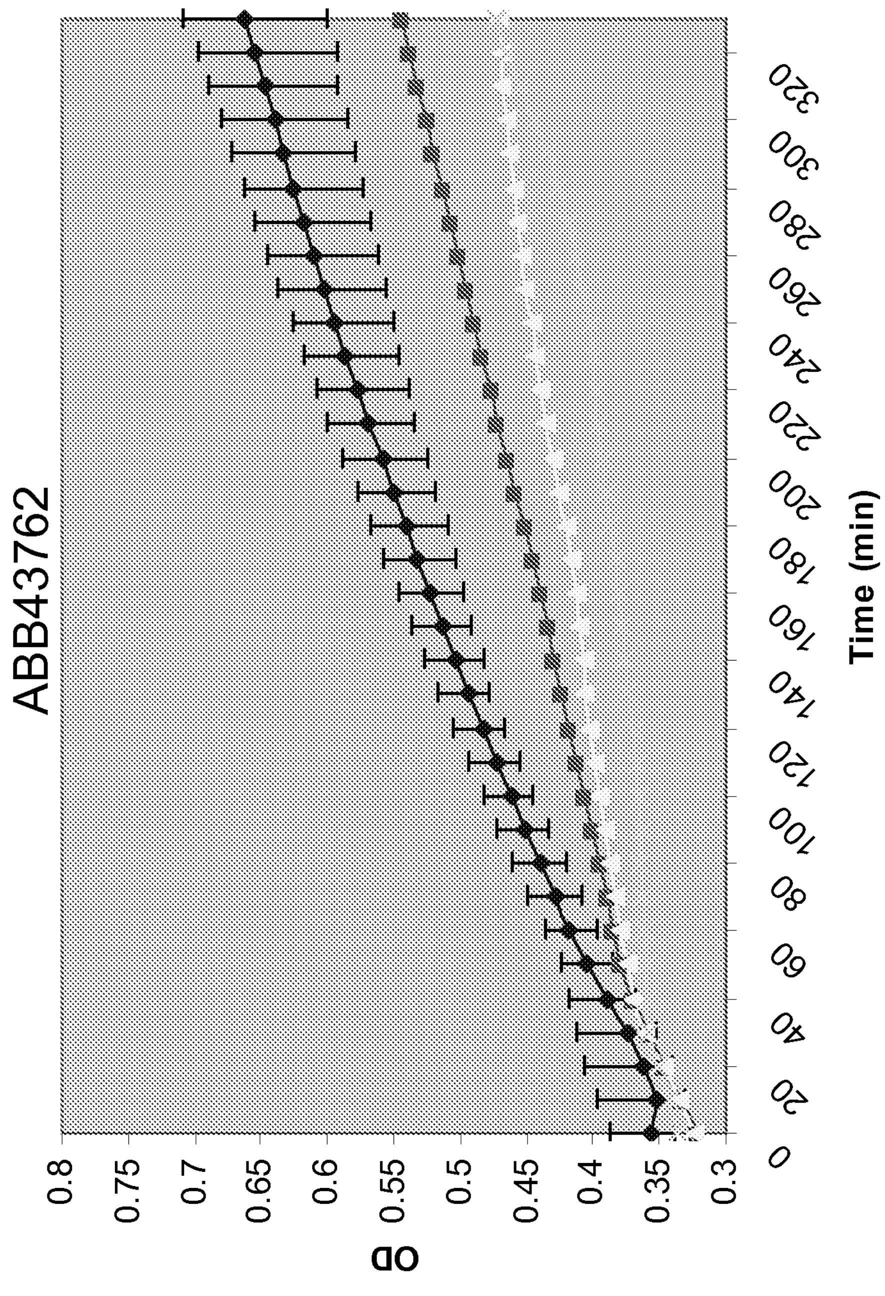
FIG. 12B, shows antimicrobial activity of protein ABB43762 (SEQ ID NO: 46).

For two of the genes and proteins shown in Table 1, growth of bacteria was inhibited in the presence of the translated toxic protein, as compared to growth without toxic proteins in the medium (FIGS. 12A and 12B). Data is not shown for all genes tested. FIGS. 12A and 12B show examples of the OD results obtained for two proteins, ABB43836 (SEQ ID NO: 30) and ABB43762 (SEQ ID NO: 46). It is anticipated that many if not all of the proteins identified in Table 1 have antimicrobial activity and inhibit growth of bacteria and other microbes. These results are significant in showing that not only internal expression of these proteins is toxic, but that the proteins exhibit antimicrobial activity and inhibit growth even if externally applied to a microbe or its environment. This aspect thus enables many of the applications described in the following sections.

These results in totality validate the presently described method in the present invention to identify toxic genes. In another embodiment, the presently described method can be used to identify other genomic elements having antimicrobial activity. Such genomic elements can include but are not limited to, genomic sequence which code for proteins such as genes, various types of RNA, small RNA, etc.

Thus, in another embodiment, the present invention further provides the genes and proteins, SEQ ID NOS:1-158 and identified in Table 1 as having antimicrobial activity. In another embodiment, the present invention provides for small toxic RNA isolated from other organisms. In one embodiment, antimicrobial genes comprise sequences SEQ ID NOS: 159-172, which encode small toxic RNA having antimicrobial activity. In another embodiment, the small toxic RNA found to have antimicrobial activity comprise SEQ ID NOS: 179-186, and are encoded by antimicrobial genes having sequences SEQ ID NOS:165-172.

Antimicrobial Polypeptides and Uses Thereof

Figure 7:
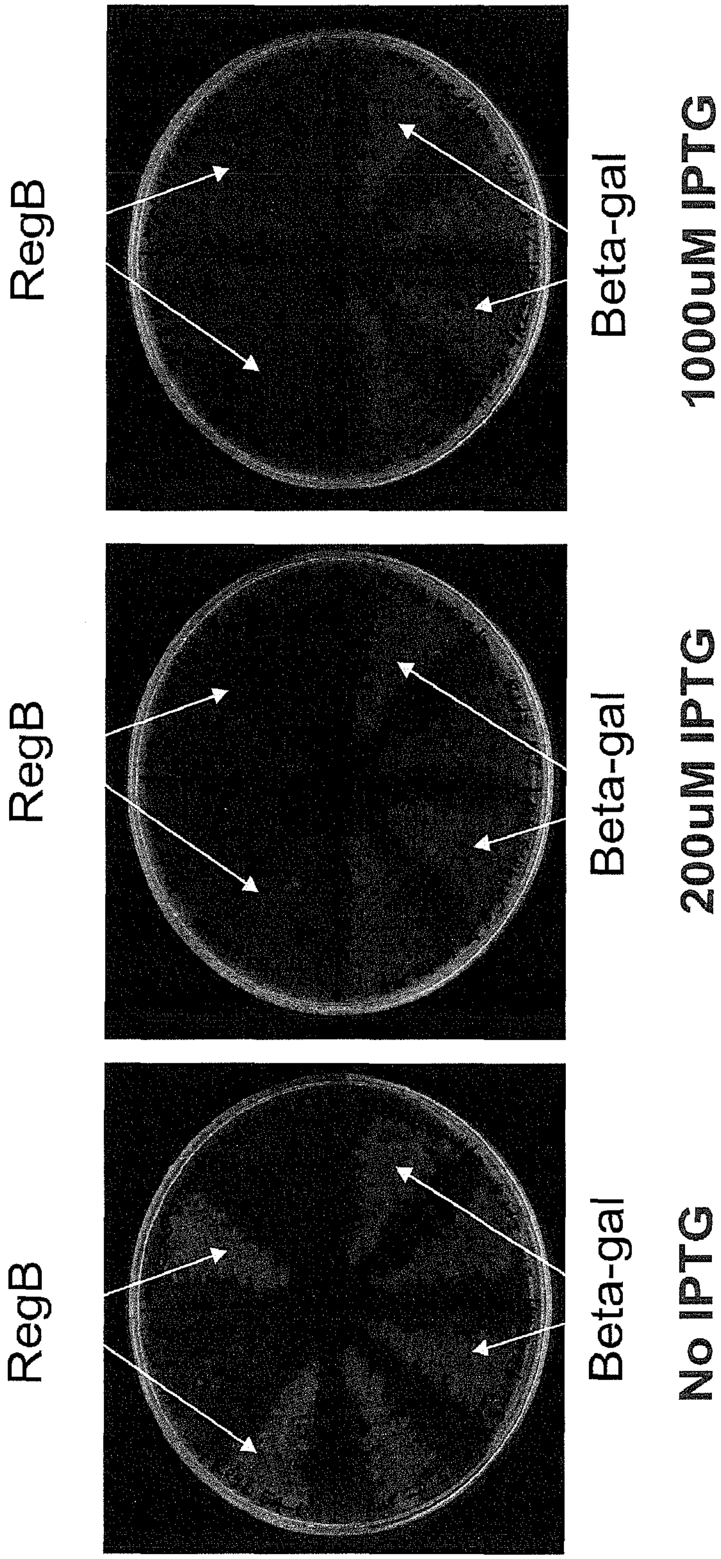
FIG. 7: Positive and negative controls. RegB, a virally encoded protein that is known to be toxic to *E. coli*, is used here as positive control for the assay, and *E. coli* beta-galactosidase, known to be non-toxic to *E. coli*, is the negative control. Two colonies containing the full length RegB gene grow in a medium without IPTG (right plate) but fail to grow in plates containing concentrations of 200 uM or 1000 uM IPTG, where expression of RegB is induced (middle and left plates). Conversely, colonies containing beta-galactosidase under the regulation of IPTG grow even in high concentrations (1000 uM) of IPTG, The genes were engineered into pET11a vector downstream to the T7 promoter. Vectors were transformed into BL21 (DE)pLys cells (Invitrogen) that contain a choromosomal copy of the T7 polymerase under the control of lac promoter. Correct sequence in the inserts was verified by direct sequencing.

In one embodiment, to determine whether a protein identified by the described method is indeed antimicrobial, the gene encoding the protein is cloned into an appropriate plasmid under a polymerase promoter, inserted into vector, and used to transform cells, such as *E. coli*. This system maintains the expression of the inserted gene silent unless an inducer molecule (e.g., IPTG) is added to the medium. As a negative control a non-toxic gene, such as beta-galactosidase (beta-gal) is similarly cloned. FIG. 7 shows that beta-galactosidase does not kill, or inhibit the growth of, *E coli* following induction of its expression.

Bacterial colonies are allowed to grow after induction of gene expression. The lack of colonies indicates that the protein expressed by the inserted gene is toxic to the cells, showing that the protein has a growth inhibition effect on cells such as *E coli*, and is thus an antimicrobial agent.

Additionally, in vitro antimicrobial assays that can be used include, for example, the addition of varying concentrations of the antimicrobial composition to paper disks and placing the disks on agar containing a suspension of the pathogen of interest. Following incubation, clear inhibition zones develop around the discs that contain an effective concentration of the antimicrobial polypeptide (Liu et al. (1994) *Plant Biology* 91:1888-1892, herein incorporated by reference). Additionally, microspectrophotometrical analysis can be used to measure the in vitro antimicrobial properties of a composition (Hu et al. (1997) *Plant Mol. Biol.* 34:949-959 and Cammue et al. (1992) *J. Biol. Chem.* 267: 2228-2233, both of which are herein incorporated by reference). Assays that specifically measure antibacterial activity are also well known in the art. See, for example, Clinical and Laboratory Standards Institute, Guideline M7-A6, *Methods for dilution antimicrobial susceptibility tests for bacteria that grow aerobically*, herein incorporated by reference.

In one embodiment, the presently described genes, proteins and/or RNA described in SEQ ID NOS: 1-172, and 179-197, and herein referred to as generally antimicrobial compositions or antimicrobial agents, are contemplated for use in any of the antimicrobial applications herein described.

In another embodiment, an antipathogenic polypeptide, selected from any of the polypeptide sequences in SEQ ID NOS:1-159, is localized in cellular compartments by addition of suitable targeting information. This can be accomplished, for example, by adding an endoplasmic reticulum retention signal encoding sequence to the sequence of the gene, or by adding a signal peptide sequence to the antipathogenic polypeptide.

In some embodiments, expression cassettes comprising a promoter operably linked to a heterologous nucleotide sequence of the invention, i.e., any nucleotide sequence in SEQ ID NOS:1-172, and 179-186, that encodes an antimicrobial RNA or polypeptide are further provided. The expression cassettes of the invention find use in generating transformed plants, plant cells, and microorganisms and in practicing the methods for inducing plant pathogen resistance disclosed herein. The expression cassette will include 5' and 3' regulatory sequences operably linked to a polynucleotide of the invention. “Operably linked” is intended to mean a functional linkage between two or more elements. For example, an operable linkage between a polynucleotide of interest and a regulatory sequence (i.e., a promoter) is functional link that allows for expression of the polynucleotide of interest. Operably linked elements may be contiguous or non-contiguous. When used to refer to the joining of two protein coding regions, by operably linked is intended that the coding regions are in the same reading frame. The cassette may additionally contain at least one additional gene to be cotransformed into the organism. Alternatively, the additional gene(s) can be provided on multiple expression cassettes. Such an expression cassette is provided with a plurality of restriction sites and/or recombination sites for insertion of the polynucleotide that encodes an antimicrobial RNA or polypeptide to be under the transcriptional regulation of the regulatory regions. The expression cassette may additionally contain selectable marker genes.

The expression cassette will include in the 5'-3' direction of transcription, a transcriptional initiation region (i.e., a promoter), translational initiation region, a polynucleotide of the invention, a translational termination region and, optionally, a transcriptional termination region functional in the host organism. The regulatory regions (i.e., promoters, transcriptional regulatory regions, and translational termination regions) and/or the polynucleotide of the invention may be native/analogous to the host cell or to each other. Alternatively, the regulatory regions and/or the polynucleotide of the invention may be heterologous to the host cell or to each other. As used herein, “heterologous” in reference to a sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide.

Where appropriate, the polynucleotides may be optimized for increased expression in the transformed organism. For example, the polynucleotides can be synthesized using preferred codons for improved expression.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassette can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). Additional selectable markers include phenotypic markers such as β-galactosidase and fluorescent proteins such as green fluorescent protein (GFP) (Su et al. (2004) *Biotechnol Bioeng* 85:610-9 and Fetter et al. (2004) *Plant Cell* 16:215-28), cyan florescent protein (CYP) (Bolte et al. (2004) *J. Cell Science* 117:943-54 and Kato et al. (2002) *Plant Physiol* 129:913-42), and yellow florescent protein (PhiYFP™ from Evrogen, see, Bolte et al. (2004) *J. Cell Science* 117:943-54). The above list of selectable marker genes is not meant to be limiting. Any selectable marker gene can be used in the present invention.

Generally, it will be beneficial to express the gene from an inducible promoter, particularly from a pathogen-inducible promoter. Such promoters include those from pathogenesis-related proteins (PR proteins), which are induced following infection by a pathogen.

In one embodiment, a plant, transformed by the antimicrobial RNA or polypeptides of the present invention is a plant (or an offspring thereof) rendered resistant to a plant-pathogenic microorganism etc., which is regenerated on the basis of host plant cells transformed with the gene of the present invention located under the control of a suitable promoter capable of functioning in plant cells, or with the gene of the present invention integrated in a suitable vector. The transformed plant of the present invention can express, in its body, the protein having an antimicrobial activity according to the present invention.

The expression vector usable in the method of transforming plant cells with the gene of the present invention include pUC vectors (for example pUC118, pUC119), pBR vectors (for example pBR322), pBI vectors (for example pBI112, pBI221), pGA vectors (pGA492, pGAH), pNC (manufactured by Nissan Chemical Industries, Ltd.). In addition, virus vectors can also be mentioned. The terminator gene to be ligated includes 35S terminator gene and Nos terminator gene.

The method of introducing the constructed expression vector into a plant includes an indirect introduction method and a direct introduction method. The indirect introduction includes, for example, a method using *Agrobacterium*. The direct introduction method includes, for example, an electroporation method, a particle gun method, a polyethylene glycol method, a microinjection method, a silicon carbide method etc.

The method of regenerating a plant individual from the transformed plant cells is not particularly limited, and may make use of techniques known in the art.

In another embodiment, the antimicrobial proteins of the present invention can be produced by methods used conventionally for protein purification and isolation by a suitable combination of various kinds of column chromatography (C18, C8, gel filtration, ion-exchange), prepared by a chemical synthesis method using a peptide synthesizer (for example, peptide synthesizer 430A manufactured by Perkin Elmer Japan) or by a recombination method using a suitable host cell selected from prokaryotes and eukaryotes.

In another embodiment, an expression vector having any one of the nucleic acid sequences in SEQ ID NOS: 1 to 172 and amplifiable in a desired host cells is used to transform bacteria, yeasts, insects or animal cells, and the transformed cells are cultured under suitable culture conditions, whereby a large amount of the protein can be obtained as a recombinant. Culture of the transformant can be carried out by general methods.

The method used in purifying the protein of the present invention from a culture mixture can be suitably selected from methods used usually in protein purification. That is, a proper method can be selected suitably from usually used methods such as salting-out, ultrafiltration, isoelectric precipitation, gel filtration, electrophoresis, ion-exchange chromatography, hydrophobic chromatography, various kinds of affinity chromatography such as antibody chromatography, chromatofocusing, adsorption chromatography and reverse phase chromatography, using a HPLC system etc. if necessary, and these techniques may be used in purification in a suitable order.

Further, the antimicrobial proteins of the present invention can also be expressed as a fusion protein with another protein or a tag (for example, glutathione S transferase, protein A, hexahistidine tag, FLAG tag, etc.). The expressed fusion protein can be cleaved off with a suitable protease (for example, thrombin etc.), and preparation of the protein can be carried out more advantageously in some cases. Purification of the protein of the present invention may be carried out by using a suitable combination of general techniques familiar to those skilled in the art, and particularly upon expression of the protein in the form of a fusion protein, a purification method characteristic of the form is preferably adopted. Further, a method of obtaining the protein by using the recombinant DNA molecule in a cell-free synthesis method (J. Sambrook, et al.: Molecular Cloning 2nd ed. (1989)) is one of the methods for producing the protein by genetic engineering techniques.

A protein of the present invention can be prepared as it is, or in the form of a fusion protein with another protein, but the protein of the present invention can be changed into various forms without limitation to the fusion protein. For example, the processing of the protein by various techniques known to those skilled in the art, such as various chemical modifications of the protein, binding thereof to a polymer such as polyethylene glycol, and binding thereof to an insoluble carrier, may be conducted. The presence or absence of addition of sugar chains or a difference in the degree of addition of sugar chains can be recognized depending on the host used. The proteins in such cases are also construed to be under the concept of the present invention insofar as they function as proteins having an antimicrobial activity.

Methods are provided for protecting a organism from a pathogen comprising applying an effective amount of an antimicrobial gene expression product, RNA, protein or other composition of the invention to the environment of the pathogen. “Effective amount” is intended to mean an amount of a protein or composition sufficient to control a pathogen. The antimicrobial proteins and compositions can be applied to the environment of the pathogen by methods known to those of ordinary skill in the art.

In one embodiment, an in-vitro transcription/translation system (e.g., Roche RTS 100 *E. coli* HY) can be used to produce cell-free antimicrobial protein or expression products of the current invention. In another embodiment, an effective amount of any of the 78 toxic proteins comprising a sequence selected from the group consisting of sequences, SEQ ID NOs:2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 79, 81, 83, 85, 87, 89, 91, 93, 95, 97, 99, 101, 103, 105, 106, 108, 110, 112, 114, 116, 118, 120, 122, 124, 126, 128, 130, 132, 134, 136, 138, 140, 142, 144, 146, 148, 150, 152, 154, 156, and/or 158, is applied to a pathogenic microorganism and/or its environment. In another embodiment, the antimicrobial protein is any of SEQ ID NOS: 187-196. In one embodiment, the antimicrobial protein is ABB43836 (SEQ_ID 30) or protein ABB43762 (SEQ_ID 46).

In another embodiment, an effective amount of any of the antimicrobial small RNA products, such as SEQ ID NOS: 179-186, or any small RNA expressed by SEQ ID NOS: 159-172, is applied to a pathogenic microorganism and/or its environment.

In some embodiments, it is preferred that the antimicrobial agents or anticmicrobial compositions, comprising the antimicrobial nucleic acids, proteins or polypeptides of the present invention described above, should demonstrate antipathogenic and antimicrobial activity, but however, be non-toxic or have low toxicity levels to humans, animals and plants or other organisms that are not the target pathogen.

The antimicrobial RNAs, proteins and expression products are preferably used as an agricultural and horticultural fungicide, an antimicrobial agent for pharmaceutical preparations and an antimicrobial agent in industrial, food, and home use.

In many cases, the antimicrobial protein of the present invention can be used alone, or may be used in combination with a suitable excipient or if necessary with other known agrochemicals, pharmaceutical preparations, industrial antimicrobial components, insecticidal components etc. Further, the protein having an antimicrobial activity used as the active ingredient in the present invention may be composed of a single protein or a mixture of several kinds of proteins.

The antimicrobial compositions of the invention may be obtained by the addition of a surface-active agent, an inert carrier, a preservative, a humectant, a feeding stimulant, an attractant, an encapsulating agent, a binder, an emulsifier, a dye, a UV protective, a buffer, a flow agent or fertilizers, micronutrient donors, or other preparations that may be used to inhibit or control microbial or bacterial infection or growth. One or more agrochemicals including, but not limited to, herbicides, insecticides, fungicides, bactericides, nematicides, molluscicides, acaracides, plant growth regulators, harvest aids, and fertilizers, can be combined with carriers, surfactants or adjuvants customarily employed in the art of formulation or other components to facilitate product handling and application for particular target pathogens. Suitable carriers and adjuvants can be solid or liquid and correspond to the substances ordinarily employed in formulation technology, e.g., natural or regenerated mineral substances, solvents, dispersants, wetting agents, tackifiers, binders, or fertilizers. The active ingredients of the present invention are normally applied in the form of compositions and can be applied to the crop area, plant, or seed to be treated. For example, the compositions of the present invention may be applied to grain in preparation for or during storage in a grain bin or silo, etc. The compositions of the present invention may be applied simultaneously or in succession with other compounds. Methods of applying an active ingredient of the present invention or an agrochemical composition of the present invention that contains at least one of the antimicrobial proteins, more particularly antibacterial proteins, of the present invention include, but are not limited to, agrochemical composition foliar application, seed coating, and soil application. The number of applications and the rate of application depend on the intensity of infestation by the corresponding pest or pathogen.

Suitable surface-active agents include, but are not limited to, anionic compounds such as a carboxylate of, for example, a metal; carboxylate of a long chain fatty acid; an N-acylsarcosinate; mono or di-esters of phosphoric acid with fatty alcohol ethoxylates or salts of such esters; fatty alcohol sulfates such as sodium dodecyl sulfate, sodium octadecyl sulfate or sodium cetyl sulfate; ethoxylated fatty alcohol sulfates; ethoxylated alkylphenol sulfates; lignin sulfonates; petroleum sulfonates; alkyl aryl sulfonates such as alkylbenzene sulfonates or lower alkylnaphtalene sulfonates, e.g., butyl-naphthalene sulfonate; salts of sulfonated naphthalene-formaldehyde condensates; salts of sulfonated phenol-formaldehyde condensates; more complex sulfonates such as the amide sulfonates, e.g., the sulfonated condensation product of oleic acid and N-methyl taurine; or the dialkyl sulfosuccinates, e.g., the sodium sulfonate or dioctyl succinate. Nonionic agents include condensation products of fatty acid esters, fatty alcohols, fatty acid amides or fatty-alkyl- or alkenyl-substituted phenols with ethylene oxide, fatty esters of polyhydric alcohol ethers, e.g., sorbitan fatty acid esters, condensation products of such esters with ethylene oxide, e.g., polyoxyethylene sorbitar fatty acid esters, block copolymers of ethylene oxide and propylene oxide, acetylenic glycols such as 2,4,7,9-tetraethyl-5-decyn-4,7-diol, or ethoxylated acetylenic glycols. Examples of a cationic surface-active agent include, for instance, an aliphatic mono-, di-, or polyamine such as an acetate, naphthenate or oleate; or oxygen-containing amine such as an amine oxide of polyoxyethylene alkylamine; an amide-linked amine prepared by the condensation of a carboxylic acid with a di- or polyamine; or a quaternary ammonium salt. Examples of inert materials include but are not limited to inorganic minerals such as kaolin, phyllosilicates, carbonates, sulfates, phosphates, or botanical materials such as cork, powdered corncobs, peanut hulls, rice hulls, and walnut shells.

The antimicrobial compositions of the present invention can be in a suitable form for direct application or as a concentrate of primary composition that requires dilution with a suitable quantity of water or other diluant before application. The concentration of the antimicrobial polypeptide will vary depending upon the nature of the particular formulation, specifically, whether it is a concentrate or to be used directly. The composition contains 1 to 98% of a solid or liquid inert carrier, and 0 to 50%, optimally 0.1 to 50% of a surfactant. These compositions will be administered at the labeled rate for the commercial product.

In a further embodiment, the compositions, as well as the transformed microorganisms and antimicrobial proteins, of the invention can be treated prior to formulation to prolong the antimicrobial, particularly antibacterial, activity when applied to the environment of a target pathogen as long as the pretreatment is not deleterious to the activity. Such treatment can be by chemical and/or physical means as long as the treatment does not deleteriously affect the properties of the composition(s). Examples of chemical reagents include but are not limited to halogenating agents; aldehydes such a formaldehyde and glutaraldehyde; anti-infectives, such as zephiran chloride; alcohols, such as isopropanol and ethanol; and histological fixatives, such as Bouin's fixative and Helly's fixative (see, for example, Humason (1967) *Animal Tissue Techniques* (W.H. Freeman and Co.).

The antimicrobial agent preparations according to the present invention may be useful in exhibiting an antimicrobial effect on pathogenic microorganisms such as *Staphylococcus aureus, Escherichia coli*, microorganisms of the genus *Staphylococcus*, microorganisms of the genus *Escherichia*, microorganisms of the genus *Aspergillus*, microorganisms of the genus *Candida*, microorganisms of the genus *Mucor*, microorganisms of the genus *Absidia*, microorganisms of the genus *Cryptococcus*, microorganisms of the genus *Blastomyces*, microorganisms of the genus *Paracoccidioides*, microorganisms of the genus *Coccidioides*, microorganisms of the genus *Sporothrix*, microorganisms of the genus *Phialophora*, microorganisms of the genus *Histoplasma*, microorganisms of the genus *Trichophyton*, microorganisms of the genus *Microsporum*, microorganisms of the genus *Epidermophyton*, microorganism of the genus *Bacillus*, and microorganisms of the genus *Yersinia*, microorganisms of the genus *Salmonella*, microorganisms of the genus *Francisella*, etc.

In another embodiment, the antimicrobial agent preparations according to the present invention may be useful in exhibiting an antimicrobial effect on plant pathogenic microorganisms such as microorganisms of the genus *Agrobacterium*, microorganisms of the genus *Burkholderia*, microorganisms of the genus *Clavibacter*, microorganisms of the genus *Erwinia*, microorganisms of the genus *Ralstonia*, microorganisms of the genus *Xanthomonas*, microorganisms of the genus *Pseudomonas*, and microorganisms of the genus *Leifsonia*, microorganisms of the genus *Xylella*, microorganisms of the genus *Spiroplasma*. In one embodiment, the antimicrobial agent exhibits an antimicrobial effect on microorganisms *Agrobacterium tumefaciens, Burkholderia cenocepacia, Clavibacter michiganensis, Erwinia carotovora, Erwinia chrysanthemi, Leifsonia xyli, Pseudomonas syringae, Ralstonia solanacearum, Xanthomonas axonopodis, Xanthomonas campestris, Xylella fastidiosa, Spiroplasma kunkelii*, and Onion yellows phytoplasma.

The protein having an antimicrobial activity used as the active ingredient for an industrial antimicrobial agent of the present invention may be blended and mixed with a suitable excipient and adjuvant, for example a binder, a stabilizer etc. to prepare a pharmaceutical preparation in a suitable form in a usual manner, such as a liquid, a hydrate, an emulsion, sol (flowable agent), etc.

In one embodiment for use in agriculture, the antimicrobial compositions of the invention can be applied to the environment of a plant pathogen by, for example, spraying, atomizing, dusting, scattering, coating or pouring, introducing into or on the soil, introducing into irrigation water, by seed treatment or general application or dusting at the time when the pathogen has begun to appear or before the appearance of pathogens as a protective measure. For example, the antimicrobial protein and/or transformed microorganisms of the invention may be mixed with grain to protect the grain during storage. It is generally important to obtain good control of pathogens in the early stages of plant growth, as this is the time when the plant can be most severely damaged. The compositions of the invention can conveniently contain an insecticide if this is thought necessary. In one embodiment of the invention, the composition is applied directly to the soil, at a time of planting, in granular form of a composition of a. Another embodiment is a granular form of a composition comprising an agrochemical such as, for example, a herbicide, an insecticide, a fertilizer, or an inert carrier.

Compositions of the invention find use in protecting plants, seeds, and plant products in a variety of ways. For example, the compositions can be used in a method that involves placing an effective amount of the antimicrobial, composition in the environment of the pathogen by a procedure selected from the group consisting of spraying, dusting, broadcasting, or seed coating.

The industrial antimicrobial agent containing the protein having an antimicrobial activity as the active ingredient according to the present invention can be used in suppression of the growth of microorganisms and fungi in emulsion products such as aqueous paints, adhesive materials, latex, acryl etc., slurry products such as starch, pigments, calcium carbonate etc., and joint cement; preservation of wood such as building materials (construction materials, civil engineering building materials etc.); sterilization and prevention of slime formation in production facilities in factories, cooling towers in building air conditioning, and pulp- and paper-making factories, etc.; antimicrobial treatment by spraying or dipping of fibers, fabrics and hides; protection from the attack of microorganisms and fungi occurring during exposure of a paint coating, particularly a paint coating of an exterior paint, to wind and rain; antimicrobial treatment of interior/exterior materials (for housing, medical facilities), building materials (construction materials, civil engineering materials etc.), home appliances, domestic sundries, sporting goods etc. made of resin such as vinyl chloride, polyurethane, polyethylene, polypropylene, silicone, modified silicone, nylon, epoxy resin etc.; protection from accumulation of slime on devices for producing sugar cane and beet sugar; prevention of accumulation and sedimentation of microorganisms in an air washer and scrubber system and an industrial freshwater-feeding system; maintenance of sanitary environments in food factories etc.; deodorization and sterilization at the time of washing production facilities and in sewage disposal plants etc.; prevention of growth of microorganisms and fungi in paper-coating materials and coating processing; prevention of contamination of cosmetics and toiletries with microorganisms; prevention of microbial growth in a pool, cooling water etc.; prevention of microbial contamination of agricultural blends, an electrodeposition system, and diagnostic and chemical products, medical instruments etc.; and prevention of accumulation of microorganisms in photographic treatment.

In another embodiment for household use as an antimicrobial agent, the present antimicrobial polypeptides are formed into a pharmaceutical preparation and used as it is, or used according to a wide variety of conventional methods of using industrial antimicrobial agents, which include, but are not limited to, a method that involves diluting it with water or a suitable organic solvent and mixing the dilution with various household materials or products, a method of applying or spraying it onto the surfaces of various household and industrial materials or products, and a method that involves dipping various industrial materials or products in a dilution of the household antimicrobial agent of the present invention, etc. The household antimicrobial agent of the present invention described above may be in the form of preparations prepared by mixing the protein with a solution, a suspension, an emulsion etc., for example in the form of tablets, powder, granules, liquids, hydrates, emulsions, injections, aerosol, sprays, sol (flowable agent), etc. The household antimicrobial agents may be used in cleaners, solvents, soaps, disposable cleaning materials, plastics, containers, etc.

In another embodiment, for pharmaceutical use, the antimicrobial polypeptides of the present invention can be prepared from the protein of the present invention alone or by compounding the protein with pharmaceutically acceptable excipients, active ingredients, fillers etc. if necessary. The preparation form includes parenteral administration forms such as injections (subcutaneous, intravenous, intramuscular or intraperitoneal injections), liquid coating agents, gel, ointments, suppositories and aerosol, and oral administration forms such as tablets, capsules, granules, pills, syrups, liquids, emulsions, suspensions etc.

For preparation of the tablets, capsules, granules and pills for oral administration, use is made of excipients such as white sugar, lactose, glucose, starch and mannitol, binders such as syrup, gum arabic, gelatin, sorbitol, tragacanth, methylcellulose and polyvinyl pyrrolidone, disintegrating agents such as starch, carboxymethyl cellulose or a calcium salt thereof, fine crystalline cellulose and polyethylene glycol, lustering agents such as talc, magnesium stearate, calcium stearate and silica, and lubricants such as sodium laurate and glycerol.

For preparation of the injections, liquids, emulsions, suspensions, syrups and aerosol, use is made of solvents for the active ingredient, such as water, ethyl alcohol, isopropyl alcohol, propylene glycol, 1,3-butylene glycol and polyethylene glycol, surfactants such as sorbitan fatty ester, polyoxyethylene sorbitan fatty ester, polyoxyethylene fatty ester, hydrogenated castor oil polyoxyethylene ether, and lecithin, cellulose derivatives such as carboxymethylcellulose sodium salt and methylcellulose, suspending agents such as natural gum such as tragacanth and gum arabic, preservatives such as paraoxybenzoate, benzalkonium chloride and sorbitate.

The clinical dose of the antimicrobial agent is varied depending on the therapeutic effect on the age, body weight, sensitivity and symptom of the patient, but usually the effective daily dose is 0.003 to 1.5 g/kg, preferably 0.01 to 0.6 g/kg. However, a dose outside of the above range can also be used if necessary.

In another embodiment, the antimicrobial agent prepared as in a cream or lotion for topical application. Typically such compositions are prepared with purified water, preservatives, emollient and emulsion stabilizers and humectants used in many cosmetic preparations including, but not limited to, propylene glycol, parabens, cetearyl alcohol, also known as cetostearyl alcohol, polysorbate 60 (polyoxyethylene sorbitan monostearate), cetyl alcohol, and glycerine. For example, a patient can topically apply an antibiotic ointment containing one or more of the antimicrobial agents of the present invention as active ingredients for fighting infection during wound repair, and thereby increasing rate of healing while reducing risk of infection.

In another embodiment of the invention, the bacteria originally producing the antimicrobial agent, or engineered bacteria that express the antimicrobial agent and are also resistant to its effect, may be used as probiotic bacteria for food preservation, livestock growth enhancement, and human health.

In another embodiment, for food processing and preservation use, antimicrobial agents of the present invention can be prepared from the genes, RNA or proteins of the present invention alone or by compounding the agent with commercially acceptable other antibacterial agents, such as chitosan or its derivatives, and/or suitable chelating agents including, but are not limited to, ethylene diaminetetraacetic acid and its salts, cyclodextrins, hydrocarboxylic acids, such as citric acid, acetic acid, lactic acid, tartaric acid, and their salts, alone or in combination. In one embodiment, the antimicrobial agents of the present invention may be combined with other antimicrobial decontaminants, such as hydrogen peroxide, citric acid, lactic acid, or acetic acid, alone, or in combination.

The antimicrobial agents can be used for treatment of whole animals and may be applied to the food animal after stunning, before the animal is bled, during the de-hairing, de-feathering, and skinning processes, and may be applied to decontaminate heads, organs, offal and other carcass parts. The antimicrobial composition of the present invention may be used in connection with any food product which is susceptible to microbial degradation. These include, but are not limited to fruits and vegetables including derived products, grain and grain derived products, dairy foods, meat, poultry, and seafood. In particularly preferred embodiments, the composition is used in connection with meat, poultry and/or seafood, more particularly with fat containing cooked meats such as hotdogs, sausages, roast beef, turkey, corned beef and deli meats. The concentration of the anti-microbial solution, contact time, temperature and other application parameters are controlled to optimize the effectiveness of the treatment.

In another embodiment, the antimicrobial agents are applied to a food surface for the purpose of food processing, preservation or to prevent food spoilage or degradation. The use of the term "food surface" is defined to include any and all internal or external surfaces of the food product being treated. The preparation form includes surface administration forms such as injections, sprays, liquid solutions, liquid coating agents, gel, ointments, and aerosol.

The composition according to the present invention can be used by applying it on the exterior surface of a blended food product, such as a hot dog or bologna, or of a solid food, such as a piece of roasted beef, so as to minimize loss of activity in the fat phase of the food. The composition may alternatively be included in the emulsion or raw ingredients of a food such as sauces or salsas, before or after cooking, or to the interior of solid products, such as hams, by injection or tumbling. In still other embodiments, the composition may be applied as a marinade, breading, seasoning rub, glaze, colorant mixture, and the like, the key criteria being that the antimicrobial composition be available to the surface subject to bacterial degradation. In a preferred embodiment, the composition may be indirectly placed into contact with the food surface by applying the composition to food packaging materials or casings and thereafter applying the packaging to the food surface. The use of surface treatment strategies, whether direct or indirect, benefits from the minimization of loss into the fat phase of the fat containing food product. The optimum effective amount to be used will depend on the composition of the particular food product to be treated and the method used for applying the composition to the food surface, but can be determined by simple experimentation.

EXAMPLE 1

Characterization of a Toxic Gene Found Using the Method

Figure 4:
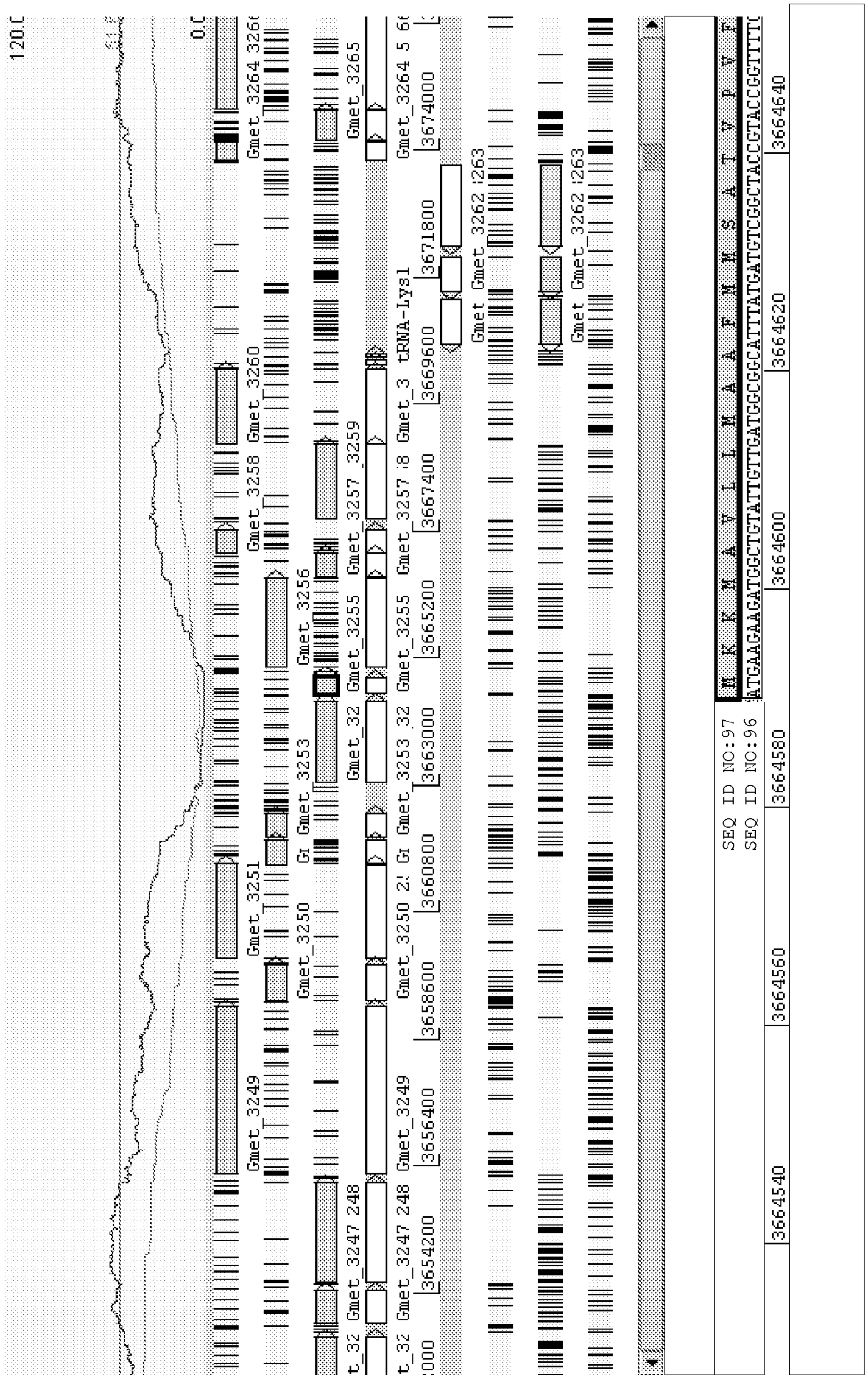
FIG. 4: Coverage of Geobacter gene YP_386193 (gmet_3255; Gene No: 48; SEQ ID NOS: 96-97). Shown is a snapshot from Artemis genome browser [Rutherford, 2000. Bioinformatics 16 (10) 944-945] of a ~20 kb region between positions 3,654,200-3,674,000 of the *Geobacter metallireducens* GS-15 genome. Clone coverage is in the above curves (red curve—small clones [up to 10 kb]; green curve—large [fosmid] clones [10-50 kb]). On the bottom of the screen in the browser (but not shown in FIG. 4) is the consensus sequence and the predicted proteins from each open reading frame. The gene and protein under the minimum coverage is YP_386193. Partial sequences of SEQ ID NOS:96 and 97 are shown and marked by a black box and highlighted)

We selected one of the proteins found in our set as an example. This protein, Genbank Accession No. YP_386193 which is hereby incorporated by reference, is found in the *Geobacter metallireducens* GS-15 genome, and is identified as Gene No. 48 in the attached Sequence Listing. The nucleic acid sequence is SEQ ID NO: 96 and the protein sequence is SEQ ID NO: 97. FIG. 4 demonstrates the deficiency in clone coverage of this gene. The gene encodes a small protein (93 amino-acids long) that has a signal sequence (as predicted by the signalP software [Nielsen, Protein Eng. 1999 January; 12(1):3-9]) and is hence probably secreted. It has an excess of basic residues over acidic ones, and is hence predicted to be positively charged in neutral pH. Homologs of this gene are found only in *Geobacter sulfurreducens* and *Geobacter uraniumreducens*, but not outside the *Geobacter* genus.

Figure 5:
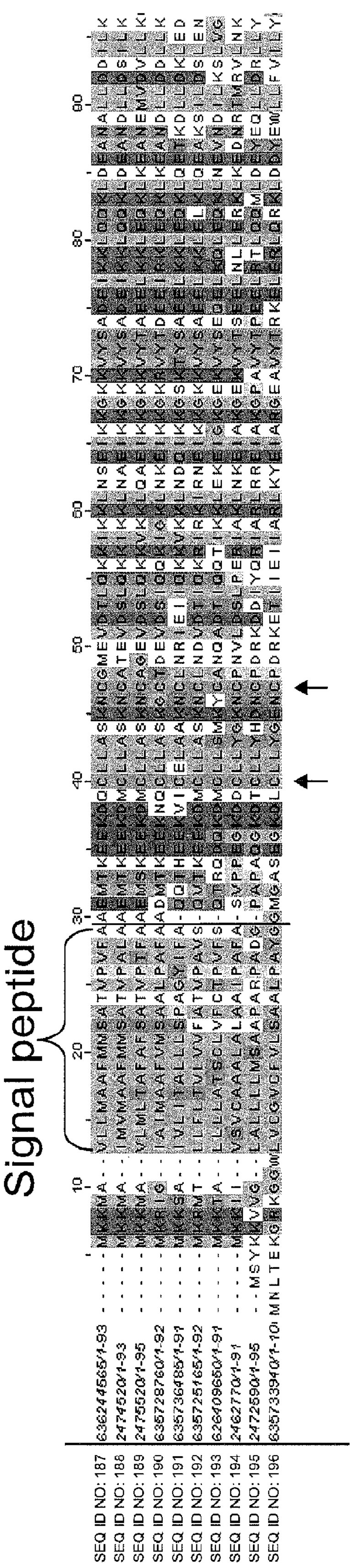
FIG. 5: Multiple alignment of YP_386193 homologs. Multiple sequence alignment of SEQ ID NOS: 187-196 was performed using clustalW. Invariant cysteine residues are marked by black arrows. The bracket above the alignment shows the conserved signal peptide region.
Figure 6:
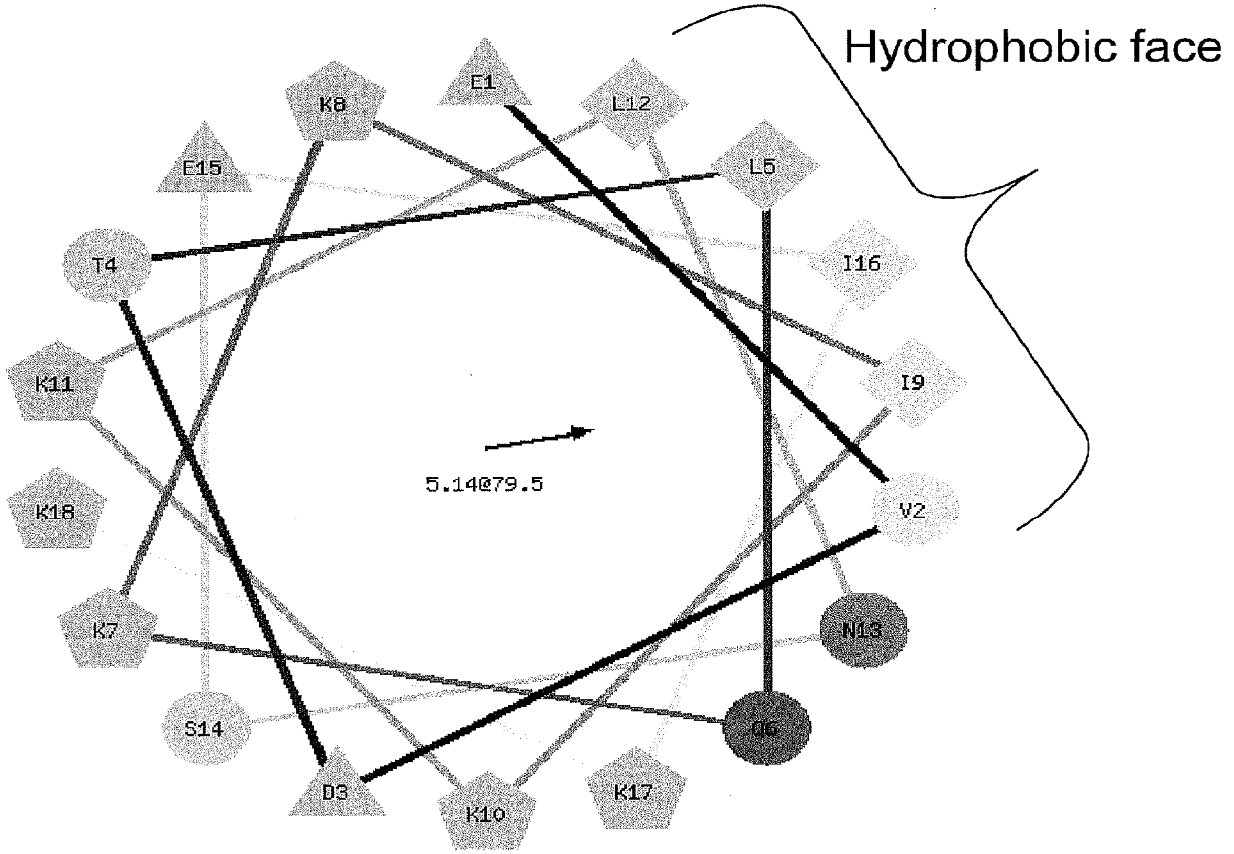
FIG. 6: Secondary structure prediction of YP_386193. Shown is the YP_386193 protein without the N-terminal signal sequence (SEQ ID NO: 197). Conserved cysteine residues are marked red. Predicted helical sequences are in blue. Secondary structure was predicted using the NNPREDICT software [Kneller, J. Mol. Biol. (214) 171-182], where only predicted helices longer than 5 residues were taken into account. A helical wheel of the first (N-terminal) helix is also presented. Hydrophobic face is marked by parenthesis; the remaining face is composed of hydrophilic residues.

FIG. 5 presents a multiple alignment of YP_386193 homologs. All homologs are short (90-100aa), positively charged proteins, with a predicted signal peptide. Two invariant cysteine residues probably indicate on a disulfide bridge formation (FIG. 5). Protein secondary structure prediction indicates that the protein contains two amphiphilic alpha helices, each containing distinct hydrophobic and hydrophilic faces (FIG. 6). From these data we predict that protein YP_386193 might be a cationic antimicrobial peptide, as these peptides are defined as short, positively charged, amphiphilic, secreted proteins that perforate bacterial membranes [Hancock, Trends Microbiol. 2000 September; 8(9): 402-10]

Figure 8:
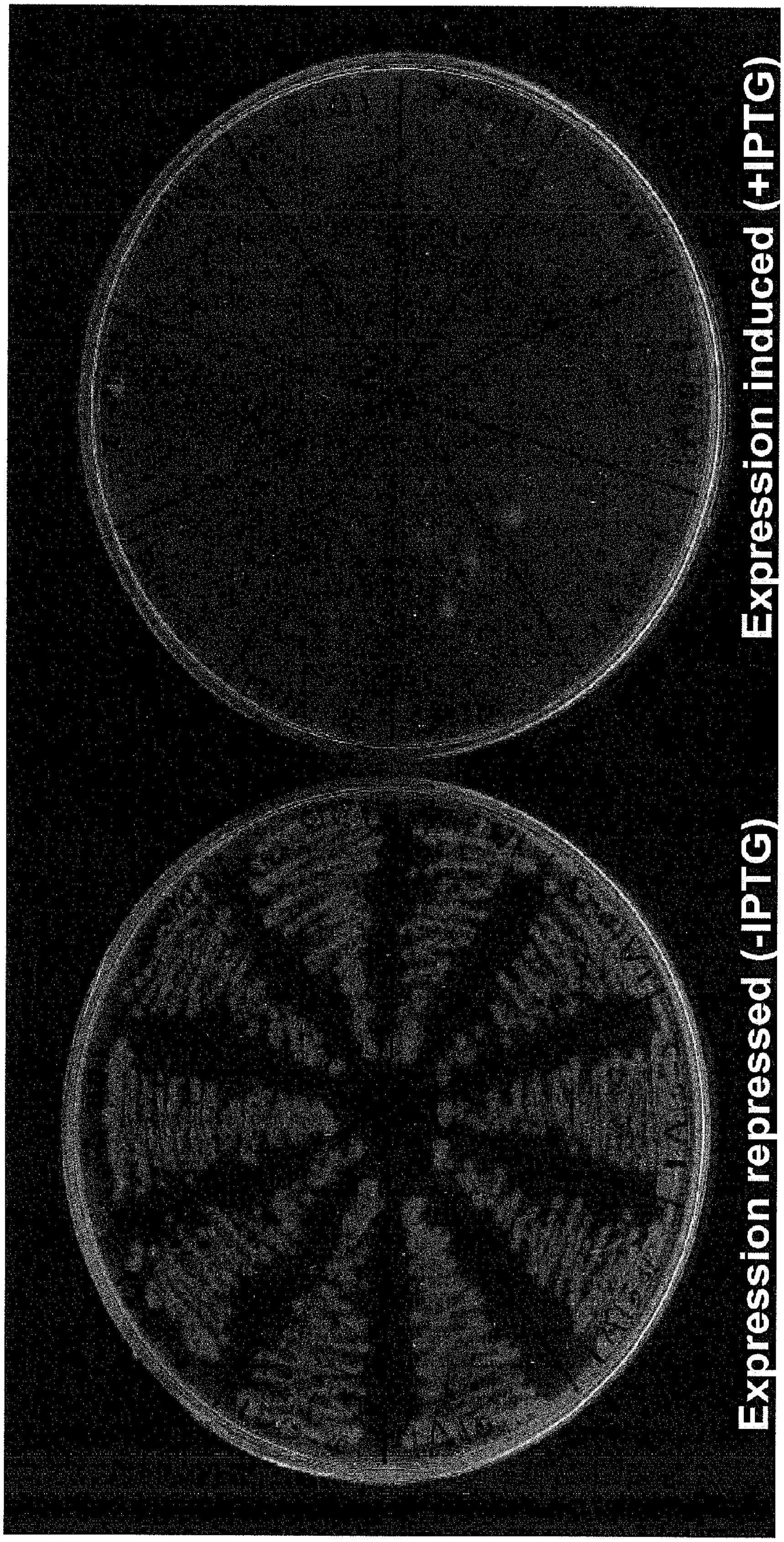
FIG. 8: The protein product of YP_386193 inhibits *E coli* growth following induction of its expression. Ten colonies containing the full length YP_386193 gene grow in a medium without IPTG (left plate) but fail to grow in the presence of IPTG, where expression of YP_386193 is induced (right plate). The gene was amplified from the Geobacter metallireducens genome and engineered into pET11a vector downstream to the T7 promoter. Vectors were transformed into BL21(DE)pLys cells (Invitrogen) that contain a choromosomal copy of the T7 polymerase under the control of lac promoter. Correct sequence in the inserts was verified by direct sequencing.
Figure 9:
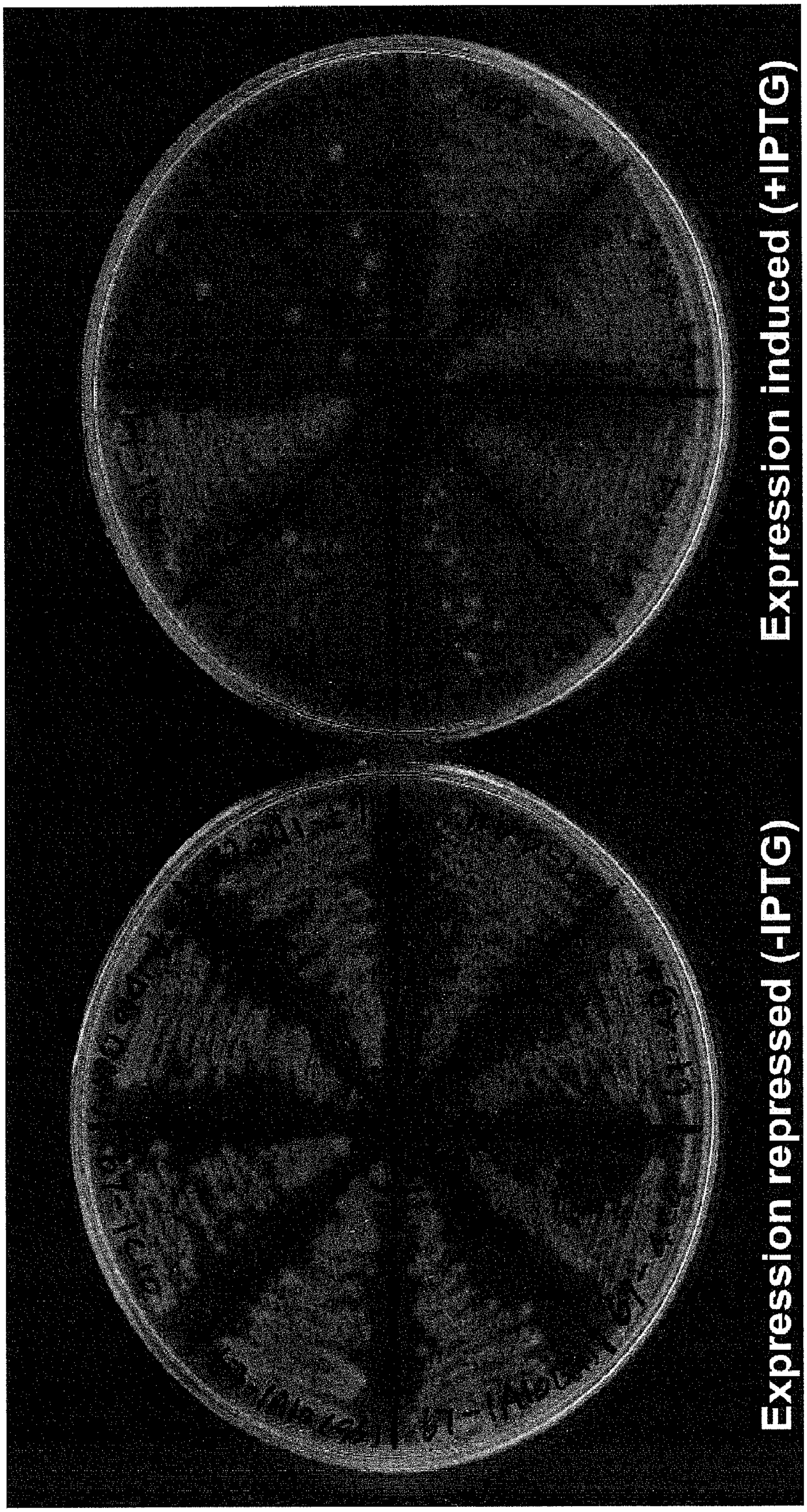
FIG. 9: Negative control: Mutated YP_386193 insertions do not kill. Experiments were done as described in FIG. 8. Colonies 1C10, 4C4, 4B4 and 4A11 contain mutated YP_386193 inserts containing various deletions in the coding sequence, as detected by direct sequencing. The remaining four colonies contain unmutated YP_386193 inserts. Bacterial growth is inhibited only upon expression induction of unmutated inserts.

To check whether protein YP_386193 indeed inhibits bacterial growth we cloned it into the pET11a plasmid (Stratagene) under a T7 polymerase promoter, and transformed the vector into BL21(DE)pLYS cells. This system maintains the expression of the inserted gene silent unless an inducer molecule (IPTG) is added to the medium. As a positive control we similarly cloned the RegB gene, which is known to be highly toxic to *E coli* [Sanson, FEMS Microbiol Rev. 1995 August; 17(1-2):141-50]. As a negative control we similarly cloned the *E. coli* beta-galactosidase gene. FIG. 7 shows that RegB indeed kills *E coli* following induction of its expression as shown by the lack of colony growth in the top half of the petri dish in the second and third panels, while beta-galactosidase does not affect bacterial growth, as shown by colony growth in the bottom of the petri dishes. FIG. 8 shows that similar to the RegB positive control, colonies containing YP_386193 cannot grow if its expression of YP_386193 is induced, demonstrating its toxicity to *E coli*. Colonies containing mutated inserts, however, were not growth inhibited following expression induction (FIG. 9). These results show that YP_386193 has a growth inhibition effect on *E coli*, and is thus an antimicrobial agent.

We tested 77 additional proteins from the set described in the attached Sequence Listing using the same experimental system as described above for protein YP_386193. It was found that each of these 77 proteins are indeed toxic when expressed in *E. coli*. Results are not shown for each protein in the set, but exemplary data (e.g., photographs of individual wells showing bacteria growth and/or inhibition as a result of induced expression of the antimicrobial protein) from several examples are found in FIG. 10 Photos were taken and the colonies were counted. Table 1 shows the gene number, internal reference number and the corresponding sequence identifier for the nucleotide and protein sequences in the first four columns. In the last column of Table 1, shown is the lowest concentration (uM) of IPTG needed to induce gene expression and inhibition of bacterial growth was observed. A protein was said to inhibit growth of bacteria if a result of no more than 10 colonies was observed in a well of a 48-well growth plate after inducing expression. In this system, IPTG influences the level of activity of the T7 promoter in the pET11a plasmid, thereby inducing expression of the toxic gene. We induced expression at varying concentrations of 100 μM, 250 μM, 400 μM, 600 μM, 800 μM and 1000 μM of IPTG. The manufacturer of the expression system recommends to use 1 mM (1000 uM) IPTG for maximum efficiency and it is generally accepted that IPTG concentrations lower than that cause partial activity. Thus, with even very low IPTG concentrations used to induce expression, it is shown that small amounts of expression of some of the disclosed genes have significant antimicrobial activity. For example, Gene No. 9, ABB43889, having a polynucleotide sequence of SEQ ID NO:17, and when expressed is SEQ ID NO:18, required only 100 μM of IPTG to express ABB43889, and inhibit growth.

To verify that the 78 proteins identified by our method are bona fide antimicrobial proteins, we used an in-vitro transcription/translation system (Roche RTS 100 *E. coli* HY) to produce cell-free protein products of the 78 toxic genes. Candidate toxic proteins were mixed with *E. coli* strain BL21 bacteria growing in liquid LB medium, and growth was then monitored for 5.5 hours by measuring Optical Density (OD) in wavelength 600 nm every 10 minutes. For each protein tested, the OD was measured for growth of control bacteria without toxic protein addition to the medium containing an in-vitro transcription/translation system. An average and standard deviation of at least 9 repetitions were performed for each control. At least three repetitions of this growth kinetics experiment for each single toxic protein mixed with the medium containing the in-vitro transcription/translation system was carried out. The OD was taken every 10 minutes and the resulting growth curves were compared to the control curve.

For each of the genes and proteins shown in Table 1, growth of bacteria may be inhibited in the presence of the translated toxic protein, as compared to growth without toxic proteins in the medium. Data not shown for all genes tested, however, FIGS. 12A and 12B show examples of the OD results obtained for two proteins identified using the method in the present invention. FIG. 12(A) shows antimicrobial activity of protein ABB43836 (SEQ_ID 30); and FIG. 12B, shows antimicrobial activity of protein ABB43762 (SEQ_ID 46). These proteins were determined empirically to have antimicrobial activity with the ability to inhibit bacteria growth by external application of the protein to bacteria or its environment. Looking at the graphs in FIGS. 12A and 12B, antimicrobial activity is evident as multiple points including the endpoint of the growth curve of the bacteria exposed to the proteins was at least 0.1 OD lower than the control, and there was an obvious deviation in the slope of the three growth curves as compared to the control. Thus, it was concluded that the two proteins had antimicrobial activity.

EXAMPLE 2

Identification of a Small Toxic RNAs Using the Method

Figure 13:
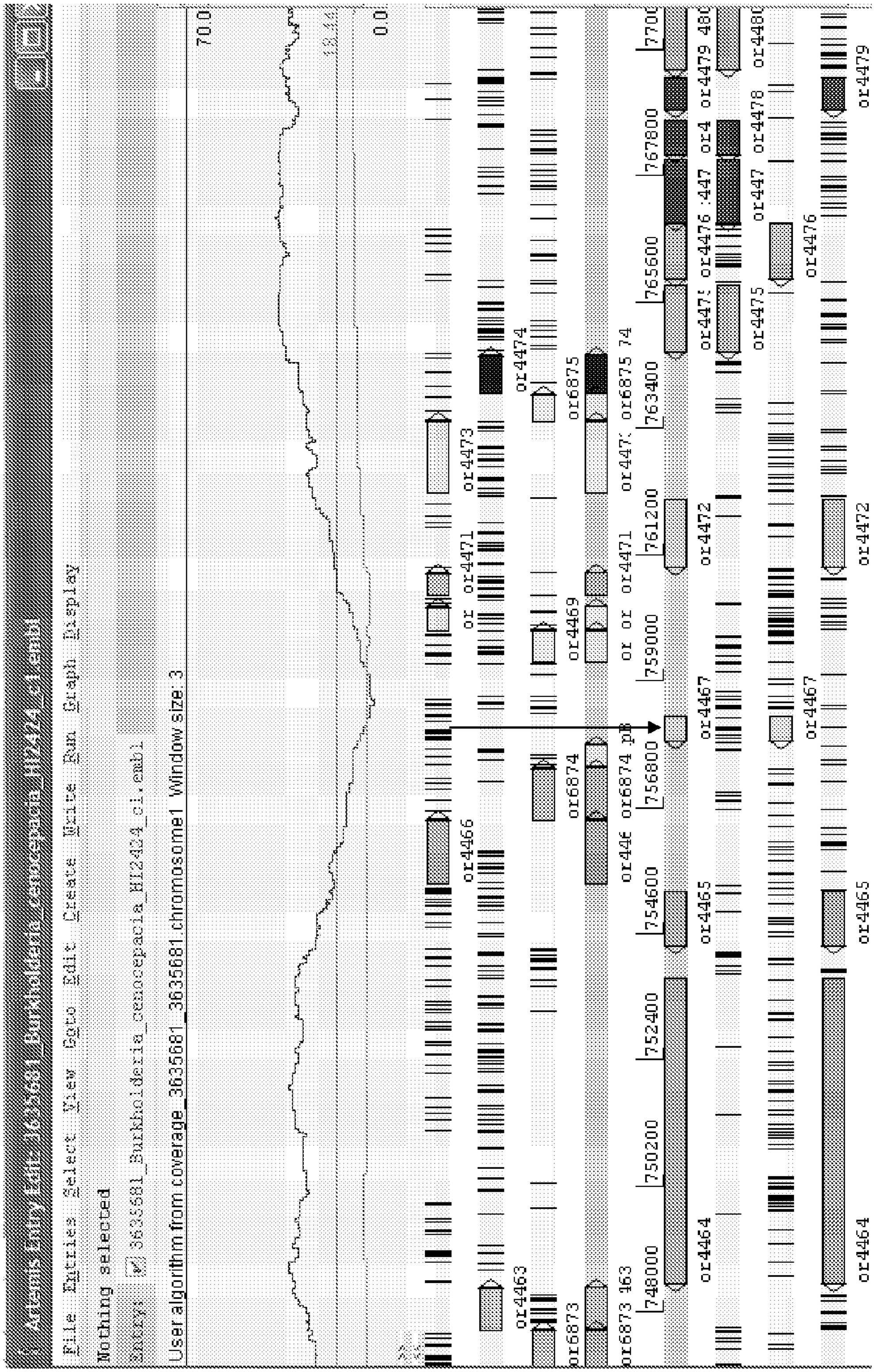
FIG. 13: Coverage deficiency in intergenic region in the *Burkholderia cenocepacia* HI2424 genome. Shown is a snapshot from Artemis genome browser [Rutherford, 2000. Bioinformatics 16 (10) 944-945] of a ~22 kb region between positions 748,000-770,000 of chromosome I of the *Burkholderia cenocepacia* HI2424 genome. Clone coverage is in the above curves (red curve—small clones [up to 10 kb]; green curve—large clones [10-50 kb]). The arrow indicates that the region that has the minimum clone coverage is an intergenic region.

The present method also enables the discovery of genome-encoded antibacterial agents that are not proteins. To demonstrate this, we looked for regions that are not predicted to contain open reading frames (ORFs), but display consistent clone coverage deficiency. One such region, found in the *Burkholderia cenocepacia* HI2424 genome displays radical reduction of clone coverage as calculated using our method (FIG. 13). This low covered region lies in the intergenic region between the genes encoding to OsmC and to ribosomal protein L13. Examining the coverage of this region in the closely related genomes of *Burkholderia cenocepacia* AU 1054, *Burkholderia* sp. strain 383, and *Burkholderia__ambifaria_*AMMD showed that it has detectable low coverage in all these genomes. The same low coverage pattern is seen in the more distantly related genomes of *Ralstonia* (*Cupriavidus*) *necator* and *Cupriavidus metallidurans* (not shown).

FIG. 14 shows a multiple sequence alignment of the DNA found in the discussed intergenic region from 4 *Burkholderia* species (*Burkholderia cenocepacia* AU 1054 (SEQ ID NO: 159), *Burkholderia* sp. strain HI2424 (SEQ ID NO: 160), *Burkholderia* sp. strain 383 (SEQ ID NO: 161), and *Burkholderia__ambifaria_*AMMD (SEQ ID NO: 162) and 2 *Ralstonia* species (*Ralstonia necator* (SEQ ID NO: 163), and *Ralstonia metallidurans* (SEQ ID NO: 164)). As seen in the figure, the sequences vary significantly, with a conserved core of 20 consecutive invariant nuclecotides in the middle of the alignment, and a conserved stretch of Thymines at the end. Deletions having sizes not divisible by 3 exclude the possibility that this region encodes a protein. Despite the lack of extensive sequence conservation, however, a strongly conserved RNA secondary structure is apparent from compensatory mutations in stem regions (FIG. 14). Therefore, this region is probably populated by an RNA gene which is toxic to *E coli*. A strongly predicted rho independent terminator defined the 3' end of the gene (FIG. 14). Scanning the region upstream to the conserved core reveals a strongly predicted promoter that defined the 5' boundary of the gene (FIG. 15, TATA box is highlighted in red).

Figure 16:
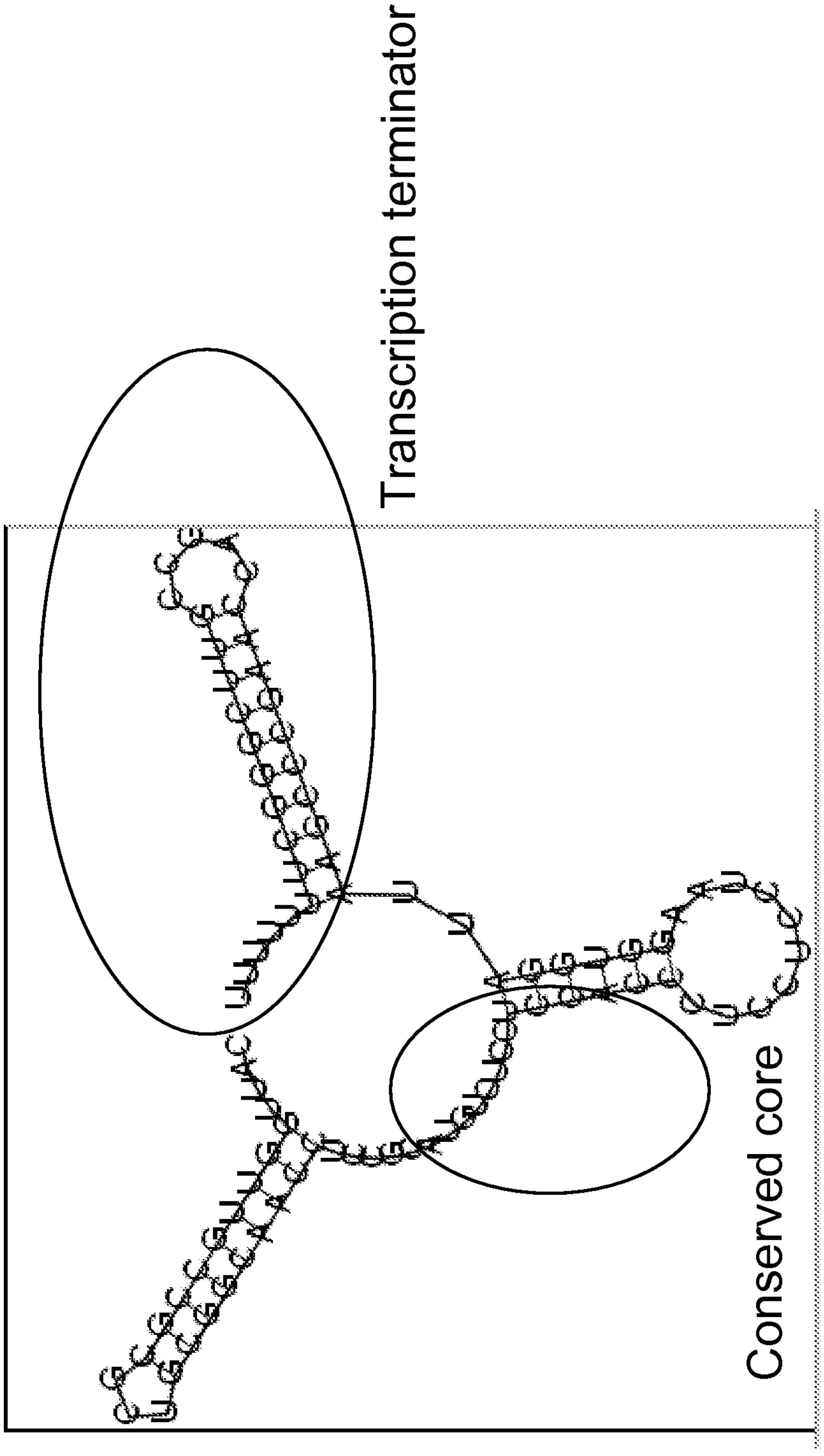
FIG. 16: Toxic small RNA gene structure in *Burkholderia* (SEQ ID NO:182). Secondary structure calculation was preformed using the RNAfold server [URL:<http://rna.tbi.univie.ac.at/cgi-bin/RNAfold.cgi>]. The transcriptional terminator is marked by blue circle; the conserved core is marked by red circle.
Figure 17:
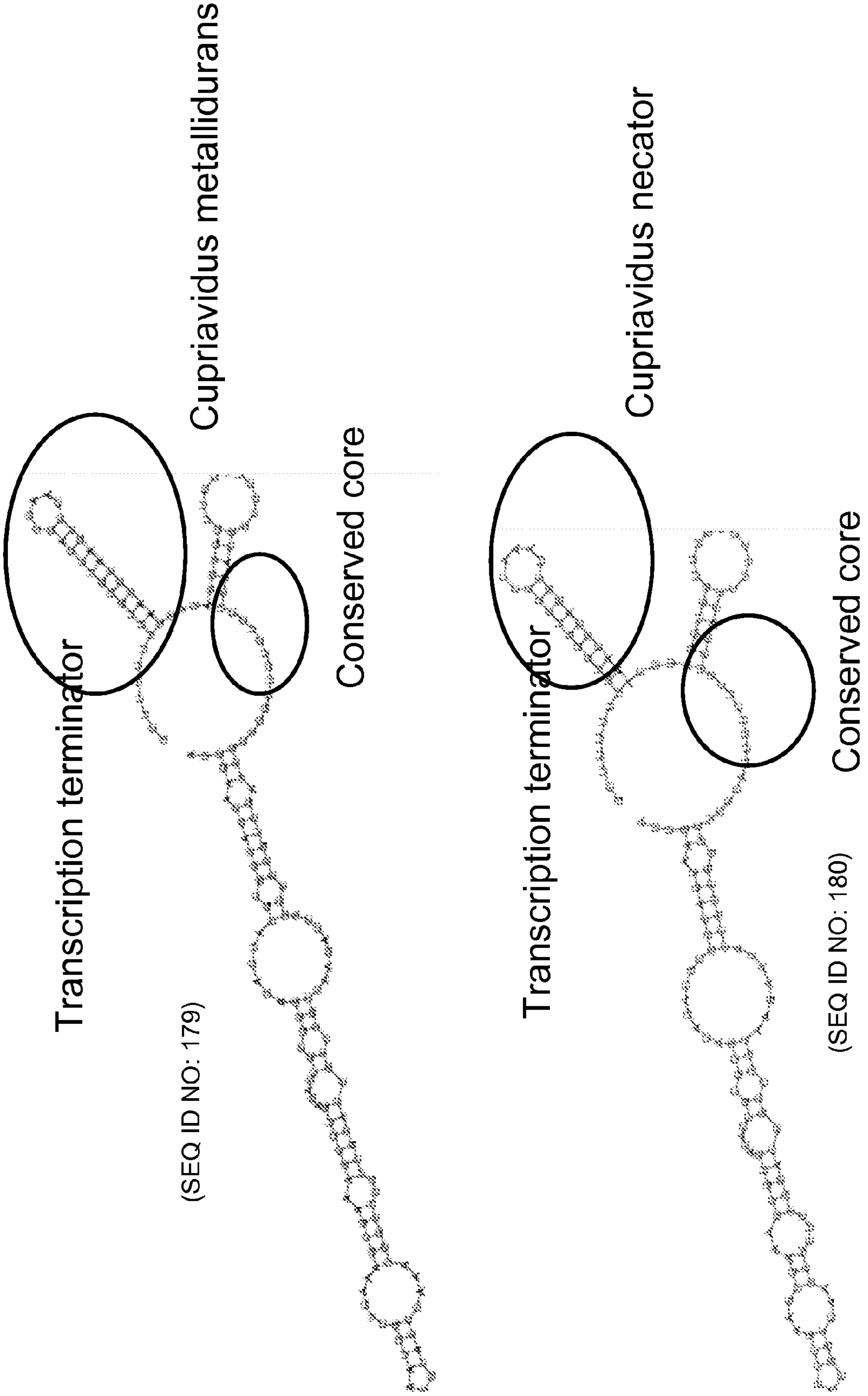
FIG. 17: Toxic small RNA genes structure in *Cupriavidus* (*Ralstonia*) genomes. Secondary structure calculation was preformed using the RNAfold server [URL:<http://rna.tbi.univie.ac.at/cgi-bin/RNAfold.cgi>]. The transcriptional terminator is marked by blue circles; the conserved core is marked by red circles. An obvious extension of the first stem structure relative to the *Burkholderia* RNA is apparent. The small RNA structure in the top panel is SEQ ID NO:179, and the bottom structure is SEQ ID NO:180.

The RNA secondary structure of this gene (as predicted by RNAfold [URL:<http://rna.tbi.univie.ac.at/cgi-bin/RNAfold.cgi>]) is shown in FIG. 16. The structure is comprised of 3 stems, of which the middle one hosts the conserved sequence core and the 3' one forms the transcriptional terminator. The first (most 5') stem is longer and more complex in the *Cupriavidus* genomes (FIG. 17). A scan by RFAM (database of known functional RNAs families [URL:<http://www.sanger.ac.uk/Software/Rfam/>]) shows that this RNA gene is not similar to any known functional RNA gene.

Figure 18:
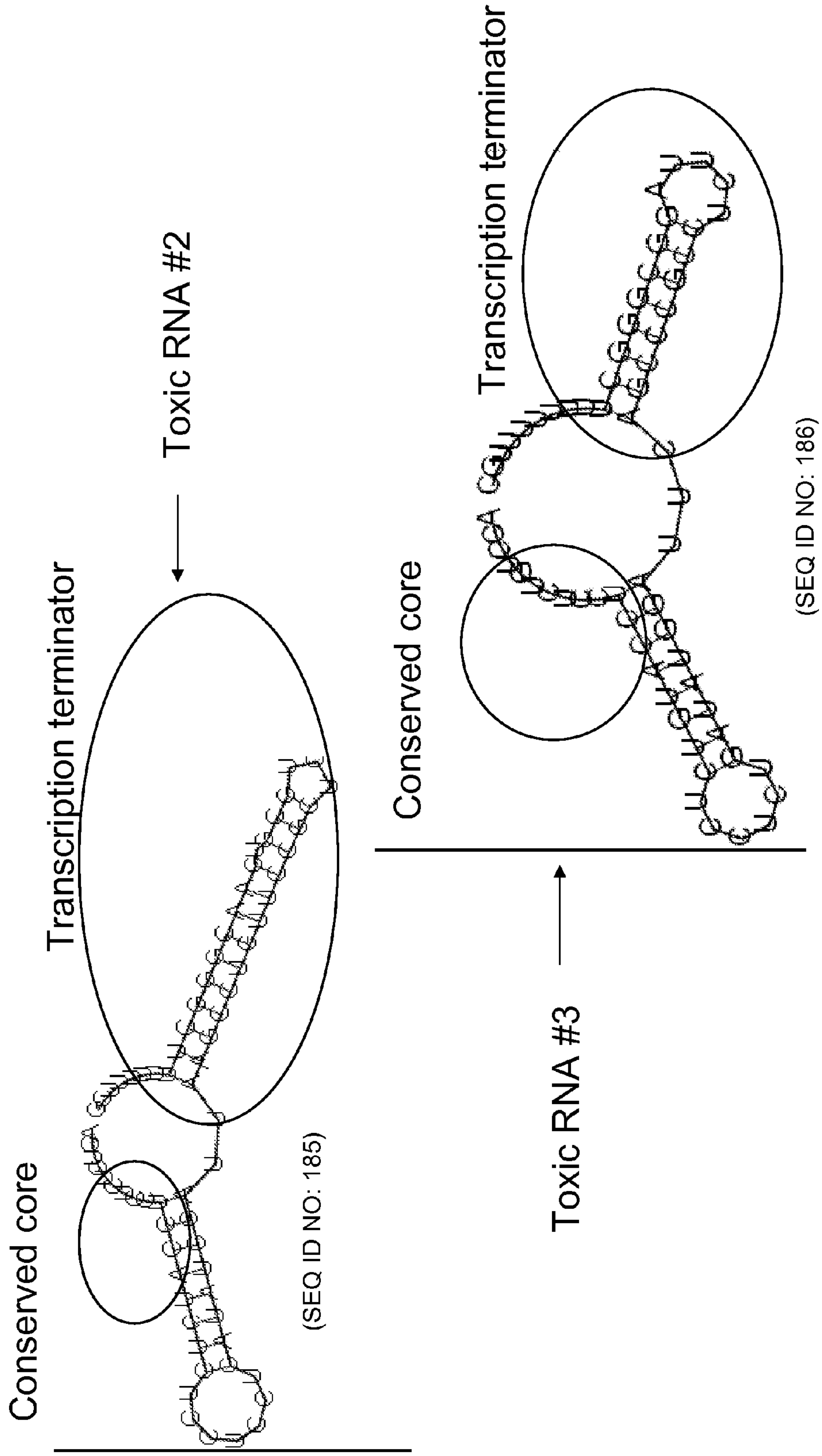
FIG. 18: Two additional RNAs in *Burkholderia*. Secondary structure calculation was preformed using the RNAfold server [URL:<http://rna.tbi.univie.ac.at/cgi-bin/RNAfold.cgi>]. The transcriptional terminator is marked by blue circles; the conserved core is marked by red circles. Structures of these two RNAs are similar to the above described one, except for the missing first stem. The top structure is SEQ ID NO:185 and the bottom structure is SEQ ID NO:186.
Figure 19:
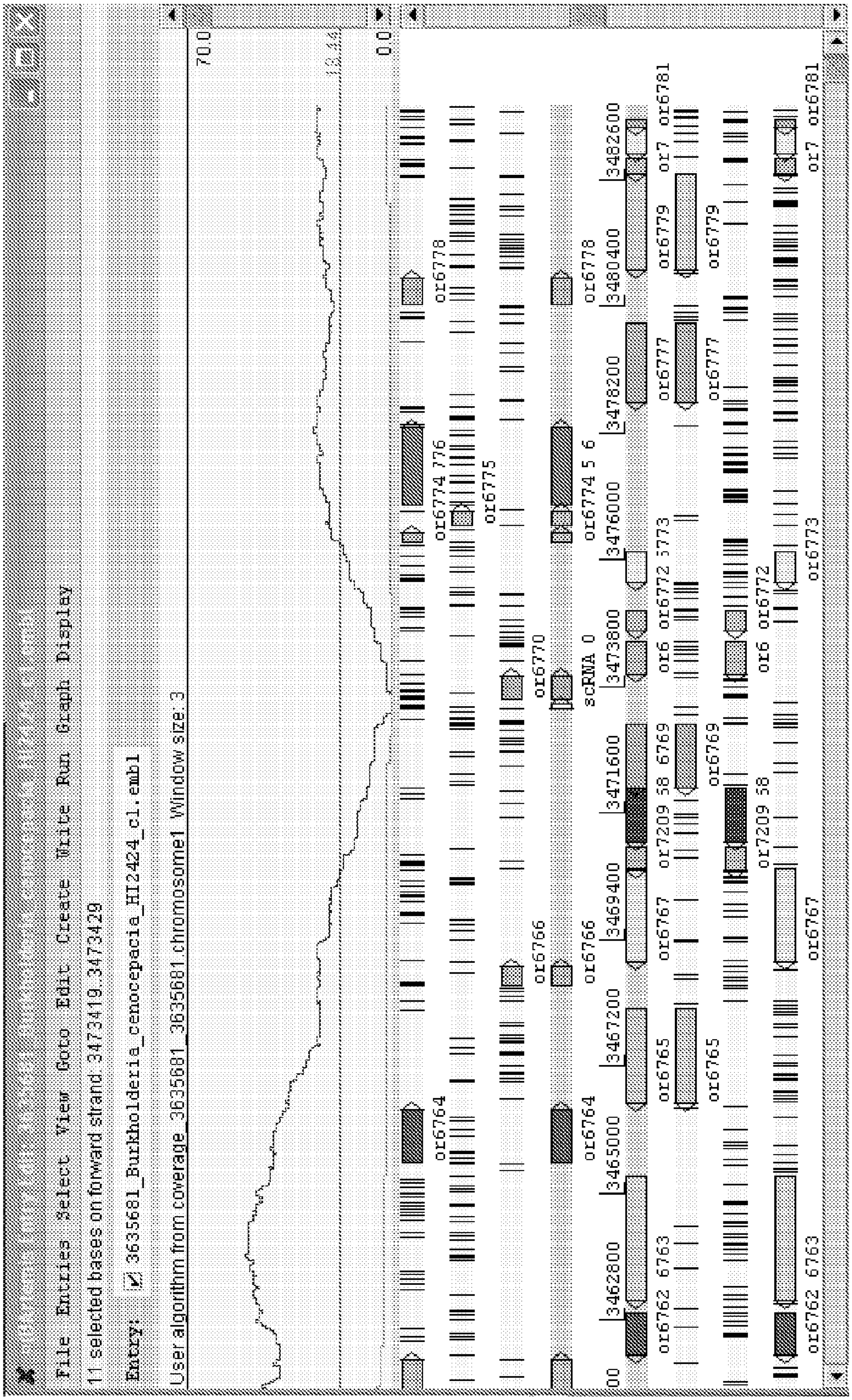
FIG. 19: Low coverage in RNA #2 (SEQ ID NO: 185). Shown is a snapshot from Artemis genome browser [Rutherford, 2000. Bioinformatics 16 (10) 944-945] of a ~22 kb region between positions 3,462,000-3,484,000 of chromosome I of the *Burkholderia cenocepacia* HI2424 genome. Clone coverage is in the above curves (red curve—small clones [up to 10 kb]; green curve—large clones [10-50 kb]). RNA #2 is marked as 'scRNA'.
Figure 20:
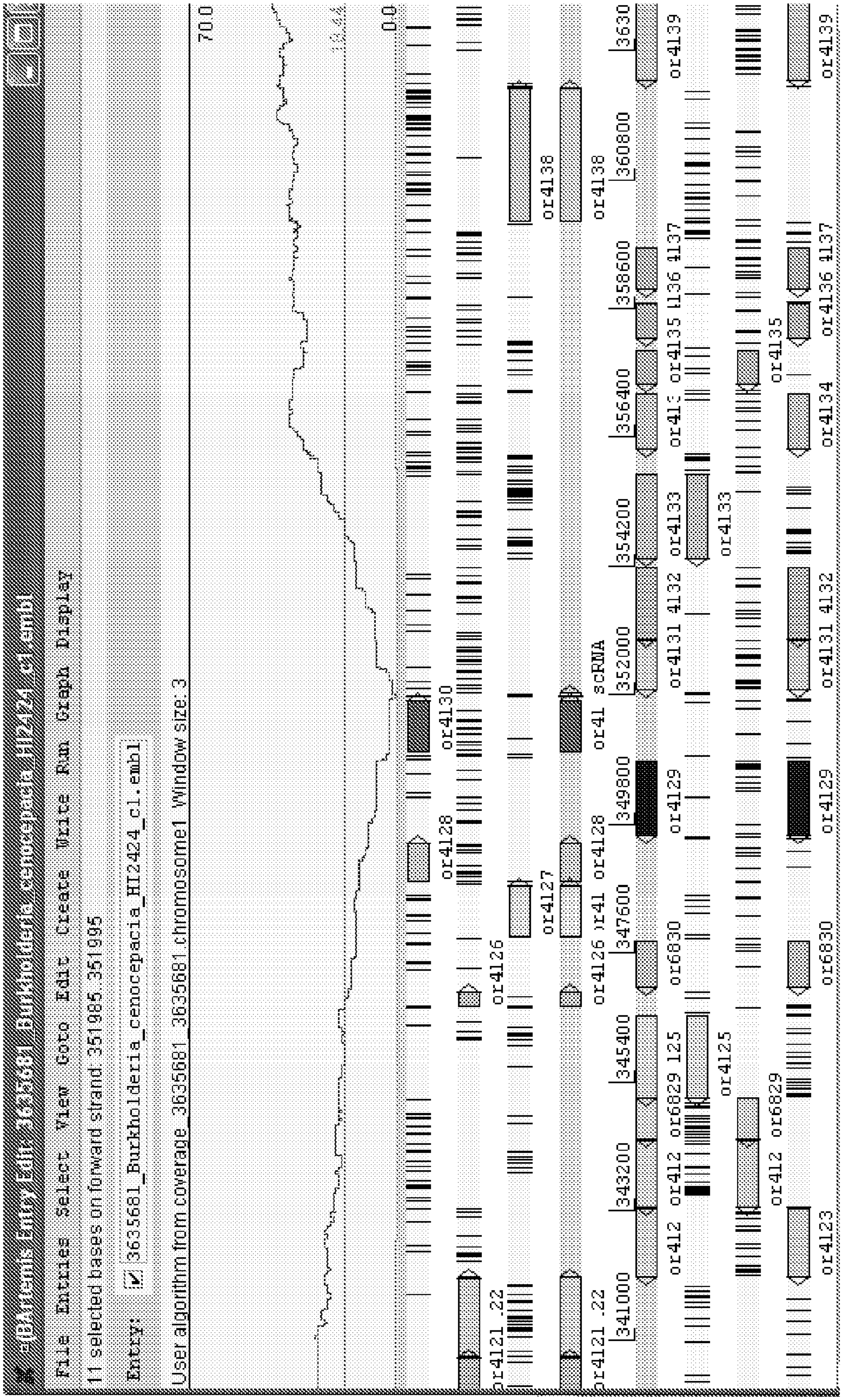
FIG. 20: Low coverage in RNA #3 (SEQ ID NO: 186). Shown is a snapshot from Artemis genome browser [Rutherford, 2000. Bioinformatics 16 (10) 944-945] of a ~22 kb region between positions 341,000-363,000 of chromosome I of the *Burkholderia cenocepacia* HI2424 genome. Clone coverage is in the above curves (red curve—small clones [up to 10 kb]; green curve—large clones [10-50 kb]). RNA #3 is marked as 'scRNA'.

To search for more RNA genes having similar structure, we used the cmalign and cmsearch software modules from the infernal software package [URL:<http://infernaljanelia.org/>]. Scanning the *Burkholderia* genome revealed two more such small predicted RNAs. In both cases, these small RNAs (SEQ ID NOS: 179, 182, 185, and 186) (as shown and identified in FIG. 21) were found in an intergenic region and had an upstream promoter and a rho-independent terminator. Two RNAs have similar structure as the above described small RNA shown in FIG. 16, but lack the first stem (FIG. 18). The clone coverage of both these additional RNAs was extremely low in both cases (FIGS. 19-20).

Figure 21:
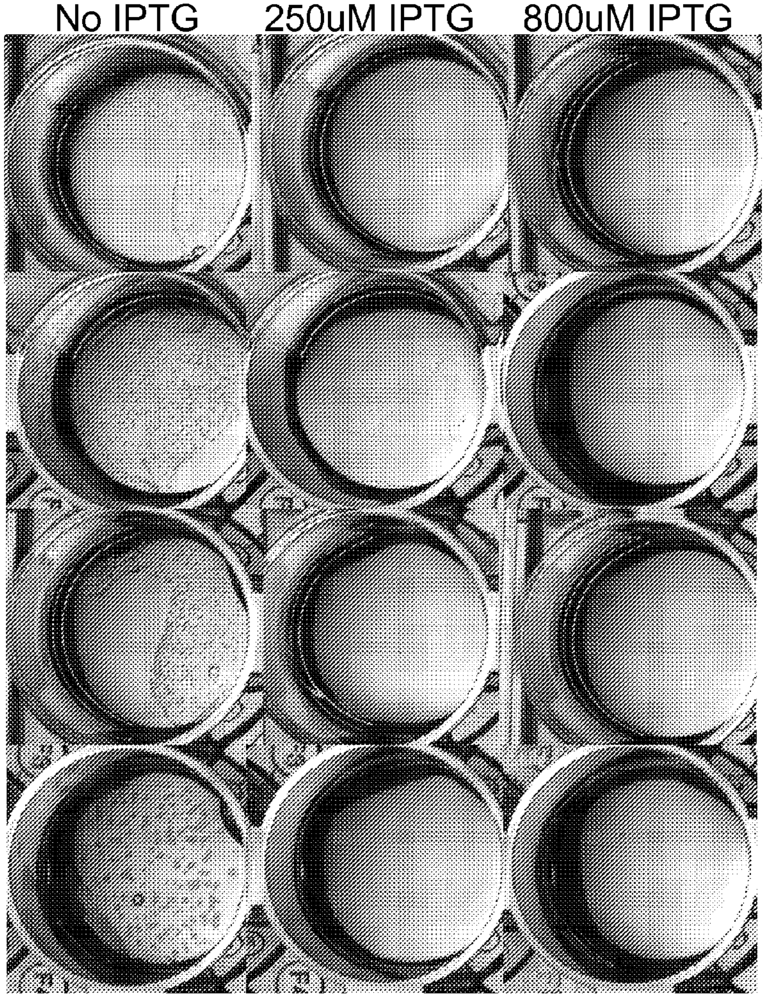
FIG. 21: Small RNAs inhibit *E. coli* growth following induction of their expression. Colonies containing four small RNA genes grow in a medium without IPTG (left plate) but fail to grow in the presence of IPTG, where expression of small RNAs is induced (right plates). The three small RNAs identified in *Burkholderia cenocepacia* HI2424 and one of the orthologous small RNA in *Ralstonia metallidurans* (SEQ ID NOS: 182, 185, 186 and 179) were amplified from their genome of origin and engineered into pcrSmart vector (Lucigen) directly downstream from the T7 promoter. Vectors were transformed into BL21 (DE)pLys cells (Invitrogen) that contain a choromosomal copy of the T7 polymerase under the control of lac promoter. Correct sequence in the inserts was verified by direct sequencing.

To check whether the identified small RNAs indeed inhibit bacterial growth we cloned 4 such RNAs (SEQ ID NOS: 165, 168, 171 and 172) into the pcrSmart plasmid (Lucigen) under a T7 polymerase promoter, and transformed the vector into BL21(DE)pLYS cells, as described above for the protein in Example 1. FIG. 21 shows that colonies containing the small RNAs cannot grow if its expression of these RNAs is induced by the addition of IPTG to the medium, demonstrating their toxicity to *E coli*. These results show that the small RNAs indeed have a growth inhibition effect (i.e., antimicrobial effect) on *E coli.*

In summary, we used our method to discover a new family of small RNAs that are toxic to *E. coli*. These RNAs have detectable homologs only in the small group of betaproteobacteria, to which the *Burkholderia* and *Cupriavidus* (*Ralstonia*) species belong. In all cases we noted these RNAs have extreme clone coverage deficiency (frequently causing zero coverage), indicating their toxicity to the *E coli* host. This demonstrates the power of our method to detect antimicrobial agents that are not necessarily proteins.

The above examples are provided to illustrate the invention but not to limit its scope. Other variants of the invention will be readily apparent to one of ordinary skill in the art and are encompassed by the appended claims. All publications, databases, and patents cited herein are hereby incorporated by reference for all purposes.

What is claimed is:

1. A plant comprising in its genome at least one stably incorporated expression cassette, said expression cassette expressing a protein sequence having at least 85% homology to SEQ ID NO: 97, wherein upon expression of said protein in the plant, said plant displays increased resistance to a plant pathogen.

2. The plant of claim 1, wherein said expression cassette comprises a heterologous nucleotide sequence that is at least 85% homologous to SEQ ID NO: 96 and operably linked to a promoter.

3. The plant of claim 2, wherein said plant pathogen is a microbe.

4. The plant of claim 3, wherein said microbe is selected from the group consisting of *Agrobacterium tumefaciens, Burkholderia cenocepacia, Clavibacter michiganensis, Erwinia carotovora, Erwinia chrysanthemi, Leifsonia xyli, Pseudomonas syringae, Ralstonia solanacearum, Xanthomonas axonopodis, Xanthomonas campestris, Xylella fastidiosa, Spiroplasma kunkelii*, and Onion yellows phytoplasma.

5. The plant of claim 2, wherein said promoter is a pathogen-inducible promoter.

6. A transformed seed of the plant of claim 1.

7. A method for inducing pathogen resistance in a plant, said method comprising introducing into a plant at least one expression cassette, said expression cassette comprising a heterologous nucleotide sequence that expresses a protein having at least 85% homology to SEQ ID NO: 97 and operably linked to an inducible promoter that drives expression in the plant; wherein the expressed protein provides pathogen resistance.

8. The method of claim 7, wherein said heterologous nucleotide sequence is at least 90% homologous to SEQ ID NO: 96.

9. The method of claim 8, wherein said heterologous nucleotide sequence is at least 90% homologous to SEQ ID NO: 96.

10. The method of claim 7, wherein said microbe is selected from the group consisting of *Agrobacterium tumefaciens, Burkholderia cenocepacia, Clavibacter michiganensis, Erwinia carotovora, Erwinia chrysanthemi, Leifsonia xyli, Pseudomonas syringae, Ralstonia solanacearum, Xanthomonas axonopodis, Xanthomonas campestris, Xylella fastidiosa, Spiroplasma kunkelii*, and Onion yellows phytoplasma.

* * * * *